(12) United States Patent
Kraus et al.

(10) Patent No.: US 12,194,082 B2
(45) Date of Patent: *Jan. 14, 2025

(54) COMPOSITIONS AND METHODS FOR TREATMENT OF HOMOCYSTINURIA

(71) Applicant: THE REGENTS OF THE UNIVERSITY OF COLORADO, Denver, CO (US)

(72) Inventors: Jan P. Kraus, Denver, CO (US); Tomas Majtan, Aurora, CO (US); Erez Bublil, Ets Efraim (IL)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/454,701

(22) Filed: Aug. 23, 2023

(65) Prior Publication Data

US 2024/0091325 A1    Mar. 21, 2024

Related U.S. Application Data

(63) Continuation of application No. 17/362,633, filed on Jun. 29, 2021, now Pat. No. 11,771,745, which is a continuation of application No. 16/824,931, filed on Mar. 20, 2020, now Pat. No. 11,077,175, which is a continuation of application No. 15/774,755, filed as application No. PCT/US2016/061050 on Nov. 9, 2016, now Pat. No. 10,653,755.

(51) Int. Cl.

| | | |
|---|---|---|
| *A61K 38/51* | (2006.01) | |
| *A61K 9/00* | (2006.01) | |
| *A61K 31/195* | (2006.01) | |
| *A61K 31/198* | (2006.01) | |
| *A61K 31/205* | (2006.01) | |
| *A61K 31/385* | (2006.01) | |
| *A61K 45/06* | (2006.01) | |
| *A61K 47/60* | (2017.01) | |
| *A61P 13/02* | (2006.01) | |
| *A61P 17/14* | (2006.01) | |
| *A61P 19/10* | (2006.01) | |
| *A61P 27/02* | (2006.01) | |
| *A61P 43/00* | (2006.01) | |
| *C12N 9/88* | (2006.01) | |
| *C12N 9/96* | (2006.01) | |

(52) U.S. Cl.
CPC ............ *A61K 38/51* (2013.01); *A61K 9/0019* (2013.01); *A61K 31/198* (2013.01); *A61K 31/205* (2013.01); *A61K 31/385* (2013.01); *A61K 45/06* (2013.01); *A61K 47/60* (2017.08); *C12N 9/88* (2013.01); *C12N 9/96* (2013.01); *C12Y 402/01022* (2013.01); *A61K 2300/00* (2013.01)

(58) Field of Classification Search
None
See application file for complete search history.

(56) References Cited

U.S. PATENT DOCUMENTS

| | | |
|---|---|---|
| 5,523,225 A | 6/1996 | Kraus |
| 5,635,375 A | 6/1997 | Kraus et al. |
| 5,643,575 A | 7/1997 | Martinez et al. |
| 5,656,425 A | 8/1997 | Kraus |
| 5,705,151 A | 1/1998 | Dow et al. |
| 5,730,990 A | 3/1998 | Greenwald et al. |
| 5,902,588 A | 5/1999 | Greenwald et al. |
| 5,919,455 A | 7/1999 | Greenwald et al. |
| 6,113,906 A | 9/2000 | Greenwald et al. |
| 6,153,655 A | 11/2000 | Martinez et al. |
| 6,174,696 B1 | 1/2001 | Seman |
| 6,177,087 B1 | 1/2001 | Greenwald et al. |
| 6,436,658 B1 | 8/2002 | Seman |
| 6,596,701 B1 | 7/2003 | Schwartz et al. |
| 6,638,500 B1 | 10/2003 | El-Tayar et al. |
| 7,485,307 B2 | 2/2009 | Kraus et al. |
| 7,816,495 B2 | 10/2010 | Kingsland et al. |
| 8,007,787 B2 | 8/2011 | Kraus |
| 8,398,989 B2 | 3/2013 | Kraus et al. |
| 9,011,844 B2 | 4/2015 | Kraus |
| 9,034,318 B2 | 5/2015 | Kraus et al. |
| 9,243,239 B2 | 1/2016 | Carrillo et al. |
| 9,284,546 B2 | 3/2016 | Kraus |
| 9,447,406 B2 | 9/2016 | Kraus et al. |
| 9,631,188 B2 | 4/2017 | Kraus |
| 9,675,678 B2 | 6/2017 | Kraus et al. |
| 10,046,036 B2 | 8/2018 | Kraus et al. |
| 10,160,962 B2 | 12/2018 | Carrillo et al. |
| 10,265,387 B2 | 4/2019 | Kraus et al. |
| 10,280,415 B2 | 5/2019 | Kraus |

(Continued)

FOREIGN PATENT DOCUMENTS

| | | |
|---|---|---|
| CA | 2898772 A1 | 8/2014 |
| CN | 1552905 A | 12/2004 |

(Continued)

OTHER PUBLICATIONS

"A novel protease for site-specific cleavage of GST fusion proteins," *Science Tools from Pharmacia Biotech* 2(1):18-19, 1997.

(Continued)

*Primary Examiner* — Suzanne M Noakes
*Assistant Examiner* — Jae W Lee
(74) *Attorney, Agent, or Firm* — Seed IP Law Group LLP

(57) ABSTRACT

Provided are compositions and methods for enzyme replacement therapy using modified human cystathionine beta synthase (CBS) in the treatment of homocystinuria and related diseases and disorders.

20 Claims, 53 Drawing Sheets

Specification includes a Sequence Listing.

(56) References Cited

U.S. PATENT DOCUMENTS

| | | | |
|---|---|---|---|
| 10,624,959 | B2 | 4/2020 | Kraus et al. |
| 10,653,755 | B2 | 5/2020 | Kraus et al. |
| 10,729,753 | B2 | 8/2020 | Kraus et al. |
| 10,941,392 | B2 | 3/2021 | Carrillo et al. |
| 11,077,175 | B2 | 8/2021 | Kraus et al. |
| 11,324,811 | B2 | 5/2022 | Majtan et al. |
| 11,400,143 | B2 | 8/2022 | Kraus et al. |
| 11,771,745 | B2 | 10/2023 | Kraus et al. |
| 2003/0091543 | A1 | 5/2003 | Klein et al. |
| 2005/0036981 | A1 | 2/2005 | Yagi et al. |
| 2006/0251641 | A1 | 11/2006 | Keimel |
| 2007/0010492 | A1 | 1/2007 | Generale |
| 2010/0016672 | A1 | 1/2010 | Segawa et al. |
| 2022/0265835 | A1 | 8/2022 | Bublil et al. |
| 2022/0290116 | A1 | 9/2022 | Sellos-Moura et al. |
| 2023/0039591 | A1 | 2/2023 | Majtan et al. |
| 2023/0042914 | A1 | 2/2023 | Kraus et al. |

FOREIGN PATENT DOCUMENTS

| | | |
|---|---|---|
| CN | 101322840 A | 12/2008 |
| CN | 102741288 A | 10/2012 |
| CN | 105452457 A | 3/2016 |
| EP | 1396537 A1 | 3/2004 |
| EP | 1878739 A1 | 1/2008 |
| JP | 6146934 B2 | 6/2017 |
| JP | 6453243 B2 | 1/2019 |
| WO | WO 9507714 A1 | 3/1995 |
| WO | WO 0102600 A2 | 1/2001 |
| WO | WO 0209515 A1 | 2/2002 |
| WO | WO 03106971 A2 | 12/2003 |
| WO | WO 2011025964 A2 | 3/2011 |
| WO | WO 2011097381 A2 | 8/2011 |
| WO | WO 2012001336 A1 | 1/2012 |
| WO | WO 2013148580 A1 | 10/2013 |
| WO | WO 2014120770 A1 | 8/2014 |
| WO | WO 2015033279 A1 | 3/2015 |
| WO | WO 2017018742 A1 | 2/2017 |
| WO | WO 2018195006 A1 | 10/2018 |

OTHER PUBLICATIONS

"Sequence alignment between SEQ ID No. 2 and AC P35520," Jun. 1, 1994, 2 pages.

Aitken et al., "Role of Active-Site Residues Thr81, Ser82, Thr85, Gln157, and Tyr158 in Yeast Cystathionine β-Synthase Catalysis and Reaction Specificity" *Biochemistry* 43(7):1963-1971, 2004.

Alexander et al., "Evolutionary relationships among pyridoxal-5'-phosphate-dependent enzymes. Regio-specific α, β and γ families," *Eur. J. Biochem.* 219: 953-960, 1994.

Allen et al., "Serum betaine, N, N-dimethylglycine and N-methylglycine levels in patients with cobalamin and folate deficiency and related inborn errors of metabolism," *Metabolism* 42(11):1448-1460, Nov. 1993.

Altschul et al., "Basic Local Allignment Search Tool," *J. Mol. Biol.* 215:403-410, 1990.

Altschul et al., "Gapped BLAST and PSI-BLAST: a new generation of protein database search programs," *Nucleic Acids Res.* 25:3389-3402, 1997.

Aoki et al., "Angiogenesis induced by hepatocyte growth factor in non-infarcted myocardium and infarcted myocardium: up-regulation of essential transcription factor for angiogenesis, ets" *Gene Therapy* 7:417-427, 2000.

Banerjee et al., "Redox regulation and reaction mechanism of human cystathionine-β-synthase: a PLP-dependent hemesensor protein," *Archives of Biochemistry and Biophysics* 433:144-156, 2005.

Barber et al., "The successful treatment of homocystinuria with pyridoxine." *J. Pediatr.* 75(3):463-78, Sep. 1969.

Bateman, "The structure of a domain common to archaebacteria and the homocystinuria disease protein." *Trends Biochem. Sci.* 22:12-13, Jan. 1997.

Belew et al., "Kinetic characterization of recombinant human cystathionine beta-synthase purified from *E. coli*," *Protein Expression and Purification Academic Press* 64(2):139-145, 2009.

Bennett et al., "Stable transgene expression in rod photoreceptors after recombinant adeno-associated virus-mediated gene transfer to monkey retina" *Proc. Natl. Acad. Sci. USA* 96:9920-9925, Aug. 1999.

Blaese et al., "T Lymphocyte-Directed Gene Therapy for ADA-SCID: Initial Trial Results After 4 Years," *Science* 270:475-480, Oct. 20, 1995.

Bordignon et al., "Gene Therapy in Peripheral Blood Lymphocytes and Bone Marrow for ADA-Immunodeficient Patients," *Science* 270(5235):470-475, Oct. 20, 1995 (7 pages).

Broun et al., "Catalytic Plasticity of Fatty Acid Modification Enzymes Underlying Chemical Diversity of Plant Lipids," *Science* 282:1315-1317, Nov. 13, 1998.

Bruno et al., "Functional Properties of the Active Core of Human Cystathione β-Synthase Crystals," *The Journal of Biological Chemistry* 276(1):16-19, Jan. 5, 2001.

Bublil et al., "Enzyme replacement with PEGylated cystathionine β-synthase ameliorates homocystinuria in murine model," *J Clin Invest.* 126(6):2372-2384, 2016.

Bukovska et al., "Expression of Human Cystathionine β-Synthase in *Escherichia coli*: Purification and Characterization," *Protein Expression and Purification* 5:442-448, Apr. 1, 1994.

Byrne et al., "DNA Sequences of the cysK Regions of *Salmonella typhimurium* and *Escherichia coli* and Linkage of the cysK Regions to ptsH," *Journal of Bacteriology* 170(7):3150-3157, Jul. 1988.

Carballal et al., "Dioxygen Reactivity and Heme Redox Potential of Truncated Human Cystathionine β-Synthase," *Biochemistry* 47(10): 3194-3201, Feb. 16, 2008.

Carson et al., "Metabolic abnormalities detected in a survey of mentally backward individuals in Northern Ireland." *Arch. Dis. Child* 37(195):505-13, Oct. 1962.

Chassaing et al., "Determination of reduced and oxidized homocysteine and related thiols in plasma by thiol-specific pre-col. derivatization and capillary electrophoresis with laser-induced fluorescence detection" *Journal of Chromatography B* 735(2):219-227, Dec. 1999.

Chassé et al., "Genomic Organization of the Human Cystathionine β-Synthase Gene: Evidence for Various cDNAs," *Biochemical and Biophysical Research Communications* 211(3):826-832, Jun. 26, 1995.

Cherney et al., "Ferrous Human Cystathionine β-Synthase Loses Activity during Enzyme Assay Due to a Ligand Switch Process," *Biochemistry* 46(45): 13199-13210, Oct. 23, 2007.

D'Souza et al., "Pharmaceutical amyloidosis associated with subcutaneous insulin and enfuvirtide administration." *Amyloid* 21(2):71-75, Jun. 2014. (NIH Public Access Author Manuscript, available in PMC Jun. 1, 2014) (9 pages).

Devos et al., "Practical Limits of Function Prediction," *PROTEINS: Structure, Function, and Genetics* 41:98-107, Jun. 12, 2000.

Ding et al., "Bioconjugated PLGA-4-arm-PEG branched polymeric nanoparticles as novel tumor targeting carriers," *Nanotechnology*: 165101, Apr. 2011. (12 pages).

Dong et al., "Secondary Structure of Recombinant Human Cystathionine β-Synthase in Aqueous Solution: Effect of Ligand Binding and Proteolytic Truncation," *Archives of Biochemistry and Biophysics* 344(1):125-132, Aug. 1, 1997.

El-Sayed et al., "PLP-Dependent Enzymes: a Potent Therapeutic Approach for Cancer and Cardiovascular diseases," Targets in Gene Therapy, Prof. Yongping You (Ed.), In Tech, pp. 119-146, Aug. 2011.

Extended European Search Report issued Aug. 7, 2020 in European patent application 20168207.7.

Fee et al., "PEG-proteins: Reaction engineering and separation issues," *Chemical Engineering Science* 61:924-939, 2006.

Fekete et al., "Theory and practice of size exclusion chromatography for the analysis of protein aggregates," *Journal of Pharmaceutical and Biomedical Analysis* 101:161-173, 2014.

Finkelstein et al., "Activation of cystathionine synthase by adenosylmethionine and adenosylethionine," *Biochem. Biophys. Res. Commun.* 66:81-87, 1975.

(56) References Cited

OTHER PUBLICATIONS

Finkelstein et al., "Inactivation of Betaine-Homocysteine Methyltransferase by Adenosylmethionine and Adenosylethionine," *Biochemical and Biophysical Research Communications* 118(1):14-19, Jan. 13, 1984.

Finkelstein et al., "Methionine metabolism in mammals. Distribution of homocysteine between competing pathways." *J. Biol. Chem.* 259(15):9508-9513, 1984.

Finkelstein, "Methionine metabolism in mammals." *J. Nutr. Biochem.* 1(5):228-37, May 1990.

First Examination Report for India Application 6010/DELNP/2015, dated Nov. 28, 2019.

Frank et al., "Purification and characterization of the wild type and truncated human cystathionine β-synthase enzymes expressed in *E. coli*," *Archives of Biochemistry and Biophysics* 470(1):64-72, 2008.

Frank et al., "Solvent-Accessible Cysteines in Human Cystathionine β-Synthase: Crucial Role of Cysteine 431 in S-Adenosyl-L-methionine Binding," *Biochemistry* 45:11021-11029, 2006.

Gallagher et al., "Structure and control of pyridoxal phosphate dependent allosteric threonine deaminase," *Structure* 6(4):465-475, Apr. 15, 1998.

Gaustadnes et al., "Prevalence of Congenital Homocystinuria in Denmark," *N. Engl. J. Med.* 340(19):1513, May 1999.

Green et al., "Molecular Cloning: A Laboratory Manual," Cold Spring Harbor Laboratory Press, Fourth Edition, vol. 1, 2012 (34 pages) (Table of Contents only).

Gupta et al., "Betaine supplementation is less effective than methionine restriction in correcting phenotypes of CBS deficient mice," *J. Inherit. Metab. Dis.* 39:39-46, 2016.

Gupta et al., "Cysthathionine beta-synthase-deficient mice thrive on a low-methionine diet," *FASEB J.* 28(2):781-90, Feb. 2014.

Gupta et al., "Mouse models of cystathionine beta-synthase deficiency reveal significant threshold effects of hyperhomocysteinemia." *FASEB J.* 23(3):883-893, Mar. 2009.

Halperin et al., "The Influences of Environmental Enrichment, Cognitive Enhancement, and Physical Exercise on Brain Development: Can we Alter the Developmental Trajectory of ADHD?" *Neurosci Biobehav Rev.* 35(3): 621-634, Jan. 2011 (NIH Public Access Author Manuscript, available in PMC Jan. 1, 2012) (31 pages).

Harris et al., "Effect of pegylation on pharmaceuticals," *Nature Reviews Drug Discovery* 2(3):214-221, Mar. 2003.

Henikoff et al., "Amino acid substitution matrices from protein blocks," *Proc. Natl. Acad. Sci. USA* 89:10915-10919, Nov. 1992.

Huang et al., "Liposomal gene delivery: A complex package," *Nature Biotechnology* 15:620-621, Jul. 1997.

International Search Report and Written Opinion, dated Jan. 23, 2017, for International Patent Application No. PCT/US2016/061050.

International Search Report, mailed Jun. 17, 2014, for International Application No. PCT/US2014/013602. (6 pages).

Jakubowski et al., "Mutations in cystathionine β-synthase or methylenetetrahydrofolate reductase gene increase N-homocysteinylated protein levels in humans," *FASEB J* 22(12):4071-4076, 2008.

Janošík et al., "Crystallization and preliminary X-ray diffraction analysis of the active core of human recombinant cystathione β-synthase: an enzyme involved in vascular disease," *Acta Crystallogr. D Biol. Crystallogr.* 57(Pt 2):289-291, 2001.

Janošík et al., "Impaired Heme Binding and Aggregation of Mutant Cystathionine β-Synthase Subunits in Homocystinuria," *Am. J. Hum. Genet.* 68(6):1506-1513, May 15, 2001.

Janošík et al., "Regulation of Human Cystathionine β-synthase by S-Adenosyl-L-methionine: Evidence for Two Catalytically Active Conformations Involving an Autoinhibitory Domain in the C-terminal Region," *Biochemistry* 40(35):10625-10633, 2001.

Jhee et al., "Domain Architecture of the Heme-Independent Yeast Cystathionine β-synthase Provides Insights into Mechanisms of Catalysis and Regulation," *Biochemistry* 39(34):10548-10556, 2000.

Jhee et al., "Forum Review: The Role of Cystathionine β-Synthase in Homocysteine Metabolism," *Antioxid. Redox Signal.* 7(5-6):813-822, 2005.

Jhee et al., "Yeast Cystathionine β-Synthase Is a Pyridoxal Phosphate Enzyme but, Unlike the Human Enzyme, Is Not a Heme Protein." *The Journal of Biological Chemistry* 275(16):11541-11544, Apr. 21, 2000.

Jinping et al., "Advance in Cystathionine beta-Synthase Research," *Med. J. West China* 18(5):657-659, Sep. 2006 (7 pages) (with English Translation).

Kabil et al., "Deletion of the Regulatory Domain in the Pyridoxal Phosphate-dependent Heme Protein Cystathionine β-Synthase Alleviates the Defect Observed in a Catalytic Site Mutant," *The Journal of Biological Chemistry*, 274(44):31256-31260, Oct. 29, 1999.

Kaneda et al., "Prevention of Restenosis by Gene Therapy," *Annals New York Academy of Sciences*, 299-310, 1997.

Kang et al., "Emerging PEGylated drugs," *Expert opinion on emerging drugs* 14(2):363-380, Jun. 2009.

Kery et al., "δ-Aminolevulinate Increases Heme Saturation and Yield of Human Cystathionine β-Synthase Expressed in *Escherichia coli*," *Archives of Biochemistry and Biophysics* 316(1):24-29, Jan. 10, 1995.

Kery et al., "Binding of Pyridoxal 5'-Phosphate to the Heme Protein Human Cystathionine β-Synthase," *Biochemistry* 38(9):2716-2724, Feb. 9, 1999.

Kery et al., "Transsulfuration Depends on Heme in Addition to Pyridoxal 5'-Phosphate. Cystathionine β-Synthase is a Heme Protein," *The Journal of Biological Chemistry* 269(41):25283-25288, Oct. 14, 1994.

Kery et al., "Trypsin Cleavage of Human Cystathionine β-Synthase into an Evolutionarily Conserved Active Core: Structural and Functional Consequences," *Arch. Biochem. Biophys.* 355(2):222-232, Jul. 1998.

Kim et al., "Functional modeling of vitamin responsiveness in yeast: a common pyridoxine-responsive cystathionine β-synthase mutation in homocystinuria," *Human Mol. Genet.* 6(13):2213-2221, 1997.

Kitano, "Biological robustness." *Nature Reviews Genetics* 5(11):826-837, Nov. 2004.

Kluijtmans et al., "Defective Cystathionine β-Synthase Regulation by S-Adenosylmethionine in a Partially Pyridoxine Responsive Homocystinuria Patient," *J. Clin. Invest.* 98(2):285-289, Jul. 1996.

Knudson et al., "Evaluating Separations of PEGylated Proteins Using Gel Filtration Chromatography," Phenomenex, Inc., Dec. 2008 (4 pages).

Koeberl et al., "Persistent expression of human clotting factor IX from mouse liver after intravenous injection of adeno-associated virus vectors," *Proc. Natl. Acad. Sci. USA* 94:1426-1431, Feb. 1997.

Komrower et al., "Dietary Treatment of Homocystinuria." *Arch. Dis. Child* 41(220):666-671, Dec. 1966.

Koza et al., "PEGylated Protein Analysis by Size-Exclusion and Reversed-Phase UPLC," Waters Corporation, pp. 1-5, 2014 (6 pages).

Kožich et al., "Screening for Mutations by Expressing Patient cDNA Segments in *E. coli*: Homocystinuria due to Cystathionine β-Synthase Deficiency," Hum. Mutation 1:113-123, 1992.

Kraus et al., "Cystathionine β-Synthase and Its Deficiency." In Carmel et al. (eds.), *Homocysteine in Health and Disease*, Cambridge University Press, Cambridge, United Kingdom, pp. 223-243, 2001.

Kraus et al., "Cystathionine β-synthase from Human Liver: Improved Purification Scheme and Additional Characterization of the Enzyme in Crude and Pure Form," *Arch. Biochem. Biophys.* 222(1):44-52, Apr. 1983.

Kraus et al., "Human cystathionine β-synthase cDNA: sequence, alternative splicing and expression in cultured cells," *Human Molecular Genetics* 2(10):1633-1638, 1993.

Kraus et al., "Purification and Properties of Cystathionine β-Synthase from Human Liver," *J. Biol. Chem.* 253(18):6523-6528, 1978.

Kraus, "Cystathionine β-synthase (human)," *Methods Enzymol.* 143:388-394, 1987.

(56) References Cited

OTHER PUBLICATIONS

Kruger et al., "A yeast system for expression of human cystathionine β-synthase: Structural and functional conservation of the human and yeast genes," *Proc. Natl. Acad. Sci. USA* 91:6614-6618, Jul. 1994.
Kutzbach et al., "Feedback inhibition of methylene-tetrahydrofolate reductase in rat liver by S-adenosylmethionine," *Biochim. Biophys. Acta* 139:217-220, 1967.
Kutzbach et al., "Mammalian Methylenetetrahydrofolate Reductase. Partial Purification, Properties, and Inhibition by S-Adenosylmethionine," *Biochim. Biophys. Acta* 250:459-477, 1971.
Levine et al., "Adenoviral-Mediated Gene Transfer to Human Adipocytes In Vitro, and Human Adipose Tissue Ex Vivo and Rabbit Femoral Adipose Tissue In Vivo," *J Nutr. Sci. Vitaminol.* 44:569-572, 1998.
Levy, "Physician's Guide to The Homocystinurias," *National Organization for Rare Disorders (NORD)*, Jan. 2010, Retrieved from Internet: URL:http://www.rarediseases.org/docs/Homocystinuria_11_29b.pdf (8 pages).
Li et al., "Homocystinuria and Phychiatric Disorder: A Case Report," *Pathology* 31(3):221-224, 1999.
Linnebank et al., "High Prevalence of the 1278T Mutation of the Human Cystathionine β-Synthase Detected by a Novel Screening Application," *Thromb. Haemost.* 85(6):986-988, Jun. 2001.
Linnebank et al., "Isolated thrombosis due to the cystathionine β-synthase mutation c.833T>C (1278T)," *J. Inherited Metabol. Dis.* 26(5):509-511, Jun. 2003.
Lodha et al., "Investigation of residues Lys112, Glu136, His138, Gly247, Tyr248, and Asp249 in the active site of yeast cystathionine β-synthase," *Biochem. Cell Biol.* 87:531-540, 2009.
Lowry et al., "Protein Measurement With the Folin Phenol Reagent." *J. Biol. Chem.* 193(1):265-275, 1951.
Lu et al., "Hcy promotes the formation of atherosclerotic and effect of liver lipid metabolism disorder in ApoE-/- mice," *Chongqing Medicine* (30):4030-4033, 2014. (with English Abstract).
MacLean et al., "A novel trangenic mouse model of CBS-deficient homocystinuria does not incur hepatic steatosis or fibrosis and exhibits a hypercoagulative phenotype that is ameliorated by betaine treatment," *Mol. Genet. Metab.* 101:153-162, Oct.-Nov. 2010.
MacLean et al., "Cystathionine beta-synthase null homocystinuric mice fail to exhibit altered hemostasis or lowering of plasma homocysteine in response to betaine treatment," *Mol. Genet. Metab.* 101:163-171, Oct.-Nov. 2010.
MacLean et al., "Cystathionine Protects against Endoplasmic Reticulum Stress-induced Lipid Accumulation, Tissue Injury, and Apoptotic Cell Death," *J. Biol. Chem.* 287(38):31994-32005, Sep. 14, 2012.
Maclean et al., "High Homocysteine and Thrombosis Without Connective Tissue Disorders Are Associated With a Novel Class of Cystathionine β-Synthase (CBS) Mutations," *Hum. Mutat.* 19:641-655, 2002.
Maclean et al., "Transsulfuration in *Saccharomyces cerevisiae* is not dependent on heme: purification and characterization of recombinant yeast cystathionine β-synthase." *Journal of Inorganic Biochemistry* 81:161-171, 2000.
Majtan et al., "Folding and activity of mutant cystathionine β-synthase depends on the position and nature of the purification tag: characterization of the R266K CBS mutant." *Protein Expr Purif.* 82(2):317-324, 2012 (NIH Public Access Author Manuscript, available in PMC Apr. 1, 2013) (21 pages).
Majtan et al., "Pharmacokinetics and pharmacodynamics of PEGylated truncated human cystathionine beta-synthase for treatment of homocystinuria," *Life Sciences* 200:15-25, 2018.
Majtan et al., "Purification and characterization of cystathionine β-synthase bearing a cobalt protoporphyrin," *Archives of Biochemistry and Biophysics* 508:25-30, 2011.
Majtan et al., "Rescue of Cystathionine β-Synthase (CBS) Mutants with Chemical Chaperones: Purification and Characterization of Eight CBS Mutant Enzymes." *J Biol Chem.* 285(21):15866-15873, May 21, 2010.

Mansoor et al., "Determination of the in Vivo Redox Status of Cysteine, Cysteinylglycine, Homocysteine, and Glutathione in Human Plasma," *Analytical Biochemistry* 200:218-229, 1992.
Mansoor et al., "Redox status and protein binding of plasma homocysteine and other aminothiols in patients with early-onset peripheral vascular disease, homocysteine and peripheral vascular disease." *Arterioscler Thromb Vasc Biol*, 15(2):232-240, Feb. 1995.
Mansoor et al., "Redox status and protein binding of plasma homocysteine and other aminothiols in patients with homocystinuria," *Metabolism* 42(11):1481-1485, Nov. 1993, 1 page (Abstract only).
Maurice et al., "Enhancement of cardiac function after adenoviral-mediated in vivo intracoronary β2-adrenergic receptor gene delivery," *J Clin. Invest.* 104(1):21-29, Jul. 1999.
Mayolo-Delosia et al., "Current advances in the non-chromatographic fractionation and characterization of PEGylated proteins," *J Chem Technol Biotechnol.*, 86:18-25, 2011.
Meier et al., "Structure of human cystathionine β-synthase: a unique pyridoxal 5'-phosphate-dependent heme protein," *EMBO J.* 20(15):3910-3916, 2001.
Melenovská et al., "Chaperone therapy for homocystinuria: the rescue of CBS mutations by heme arginate." *J. Inherit. Metab. Dis.* 38(2); 284-297, Mar. 2015.
Miles et al., "Cystathionine β-synthase: structure, function, regulation, and location of homocystinuria-causing mutations." *J. Biol. Chem.* 279(29):29871-29874, 2004.
Millecamps et al., "Neuron-restrictive silencer elements mediate neuron specificity of adenoviral gene expression," *Nature Biotechnology* 17:865-869, Sep. 1999.
Mudd et al., "Disorders of transsulfuration," in Stanbury et al. (eds.), *The Metabolic and Molecular Bases of Inherited Disease*, 8 Ed., McGraw-Hill, New York , pp. 2007-2056, 2001.
Mudd et al., "Homocysteine and its disulfide derivatives: A suggested consensus terminology," *Arterioscler. Thromb. Vasc. Biol.* 20:1704-1706, Jul. 2000.
Mudd et al., "Homocystinuria: An enzymatic defect." *Science* 143(3613):1443-1445, Mar. 1964.
Mudd et al., "The natural history of homocystinuria due to cystathionine β-synthase deficiency," *Am. J. Hum. Genet.* 37(1):1-31, Jan. 1985.
Münke et al., "The gene for cystathionine β-synthase (CBS) maps to the subtelomeric region on human chromosome 21q and to proximal mouse chromosome 17," *Am. J. Hum. Genet.* 42(4):550-559, Apr. 1988.
Needleman et al., "A general method applicable to the search for similarities in the amino acid sequence of two proteins," *J. Mol. Biol.* 48(3):443-453, Mar. 1970.
NOF America Corporation, "Sunbright MA series (Maleimide PEG)," URL=https://www.nofamerica.com/, download date Sep. 3, 2017. (5 pages).
NOF Corporation, "Activated PEGs," URL=https://www.dds-drug.cm/dds-products/index/php?dispatch=categories.view&category, download date Jun. 30, 2021. (10 pages).
Nozaki et al., "Characterization of Transsulfuration and Cysteine Biosynthetic Pathways in the Protozoan Hemoflagellate, *Trypanosoma cruzi*. Isolation and Molecular Characterization of Cystathionine β-Synthase and Serine Acetyltransferase from *Trypanosoma*," *The Journal of Biological Chemistry* 276(9):6516-6523, Mar. 2, 2001.
O'Shannessy et al., "Determination of Rate and Equilibrium Binding Constants for Macromolecular Interactions Using Surface Plasmon Resonance: Use of Nonlinear Least Squares Analysis Methods," *Analytical Biochemistry* 212:457-468, 1993.
Office Action, dated Apr. 18, 2018, for Japanese Application No. 2015555429. (with English Translation).
Office Action, dated Apr. 26, 2018, for Chinese Application No. 201480006554.0. (with English Translation).
Office Action, dated Jun. 2, 2020, for Japanese Application No. 2018232350.
Office Action, dated Jun. 24, 2018, for Israel Application No. 239783.
Office Action, dated Nov. 6, 2019, for Japanese Application No. 2018232350.
Office Action, dated Oct. 12, 2020, for Chinese Application No. 2016800762750.

(56) References Cited

OTHER PUBLICATIONS

Office Action, dated Oct. 13, 2020, for Brazil Application No. BR112018007768-2.
Office Action, dated Oct. 18, 2019, for Canadian Application 2,898,772.
Office Action, dated Sep. 29, 2020, for Japanese Application No. 2018-523444.
Ojha et al., "Effects of Heme Ligand Mutations Including a Pathogenic Variant, H65R, on the Properties of Human Cystathionine β-Synthase," *Biochemistry* 41(14):4649-4654, 2002.
Oligino et al., "Intra-articular delivery of a herpes simplex virus IL-1Ra gene vector reduces inflammation in a rabbit model of arthritis," *Gene Therapy* 6:1713-1720, Jun. 16, 1999.
Ono et al., "Purification and Properties of *Saccharomyces cerevisiae* Cystathionine β-Synthase," *Yeast* 10:333-339, 1994.
Park et al., "Recombinant adeno-associated virus mediated gene transfer in a mouse model for homocystinuria," *Exp. Mol. Med.* 38(6):652-661, Dec. 2006.
Pasut et al., "Pegylation for improving the effectiveness of therapeutic biomolecules," *Drugs of Today* 45(9):687-695, 2009.
Pasut et al., "State of the art in PEGylation: The great versatility achieved after forty years of research," *Journal of Controlled Release* 161(2):461-472, 2012.
Pearson et al., "Improved tools for biological sequence comparison," *Proc. Nat'l. Acad. Sci. USA* 85(8):2444-2448, Apr. 1988.
Pfister et al., "Process for protein PEGylation," *Journal of Controlled Release* 180:134-149, 2014.
Preliminary Office Action, dated Jun. 10, 2020, for Brazil Patent Application No. BR112014023570-8.
Refsum et al., "Facts and recommendations about total homocysteine determinations: an expert opinion," *Clin. Chem.* 50:3-32, Jan. 2004.
Robert et al., "Cystathionine β Synthase Deficiency Promotes Oxidative Stress, Fibrosis, and Steatosis in Mice Liver," *Gastroenterology* 128:1405-1415, 2005.
Robichon et al., "Engineering *Escherichia coli* BL21(DE3) Derivative Strains To Minimize *E. coli* Protein Contamination after Purification by Immobilized Metal Affinity Chromatography," *Applied and Environmental Microbiology* 77(13):4634-4646, Jul. 2011.
Rolland et al., "O-Acetylserine(thiol)lyase from Spinach (*Spinacia oleracea* L.) Leaf: cDNA Cloning, Characterization, and Overexpression in *Escherichia coli* of the Chloroplast Isoform," *Archives of Biochemistry and Biophysics* 300(1):213-222, Jan. 1993.
Roper et al., "Rat cystathionine β-synthase: expression of four alternatively spliced isoforms in transfected cultured cells." *Arch. Biochem. Biophys.* 298(2):514-521, 1992.
Régnier et al., "Brain Phenotype of Transgenic Mice Overexpressing Cystathionine β-Synthase," *PLOS One* 7(1):e29056 (10 pages).
Sacharow et al., "Homocystinuria Caused by Cystathionine Beta-Synthase Deficiency," *GeneReviews*:1-21, Jan. 15, 2004.
Saluta et al., "Troubleshooting GST fusion protein expression in *E. coli*," *Life Science News* 1: 1-3, 1998.
Salzmann et al., "Rates of Evolution of Pyridoxal-5'-Phosphate-Dependent Enzymes," *Biochemical and Biophysical Research Communications* 270(2):576-580, 2000.
Schiff et al., "Treatment of Inherited Homocystinurias," *Neuropediatrics* 43:295-304, 2012 (10 Pages).
Schuster et al., "Assembly and function of a quaternary signal transduction complex monitored by surface plasmon resonance," *Nature* 365:343-347, Sep. 23, 1993.
Seffernick et al., "Melamine Deaminase and Atrazine Chlorohydrolase: 98 Percent Identical but Functionally Different, " *J. Bacteriol.* 183(8):2405-2410, Apr. 2001.
Sen et al., "Cystathionine-β-synthase gene transfer and 3-deazaadenosine ameliorate inflammatory response in endothelial cells," *Am J Physiol Cell Physiol* 293: C1779-C1787, Sep. 13, 2007.
Shan et al., "Correction of disease-causing CBS mutation in yeast," *Nature Genetics* 19:91-93, May 1998.
Shan et al., "Mutations in the regulatory domain of cystathionine β-synthase can functionally suppress patient-derived mutations in cis," *Human Molecular Genetics* 10(6):635-643, 2001.
Singh et al., "Functional Rescue of Mutant Human Cystathionine β-Synthase by Manipulation of Hsp26 and Hsp70 Levels in *Saccharomyces cerevisiae*," *The Journal of Biological Chemistry* 284(7):4238-4245, Feb. 13, 2009.
Singh et al., "Modulation of the Heme Electronic Structure and Cystathionine β-synthase Activity by Second Coordination Sphere Ligands: The Role of Heme Ligand Switching in Redox Regulation," *J Inorg Biochem* 103(5):689-697, May 2009 (NIH Public Access Author Manuscript, available in PMC May 1, 2010) (23 pages).
Skovby et al., "Assignment of the genes for cystathionine β-synthase to human chromosome 21 in somatic cell hybrids," *Hum. Genet.* 65(3):291-294, Apr. 1984.
Smith et al., "Comparison of biosequences," *Adv. Appl. Math.* 2(4):482-489, Dec. 1981.
Sokolova et al., "Cystathionine beta-synthase deficiency in Central Europe: discrepancy between biochemical and molecular genetic screening for homocystinuric alleles," *Hum. Mutat* 18(6):548-549, Dec. 2001.
Stabler et al., "Elevated plasma total homocysteine in severe methionine adenosyltranferase I/III deficiency," *Metabolism* 51(8):981-988, Aug. 2002.
Stribling et al., "Aerosol gene delivery in vivo," *Proc. Natl. Acad. Sci. USA* 89:11277-11281, Dec. 1992.
Tan et al., "Polyethylene Glycol Conjugation of Recombinant Methionase for Cancer Therapy, " *Protein Expression and Purification* 12:45-52, Feb. 1998.
Taoka et al., "Assignment of Enzymatic Functions to Specific Regions of the PLP-Dependent Heme Protein Cystathionine β-Synthase," *Biochemistry* 38(40):13155-13161, 1999.
Taoka et al., "Characterization of NO binding to human cystathionine β-synthase: Possible implications of the effects of CO and NO binding to the human enzyme," *Journal of Inorganic Biochemistry* 87:245-251, 2001.
Taoka et al., "Characterization of the Heme and Pyridoxal Phosphate Cofactors of Human Cystathionine β-Synthase Reveals Nonequivalent Active Sites," *Biochemistry* 38:2738-2744, Feb. 5, 1999.
Taoka et al., "Evidence for Heme-mediated Redox Regulation of Human Cystathionine β-Synthase Activity," *The Journal of Biological Chemistry* 273(39):25179-25184, Sep. 25, 1998.
Taoka et al., "Stopped-flow Kinetic Analysis of the Reaction Catalyzed by the Full-Length Yeast Cystathionine β-Synthase," *The Journal of Biological Chemistry* 277(25):22421-22425, Jun. 21, 2002.
Van Guldener et al., "Homocysteine-lowering treatment: an overview," *Expert Opin Pharmacother.* 2(9): 1449-1460, 2001.
Vargas et al., "Detection of c-type cytochromes using enhanced chemiluminescence." *Anal. Biochem.* 209(2):323-326, 1993.
Volpe et al., "Transsulfuration in fetal and postnatal mammalian liver and brain. Cysthathionine synthase, its relation to hormonal influences and cystathionine," *Biol. Neonate* 20(5):385-403, 1972.
Von der Leyen et al., "Gene therapy inhibiting neointimal vascular lesion: In vivo transfer of endothelial cell nitric oxide synthase gene," *Proc. Natl. Acad. Sci. USA* 92:1137-1141, Feb. 1995.
Vozdek et al., "Novel structural arrangement of nematode cystathionine β-synthases:characterization of Caenorhabditis elegans CBS-1," *Biochem. J.* 443:535-547, 2012.
Vugmeyster et al., "Pharmacokinetics and toxicology of therapeutic proteins: Advances and challenges," *World Journal of Biological Chemistry* 3(4):73-92, Apr. 2012.
Walter et al., "Strategies for the treatment of cystathionine β-synthase deficiency: the experience of the Willink Biochemical Genetics Unit over the past 30 years," *Eur. J. Pediatr.* 157(Suppl 2):S71-6, Apr. 1998.
Wang et al., "Expression of mutant human cystathionine β-synthase rescues neonatal lethality but not homocystinuria in a mouse model," *Human Molecular Genetics* 14(15):2201-2208, Jun. 22, 2005.
Wang et al., "Expression, Purification and Characterization of Recombinant Human CBS in *Escherichia coli*," *Progress in Modern Biomedicine* 11(5):830-833, Mar. 2011 (with English Abstract).

(56) References Cited

OTHER PUBLICATIONS

Watanabe et al., "Mice deficient in cysthathionine β-synthase: animal models for mild and severe homocyst(e)inemia," *Proc. Natl. Acad. Sci. U.S.A.* 92(5):1585-1589, Feb. 1995.

Whisstock et al., "Prediction of protein function from protein sequence and structure," *Quarterly Reviews of Biophysics* 36(3):307-340, 2003.

Wilcken et al., "Homocystinuria—the effects of betaine in the treatment of patients not responsive to pyridoxine," *N. Engl. J. Med.* 309(8):448-453, 1983.

Witkowski et al., "Conversion of a β-Ketoacyl Synthase to a Malonyl Decarboxylase by Replacement of the Active-Site Cysteine with Glutamine," *Biochemistry* 38:11643-11650, Aug. 1999.

Yamanishi et al., "Structural insights into pathogenic mutations in heme-dependent cystathionine-β-synthase," *Journal of Inorganic Biochemistry* 100:1988-1995, Sep. 20, 2006.

Yap et al., "Vascular outcome in patients with homocystinuria due to cystathionine beta-synthase deficiency treated chronically: a Multicenter observational study," *Arterioscler. Thromb. Vasc. Biol.* 21(12):2080-2085, Dec. 2001.

Yap, "Classical homocystinuria: Vascular risk and its prevention," *J. Inherit. Metab. Dis.* 26:259-265, 2003.

Yap, "Homocystinuria due to cystathionine β-synthase deficiency," *Orphanet Encyclopedia*, Feb. 2005, Retrieved from Internet: URL: http://www.orpha.net/data/patho/GB/uk-CbS.pdf (13 Pages).

Zhang et al., "Characteristics and Crystal Structure of Bacterial Inosine-5'-monophosphate Dehydrogenase," *Biochemistry* 38(15):4691-4700, Mar. 26, 1999.

Zou et al., "Tumor Necrosis Factor-α-induced Targeted Proteolysis of Cystathionine β-Synthase Modulates Redox Homeostasis," *The Journal of Biological Chemistry* 278(19):16802-16808, May 9, 2003.

Baranov et al., "Homocystinuria in children*," *Issues of modern pediatrics* 16(6): 457-467, 2017.

Izutsu et al., "Freeze-drying of protein pharmaceuticals," *Pharmacology* 72(6):353-358, 2012 (with Machine Translation). (12 pages).

Izutsu et al., "Characterization of Frozen Aqueous Solution for Formulation and Process Design of Freeze-dried Pharmaceuticals," *Netsu Sokutei* 36(2):112-120, 2009 (with English abstract). (9 pages).

James et al., "Metabolic biomarkers of increased oxidative stress and impaired methylation capacity in children with autism," *Am J Clin Nutr* 80:1611-1617, Dec. 2004. (7 pages).

Zhao, Applications of Capillary Electrophoresis—Mass Spectrometry Interfaced By a Flow-Through Microvial Electrospray Ionization Sprayer, Ph.D., Thesis, The University of British Columbia, Canada, Dec. 2014. (205 pages).

KO1982 (-/-) PBS injected MODERATE TO SEVERE HEPATOPATHY

KO2276 (-/-) 20NHS C15S/ME-200GS injected MILD CHANGES

KO1985 (+/-) healthy control MINIMAL CHANGES

KO1982 (-/-) PBS injected MODERATE
TO SEVERE HEPATOPATHY

KO2276 (-/-) 20NHS PEG-CBS injected
MILD CHANGES

KO1985 (+/-) healthy control
MINIMAL CHANGES

+/- (1984)

KO-PBS (1981)

KO-CBS (2276)

SEQUENCE LISTING

```
Sequence total quantity: 16
SEQ ID NO: 1              moltype = DNA  length = 1656
FEATURE                   Location/Qualifiers
source                    1..1656
                          mol_type = other DNA
                          organism = Homo sapiens
SEQUENCE: 1
atgccgtcag aaacccgca  ggcagaagtg ggtccgacgg gttgcccgca ccgtagcggt   60
ccgcattctg caaaaggcag tctggaaaaa ggttccccgg aagataaaga agccaaagaa  120
ccgctgtgga ttcgtccgga cgcaccgtca cgctgtacct ggcagctggg tcgtccggca  180
agcgaatctc cgcatcacca tacggctccg gcgaaaagtc cgaaaattct gccggatatc  240
ctgaagaaaa ttggtgacac cccgatggtt cgtatcaaca aatcggcaa aaaattcggt  300
ctgaaatgcg aactgctggc taaatgtgaa tttttcaatg cgggcggttc cgtgaaagat  360
cgtatctcac tgcgcatgat tgaagatgct gaacgcgacg gcaccctgaa accgggtgat  420
acgattatcg aaccgacctc tggcaacacg ggtatcggtc tggcactggc ggcggcagtc  480
cgtggttatc gctgcattat cgtgatgccg gaaaaaatga gctctgaaaa agttgatgtc  540
ctgcgtgctc tgggcgcgga aattgttcgt accccgacga atgcccgctt cgacagtccg  600
gaatcccatg tgggtgttgc atggcgcctg aaaaacgaaa tcccgaattc gcacattctg  660
gatcagtatc gtaacgctag caatccgctg gcgcattacg ataccacggc cgacgaaatc  720
ctgcagcaat gtgatggcaa actggacatg ctggtcgctt ctgtgggtac cggcggtacc  780
attacgggca tcgcgcgtaa actgaaagaa aaatgcccgg gctgtcgcat tatccggtgtg  840
gatccggaag gcagtattct ggcggaaccg gaagaactga accagaccga acaaaccacg  900
tatgaagttg aaggcatcgg ttacgatttt attccgaccg tcctggatcg cacggtggtt  960
gacaaatggt tcaaaagcaa tgacgaagaa gcctttacct tcgcacgtat gctgatcgct 1020
caggaaggtc tgctgtgcgg tggttcagca ggttcgacgg tcgcagtggc agttaaagct 1080
gcgcaggaac tgcaagaagg tcaacgttgt gtcgtgattc tgccggattc tgttcgcaac 1140
tacatgacca aatttctgag tgaccgttgg atgctgcaaa aaggcttcct gaaagaagaa 1200
gatctgaccg agaaaaaacc gtgtgggtgg cacctgcgcg tgcaggaact gggtctgtcc 1260
gcaccgctga ccgttctgcc gaccatcacg tgcggccata cgattgaaat cctgcgtgaa 1320
aaaggttttg atcaggcccc ggttgtcgac gaagcaggcg tgattctggg tatggttacc 1380
ctgggtaaca tgctgagttc cctgctggcg ggcaaagtgc aaccgagcga tcaggttggt 1440
aaagtcatct acaaacaatt caaacagatt cgtctgaccg atacgctggg ccgcctgtcg 1500
cacatcctgg aaatggacca tttcgcgctg gttgtgcacg aacagattca ataccatagc 1560
accggcaaat catcgcagcg ccaaatggtc tttggtgtcg tgacggccat tgatctgctg 1620
aatttcgtgg ccgcacaaga acgtgaccag aaataa                            1656

SEQ ID NO: 2              moltype = AA  length = 551
FEATURE                   Location/Qualifiers
source                    1..551
                          mol_type = protein
                          organism = Homo sapiens
SEQUENCE: 2
```

```
MPSETPQAEV GPTGCPHRSG PHSAKGSLEK GSPEDKEAKE PLWIRPDAPS RCTWQLGRPA    60
SESPHHHTAP AKSPKILPDI LKKIGDTPMV RINKIGKKFG LKCELLAKCE FFNAGGSVKD   120
RISLRMIEDA ERDGTLKPGD TIIEPTSGNT GIGLALAAAV RGYRCIIVMP EKMSSEKVDV   180
LRALGAEIVR TPTNARFDSP ESHVGVAWRL KNEIPNSHIL DQYRNASNPL AHYDTTADEI   240
LQQCDGKLDM LVASVGTGGT ITGIARKLKE KCPGCRIIGV DPEGSILAEP EELNQTEQTT   300
YEVEGIGYDF IPTVLDRTVV DKWFKSNDEE AFTFARMLIA QEGLLCGGSA GSTVAVAVKA   360
AQELQEGQRC VVILPDSVRN YMTKFLSDRW MLQKGFLKEE DLTEKKPWWW HLRVQELGLS   420
APLTVLPTIT CGHTIEILRE KGFDQAPVVD EAGVILGMVT LGNMLSSLLA GKVQPSDQVG   480
KVIYKQFKQI RLTDTLGRLS HILEMDHFAL VVHEQIQYHS TGKSSQRQMV FGVVTAIDLL   540
NFVAAQERDQ K                                                       551

SEQ ID NO: 3            moltype = AA  length = 413
FEATURE                 Location/Qualifiers
source                  1..413
                        mol_type = protein
                        organism = synthetic construct
SEQUENCE: 3
MPSETPQAEV GPTGCPHRSG PHSAKGSLEK GSPEDKEAKE PLWIRPDAPS RCTWQLGRPA    60
SESPHHHTAP AKSPKILPDI LKKIGDTPMV RINKIGKKFG LKCELLAKCE FFNAGGSVKD   120
RISLRMIEDA ERDGTLKPGD TIIEPTSGNT GIGLALAAAV RGYRCIIVMP EKMSSEKVDV   180
LRALGAEIVR TPTNARFDSP ESHVGVAWRL KNEIPNSHIL DQYRNASNPL AHYDTTADEI   240
LQQCDGKLDM LVASVGTGGT ITGIARKLKE KCPGCRIIGV DPEGSILAEP EELNQTEQTT   300
YEVEGIGYDF IPTVLDRTVV DKWFKSNDEE AFTFARMLIA QEGLLCGGSA GSTVAVAVKA   360
AQELQEGQRC VVILPDSVRN YMTKFLSDRW MLQKGFLKEE DLTEKKPWWW HLR          413

SEQ ID NO: 4            moltype = DNA  length = 1242
FEATURE                 Location/Qualifiers
source                  1..1242
                        mol_type = other DNA
                        organism = synthetic construct
SEQUENCE: 4
atgccgtcag aaaccccgca ggcagaagtg ggtccgacgg gttgcccgca ccgtagcggt    60
ccgcattctg caaaaggcag tctggaaaaa ggttccccgg aagataaaga agccaaagaa   120
ccgctgtgga ttcgtccgga cgcaccgtca cgctgtacct ggcagctggg tcgtccggca   180
agcgaactc cgcatcacca tacggctccg gcgaaaagtc cgaaaattct gccggatatc    240
ctgaagaaaa ttggtgacac cccgatggtt cgtatcaaca aaatcggcaa aaaattcggt   300
ctgaaatgcg aactgctggc taaatgtgaa ttttttcaatg cggcggttc cgtgaaagat   360
cgtatctcac tgcgcatgat tgaagatgct gaacgcgacg gcaccctgaa accgggtgat   420
acgattatcg aaccgacctc tggcaacacg ggtatcggtc tggcactggc ggcggcagtc   480
cgtggttatc gctgcattat cgtgatgccg gaaaaaatga gctctgaaaa agttgatgtc   540
ctgcgtgctc tgggcgcgga aattgttcgt accccgacga atgcccgctt cgacagtccg   600
gaatcccatg tgggtgttgc atggcgcctg aaaaacgaaa tcccgaattc gcacattctg   660
gatcagtatc gtaacgctag caatccgctg gcgcattacg ataccacgg cgacgaaatc    720
ctgcagcaat gtgatggcaa actggacatg ctggtcgctt ctgtgggtac cggcggtacc   780
attacgggca tcgcgcgtaa actgaaagaa aaatgcccgg gctgtcgcat tatcggtgtg   840
gatccggaag gcagtattct ggcggaaccg gaagaactga accagaccga acaaaccacg   900
tatgaagttg aaggcatcgg ttacgatttt attccgacct cctggatcg cacggtggtt    960
gacaaatggt tcaaaagcaa tgacgaagaa gcctttacct tcgcacgtat gctgatcgct   1020
caggaaggtc tgctgtgcgg tggttcagca ggttcgacgg tcgcagtggc agttaaagct   1080
gcgcaggaac tgcaagaagg tcaacgttgt gtcgtgattc tgccggattc tgttcgcaac   1140
tacatgacca aatttctgag tgaccgttgg atgctgcaaa aaggcttcct gaaagaagaa   1200
gatctgaccg agaaaaaacc gtggtggtgg cacctgcgct aa                     1242

SEQ ID NO: 5            moltype = DNA  length = 30
FEATURE                 Location/Qualifiers
misc_feature            1..30
                        note = Synthetic oligonucleotide
source                  1..30
                        mol_type = other DNA
                        organism = synthetic construct
SEQUENCE: 5
cgtagaattc acctttgccc gcatgctgat                                    30

SEQ ID NO: 6            moltype = DNA  length = 35
FEATURE                 Location/Qualifiers
misc_feature            1..35
                        note = Synthetic oligonucleotide
source                  1..35
                        mol_type = other DNA
                        organism = synthetic construct
SEQUENCE: 6
tacgggtacc tcaacggagg tgccaccacc agggc                              35

SEQ ID NO: 7            moltype = DNA  length = 29
FEATURE                 Location/Qualifiers
misc_feature            1..29
                        note = Synthetic oligonucleotide
source                  1..29
                        mol_type = other DNA
```

```
                            organism = synthetic construct
SEQUENCE: 7
agtcgcccat ggcgtcagaa accccgcag                                              29

SEQ ID NO: 8               moltype = DNA   length = 31
FEATURE                    Location/Qualifiers
misc_feature               1..31
                           note = Synthetic oligonucleotide
source                     1..31
                           mol_type = other DNA
                           organism = synthetic construct
SEQUENCE: 8
atcgcgctcg agttagcgca ggtgccacca c                                           31

SEQ ID NO: 9               moltype = DNA   length = 30
FEATURE                    Location/Qualifiers
misc_feature               1..30
                           note = Synthetic oligonucleotide
source                     1..30
                           mol_type = other DNA
                           organism = synthetic construct
SEQUENCE: 9
ggagatatac catgccgtca gaaaccccgc                                             30

SEQ ID NO: 10              moltype = DNA   length = 30
FEATURE                    Location/Qualifiers
misc_feature               1..30
                           note = Synthetic oligonucleotide
source                     1..30
                           mol_type = other DNA
                           organism = synthetic construct
SEQUENCE: 10
gcggggtttc tgacggcatg gtatatctcc                                             30

SEQ ID NO: 11              moltype = DNA   length = 23
FEATURE                    Location/Qualifiers
misc_feature               1..23
                           note = Synthetic oligonucleotide
source                     1..23
                           mol_type = other DNA
                           organism = synthetic construct
SEQUENCE: 11
tgggtccgac gggtagcccg cac                                                    23

SEQ ID NO: 12              moltype = DNA   length = 23
FEATURE                    Location/Qualifiers
misc_feature               1..23
                           note = Synthetic oligonucleotide
source                     1..23
                           mol_type = other DNA
                           organism = synthetic construct
SEQUENCE: 12
gtgcgggcta cccgtcggac cca                                                    23

SEQ ID NO: 13              moltype = AA    length = 413
FEATURE                    Location/Qualifiers
REGION                     1..413
                           note = Truncated human C15S mutant CBS polypeptide
source                     1..413
                           mol_type = protein
                           organism = synthetic construct
SEQUENCE: 13
MPSETPQAEV GPTGSPHRSG PHSAKGSLEK GSPEDKEAKE PLWIRPDAPS RCTWQLGRPA   60
SESPHHHTAP AKSPKILPDI LKKIGDTPMV RINKIGKKFG LKCELLAKCE FFNAGGSVKD  120
RISLRMIEDA ERDGTLKPGD TIIEPTSGNT GIGLALAAAV RGYRCIIVMP EKMSSEKVDV  180
LRALGAEIVR TPTNARFDSP ESHVGVAWRL KNEIPNSHIL DQYRNASNPL AHYDTTADEI  240
LQQCDGKLDM LVASVGTGGT ITGIARKLKE KCPGCRIIGV DPEGSILAEP EELNQTEQTT  300
YEVEGIGYDF IPTVLDRTVV DKWFKSNDEE AFTFARMLIA QEGLLCGGSA GSTVAVAVKA  360
AQELQEGQRC VVILPDSVRN YMTKFLSDRW MLQKGFLKEE DLTEKKPWWW HLR         413

SEQ ID NO: 14              moltype = DNA   length = 1242
FEATURE                    Location/Qualifiers
misc_feature               1..1242
                           note = Truncated human C15S mutant CBS Nucleotide
source                     1..1242
                           mol_type = other DNA
                           organism = synthetic construct
SEQUENCE: 14
atgccgtcag aaaccccgca ggcagaagtg ggtccgacgg gtagcccgca ccgtagcggt   60
```

```
ccgcattctg caaaaggcag tctggaaaaa ggttccccgg aagataaaga agccaaagaa    120
ccgctgtgga ttcgtccgga cgcaccgtca cgctgtacct ggcagctggg tcgtccggca    180
agcgaatctc cgcatcacca tacggctccg gcgaaaagtc cgaaaattct gccggatatc    240
ctgaagaaaa ttggtgacac cccgatggtt cgtatcaaca aaatcggcaa aaaattcggt    300
ctgaaatgcg aactgctggc taaatgtgaa tttttcaatg cgggcggttc cgtgaaagat    360
cgtatctcac tgcgcatgat tgaagatgct gaacgcgacg gcaccctgaa accgggtgat    420
acgattatcg aaccgacctc tggcaacacg gtatcggtc tggcactggc ggcggcagtc    480
cgtggttatc gctgcattat cgtgatgccg gaaaaaatga gctctgaaaa agttgatgtc    540
ctgcgtgctc tgggcgcgga aattgttcgt accccgacga tgcccgctt cgacagtccg    600
gaatcccatg tgggtgttgc atggcgcctg aaaaacgaaa tcccgaattc gcacattctg    660
gatcagtatc gtaacgctag caatccgctg gcgcattacg ataccacggc cgacgaaatc    720
ctgcagcaat gtgatggcaa actggacatg ctggtcgctt ctgtgggtac cggcggtacc    780
attacgggca tcgcgcgtaa actgaaagaa aaatgcccgg gctgtcgcat tatcggtgtg    840
gatccggaag gcagtattct ggcggaaccg gaagaactga accagaccga acaaaccacg    900
tatgaagttg aaggcatcgg ttacgatttt attccgaccg tcctggatcg cacggtggtt    960
gacaaatggt tcaaaagcaa tgacgaagaa gcctttacct tcgcacgtat gctgatcgct   1020
caggaaggtc tgctgtgcgg tggttcagca ggttcgacgg tcgcagtggc agttaaagct   1080
gcgcaggaac tgcaagaagg tcaacgttgt gtcgtgattc tgccggattc tgttcgcaac   1140
tacatgacca aatttctgag tgaccgttgt atgctgcaaa aaggcttcct gaagaagaa    1200
gatctgaccg agaaaaaacc gtggtggtgg cacctgcgct aa                       1242

SEQ ID NO: 15           moltype = DNA  length = 1656
FEATURE                 Location/Qualifiers
misc_feature            1..1656
                        note = Full length human C15S mutant CBS nucleotide
source                  1..1656
                        mol_type = other DNA
                        organism = synthetic construct
SEQUENCE: 15
atgccgtcag aaaccccgca ggcagaagtg ggtccgacgg gtagcccgca ccgtagcggt     60
ccgcattctg caaaaggcag tctggaaaaa ggttccccgg aagataaaga agccaaagaa    120
ccgctgtgga ttcgtccgga cgcaccgtca cgctgtacct ggcagctggg tcgtccggca    180
agcgaatctc cgcatcacca tacggctccg gcgaaaagtc cgaaaattct gccggatatc    240
ctgaagaaaa ttggtgacac cccgatggtt cgtatcaaca aaatcggcaa aaaattcggt    300
ctgaaatgcg aactgctggc taaatgtgaa tttttcaatg cgggcggttc cgtgaaagat    360
cgtatctcac tgcgcatgat tgaagatgct gaacgcgacg gcaccctgaa accgggtgat    420
acgattatcg aaccgacctc tggcaacacg gtatcggtc tggcactggc ggcggcagtc    480
cgtggttatc gctgcattat cgtgatgccg gaaaaaatga gctctgaaaa agttgatgtc    540
ctgcgtgctc tgggcgcgga aattgttcgt accccgacga tgcccgctt cgacagtccg    600
gaatcccatg tgggtgttgc atggcgcctg aaaaacgaaa tcccgaattc gcacattctg    660
gatcagtatc gtaacgctag caatccgctg gcgcattacg ataccacggc cgacgaaatc    720
ctgcagcaat gtgatggcaa actggacatg ctggtcgctt ctgtgggtac cggcggtacc    780
attacgggca tcgcgcgtaa actgaaagaa aaatgcccgg gctgtcgcat tatcggtgtg    840
gatccggaag gcagtattct ggcggaaccg gaagaactga accagaccga acaaaccacg    900
tatgaagttg aaggcatcgg ttacgatttt attccgaccg tcctggatcg cacggtggtt    960
gacaaatggt tcaaaagcaa tgacgaagaa gcctttacct tcgcacgtat gctgatcgct   1020
caggaaggtc tgctgtgcgg tggttcagca ggttcgacgg tcgcagtggc agttaaagct   1080
gcgcaggaac tgcaagaagg tcaacgttgt gtcgtgattc tgccggattc tgttcgcaac   1140
tacatgacca aatttctgag tgaccgttgt atgctgcaaa aaggcttcct gaagaagaa    1200
gatctgaccg agaaaaaacc gtggtggtgg cacctgcgcg tgcaggaact gggtctgtcc   1260
gcaccgctga ccgttctgcc gaccatcacg tgcggccata cgattgaaat cctgcgtgaa   1320
aaaggttttg atcaggcccc ggttgtcgac gaagcaggcg tgattctggg tatggttacc   1380
ctgggtaaca tgctgagttc cctgctggcg ggcaaagtgc aaccgagcga tcaggttggt   1440
aaagtcatct acaaacaatt caaacagatt cgtctgaccg atacgctggg ccgcctgtcg   1500
cacatcctgg aaatggacca tttcgcgctg gttgtgcacg aacagattca ataccatagc   1560
accggcaaat catcgcagcg ccaaatggtc tttggtgtcg tgacggccat tgatctgctg   1620
aatttcgtgg ccgcacaaga acgtgaccag aaataa                              1656

SEQ ID NO: 16           moltype = AA  length = 551
FEATURE                 Location/Qualifiers
REGION                  1..551
                        note = Full length human C15S mutant CBS polypeptide
source                  1..551
                        mol_type = protein
                        organism = synthetic construct
SEQUENCE: 16
MPSETPQAEV GPTGSPHRSG PHSAKGSLEK GSPEDKEAKE PLWIRPDAPS RCTWQLGRPA     60
SESPHHHTAP AKSPKILPDI LKKIGDTPMV RINKIGKKFG LKCELLAKCE FFNAGGSVKD    120
RISLRMIEDA ERDGTLKPGD TIIEPTSGNT VSVLALAAAV RGYRCIIVMP EKMSSEKVDV    180
LRALGAEIVR TPTNARFDSP ESHVGVAWRL KNEIPNSHIL DQYRNASNPL AHYDTTADEI    240
LQQCDGKLDM LVASVGTGGT ITGIARKLKE KCPGCRIIGV DPEGSILAEP EELNQTEQTT    300
YEVEGIGYDF IPTVLDRTVV DKWFKSNDEE AFTFARMLIA QEGLLCGGSA GSTVAVAVKA    360
AQELQEGQRC VVILPDSVRN YMTKFLSDRW MLQKGFLKEE DLTEKKPWWW HLRVQELGLS    420
APLTVLPTIT CGHTIEILRE KGFDQAPVVD EAGVILGMVT LGNMLSSLLA GKVQPSDQVG    480
KVIYKQFKQI RLTDTLGRLS HILEMDHFAL VVHEQIQYHS TGKSSQRQMV FGVVTAIDLL    540
NFVAAQERDQ K                                                         551
```

COMPOSITIONS AND METHODS FOR TREATMENT OF HOMOCYSTINURIA

CROSS-REFERENCE TO RELATED APPLICATIONS

This application claims priority to U.S. application Ser. No. 17/362,633, filed Jun. 29, 2021, which claims priority to U.S. application Ser. No. 16/824,931, filed Mar. 20, 2020, which has issued as U.S. Pat. No. 11,077,175, which claims priority to U.S. application Ser. No. 15/774,755, filed May 9, 2018, which has issued as U.S. Pat. No. 10,653,755, which is a national stage application of PCT/US2016/061050 entitled COMPOSITIONS AND METHODS FOR TREATMENT OF HOMOCYSTINURIA filed Nov. 9, 2016, which is an international application of and claims priority to U.S. application Ser. No. 14/935,690, filed Nov. 9, 2015, which has issued as U.S. Pat. No. 9,675,678, the contents of each of which are incorporated by reference herein in their entireties.

SEQUENCE LISTING

The present application is being filed along with a Sequence Listing in electronic format. The sequence listing file, entitled 43101C3_SeqListing.xml, was created on Aug. 23, 2023 and is 27,509 bytes in size. The information in electronic format of the Sequence Listing is hereby incorporated by reference herein in its entirety.

FIELD OF THE INVENTION

The present invention generally relates to enzyme replacement therapy (ERT) using human Cystathionine Beta-Synthase (CBS), or a modified version thereof (e.g., human truncated CBS (htCBS) or a variant thereof), to significantly reduce serum homocysteine (Hcy) concentrations, and restore levels of its downstream metabolites such as cystathionine and cysteine. Further, ERT with CBS, htCBS or a modified version thereof, such as a htCBS mutant C15S, can be used for treatment of diseases such as homocystinuria and homocysteine remethylation disorders.

BACKGROUND OF THE INVENTION

Cystathionine beta-synthase (CBS) is the first enzyme in the transsulfuration pathway, catalyzing the condensation of serine and homocysteine (Hcy) to cystathionine, which is then hydrolyzed to cysteine by cystathionine gamma-lyase (CGL). In systems biology, robustness of a biological system is defined as its ability to function properly in face of perturbations, and redundancy of elements in the system is one of the mechanisms by which such robustness is achieved (Kitano, H. 2004, Nature Reviews Genetics, 5:826-837). However, the biological transsulfuration system seems to largely lack redundancy of components, making this system prone to mutational perturbations. For example, the CBS enzyme is the only component that can process homocysteine to cystathionine. A limited system redundancy partly exists as homocysteine, the first metabolite that funnels into the pathway, can alternatively be converted to methionine through the remethylation pathway, thus relieving the homocysteine load. In addition, cysteine, a downstream product, can be obtained directly from diet. Nevertheless, these pathways are limited in their capacity to maintain normal levels of metabolites, and lack of CBS function has detrimental consequences for human patients if left untreated. Inactivation of CBS results in cystathionine beta-synthase-deficient homocystinuria (CBSDH), more commonly referred to as classical homocystinuria.

There exist limited therapeutic options to treat CBSDH and current treatment options reduce homocysteine but do not tend to normalize cystathionine (Cth) or cysteine (Cys) and thus these treatment options may be inadequate for providing robust and effective treatment options. Thus, there remains a need in the art for more effective treatment strategies for individuals with homocystinuria.

The present invention addresses this need by providing compositions and methods of using these compositions for the treatment of CBSDH.

SUMMARY OF THE INVENTION

The present disclosure provides compositions suitable for enzyme replacement therapy comprising human truncated cystathionine beta synthase (htCBS) and variants thereof which may also be PEGylated. The htCBS composition may be used to reduce homocysteine levels and raise levels of downstream metabolites cystathionine and cysteine, may be used to treat conditions and diseases such as homocystinuria (e.g., CBSDH) and homocysteine remethylation disorders and they also may be used to improve liver pathology.

Provided herein are methods for treating homocystinuria in a subject by administering to a subject a composition comprising an isolated htCBS or htCBS mutant polypeptide. The htCBS or htCBS mutant polypeptide may be PEGylated with a low molecular weight or high molecular weight PEG. In certain embodiments, the htCBS or htCBS mutant polypeptide may be PEGylated with PEG molecules having various geometries and different chemistries for conjugation. In some embodiments, the htCBS or htCBS mutant polypeptides may be administered at a dose between 0.01 and 10 mg/kg and may be administered at least once a week. The htCBS or htCBS mutant polypeptide may be administered at a dose between 5 and 7.5 mg/kg and may be administered at least twice a week. Further, the htCBS or htCBS mutant polypeptide may be co-administered with betaine, or other known CBSDH therapies.

Provided herein are methods for increasing the amount of a metabolite such as, but not limited to, cystathionine and cysteine, in a subject by administering to a subject a composition comprising an htCBS or htCBS mutant polypeptide. The htCBS or htCBS mutant polypeptide may be PEGylated with a low molecular weight or high molecular weight PEG. In some embodiments, the htCBS or htCBS mutant polypeptides may be administered at a dose between 0.01 and 10 mg/kg and may be administered at least once a week. The htCBS or htCBS mutant polypeptide may be administered at a dose between 5 and 7.5 mg/kg and may be administered at least twice a week. Further, the htCBS or htCBS mutant polypeptide may be co-administered with betaine. The amount of cystathionine may be increased to 0.005-0.35 µM. The amount of cysteine may be increased to above 140 µM (e.g., between 200 µM to 400 µM)

Provided herein are methods for decreasing the amount of a metabolite such as, but not limited to, homocysteine, methionine S-adenosyl homocysteine, and S-adenosyl methionine in a subject by administering to a subject a composition comprising an htCBS or htCBS mutant polypeptide. The htCBS or htCBS mutant polypeptide may be PEGylated with a low molecular weight or high molecular weight PEG. In some embodiments, the htCBS or htCBS mutant polypeptides may be administered at a dose between 0.01 and 10 mg/kg. For example, the dose is about 0.4 mg/kg. The htCBS or htCBS mutant polypeptide may be administered at a dose between 5 and 7.5 mg/kg and may be administered at least twice a week. Further, the htCBS or htCBS mutant polypeptide may be co-administered with betaine. The amount of homocysteine may be decreased to less than 100 µM (e.g., about 10 µM). The amount of methionine may be decreased to less than 50 µM (e.g., about 30 µM). The amount of S-adenosyl homocysteine may be decreased to less than 0.14 µM (e.g., about 0.015 µM)

Provided herein are methods for treating liver disease in a subject by administering to a subject a composition comprising an htCBS or htCBS mutant polypeptide. The htCBS or htCBS mutant polypeptide may be PEGylated with a low molecular weight or high molecular weight PEG. In some embodiments, the htCBS or htCBS mutant polypeptides may be administered at a dose between 0.01 and 10 mg/kg and may be administered at least once a week. For example, the dose is about 0.4 mg/kg. The htCBS or htCBS mutant polypeptide may be administered at a dose between 5 and 7.5 mg/kg and may be administered at least twice a week.

Certain embodiments of the invention herein provide a method of treating homocystinuria in a subject, the method including the steps of administering to a subject a composition comprising an isolated human truncated cystathionine beta synthase (htCBS) mutant polypeptide comprising a mutation at amino acid position 15 of SEQ ID NO: 3, such that the isolated htCBS mutant polypeptide is PEGylated with an ME-200GS PEG molecule.

In some embodiments, the mutation is a substitution of a serine for a cysteine (C15S). In some embodiments, the subject is a human. In some embodiments, the composition is administered in a dose selected from the range of about 0.01 mg/kg to about 10 mg/kg. For example, the dose is about 0.4 mg/kg.

In some embodiments, the disease, disorder, or condition is selected osteoporosis, alopecia, thinning hair, or eye defects, the method comprising administering to a subject a composition comprising an isolated human truncated cystathionine beta synthase (htCBS) mutant polypeptide comprising a mutation at amino acid position 15 of SEQ ID NO: 3, wherein said isolated htCBS polypeptide mutant has been PEGylated with an ME-200GS PEG molecule.

Additional embodiments of the present compositions and methods, and the like, will be apparent from the following description, drawings, examples, and claims. As can be appreciated from the foregoing and following description, each feature described herein, and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIG. 1A shows enzyme retention time in plasma is maintained suggesting that rapid loss of activity in vivo is a result of clearance. FIG. 1B shows enzyme retention time is in vivo is enhanced for PEGylated htCBS. Mouse #1 and Mouse #2 in FIG. 1B are also described as FIG. 1B in International Patent Publication No. WO2014120770, the contents of which are herein incorporated by reference in its entirety.

FIG. 5A is also described as FIG. 5A in International Patent Publication No. WO2014120770, the contents of which are herein incorporated by reference in its entirety. FIG. 5B is also described as FIG. 5B in International Patent Publication No. WO2014120770, the contents of which are herein incorporated by reference in its entirety. FIG. 5C is also described as FIG. 5C in International Patent Publication No. WO2014120770, the contents of which are herein incorporated by reference in its entirety. FIG. 5F is also described as FIG. 6A in International Patent Publication No. WO2014120770, the contents of which are herein incorporated by reference in its entirety. FIG. 5G is also described as part of FIG. 7A and FIG. 7B in International Patent Publication No. WO2014120770, the contents of which are herein incorporated by reference in its entirety. FIG. 5H is also described as FIG. 6C in International Patent Publication No. WO2014120770, the contents of which are herein incorporated by reference in its entirety.

FIG. 11A-11C show the changes in survival rates and metabolite levels in KO mice after administration of C15S PEGylated with either ME-200GS, ME-200MA0B or ME-400MA.

DETAILED DESCRIPTION

Figure 1A:
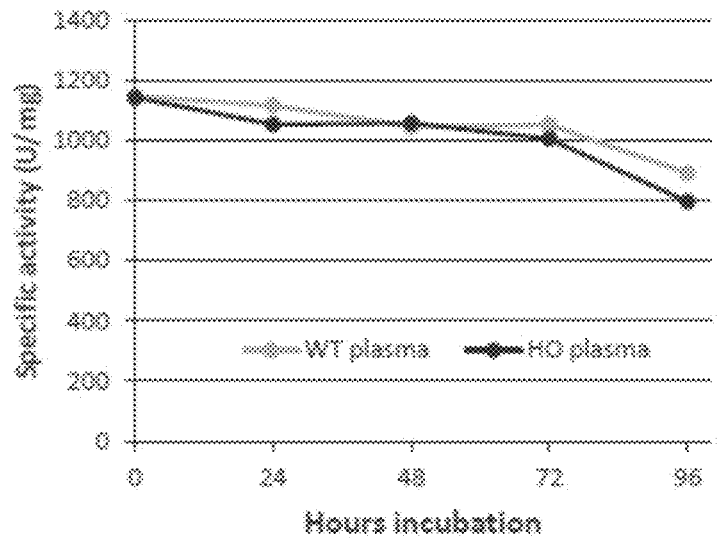
FIG. 1A-1B show enzyme retention in plasma and in vivo.

Provided herein are compositions and methods for treating cystathionine beta-synthase-deficient homocystinuria (CBSDH). As a non-limiting example, CBSDH may be treated by enzyme replacement of CBS or a variant thereof.

Inactivation of CBS results in cystathionine beta-synthase-deficient homocystinuria (CBSDH), more commonly referred to as classical homocystinuria. CBSDH is an autosomal recessive disorder characterized by markedly elevated plasma total homocysteine (tHcy) and methionine levels, and greatly reduced concentrations of cystathionine and cysteine; it is the most common sulfur-amino acid defect. If untreated, CB SDH results in diseases, disorders and/or conditions in a variety of different organ systems and severe phenotypic changes. Non-limiting examples of diseases, disorders and/or conditions from CBSDH include mental retardation, psychiatric disturbances, central nervous system problems including seizures, cardiovascular disease with a predisposition to thromboembolic complications resulting in a high rate of mortality in untreated and partially treated individuals, and a range of connective tissue disorders affecting the ocular system (e.g., progressive myopia and lens dislocation, ectopia lentis), and skeletal system (e.g., marfanoid habitus, osteoporosis, scoliosis, fine fair hair and brittle, thin skin).

There is a functional trichotomy in the nature of pathogenic mutations associated with CBSDH. One group of mutations is classified as "pyridoxine-responsive," where CBS enzyme function may be partially restored by high dose Vitamin $B_6$ therapy. This treatment can be effective, but does not always mitigate the pathological events in these individuals, and some of the events occur even in these individuals over time. In a clinical setting "Vitamin B6 responsive" is defined as a 20% relative drop in Hcy that occurs 24 hours after an individual is given an oral dose of 100-500 mg of B6, meaning that a B6 responsive individual may still have abnormally high homocysteine levels. The second group of functional mutations is represented by the "C-terminal CBS mutants" that are defective in their ability to respond to post-translational up-regulation by S-adenosylmethionine. Individuals with this class of mutations usually lack the mental retardation and connective tissue aspects of the phenotype. This class is detected after measurement of plasma Hcy levels following an idiopathic thrombotic event before the age of 40 years (Maclean et al., 2002, *Hum. Mutat.* 19:641-55). The final group of CB SDH mutations is "classical homocystinuria," which represents the most severe form of the disease. For these latter two groups of individuals Vitamin B6 therapy in isolation does not effectively lower serum Hcy levels. These mutational groups may show phenotypic distinctions, but can be treated similarly.

The most common mutated CBS allele is 833T>C (I278T), which is associated with pyridoxine-responsive homocystinuria. Thus, $B_6$ responsive individuals account for approximately half of the homocystinuric patient population (Barber and Spaeth, 1969; Mudd et al., 1985). Of these $B_6$ responsive individuals, however, many are only partial responders, and in combination with $B_6$ non-responsive individuals, there arises a need for additional therapeutic options. Unfortunately, such therapeutic options are currently limited to reducing intake of methionine by following a strict low protein diet with supplemented cysteine (now essential) and decreasing homocysteine concentration via the use of betaine (N,N,N-trimethylglycine), a methyl donor able to re-methylate homocysteine back to methionine. Therefore, enzyme replacement therapy (ERT) using CBS (e.g., PEGylated htCBS described herein) may be the best therapy for both the $B_6$ partial and non-responsive patients.

As a result of CBS dysfunction, homocysteine (Hcy) levels are dramatically altered in CB SDH patients. In healthy individuals, total Hcy levels are in the range of ~5-15 μM (Stabler et al., 2002, *Metabolism*, 51:981-988), 98% of which is in the form of disulfides or is protein-bound. Only 2% of the tHcy exists as a free (non-protein-bound) reduced homocysteine, which can serve as a substrate for CBS (Mansoor et al., 1992, *Anal. Biochem.* 200:218-229; Mudd et al., 2000, *Arterioscler. Thromb. Vasc. Biol.* 20:1704-1706). This balance is dramatically altered in CBSDH patients, with free reduced homocysteine reaching 10-25% of tHcy values that are observed in these patients (up to ~400 μM) (Mansoor et al., 1993, *Metabolism*, 42:1481-1485).

Higher tHcy levels (e.g., greater than 54 times the wild type levels) may also cause diseases, disorders and/or conditions such as, but not limited to, facial alopecia in mice, osteoporosis and reduction in mean survival. As a non-limiting example, model mice having at least 54 times higher tHcy as compared to wild type demonstrated several diseases, disorders and/or conditions, including facial alopecia, osteoporosis and reduction in mean survival. However, no such signs were observed in mice which had tHcy levels of about 30 times the normal values and thus homocysteine elevation may only pathogenic only above a threshold level (Gupta et al., 2009, *FASEB J.* 23:883-893). In a multicenter observational study of CBSDH in humans, it was found that even though various treatment combinations failed to restore normal homocysteine levels in CBSDH patients, and $B_6$ non-responders continued to exhibit homocysteine levels 3-5 times higher than the upper limit in the normal population, the risk of thromboembolism in these patients was significantly reduced (Yap et al., 2001, *Arterioscler. Thromb. Vasc. Biol.* 21, 2080-2085). Collectively, these data indicate that to ameliorate the clinical manifestation of CBSDH, an incomplete reduction of tHcy, if it is below a threshold level, may be sufficient to treat disease.

While a low methionine diet can be effective in establishing and maintaining some metabolic control of homocysteine levels in patients, its effect may be hindered by lack of dietary compliance especially in late-diagnosed patients, resulting in a concomitant increase in homocysteine accompanied by development of symptoms, especially in children (Walter et al., 1998, *Eur. J. Pediatr.* 157 Suppl 2, S71-76). Failure of dietary compliance causes increased serum Hcy, resurgence of complications in the vascular and connective tissue including fatal and incapacitating events, and risk of severe side-effects such as cerebral edema (from excessive serum Met concentration) or severe malnutrition (from lack of essential amino acids). The most effective therapeutic strategy is to increase enzyme activity, as is evident when given pyridoxine to Vitamin $B_6$ responsive homocystinuria. This strategy is not possible for Vitamin $B_6$ non-responsive individuals due to the mutation status. Betaine may help to achieve a metabolic control in less compliant patients and its combination with the diet may represent the best available treatment. However, current therapies for $B_6$ non-responders do not increase cystathionine, and cysteine supplementation may be warranted to maintain proper levels. Increased enzyme activity in these individuals may therefore depend on the delivery of exogenous enzyme, i.e. enzyme replacement therapy (ERT).

Considerable evidence suggests a possible function for cystathionine independent of its role as an intermediate in transsulfuration. A positive role for cystathionine has been suggested by studies of a particular transgenic mouse model of CBS-deficient homocystinuria. In this model of classical homocystinuria, the mouse cbs gene is inactivated and survives on low-level expression of the human CBS transgene under the control of the human CBS promoter; thus, it has been designated as "human only" (HO). The HO mouse exhibits severe elevations in both plasma and tissue levels of Hcy, methionine, S-adenosylmethionine, and S-adenosylhomocysteine and a concomitant decrease in plasma and hepatic levels of cysteine. However, in contrast to previous CBS knockout models of classical homocystinuria (also known as CBS knockout mice (KO) which suffer a severe growth retardation and hepatopathy and most die within three weeks after birth, even while mothers are on betaine (Maclean et al., 2010b. *Mol. Genet. Metab.* 101, 153-162)), which suffer severe growth retardation and hepatopathy, incur hepatic steatosis, fibrosis, and neonatal death within three weeks after birth even while mothers are treated with betaine, the HO mice exhibit mild hepatopathy and approximately 90% of HO mice live for at least 6 months (Maclean et al., 2012, *J. Biol. Chem.* 287, 31994-32005, the contents of which are herein incorporated by reference in its entirety). Tail bleeding determinations indicate that HO mice are in a hypercoagulative state that is significantly ameliorated by betaine treatment in a manner that recapitulates the disease as it occurs in humans (Maclean et al., 2010b. Mol. Genet. Metab. 101, 153-162; the contents of which are herein incorporated by reference in its entirety). HO mice have high levels of tHcy, but suffer only minor consequences. There is little or no difference in metabolite levels between these two murine models, except the level of cystathionine, which is significantly elevated in HO mice (~10 µM) as compared to KOs (~1 µM). Thus, it has been suggested that cystathionine may exert protective effects against hepatic and renal lipid accumulation, tissue injury and apoptotic cell death induced by prolonged endoplasmic reticulum stress.

Cystathionine may exert protective effects in a mouse model of acetaminophen-induced liver injury by serving as a cysteine prodrug. The use of the CGL inactivating compound D,1-2-amino-4-pentynoic acid in experiments to induce hypercystathionemia by blocking the conversion of cystathionine to cysteine coupled with the observation that cystathionine exerts significant protective effects in a23 cells that are incapable of converting this compound to cysteine, indicate that the protective effects observed are not a result of cystathionine acting as a precursor for cysteine synthesis.

Cystathionine may be important to the normally functioning brain. It is possible that cystathionine specifically accumulates in the normal mammalian brain to serve as a cytoprotectant and that the abolition of its synthesis could contribute to mental retardation in homocystinuria by increasing sensitivity of neural tissues to the toxic insult of elevated Hcy and/or derivatives thereof (Maclean et al., 2012, J. Biol. Chem. 287, 31994-32005). There are considerable regional differences in concentrations of cystathionine within the brain, and there is a higher concentration in white matter than in grey matter, suggesting a possible role in myelination. Cystathionine has been found in higher levels in occipital lobes of human and monkey brains than in the whole brain of lower animal species, and the role of cystathionine has been suggested to be more important in primate than in rodent brain (Volpe and Laster, 1972, *Biol. Neonate* 20, 385-403; the contents of which are herein incorporated by reference in its entirety).

A number of indirect lines of evidence support possible physiological roles for either cystathionine or a derivative thereof. In primate brain and central nervous system (CNS), there appears to be an imbalance between the relative activity levels of CBS and CGL leading to an accumulation of cystathionine. Similarly, during embryonic development, CBS is expressed in multiple tissues such as the heart and lungs that do not express any detectable CBS in adult tissues. A range of data indicates that CGL is not expressed during early mammalian development. In human liver samples for instance, CGL activity is only detected in post-natal tissue whereas activity in fetal, premature and full-term neonatal liver tissue is essentially undetectable. Collectively, these results indicate that at certain stages of development and in adult neural tissues, CBS is expressed specifically for the production of cystathionine distinct from its role as an intermediate in cysteine synthesis (Maclean et al., 2012, *J. Biol. Chem.* 287, 31994-32005; the contents of which are herein incorporated by reference in its entirety). Taken with the knowledge that rigorous control over cystathionine γ-lyase (CGL) and CBS expression occurs during mammalian development, these observations come together to suggest a possible protective role for cystathionine in addition to being a precursor to cysteine.

Cysteine biosynthesis from cystathionine is catalyzed by CGL. Cystathionine is present inside the cells, and it is believed to not exist as a plasma protein. Accordingly, it is believed that the cystathionine produced upon injection of the PEGylated human truncated (htCBS) enzyme described herein may also serve as an intracellular substrate for CGL. Additionally, it may be possible that reduced levels of tHcy may impede the formation of cysteine-homocysteine adducts (which can be rapidly cleared in urine), generating higher levels of free cysteine in plasma (Gupta et al., 2014, FASEB J. 28:781-790).

Various aspects of the present invention now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The CBS Enzyme

The CBS gene resides on human chromosome 21 at q22.3 (Skovby et al., Hum. Genet. 65:291-294 (1984); Munke et al., Am. J. Hum. Genet. 42:550-559 (1988); the contents of which are herein incorporated by reference in their entirety). The nucleic acid sequence encoding human CBS and the amino acid sequence encoded thereby are available through GenBank Accession No. L19501, and these sequences are also disclosed in U.S. Pat. No. 5,523,225, which is incorporated herein by reference in its entirety. The nucleic acid sequence of the genomic DNA encoding CBS is also publicly available through sequence databases such as GenBank and at University of Colorado-Denver webpage (Kraus Laboratory).

While not wishing to be bound by theory, the protein encoded by the CBS gene acts as a homotetramer to catalyze the conversion of homocysteine to cystathionine, the first step in the transsulfuration pathway. The encoded protein is allosterically activated by S-adenosyl-methionine and uses pyridoxal phosphate as a cofactor. Multiple alternatively spliced transcript variants have been found for this gene.

CBS governs the unidirectional flow of sulfur from methionine to cysteine by operating at the intersection of the transmethylation, transsulfuration and re-methylation pathways. It catalyzes a β-replacement reaction in which serine condenses with homocysteine in a pyridoxal 5'-phosphate (PLP)-dependent manner, to form cystathionine (Miles and Kraus, 2004, J. Biol. Chem. 279:29871-29874; the contents of which are herein incorporated by reference in its entirety). Cystathionine can then be converted to cysteine by Cystathionine Gamma Lyase (CGL). Thus, proper function of the CBS enzyme is critical for the regulation of both cysteine and methionine metabolism (Mudd et al., 2001, "Disorders of Transsulfuration." In the Metabolic and molecular bases of inherited disease. C. R. Scriver, A. L. Beudet, W. S. Sly, V. D., C. B., K. K. W., and V. B., eds. (New York: McGraw-Hill), pp. 2007-2056; the contents of which are herein incorporated by reference in its entirety), and accordingly, a compromised CBS activity or lack thereof, leads to the biochemical and clinical manifestations of CBS-deficient homocystinuria (CBSDH).

Inactivation of CBS results in cystathionine beta-synthase-deficient homocystinuria (CBSDH), more commonly referred to as classical homocystinuria. Classical homocystinuria was first described by Carson and Neill in 1962 (Carson and Neill, 1962. Arch. Dis. Child 37:505-513; the contents of which are herein incorporated by reference in its entirety) and is recognized as the most common inborn error of sulfur amino acid metabolism. The underlying cause of homocystinuria, a deficiency of the Cystathionine β-Synthase (CBS) enzyme, was discovered shortly thereafter (Mudd et al., 1964, Science 143:1443-1445; the contents of which are herein incorporated by reference in its entirety).

Missense mutations represent the most common cause of cystathionine β-synthase (CBS) deficiency. Many of these mutations result in misfolded proteins, which lack biological function. The presence of chemical chaperones (e.g., such as ethanol, dimethyl sulfoxide, or trimethylamine-N-oxide) can sometimes alleviate or even restore protein folding and activity of mutant proteins. Eight CBS mutant enzymes (P49L, P78R, A114V, R125Q, E176K, P422L, I435T, and S466L) were purified and characterized, and could be rescued with chemical chaperones by improving their protein folding. The tetrameric mutant enzymes fully saturated with heme had the same or higher specific activities than wild type CBS. Thermal stability measurements demonstrated that the purified mutants are equally or more thermostable than wild type CBS. The response to S-adenosyl-L-methionine stimulation or thermal activation varied. The lack of response of R125Q and E176K to both stimuli indicated that their specific conformations were unable to reach the activated state. Increased levels of molecular chaperones in crude extracts, particularly DnaJ, indicated a rather indirect effect of the chemical chaperones on folding of CBS mutants (Majtan, et al., 2010, J. Biol. Chem. 285(21): 15866-15873; the contents of which are herein incorporated by reference in its entirety).

The extent of misfolding of 27 CBS mutations previously tested in E. coli have been tested for the ability of chaperones to rescue the conformation of these mutations under the more folding-permissive conditions of mammalian CHO-K1 cells. Expression of mutations in mammalian cells increased the median activity 16-fold and the amount of tetramers 3.2-fold compared with expression in bacteria. Subsequently, the responses of seven selected mutations to three compounds with chaperone-like activity were tested. Aminooxyacetic acid and 4-phenylbutyric acid exhibited only a weak effect. In contrast, heme arginate substantially increased the formation of mutant CBS protein tetramers (up to six fold) and rescued catalytic activity (up to nine fold) of five out of seven mutations (p.A114V, p.K102N, p.R125Q, p.R266K, and p.R369C). The greatest effect of heme arginate was observed for the mutation p.R125Q, which is non-responsive to in vivo treatment with vitamin B6. Moreover, the heme responsiveness of the p.R125Q mutation was confirmed in fibroblasts derived from a patient homozygous for this genetic variant. Based on these data, a distinct group of heme-responsive CBS mutations was proposed and the heme pocket of CBS was predicted to be an important target for designing novel therapies for homocystinuria (Melenovska, et al., 2014, J. Inherit. Metab. Dis. 38(2); the contents of which are herein incorporated by reference in its entirety).

Biochemically, CB SDH is characterized by highly elevated blood levels of homocysteine, methionine and S-adenosyl-homocysteine (also known as "SAH" or "AdoHcy"), accompanied by low levels of cysteine and cystathionine. Some of the clinical manifestations of untreated homocystinuria include thromboembolism, connective tissue problems such as dislocation of the optic lens, marfanoid features and osteoporosis, cognitive impairment and other signs (Kraus, J., and Kozich, V. (2001). "Cystathionine beta-synthase and its deficiency." In Homocysteine in health and disease. J. D. Carmel R, ed. (New York: Cambridge University Press), pp. 223-243; Mudd et al., 2001, "Disorders of Transsulfuration." In the Metabolic and molecular bases of inherited disease. C. R. Scriver, A. L. Beudet, W. S. Sly, V. D., C. B., K. K. W., and V. B., eds. (New York: McGraw-Hill), pp. 2007-2056).

Initial attempts to treat homocystinuria employed dietary restrictions to decrease the methionine intake, thus avoiding the build-up of the toxic homocysteine (Komrower et al., 1966, *Arch. Dis. Child* 41:666-671). It was later found that supplementation with the PLP-cofactor precursor, pyridoxine (vitamin $B_6$), relieves the clinical manifestations for slightly less than half of patients, and a subset of these are only partial responders (Barber and Spaeth, 1969. *J. Pediatr.* 75:463-478; Mudd et al., 1985, *Am. J. Hum. Genet.* 37:1-31). The "$B_6$ responders" need to take supplemental vitamin $B_6$ for the rest of their lives. In many cases, even full $B_6$-responsive patients require a milder protein restricted diet to be able to achieve a metabolic control (Picker, J. D., and Levy, H. L. (2004). Homocystinuria Caused by Cystathionine Beta-Synthase Deficiency. In GeneReviews. R. A. Pagon, M. P. Adam, T. D. Bird, C. R. Dolan, C. T. Fong, and K. Stephens, eds. (Seattle (WA): University of Washington, Seattle; the contents of each of which are herein incorporated by reference in their entirety). The remaining subset, the non-responders, are subjected to an extremely limited diet, with which many patients poorly comply (Walter et al., 1998, Eur. J. Pediatr. 157 Suppl 2, S71-76; the contents of which are herein incorporated by reference in its entirety). The diet is combined with a methionine-free and cysteine enriched amino acid mixture along with betaine, which can serve as a methyl donor for the enzyme betaine-homocysteine methyltransferase (BHMT) to produce dimethylglycine and methionine from homocysteine (Finkelstein, 1990, *J. Nutr. Biochem.* 1:228-237). Glutathione is synthesized from cysteine, and thus the addition of cysteine can be important to reduce oxidative stress. Most patients are also treated with trimethylglycine, and a normal dose of folic acid supplement. This improves the metabolic control by lowering homocysteine levels, in conjunction with the strict diet.

Betaine (N,N,N-trimethylglycine) is used to reduce concentrations of homocysteine by promoting the conversion of homocysteine back to methionine, i.e., increasing flux through the remethylation pathway independent of folate derivatives (which is mainly active in the liver and in the kidneys). A small portion of the re-formed methionine is then gradually removed by incorporation into body protein. The methionine that is not converted into protein is converted to S-adenosyl-methionine which goes on to form homocysteine again. Betaine is, therefore, most effective if the quantity of methionine to be removed is small. Hence treatment includes both betaine and a diet low in methionine. In classical homocystinuria, the plasma methionine level usually increases above the normal range of 30 micromoles/L and the concentrations should be monitored as potentially toxic levels (more than 400 micromoles/L) may be reached.

An alternative treatment strategy for CBSDH has long been sought to provide the $B_6$ non-responders and partial responders with a therapy that improves the metabolic abnormalities, reduces the accumulation of toxic homocysteine in circulation, and increases the levels of cystathionine and cysteine. Such metabolic changes may reverse, or delay, the onset of CBSDH symptoms, and allow this group of affected individuals to enjoy an unrestricted or only mildly restricted diet and significantly improve their quality of life. To provide these benefits, a therapy must improve the core deficiency that underlies this condition, namely, aberrant CBS levels and/or function. Accordingly, systemic introduction of CBS, in the form of Enzyme Replacement Therapy (ERT), should be beneficial for homocystinuric patients.

Without being bound by theory, a significant decrease in extracellular homocysteine due to CBS administration is believed to generate a concentration gradient, triggering a flux of homocysteine from intra- to extra-cellular spaces, where the administered enzyme can further process it, and thus the extracellular CBS can serve as a homocysteine "sink."

The structure and mode of activation of native human CBS, which exists as a tetramer, comprised of four identical monomers may be difficult to use as ERT. This form of the enzyme has a high tendency for aggregation, which poses a major constraint on the purification efforts (Kraus and Rosenberg, 1983, *Arch. Biochem. Biophys.* 222:44-52; the contents of which are herein incorporated by reference in its entirety). Additionally, CBS activation requires the binding of S-Adenosyl-methionine (SAM) to the C-terminal tail, in order to relieve the auto-inhibition exerted on the enzyme by its C-terminal regulatory region.

A truncated recombinant human CBS (htCBS) is provided (SEQ ID NO: 3) where the C-terminal regulatory region has been removed. In one embodiment, the htCBS may be mutated where cysteine at amino acid position 15 has been changed to serine (htCBS mutant or C15S) (SEQ ID NO: 13).

In one embodiment, PEGylated htCBS or PEGylated htCBS mutant enzyme improved the pharmacokinetic and pharmacodynamic properties of the enzyme in vivo. Therapeutic proteins, unlike small molecules, are delivered via parenteral routes, and treatment efficacy may be greatly impacted by their absorption, distribution, metabolism and excretion ("ADME") (Vugmeyster et al., 2012, *World Journal of Biological Chemistry* 3:73-92; the contents of which are herein incorporated by reference in its entirety). High molecular weight compounds, such as enzymes, have limited tissue penetration capability, and are thus mainly present in the plasma until they are removed from circulation by at least one mechanism.

In one embodiment, administration of htCBS or htCBS mutant for ERT maintains high activity in plasma for a period of time that is sufficient to deliver a steady and significant effect on sulfur amino acid metabolism. Enhancing ERT efficacy may require additional modifications to the protein, in order to increase retention time in vivo. This may be achieved by PEGylation, the addition of Poly-Ethylene-Glycol (PEG) moieties onto the surface of the protein, in order to extend the retention time in a subject. PEGylation was found to minimize proteolysis, immune response and antigenicity, while increasing protein stability and size, and reducing renal excretion (Kang et al., 2009, *Expert opinion on emerging drugs* 14:363-380; the contents of which are herein incorporated by reference in its entirety).

Cysteine biosynthesis from cystathionine is catalyzed solely by CGL. Cystathionine is only present inside the cells, and does not exist as a plasma protein. Accordingly, it is believed that the cystathionine produced upon injection of the PEGylated htCBS or PEGylated htCBS mutant enzyme described herein may also serve as an intracellular substrate for CGL. Additionally, and not mutually exclusively, it is also possible that reduced levels of tHcy may impede the formation of cysteine-homocysteine adducts (which can be rapidly cleared in urine), generating higher levels of free cysteine in plasma, as was recently suggested (Gupta et al., 2014, *FASEB J.* 28, 781-790). Normalizing cysteine levels without cysteine supplementation is another potential advantage of the presently described htCBS and htCBS mutant in ERT.

In one embodiment, normalization of cysteine levels may be observed following administration of the PEGylated htCBS or PEGylated htCBS mutant enzyme. In addition to a change in metabolite levels, another positive effect of htCBS or htCBS mutant administration may be predicted to be a significant impact on liver disease and survival of affected CBSDH patients.

Methods of Using Pegylated htCBS

In one embodiment, the compositions and methods described herein may be used to treat CBSDH. There are three groups of pathogenic mutations associated with CBSDH, (1) pyridoxine-responsive mutations, (2) C-terminal CBS mutants and (3) classical homocystinuria.

In one embodiment, htCBS and htCBS mutant enzyme replacement may be used to treat CBSDH. The htCBS and htCBS mutant enzyme may be PEGylated by a method known in the art or described herein. As a non-limiting example, the PEG may be a low molecular weight (e.g., 2 kDa) PEG or a high molecular weight (e.g., 40 kDa) four arm branched PEG. For example, the htCBS or htCBS mutant polypeptide is PEGylated with one of the following PEG molecules: ME-200MA0B, ME-400MA, ME-050GS, GL4-400MA, and ME-200GS. For example, the htCBS or htCBS mutant polypeptide PEG conjugate is a 20NHS PEG-htCBS C15S conjugate.

In one embodiment, PEGylated htCBS or PEGylated htCBS mutant and methods of using the PEGylated htCBS or PEGylated htCBS mutant described herein may be used to treat subjects with pyridoxine-responsive mutations. PEGylated htCBS or PEGylated htCBS mutant may be used alone or in combination with current therapies (e.g., Vitamin B6 or Betaine) to treat subjects with pyridoxine-responsive mutations. As a non-limiting example, the PEGylated htCBS or PEGylated htCBS mutant may be used to mitigate or reduce pathological events in subjects with pyridoxine-responsive mutations. As a non-limiting example, the PEGylated htCBS or PEGylated htCBS mutant may be used to treat a subject with pyridoxine-responsive mutations who is a partial responder to Vitamin B6 therapy. As another non-limiting example, the PEGylated htCBS or PEGylated htCBS mutant may be used to treat a subject with pyridoxine-responsive mutations who is a non-responder to Vitamin B6 therapy.

In one embodiment, PEGylated htCBS or PEGylated htCBS mutant and methods of using the PEGylated htCBS or PEGylated htCBS mutant described herein may be used to treat subjects with C-terminal CBS mutations. PEGylated htCBS or PEGylated htCBS mutant may be used alone or in combination with current therapies (e.g., Vitamin B6 or Betaine) to treat subjects with C-terminal CBS mutations. As a non-limiting example, the PEGylated htCBS or PEGylated htCBS mutant may be used to lower serum Hcy levels in subjects with C-terminal CBS mutations. As a non-limiting example, the PEGylated htCBS or PEGylated htCBS mutant may be used to treat a subject with C-terminal CBS mutations who is a partial responder to Vitamin B6 therapy. As another non-limiting example, the PEGylated htCBS or PEGylated htCBS mutant may be used to treat a subject with C-terminal CBS mutations who is a non-responder to Vitamin B6 therapy.

In one embodiment, PEGylated htCBS or PEGylated htCBS mutant and methods of using the PEGylated htCBS or PEGylated htCBS mutant described herein may be used to treat subjects with classical homocystinuria. PEGylated htCBS or PEGylated htCBS mutant may be used alone or in combination with current therapies (e.g., Vitamin B6 or Betaine) to treat subjects with classical homocystinuria. As a non-limiting example, the PEGylated htCBS or PEGylated htCBS mutant may be used to lower serum Hcy levels in subjects with classical homocystinuria. As a non-limiting example, the PEGylated htCBS or PEGylated htCBS mutant may be used to treat a subject with classical homocystinuria who is a partial responder to Vitamin B6 therapy. As another non-limiting example, the PEGylated htCBS or PEGylated htCBS mutant may be used to treat a subject with classical homocystinuria who is a non-responder to Vitamin B6 therapy. In certain embodiments, the subject is a human, a rat, a mouse, and a non-human primate. In certain embodiments, 20NHS PEG-htCBS C15S is used to treat at least one disease, disorder, condition, or clinical symptom selected from the group consisting of osteoporosis, thinning hair, or eye defects.

In one embodiment, the compositions and methods described herein may be used to reduce a symptom, disease or disorder associated with CBSDH. The symptom, disease or disorder may be in an organ system or a severe phenotypic change. Non-limiting examples of diseases, disorders and/or conditions from CBSDH include mental retardation, psychiatric disturbances, central nervous system problems including seizures, cardiovascular disease with a predisposition to thromboembolic complications resulting in a high rate of mortality in untreated and partially treated individuals, and a range of connective tissue disorders affecting the ocular system (e.g., progressive myopia and lens dislocation, ectopia lentis), and skeletal system (e.g., marfanoid habitus, osteoporosis, scoliosis, fine fair hair and brittle, thin skin).

In one embodiment, the compositions and methods described herein may be used to treat a disease, disorder and/or condition such as, but not limited to, thromboembolism, connective tissue problems such as dislocation of the optic lens, marfanoid features, osteoporosis, and cognitive impairment.

In one embodiment, the PEGylated htCBS or PEGylated htCBS mutant enzyme described herein may reduce the effects and/or treat liver disease. The liver disease may be in a subject with CBSDH. The treatment and/or reduction of the effects of liver disease may thus increase the rate of survival of CBSDH patients. As a non-limiting example, PEGylated htCBS or PEGylated htCBS mutant may be used to reduce liver parenchyma damage.

In one embodiment, PEGylated htCBS or PEGylated htCBS mutant may be used to increase cystathionine and treat or reduce the effects of liver disease or injury.

In one embodiment, the compositions and methods described herein (e.g., enzyme replacement therapy (ERT)) using the PEGylated htCBS or PEGylated htCBS mutant enzyme can ameliorate the disease manifestations and metabolic abnormalities that characterize the homocystinuria. In some embodiments, the PEGylated htCBS or PEGylated htCBS mutant enzyme modulates toxic metabolites for at least 24 hours, at least 48 hours, or at least 72 hours. In additional embodiments, the PEGylated htCBS or PEGylated htCBS mutant enzyme ameliorates the disease manifestations for at least 3 months, 6 months, 12 months, or 24 months.

In one embodiment, ERT using PEGylated htCBS or PEGylated htCBS mutant enzyme offers an effective therapy for CBSDH patients to allow prevention and treatment of and/or amelioration of symptoms of homocystinuria, and relieving the need to maintain such a strict protein-excluding diet. Alternatively, a subject is administered a PEGylated htCBS C15S, and the subject is on protein-excluding or on a Met-restricted diet.

In one embodiment, PEGylated htCBS or PEGylated htCBS mutant may be used to increase cystathionine and treat or reduce the effects of mental retardation in homocystinuria subjects. The amount of cystathionine may be increased in a region or area of the brain such as, but not limited to, occipital lobes grey matter and white matter.

In one embodiment, PEGylated htCBS or PEGylated htCBS mutant may be used to increase sensitivity of neural tissues in the brain of homocystinuria subjects. The amount of cystathionine may be increased in a region or area of the brain such as, but not limited to, occipital lobes grey matter and white matter.

In one embodiment, PEGylated htCBS or PEGylated htCBS mutant may be used to extend the life of a subject with CBSDH.

In one embodiment, PEGylated htCBS or PEGylated htCBS mutant is used as part of CBS enzyme replacement therapy (ERT) for the treatment of homocystinuria. The administration of PEGylated htCBS and htCBS mutant may not necessitate introduction of the deficient enzyme into its natural intracellular compartment.

In one embodiment, administration of PEGylated htCBS or PEGylated htCBS mutant decrease homocysteine levels by 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95%. As a non-limiting example, the decrease of homocysteine may be a decrease of about 69%. As a non-limiting example, the decrease of homocysteine may be a decrease of about 67%. As a non-limiting example, the decrease of homocysteine may be a decrease of about 52%. As a non-limiting example, the decrease of homocysteine may be a decrease of about 33%.

In one embodiment, PEGylated htCBS or PEGylated htCBS mutant may be administered before, after or concurrently with traditional betaine treatment. The combination therapy may result in synergistic effects on homocysteine levels.

In one embodiment, administration of PEGylated htCBS or PEGylated htCBS mutant to a subject may alter the extra- and intra-cellular equilibrium of sulfur amino acids.

In one embodiment, the alteration of extra- and intra-cellular equilibrium may be a decrease in the plasma homocysteine such as, but not limited to, a decrease of about 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95%. As a non-limiting example, the decrease of plasma homocysteine may be a decrease of about 75%.

In one embodiment, the alteration of extra- and intra-cellular equilibrium may be an increase in cystathionine such as, but not limited to, an increase of about 10%, 20%, 30%, 40%, 50%, 60%, 70%, 80%, 90%, 100%, 110%, 1120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, 1000% or more than 1000%. As a non-limiting example, increase in cystathionine may be about 900%.

In one embodiment, the alteration of extra- and intra-cellular equilibrium may be the normalization of cysteine concentrations that is reflected in improvement of histopathological changes in the liver and increased survival.

In one embodiment, PEGylated htCBS or PEGylated htCBS mutant may be used to reduce tHcy levels in a subject with CBSDH. The tHcy levels may be reduced to 1, 2, 3, 4, 5, 6, 7, 8, 9, 10, 11, 12, 13, 14, 15, 16, 17, 18, 19, 20 21, 22, 23, 24, 15, 26, 27, 28, 29, 30, 31, 32, 33, 34, 35, 36, 37, 38, 39, 40, 41, 42, 43, 44, 45, 46, 47, 48, 49, 50, 51, 52, 53, 54, 1-5, 1-10, 1-20, 1-30, 1-40, 1-50, 2-5, 2-10, 2-20, 2-30, 2-40, 2-50, 3-5, 3-10, 3-20, 3-30, 3-40, 3-50, 4-6, 4-10, 4-20, 4-30, 4-40, 4-50, 5-7, 5-10, 5-20, 5-30, 5-40, 5-50, 6-8, 6-10, 6-20, 6-30, 6-40, 6-50, 7-10, 7-20, 7-30, 7-40, 7-50, 8-10, 8-20, 8-30, 8-40, 8-50, 9-10, 9-20, 9-30, 9-40, 9-50, 10-20, 10-30, 10-40, 10-50, 20-30, 20-40, 20-50, 30-40, 30-50 or 40-50 times the wild type level. As a non-limiting example, the tHCY level is reduced to about 30 times the wild type level. As a non-limiting example, the tHCY level is reduced to about 3-5 times the wild type level.

In one embodiment, PEGylated htCBS or PEGylated htCBS mutant may be used to lower tHcv levels and thus treat or reduce the effects of diseases, disorders and/or conditions associated with high tHCY levels (e.g., greater than 54 times the wild type level). Non-limiting examples, of diseases, disorder and/or conditions associated with high tHCY levels include facial alopecia, osteoporosis, dislocation of eye lenses, and reduction in mean survival.

In one embodiment, the PEGylated htCBS or PEGylated htCBS mutant described herein may be used to normalizing cysteine levels without cysteine supplementation.

In one embodiment, the PEGylated htCBS or PEGylated htCBS mutant described herein may be used in combination with Betaine to reduce concentrations of homocysteine in a subject. Homocysteine may be reduced about 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95% or more than 95% in a subject using the combination therapy. As a non-limiting example, homocysteine may be reduced 77%. As a non-limiting example, homocysteine may be reduced 76%. As a non-limiting example, homocysteine may be reduced 74%. As a non-limiting example, homocysteine may be reduced 40%.

In one embodiment, the PEGylated htCBS or PEGylated htCBS mutant described herein may be used to cause a change such as an increase and/or decrease in metabolite levels.

In one embodiment, the PEGylated htCBS or PEGylated htCBS mutant described herein may be used to cause a change such as an increase in metabolite levels. As a non-limiting example, the metabolite may be cystathionine and cysteine which may be increased 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95%, 100%, 110%, 1120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, 1000% or more than 1000%. As a non-limiting example, the amount of cystathionine may be increased to be above 0.008, 0.01, 0.015, 0.020, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, or 0.35 µM or cystathionine may be increased to be between 0.05 and 0.35 µM. As another non-limiting example, the amount of cysteine may be increased to be above 140, 150, 160, 170, 180, 190, 200, 210, 220, 230, 240, 250, 260, 270, 280, 290, 300, 310, 320, 330, 340, 350, 360, 370, 380, 390, 400 or cysteine may be increased to be between 200 µM and 400 µM.

In one embodiment, the PEGylated htCBS or PEGylated htCBS mutant described herein may be used to cause a change such as a decrease in metabolite levels. As a non-limiting example, the metabolite may be homocysteine, methionine and S-adenosyl homocysteine which may be decreased by 5%, 10%, 15%, 20%, 25%, 30%, 33%, 35%, 40%, 45%, 50%, 52% 55%, 60%, 65%, 67%, 69%, 70%, 74%, 75%, 76%, 77%, 80%, 85%, 90%, 95%, 99% or 100%. As a non-limiting example, the amount of homocysteine may be decreased to be about 100, 95, 90, 85, 80, 75, 70, 65, 60, 55, 50, 45, 40, 35, 30, 25, 20, 15, 10, 5, 4, 3, 2 or 1 µM. As a non-limiting example, the amount of methionine may be decreased to be about 50, 45, 40, 35, 30, 25, 20, 15, 10, 5, 4, 3, 2 or 1 µM. As another non-limiting example, the amount of S-adenosyl homocysteine is decreased to be about 0.15, 0.14, 0.13, 0.12, 0.11, 0.10, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.009, 0.008, 0.007, 0.006, 0.005, 0.004, 0.003, 0.002, 0.001 or less than 0.001 µM.

In one embodiment, the PEGylated htCBS or PEGylated htCBS mutant described herein may be used to reduce levels of homocysteine, methionine, S-adenosyl-methionine and S-adenosyl-homocysteine in a subject.

In one embodiment, the PEGylated htCBS or PEGylated htCBS mutant may be used to increase the levels of cysteine and cystathionine in a subject.

In a further aspect, the present invention relates to a method to recombinantly produce and purify a human cystathionine synthase. The method includes the step of cloning a nucleic acid sequence encoding a human CBS enzyme or a truncated or mutated variant thereof into an expression vector. As a non-limiting example, the enzyme and method may be as set forth in International publication WO2014120770, the contents of which are herein incorporated by reference, and specifically as in SEQ ID NO: 01, SEQ ID NO: 02, SEQ ID NO: 3, SEQ ID NO: 4, SEQ ID NO: 13, SEQ ID NO: 14, SEQ ID NO: 15, and SEQ ID NO: 16.

Administration and Dosing

In one embodiment, PEGylated htCBS or PEGylated htCBS mutant may be administered to a subject by parenteral administration.

In one embodiment, PEGylated htCBS or PEGylated htCBS mutant may be administered to a subject by subcutaneous (SC), intravenous (IV) or intraperitoneal (IP) injection. As a non-limiting example, PEGylated htCBS or PEGylated htCBS mutant may be administered to a subject by subcutaneous administration. As a non-limiting example, PEGylated htCBS or PEGylated htCBS mutant may be administered to a subject by intravenous administration. As a non-limiting example, PEGylated htCBS or PEGylated htCBS mutant may be administered to a subject by intraperitoneal administration. As a non-limiting example, PEGylated htCBS or PEGylated htCBS mutant may be administered to a subject by an osmotic pump.

In one embodiment, the PEGylated htCBS or PEGylated htCBS mutant may be administered to a subject at least 1, 2, 3, 4, 5, 6, 7, 8, 9, 10, 11, 12, 13, 14, 15, 16, 17, 18, 19, 20 or more than 20 times.

In one embodiment, the administration of the PEGylated htCBS or PEGylated htCBS mutant may be repeated every minute, 2 minutes, 3 minutes, 4 minutes, 5 minutes, six 6, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, hourly, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, daily, 2 days, 3 days, 4 days, 5 days, 6 days, weekly, biweekly, 3 weeks, monthly, 2 months, quarterly, 4 months, 5 months, 6 months, 7 months, 8 months, 9 months, 10 months, 11 months, yearly, 13 months, 14 months, 15 months, 16 months, 17 months, or 18 months.

In one embodiment, the administration of the PEGylated htCBS or PEGylated htCBS mutant may be a series of doses which are minutes, hours, days or weeks apart. The number of doses in a series may be 2, 3, 4, 5 or 6. As a non-limiting example, a subject is administered 3 doses 24 hours apart. As another non-limiting example, a subject is administered 5 doses 12 hours apart.

In one embodiment, the administration of the PEGylated htCBS or PEGylated htCBS mutant may follow a dosing schedule of a series of doses that has a gap between the first series and the second series of doses. The gap between the doses may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. The number of doses in a series may be 2, 3, 4, 5 or 6. As a non-limiting example, a subject may be administered a first series of 5 doses 12 hours apart and then 14 days after the first dose a subject is administered a second series of 5 doses 12 hours apart. As another non-limiting example, a subject is administered two series of doses over a period of 8 weeks where the first series is one dose twice a week for two weeks and the second series of doses is three times a week for 6 weeks.

In one embodiment, PEGylated htCBS or PEGylated htCBS mutant may be administered at least once after a subject has been administered Betaine. The time between the Betaine administration the PEGylated htCBS may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the PEGylated htCBS may be administered 14 days after the subject was administered Betaine. As another non-limiting example, a subject may be administered two doses after the subject was administered Betaine. The PEGylated htCBS or PEGylated htCBS mutant may be administered 14 and 15 days after Betaine administration.

In one embodiment, PEGylated htCBS or PEGylated htCBS mutant may be administered in combination with Betaine to a subject. The combination may be administered at least 1, 2, 3, 4, 5, 6, 7, 8, 9, 10, 11, 12, 13, 14, 15 or more than 15 times.

In one embodiment, PEGylated htCBS or PEGylated htCBS mutant may be administered in combination with Betaine to a subject after the subject has initially received Betaine. The time between the combination treatment and the original Betaine administration may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the combination may be administered 14 days after the subject was first administered Betaine. As another non-limiting example, a subject may be administered two doses after the subject was first administered Betaine. The combination may be administered 14 and 15 days after Betaine administration.

In one embodiment, the dose of PEGylated htCBS or PEGylated htCBS mutant administered to a subject may be between 5 and 8 mg/kg such as 5 mg/kg, 5.5 mg/kg, 6 mg/kg, 6.5 mg/kg, 7 mg/kg, 7.5 mg/kg or 8 mg/kg. In certain embodiments, the dose is selected from the range of about 2 mg/kg to about 24 mg/kg. For example, the dose is about 2 mg/kg, about 6 mg/kg, about 8 mg/kg, about 10 mg/kg, or about 24 mg/kg. In certain embodiments, the dose is selected from the range of about 0.01 to about 10 mg/kg. For example, the dose is about 0.4 mg/kg. In certain embodiments, the PEGylated htCBS or PEGylated htCBS mutant polypeptide is administered to a subject on a methionine-restricted diet. Alternatively, the PEGylated htCBS or PEGylated htCBS mutant polypeptide is administered to a subject that is not on a methionine-restricted diet.

In one embodiment, the PEGylated htCBS or PEGylated htCBS mutant polypeptide may be co-administered with another therapeutic for treating CB SDH. As used herein, "co-administered" means the administration of two or more components. These components for co-administration include, but are not limited to PEGylated htCBS, PEGylated htCBS mutant, betaine or Vitamin B6. Co-administration refers to the administration of two or more components simultaneously or with a time lapse between administration such as 1 second, 5 seconds, 10 seconds, 15 seconds, 30 seconds, 45 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 1 hour, 1.5 hours, 2 hours, 2.5 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 1.5 days, 2 days, or more than 3 days.

Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure and specifically disclosed. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

"Coding sequence" refers to that portion of a nucleic acid (e.g., a gene) that encodes (i) an mRNA that is translated into an amino acid sequence of a protein; or (ii) a functional RNA, such as an interfering RNA or antisense molecule.

"Recombinant," when used with reference to, e.g., a cell, nucleic acid, polypeptide, expression cassette or vector, refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell (i.e., "exogenous nucleic acids") or express native genes that are otherwise expressed at a different level, typically, under-expressed or not expressed at all.

Recombinant techniques can include, e.g., use of a recombinant nucleic acid such as a cDNA encoding a protein or an antisense sequence, for insertion into an expression system, such as an expression vector; the resultant construct is introduced into a cell, and the cell expresses the nucleic acid, and the protein, if appropriate. Recombinant techniques also encompass the ligation of nucleic acids to coding or promoter sequences from different sources into one expression cassette or vector for expression of a fusion protein, constitutive expression of a protein, or inducible expression of a protein.

The terms "subject", "individual" or "patient" are used interchangeably herein and refer to a vertebrate, preferably a mammal. Mammals include, but are not limited to, humans.

"Associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

"Physiological conditions" or "physiological solution" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl, pH 6.5-7.6, and a temperature of approximately 22-37 degrees C. Generally, physiological conditions are suitable binding conditions for intermolecular association of biological macromolecules. For example, physiological conditions of 150 mM NaCl, pH 7.4, at 37 degrees C. are generally suitable.

"Pharmaceutically acceptable excipient or carrier" refers to an excipient that may optionally be included in the compositions of the invention and that causes no significant adverse toxicological effects to the patient. In particular, in the present instance, such refers to an excipient that can be taken into the mammalian subject's body in association with an active compound (here PEGylated htCBS) with no significant adverse toxicological effects to the subject.

The term "excipient" or "vehicle" as used herein means any substance, not itself a therapeutic agent, used as a carrier for delivery of a therapeutic agent and suitable for administration to a subject, e.g. a mammal or added to a pharmaceutical composition to improve its handling or storage properties or to permit or facilitate formation of a dose unit of the composition into a discrete article such as a capsule or tablet suitable for oral administration. Excipients and vehicles include any such materials known in the art, e.g., any liquid, gel, solvent, liquid diluent, solubilizer, or the like, which is nontoxic and which does not interact with other components of the composition in a deleterious manner. Administration can mean oral administration, inhalation, enteral administration, feeding or inoculation by intravenous injection. The excipients may include standard pharmaceutical excipients, and may also include any components that may be used to prepare foods and beverages for human and/or animal consumption, feed or bait formulations or other foodstuffs.

"Permeant," "drug," or "pharmacologically active agent" or any other similar term means any chemical or biological material or compound, inclusive of peptides, suitable for administration by the methods previously known in the art and/or by the methods taught in the present disclosure, that induces a desired biological or pharmacological effect, which may include, but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anesthetic effect, or it may be systemic. This disclosure is not drawn to novel permeants or to new classes of active agents. Rather it is limited to the mode of delivery of agents or permeants which exist in the state of the art or which may later be established as active agents and which are suitable for delivery by the present disclosure.

The term "about," particularly in reference to a given quantity, is meant to encompass deviations of plus or minus five percent.

"Optional" or "optionally" means that the subsequently described circumstance may or may not be present or occur, so that the description includes instances where the circumstance is present or occurs and instances where it is not present or does not occur.

"Substantially absent" or "substantially free" of a certain feature or entity means nearly totally or completely absent the feature or entity. For example, for a subject administered PEGylated htCBS, the substantial absence of an observable side effect means that such side effect is either non-detectable, or occurs only to a negligible degree, e.g., to an extent or frequency that is reduced by about 50% or more when compared to either the frequency or intensity of the same side effect observed in an untreated patient.

The terms "pharmacologically effective amount" or "therapeutically effective amount" as related to the present composition refer to a non-toxic, but sufficient amount of the active agent (or composition containing the active agent) to provide the desired level in the bloodstream or at the site of action (e.g. intracellularly) in the subject to be treated, and/or to provide a desired physiological, biophysical, biochemical, pharmacological or therapeutic response, such as amelioration of the manifestations of homocystinuria. The exact amount required will vary from subject to subject, and will depend on numerous factors, such as the active agent, the activity of the composition, the delivery device employed, the physical characteristics of the composition, intended patient use (i.e., the number of doses administered per day), as well as patient considerations, such as species, age, and general condition of the subject, the severity of the condition being treated, additional drugs being taken by the subject, mode of administration, and the like. These factors and considerations can readily be determined by one skilled in the art, based upon the information provided herein. An appropriate "effective" amount in any individual case may be determined by one of ordinary skill in the art using routine experimentation, based upon the information provided herein.

The term "biological activity" refers to any biological activity typically attributed to a nucleic acid or protein by those skilled in the art. Examples of biological activities are enzymatic activity, ability to dimerize, fold or bind another protein or nucleic acid molecule, etc.

The term "nucleic acid" may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand.

As used herein, a "variant" is a nucleic acid, protein or polypeptide which is not identical to, but has significant homology (for example, 80%, 85%, 90%, 91%, 92%, 93%, 94%, 95%, 96%, 97%, 98% or 99% sequence identity) over the entire length of the wild type nucleic acid or amino acid sequence, as exemplified by sequences in the public sequence databases, such as GenBank. As used herein, a "protein, polypeptide or peptide fragment thereof" means the full-length protein or a portion of it having an amino acid sequence usually at least 5, 6, 7, 8, 9, 10, 11, 12, 13, 14 or 15 amino acids in length, although dipeptides, tripeptides and tetrapeptides are also contemplated and encompassed by the present disclosure.

As used herein, a "mutant" is a mutated protein designed or engineered to alter properties or functions relating to glycosylation, protein stabilization and/or ligand binding.

As used herein, the terms "native" or "wild-type" relative to a given cell, polypeptide, nucleic acid, trait or phenotype, refers to the form in which that is typically found in nature.

As used herein, the terms "protein," "polypeptide," "oligopeptide" and "peptide" have their conventional meaning and are used interchangeably to denote a polymer of at least two amino acids covalently linked by an amide bond, regardless of length or post-translational modification (e.g., glycosylation, phosphorylation, lipidation, myristylation, ubiquitination, etc.). Furthermore, the polypeptides described herein are not limited to a specific length. Included within this definition are D- and L-amino acids, and mixtures of D- and L-amino acids. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Polypeptides can also refer to amino acid subsequences comprising epitopes, i.e., antigenic determinants substantially responsible for the immunogenic properties of a polypeptide and being capable of evoking an immune response.

"Position corresponding to" refers to a position of interest (i.e., base number or residue number) in a nucleic acid molecule or protein relative to the position in another reference nucleic acid molecule or protein. Corresponding positions can be determined by comparing and aligning sequences to maximize the number of matching nucleotides or residues, for example, such that identity between the sequences is greater than 90%, greater than 95%, greater than 96%, greater than 97%, greater than 98% or greater than 99%. The position of interest is then given the number assigned in the reference nucleic acid molecule. For example, if a particular polymorphism in Gene-X occurs at nucleotide 2073 of SEQ ID No. X, to identify the corresponding nucleotide in another allele or isolate, the sequences are aligned and then the position that lines up with 2073 is identified. Since various alleles may be of different length, the position designating 2073 may not be nucleotide 2073, but instead is at a position that "corresponds" to the position in the reference sequence.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as "seeds" for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89:10915 (1989)).

While all of the above mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (Accelrys, Madison WI), using default parameters provided.

The term "NH2 Terminal Modifications" may be used to refer to the peptides described herein. The terminus of the peptide compounds of the invention corresponding to the amino terminus, if present, may be in the "free" form (e.g., $H_2N$—), or alternatively may be acylated with a group of the formula $R^2C(O)$— or $R^2S(O)_2$—, wherein $R^2$ is as previously defined. In one embodiment, $R^2$ is selected from the group consisting of ($C_1$-$C_6$) alkyl, ($C_5$-$C_{10}$) aryl, ($C_6$-$C_{16}$) arylalkyl, 5-10 membered heteroaryl or 6-16 membered heteroarylalkyl.

In another embodiment, the amino terminus may be "blocked" with a blocking group designed to impart the compound with specified properties, such as a low antigenicity. Non-limiting examples of such blocking groups include polyalkylene oxide polymers such as polyethylene glycol (PEG). A variety of polymers useful for imparting compounds, and in particular peptides and proteins, with specified properties are known in the art, as are chemistries suitable for attaching such polymers to the compounds. Specific non-limiting examples may be found in U.S. Pat. Nos. 5,643,575; 5,730,990; 5,902,588; 5,919,455; 6,113,906; 6,153,655; and 6,177,087, the disclosures of which are incorporated herein by reference.

The term "Carboxy Terminus Modifications" may be used in relation to the peptides described herein. The terminus of the peptide compounds corresponding to the C-terminus, if present, may be in the form of an underivatized carboxyl group, either as the free acid or as a salt, such as a sodium, potassium, calcium, magnesium salt or other salt of an inorganic or organic ion, or may be in the form of a derivatized carboxyl, such as an ester, thioester or amide. Such derivatized forms of the compounds may be prepared by reacting a compound having a carboxyl terminus with an appropriate alcohol, thiol or amine. Suitable alcohols, thiols or amines include, by way of example and not limitation, alcohols of the formula $R^2OH$, thiols of the formula $R^2SH$ and amines of the formula $R^2NH_2$, $R^2R^2NH$ or $NH_3$, where each R 2 is, independently of the others, as previously defined.

The term "L or D form amino acids" may be used in relation to the peptide described herein. As will be recognized by skilled artisans, the various $X''$ residues comprising the compounds of the invention may be in either the L- or D-configuration about their $C_\alpha$ carbons. In one embodiment, all of the $C_\alpha$ carbons of a particular compound are in the same configuration. In some embodiments of the invention, the compounds comprise specific chiralities about one or more $C_\alpha$ carbon(s) and/or include non-peptide linkages at specified locations so as to impart the compound with specified properties. For example, it is well-known that peptides composed in whole or in part of D-amino acids are more resistant to proteases than their corresponding L-peptide counterparts. Thus, in one embodiment, the compounds are peptides composed in whole or in part of D-amino acids. Alternatively, compounds having good stability against proteases may include peptide analogs including peptide linkages of reversed polarity at specified positions. For example, compounds having stability against tryptic-like proteases include peptide analogs having peptide linkages of reversed polarity before each L-Arg or L-Lys residue; compounds having stability against chymotrypsin-like proteases include peptide analogs having peptide linkages of reversed polarity before each small and medium-sized L-aliphatic residue or L-non-polar residue. In another embodiment, compounds having stability against proteases include peptide analogs composed wholly of peptide bonds of reversed polarity. Other embodiments having stability against proteases will be apparent to those of skill in the art. Additional specific embodiments of the compounds are described herein.

As used herein, the term "long-term administration" refers to administration of the CBS enzyme, htCBS, or htCBS mutant (e.g., with a C15S mutation) conjugated to a PEG moiety over a time-period of 6 weeks or longer.

As used herein, the term "continuous administration" refers to repeated administration of the CBS enzyme, htCBS, or htCBS mutant (e.g., with a C15S mutation) conjugated to a PEG moiety throughout the course of a study via SC injection or implanted osmotic pump.

As used herein, the term "I278T", "I278T homozygous", or "I278T −/− homozygous" mice refers to a mouse model in which the endogenous mouse cbs gene has been knocked out and a human CBS transgene having the most common mutation in the CBS allele, 833T>C (I278T), which is associated with homocystinuria, has been inserted as a cDNA clone under the control of zinc-inducible promoter on a plasmid integrated to the mouse genome.

EXAMPLES

The following examples are illustrative in nature and are in no way intended to be limiting.

Example 1. Experimental Procedures

A. Construction of Sequence-Optimized, Truncated Human CBS in PET29A(+) Vector

As previously described in International Publication No. WO2014120770, the disclosure of which is incorporated herein by reference in its entirety, full length (551 aa) human CBS coding sequence was optimized for bacterial expression and cloned into the pUC57 vector following digestion with the EcoRV restriction enzyme, by GenScript USA Inc (NJ, USA). The CBS sequence was then amplified by PCR using primers A1 and A2 to generate a sequence coding for the truncated enzyme (aa 1-413). The PCR product was then digested with the restriction enzymes NcoI and XhoI, and ligated into the pET-28a(+) vector that was digested with the same enzymes. Cloning into the optimal NcoI site of pET-28a(+) results in a G to C mutation as compared to the CBS wild-type sequence. Site-Directed Mutagenesis kit (Stratagene, CA, USA) utilizing primers B1 and B2, was used to re-generate the wild type sequence (htCBS). The same strategy was used to generate the C15S mutant (T to A mutation; htCBSC15) by using primers C1 and C2. All sequences were verified by sequencing. Expression of the truncated CBS is controlled by an upstream T7 promoter in the pET-28a(+) vector, which requires transformation into DE3 bacteria and induction by IPTG. Table 1 describes the primers and their sequence identifier.

TABLE 1

| Primers | |
| --- | --- |
| Primer name | SEQ ID NO. |
| A1 | 7 |
| A2 | 8 |
| B1 | 9 |
| B2 | 10 |
| C1 | 11 |
| C2 | 12 |
| pKK-F (SphI) | 5 |
| pKK-R (Kpn I) | 6 |

B. Expression and Purification

The pET-28a(+) vector, harboring the sequence coding for the truncated human CBS, was transformed into DE3 bacteria, i.e., *E. coli* BL-21 (DE3) or HMS174(DE3), and bacteria from kanamycin-resistant clones were grown in 5 ml of Luria-Bertani (LB) medium, with 30 µg/ml kanamycin, overnight at 37° C. on a rotational shaker at 275 RPM. One ml of the overnight culture was added to a 100 ml Terrific Broth (TB) medium with 30 ug/ml kanamycin and grown overnight. 10 ml of was then added to a 1 liter TB medium containing 0.001% of thiamine-HCl pH 8.0, 0.0025% of pyridoxine-HCl pH 8.0, 0.3 mM δ-ALA pH 8.0, 150 µM ferric chloride, 30 ug/ml of kanamycin. The culture was then grown at 30° C. on a rotational shaker at 275 RPM until $OD_{600}$ reached the value of ~0.6-0.7 and protein expression was induced by addition of 1 mM IPTG. Fermentation was continued for additional 16 hours. Cells were harvested by a 10 minute, 6000 RCF centrifugation at 4° C., washed with ice-cold 0.9% NaCl, re-centrifuged as above, and frozen at −80° C. 4.45 ml of lysis buffer (20 mM $NaH_2PO_4$, pH=7.2, 40 mM NaCl, 0.1 mM PLP) per 1 gram of pellet was then added to the cell pellet and the latter was homogenized in a Dounce homogenizer and treated with lysozyme (2 mg/ml final), incubated for 1 hour at 4° C. on a rocking platform, sonicated to reduce viscosity, and centrifuged at 53000 RCF. The supernatant, comprising the soluble fraction was then stored at −80° C. The lysate was processed through a multi-step chromatographic procedure. The core process consists of an anion exchange capture column (DEAE Sepharose-FF), followed by an affinity column. This attains purity of approximately 90%. The final purity of >99% is achieved by the use of one or two polishing chromatography steps. The final column eluate was diafiltered into PBS.

C. Enzyme Activity Assay

CBS activity was determined by a radioisotope assay with $C^{14}$-labeled serine as a substrate. Ten μl (total 490 ng) of pure htCBS in dilution buffer (0.1 M Tris-HCl pH=8.6, 1 mM DTT, 10 μM PLP, 0.5 mg/ml BSA) or 10 μl of plasma were added to 85 μl of reaction mixture containing 0.1 M Tris-HCl pH=8.6, 10 mM L-serine, 0.5 mM PLP, 0.5 mg/ml BSA and 0.3 μCi (for pure enzyme) or 0.45 μCi (for plasma) of L-[$C^{14}$(U)]-Serine. Samples were incubated for 5 min at 37° C. and reaction was initiated by addition of 5 μl of 0.2 M Hcy (10 mM final concentration). Following 30 min of incubation at 37° C., a 20 μl aliquot of the assay mixture was applied onto a grade 3 CHR Whatman (NJ, USA) paper. Assay initiation and sampling of the resulting mixture were staggered so that each reaction time was 30 minutes. Descending paper chromatography was used to isolate the radioactive product (Cth) from a labeled substrate (Ser). The $C^{14}$-cystathionine formed in the reaction was separated from $C^{14}$-serine by an overnight descending paper chromatography in 2-propanol/formic acid/$H_2O$ (75:5.7:18.9 v/v). Radioactivity in the area of the marker cystathionine (detected by staining the marker lane with ninhydrin) was determined by cutting the chromatogram into strips that were submerged in 5 ml of Opti-fluor scintillation cocktail (PerkinElmer, MA, USA) and counted in a Beckman LS-3801 scintillation counter. An enzyme-free sample was used as a blank to monitor the background radioactivity that was then subtracted from each sample. For pure enzyme, specific activity values are expressed as enzyme units (the amount of enzyme that produces 1 μmol of cystathionine/hour) per mg of CBS, and for plasma samples as units per μl plasma. In the pharmacokinetic (PK) studies, this has been designated: mU/μl of plasma.

D. In Gel Activity Assay

Protein samples were separated using Native Page (Bio-Rad, CA, USA). The gel was then incubated for 15-30 minutes in a staining solution (100 mM Tris-HCl pH=8, 20 mM L-cysteine, 50 mM 2-mercaptoethanol, 0.1 mM PLP and 0.2 lead nitrate). Reaction was stopped by submerging the gel in 7% acetic acid.

E. Determination of Metabolite Concentrations

Plasma metabolites homocysteine, cystathionine and cysteine were determined by stable-isotope-dilution liquid chromatography mass spectrometry as previously described in (Allen et al., 1993, *Metabolism*, 42: 1448-1460). Measurements of total non-protein bound homocysteine and other aminothiols as well as of amino acids in tissue were performed as described in (Maclean et al., 2010b. *Mol. Genet. Metab.* 101, 153-162). Metabolites were determined by stable-isotope-dilution liquid chromatography mass spectrometry.

F. PEGylation

Polyethylene glycol molecules were purchased from the NOF Corporation (Tokyo, Japan). PEGylation was carried out according to manufacturer instructions. For example, coupling of PEG maleimide derivatives to the SH groups of htCBS (5 mg/ml) was carried out in a 100 mM phosphate buffer pH=6.5 overnight at 4° C. Molar Ratio between PEG molecules to the CBS protein was 10:1 or 5:1.

Alternatively, PEGylation was achieved by conjugation of 20 kDa NHS-ester PEG (ME-200GS) with htCBS C15S (truncated human CBS having a C15S mutation). The protocol below outlines the PEGylation procedure.

Chromatographically purified htCBS C15S was buffer exchanged and formulated in 100 mM sodium phosphate buffer pH 7.2 and concentrated to at least 10 mg/ml. The enzyme aliquot was stored at −80° C., and was thawed out in a 37/42° C. water bath with occasional mixing. The enzyme aliquot was spun down to remove generated foam, if any, and kept on ice until needed.

The PEGylation molar ratio was 1:10 (per htCBS C15S subunit), which translates into 431 mg of ME-200GS per 100 mg of htCBS C15S. The calculated amount of protein, water, and 2× buffer (needed only if concentration of the enzyme was higher than 10 mg/ml) were mixed in a sterile endotoxin-free 50 ml Falcon tube. For example, PEGylation of 200 mg of htCBS C15S of 20 mg/ml required 10 ml of the protein, 12 ml of sterile water, and 10 ml of 100 mM Na-P pH7.2 buffer. The tube contained a total volume of 32 ml and was kept on ice. In a separate tube, 862 mg of ME-200GS PEG was dissolved in sterile water or DMSO by mixing, vortexing, or optional warming up in a 37/42° C. water bath for a brief amount of time. The PEG quickly dissolved into a clear, highly viscous solution. Diluted enzyme was transferred into the tube containing dissolved PEG swiftly by either pouring or pipetting. The tube was closed tightly and immediately vortexed for 10-15 seconds to generate a homogenous mixture. The tube was incubated at RT on a rocking platform for 4-6 hours or at 4° C. overnight.

G. Enzyme Storage

PEGylated htCBS C15S was formulated using PBS pH7.4 and concentrated to approximately at least 5 mg/ml, and typically to a concentration between 10 and 25 mg/ml. The enzyme was stored at −80° C. in (1.2 ml) aliquots. For each dosing day, a single use, fresh, solution of enzyme was prepared by dilution into PBS to a final concentration of 1 mg/ml. Any solution remaining upon completion of dosing was discarded.

H. Animal Procedures

All animal procedures were approved by the University of Colorado-Denver IACUC, which is an AAALAC Accredited (#00235), Public Health Service Assured (#A 3269-01) and USDA Licensed (#84-R-0059) Institution. C576BL/6J and CBS knock out (KO) mice were obtained from the Jackson Laboratory (ME, USA). Human Only (HO) mice were previously generated (Maclean et al., 2010b. *Mol. Genet. Metab.* 101, 153-162) in the laboratory. Animals were maintained on extruded standard diet 2918 (Harlan, CA, USA) with unlimited access to food and water.

Representative pups were routinely analyzed for homozygosity. A single-use lancet for submandibular bleeding was used for blood collection into Capiject T-MLHG lithium heparin (12.5 IU) tubes with gel (Terumo Medical Corporation, NJ, USA). Tubes were then centrifuged at 1200 G for 10 min, followed by collection of plasma to 1.5 ml tubes and storage at −80° C.

Genotyping: Representative pups were routinely analyzed for homozygosity qPCR. Tail biopsies were generated by the DNeasy Blood and Tissue kit (Qiagen, Hilden, Germany). DNA quality was monitored by NanoDrop 1000 (Thermo Scientific, DE, USA). Twenty ng samples of DNA were run single-plex in triplicate using Applied Biosystem's (CA, USA) Gene Expression master mix (Item #4369016). Amplification was performed on Applied Biosystem's 7500 Fast Instrument using the standard curve method. Applied Biosystems' Tert (Item #4458366) or Tfrc (Item #4458368)

copy number reference assays were used as the homozygous one copy calibrator. Applied Biosystem's assay Mr00299300 was used to detect the Neo gene.

Wild type Sprague Dawley rats were housed in cages and maintained under standard conditions with unlimited access to food and water.

Wild-type cynomolgus monkeys (*Macaca fascicularis*) were housed in sex-segregated pens with unlimited access to food and water. Twelve-hour light/dark cycles, temperature, and humidity were continuously monitored and controlled. Additional environmental enrichment in the form both natural auditory background sounds and visual nature video enrichment were provided daily. All monkeys were screened for general health prior to the study.

I. Sample Collection

After injection with a PEGylated form of htCBS, such as 20NHS PEG-htCBS C15S, blood was collected at various time-points into Capiject T-MLHG lithium heparin tubes (12.5 IU) with gel (Terumo Medical Corporation, NJ, USA) from the submandibular vein of conscious study animals using a disposable lancet designed for submandibular sampling. Plasma was collected from blood samples after centrifugation at 1200 G for 10 minutes and stored at −80° C. in 1.5 mL tubes.

J. Pharmacokinetics

The pharmacokinetic (PK) parameters were calculated using a non-compartmental curve stripping model which resolves a curve into a series of exponential terms corresponding to the absorption, distribution and elimination phases occurring during the time course of the enzyme in the blood. The curve stripping approach assumes that the disposition phases of the drug follow apparent first-order kinetics, which is evidenced by the linearity in the terminal portion of a semi-log plot. These calculations were made using a modeling program called PK Solutions 2.0 (Summit Solutions, Montrose, CO) using the mean plasma enzyme activity for each route of administration. The bioavailability was calculated by dividing the area under the curve (AUC) for the SC or IP route by the AUC observed after IV administration.

K. Preparation of Samples for NHS PEGylation Mapping

Each sample (300 µg), including the non-PEGylated CBS control, was diluted with HPLC water (ThermoFisher) to 80 µL. The sample was then mixed 1:1 (v/v) with 0.24 M CAPS buffer (Sigma) pH 11.5, and incubated at 37° C. for 22 hours to remove the PEGs. The de-PEGylated sample was transferred to Amicon Ultra 30K Centrifugal filter (Millipore), and 320 µL of 8M guanidine HCl solution (Sigma) was added. The filter was spun at 13,000 rpm for 10 minutes. This process was repeated twice to buffer exchange the samples into 8M guanidine HCl and remove the residual free PEG.

The sample was combined with 1M Tris HCl (pH 7.5) to a final concentration of 100 mM Tris. The sample was reduced with 10 mM DTT (Sigma) at 56° C. for 45 minutes and cooled. Iodoacetamide was added to a final concentration of 30 mM and the samples were incubated in the dark at room temperature for 1 hour. The sample was then diluted with 50 mM Tris (pH 7.5) solution to reach a guanidine concentration of 1 M. The reduced/alkylated samples were used for Asp-N endopeptidase digestion.

Two µg of Asp-N was added to 100 µg of the reduced and alkylated sample (enzyme: protein ratio=1:50 (w:w)). The digestion was conducted overnight at 37° C.

L. Preparation of Samples for Histopathological Analysis

The PBS-injected or PEGylated htCBS conjugate, such as 20NHS PEG-htCBS C15S, treated KO mice were sacrificed on day 17-19 and liver samples were processed for histological analysis by optical microscopy. The histological assessment was carried out in a blinded fashion. Livers were removed and were fixed for 24 hours with 4% paraformaldehyde in PBS (pH 7.4). Tissue blocks for histology were trimmed, dehydrated with an ethanol series followed by acetone, acetone-xylene mixture, and xylene, then embedded in paraffin. In parallel, small tissue blocks (around 4 mm×2 mm) fixed with paraformaldehyde were rapidly frozen in petrol ether cooled with dry ice, and stored at −50° C. for detection of apolar lipids. Paraffin sections 4 µm thick were deparaffinized in xylene and after isopropyl alcohol step rehydrated with ethanol (96%, 70%, 60%). Tissue sections were stained with hematoxylin and eosin (H&E) to evaluate histopathological changes. Masson trichrome staining was performed for detection of fibrosis. Steatosis was verified using Oil Red O staining for detection of apolar lipids in fixed-frozen sections that was 10 µm thick and cut with a Leica Cryomicrotome (CM 1850). The sections were viewed and photographed with a Nikon light microscope (E800) equipped with Olympus digital camera (DP70).

For electron microscopy, one third of each of the livers was processed for electron microscopy by cutting it into 1-2 mm thick slices and immersed post-fixation into 3% glutaraldehyde. Samples were subsequently embedded into an Epon-Araldite mixture, double stained, and examined using a JEOL 1200 electron microscope at 3000× magnification.

M. Dual-Energy X-Ray Absorptiometry (DEXA)

A PIXImusII DEXA scanner (GE Lunar Medical Systems) specifically designed for scanning small animals such as mice was used for DEXA analysis. This machine enabled quick and efficient determination of the body composition (lean, fat mass, and bone density) of a mouse before terminal tissue extraction procedures. Mice were fasted for 4 hours prior to the DEXA measurement to remove food from the gastro-intestinal tract. Mice were then anesthetized using IP bolus injection of 60 mg/kg ketamine and 15 mg/kg xylazine and placed on a tray in the DEXA machine. After the measurement was done (3~5 minutes), the mice were removed from the DEXA machine and used in terminal procedures, such as tissue extractions.

N. Preparation of Eye Samples for Observation by Microscopy

Mice were subjected to perfusion fixation with 4% paraformaldehyde in 1×PBS pH 7.4 (4% PFA) to preserve the walls of the eye globe. Eyes were carefully surgically removed, submerged into 4% PFA and a small hole was carefully made in the posterior globe of the eye right below the optic nerve to allow the fixative to permeate to the interior of the eye and fixate the structures overnight at 4° C. The samples were washed 3 times using filtered 1×PBS pH 7.4. After washing, the posterior globe of the eye was carefully dissected down to the level of the ciliary epithelium to expose the ciliary zonule. The sample was placed in 8% BSA blocking solution for 2 hours with shaking. After blocking, MAGP1 antibodies (Sigma) diluted 1:50 in 4% BSA were added to the sample and stored at 4° C. overnight. The next day, the sample was washed 6 times using 1×PBS pH 7.4, and Alexa 488 secondary antibodies (1:200, Invitrogen) were added to the sample and incubated for 2 hours at room temperature with shaking. The sample was wash 6 times and counterstained with methylgreen (nuclear staining) for 15 minutes.

A solution containing 4% agarose was heated, poured into a covered slip glass pertri dish, and allowed to solidify at room temperature. The solidified gel served as an imaging chamber for the eye. A small hole was made in the gel to serve as a secure chamber for the eye. To observe the ciliary zonule, the chamber was filled with 1×PBS, and the stained eye sample was placed in the hole with the posterior surface of the lens touching the gel bed. The 3-dimensional images were generated using an inverted LSM 510 confocal microscope at 10× magnification and 0.7× zoom.

Example 2. htCBS Retention Time

A. Unmodified htCBS Exhibits a Short Retention Time in Circulation

The pharmacokinetic properties of a pharmacologically active substance that is administered to circulation is greatly affected by natural mechanisms of ADME. Rapid clearance of the injected molecule may greatly impact treatment efficacy and thus longer circulating half-lives are desired, which may translate into less frequent administrations or smaller doses that in turn minimize the side effects. To determine the pharmacokinetics of htCBS in plasma circulation, a single dose of 5 mg/kg was injected via subcutaneous (SC), intravenous (IV) or intraperitoneal (IP) routes to C57BL/6J mice. Administration of htCBS via IV or IP routes exhibited the highest specific activity values during the first 4 hours post injection (observed peak plasma levels of up to 123 and 76 mU/μL, respectively; Table 2 shows Area Under Curve (AUC) values). The pharmacokinetic parameters calculated from plasma samples (Table 2) show that the half-life for htCBS was 2.7 hours, suggesting that after roughly 6 half-lives (less than 20 hours) htCBS levels should be undetectable.

The bioavailablity of htCBS was 50% for SC routes suggesting that SC delivery may be a clinical option for this therapeutic approach. The slower apparent half-lives for SC and IP (Table 2) can be explained by a slow absorption phase that is occurring during the elimination phase thereby extending the mean residency time and apparent half-life, however, for the present purpose a much longer half-life was desirable and thus PEGylated derivatives of htCBS were tested.

TABLE 2

Pharmacokinetic Parameters

| Pharmacokinetic Parameter | Units | IP | SC | IV |
|---|---|---|---|---|
| Dose Amount | Mg/Kg | 5 | 5 | 5 |
| AUC(0-t) (obs area) | mU-hr/μL | 932.4 | 500.9 | 1011 |
| Bioavailability | % | 92% | 50% | — |
| E Half-life | hr | 4.3 | 6.1 | 2.7 |
| $C_{max}$ (obs) | Mu/μL | 75.9 | 34.5 | — |
| MRT (area) | hr | 7.9 | 9.5 | 4.9 |

Figure 1B:
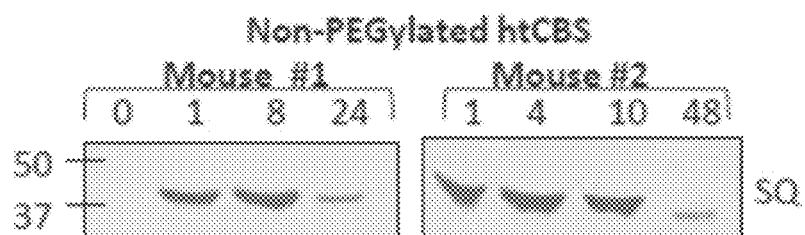
Figure 1B:
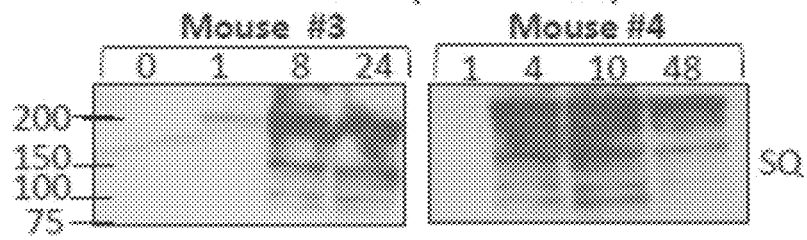

The rapid decline in htCBS activity in vivo may be attributed to a facilitated clearance from circulation and may also be attributed to the loss of enzymatic activity of htCBS once introduced to the environment in circulation. To test the latter, htCBS was incubated in vitro in mouse plasma of wild type or HO mice at 37° C. for up to 96 hours, with activity measured every 24 hours. As shown in FIG. 1A, no significant loss of activity was recorded for up to 72 hours of incubation in the plasma of either mouse model. A modest 25% loss of activity was recorded after 96 hours of incubation. Furthermore, as shown in FIG. 1B, western blot (WB) analyses of plasma from the SC injected animals, revealed that the amount of htCBS decreases as a function of time, hence, clearance accounts for the rapid loss of htCBS activity in circulation, rather than loss of activity in plasma.

B. PEGylation of htCBS Enhances Plasma Half-Life In Vivo

In order to determine the impact of PEG molecules on the pharmacokinetics CBS, htCBS was PEGylated with a low molecular weight (2 kDa) linear PEG, and with a high molecular weight (40 kDa) four arm branched PEG (designated ME020MA and GL4-400MA, respectively). As shown in Table 3, PEGylation did not affect the specific activity of the enzyme. Table 3 shows the results of the Coomassie-stained SDS-PAGE of the PEGylated and non-PEGylated htCBS with corresponding specific activity values showing that PEGylation does not influence the activity of the enzyme. Mice were injected SC as described in A (n=4-5), with the ME200MA- or GL4-400MA-PEGylated htCBS as compared to the non-PEGylated htCBS.

TABLE 3

| Activity | |
|---|---|
| htCBS tested | Specific Activity |
| Non-PEG CBS | 1193 |
| ME-200MA CBS | 1184 |
| GL4-400MA CBS | 1075 |

A dose of 5 mg/kg body weight (BW) of PEGylated htCBS (PEGhtCBS) was administered to C57BL/6J mice via the SC and IV route, and CBS activity was monitored at different time points. Two experimental arms (n=5 each) were used for each injection route. Blood was collected post injection from group 1 at 0, 1, 8 and 24 hours and from group 2 at 1, 4, 10, and 48 hours.

As shown in FIG. 1B (bottom panel) for the GL4-400MA PEGhtCBS, the activity in plasma was significantly extended for the PEGylated protein as compared to the non-PEGylated counterpart. As shown in Table 4 the half-life increased from 2.7 hours for the non-PEGylated htCBS to 16.7 and 30.4 hours with the ME020MA and GL4-400MA PEGylation, respectively.

TABLE 4

Pharmacokinetic Modeling Results

| Pharmacokinetic Modeling Results | | PEGylated htCBS ME020MA | | PEGylated htCBS GL400MA | |
|---|---|---|---|---|---|
| Parameter | Units | SC | IV | SC | IV |
| Dose Amount | Mg/Kg | 5 | 5 | 5 | 5 |
| AUC(0-t) (obs area) | Mu-hr/μL | 1637.0 | 3193.2 | 2286.3 | 2836.5 |
| Bioavailability | % | 51.2% | — | 80.6% | — |
| E Half-life | hr | 15.1 | 16.7 | 20.1 | 30.4 |
| $c_{max}$ (obs) | Mu/μL | 54.6 | — | 64.9 | — |
| MRT (area) | hr | 27.0 | 25.7 | 37.0 | 43.1 |

This means that the time of exposure after a single dose would be 5 to 10-fold longer for the PEGylated forms. Additionally, the bioavailability after SC administration ranged from 50 to 80% suggesting that the SC route would be reasonable for clinical studies.

Example 3. Administration of htCBS and Serum Levels of Homocysteine, Cystathionine and Cysteine The ultimate goal for the use of htCBS for CB SDH is to lower the toxic tHcy load, to elevate cystathionine and cysteine levels. These changes are expected to prevent, reverse or delay the onset of CB SDH symptoms. Homocystinuria research, however, has long been hindered by a lack of a suitable animal model. Mice that are complete knockout for the mouse gene die within 2-3 weeks after birth. The HO (Human Only) mice are different from other knockout mice because, in addition to having the mouse gene knocked out, they express low levels of the human gene which allows their survival to adulthood (Maclean et al., 2010b. *Mol. Genet. Metab.* 101, 153-162). HO mice exhibit severe elevations of Hcy, methionine, S-adenosylmethionine, and S-adenosylhomocysteine and present with a concomitant decrease in plasma and hepatic levels of cysteine. Accordingly, these mice exhibit characteristics that in several aspects, recapitulate the disease as it occurs in humans.

A. htCBS Administration Does Not Improve tHcy and Cystathionine Concentrations

Figure 2:
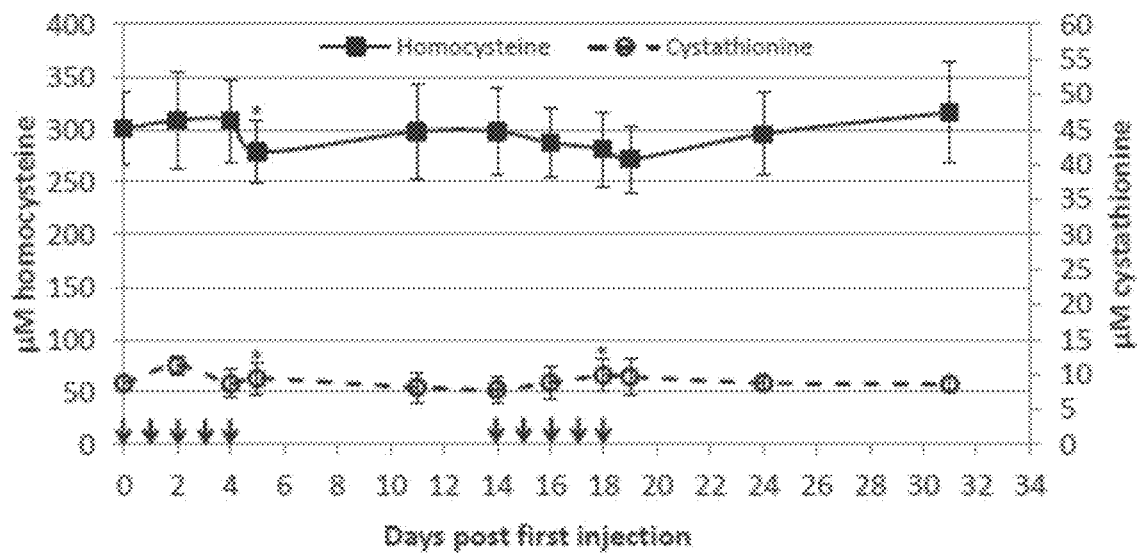
FIG. 2 shows that repeated administration of non-PEGylated htCBS results in no changes in homocysteine or cystathionine levels in HO mice.

HO mice administered non-PEGylated htCBS at 5 mg/kg for 5 consecutive days on weeks 1 and 3 (10 days between sets of treatments) demonstrated no change in serum homocysteine levels. FIG. 2 shows the mean homocysteine and cystathionine levels in HO mice. This lack of metabolic modulation by non-PEGylated htCBS further confirms the necessity to modify htCBS by covalent attachment of polyethylene glycol molecules.

Figure 3:
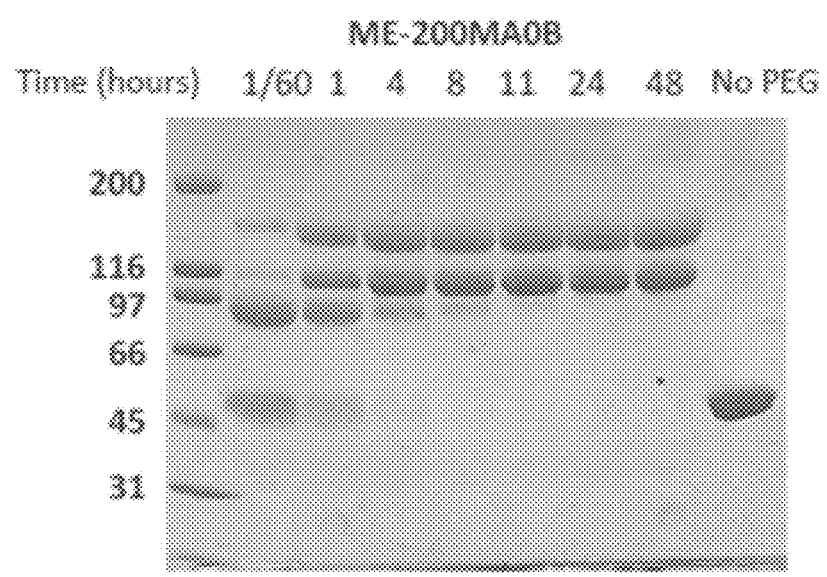
FIG. 3 shows a PEGylation time course with the selected linear 20 kDa PEG molecule designated ME200MAB.

Several different chemistries of PEGs were tested as described in International Publication No. WO2014120770, the contents of which are herein incorporated by reference in its entirety, (See Table 5) and the data indicate that CBS that is PEGylated with lower than 20 kDa PEGs demonstrates a more rapid loss of activity in plasma, than CBS with PEGs of higher molecular weight. For that reason, the linear 20 kDa PEG designated ME200MA0B was chosen for further analyses. FIG. 3 presents a Coomassie-stained SDS-PAGE showing the time course of htCBS PEGylation with ME200MA0B. PEGylation reaction was initiated by adding the PEG, and samples were withdrawn from the tube at the indicated time points to be analyzed.

TABLE 5

PEG chemistry evaluation

| PEG molecule | Structure | Target group | Size (kDa) |
|---|---|---|---|
| ME020MA | linear | —SH | 2 |
| ME050GS | linear | —NH2, —OH, —SH | 5 |
| ME200GS | linear | —NH2, —OH, —SH | 20 |
| ME200MA0B | linear | —SH | 20 |
| ME400MA | linear | —SH | 40 |
| GL2400MA | 2 arms | —SH | 40 |
| GL4400MA | 4 arms | —SH | 40 |
| GL2800MA | 4 arms | —SH | 80 |

B. Repeated PEGhtCBS Administration Improves tHcy and Cystathionine Concentrations and Restores Normal Cysteine Levels.

Figure 4A:
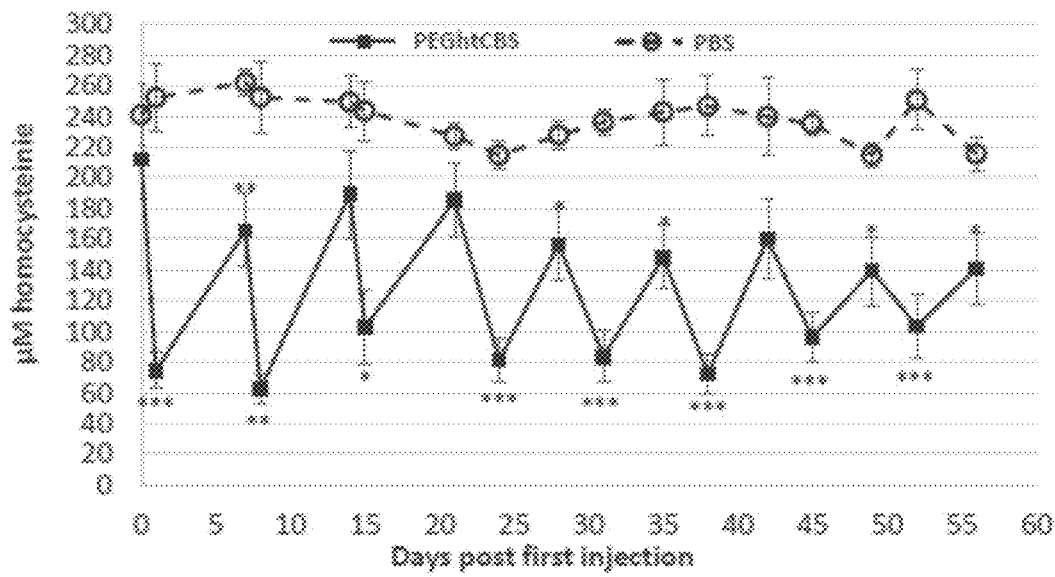
FIG. 4A-4D show that long term repeated injection of the PEGylated htCBS significantly impacts homocysteine, cystathionine and cysteine plasma and tissue levels.
Figure 4B:
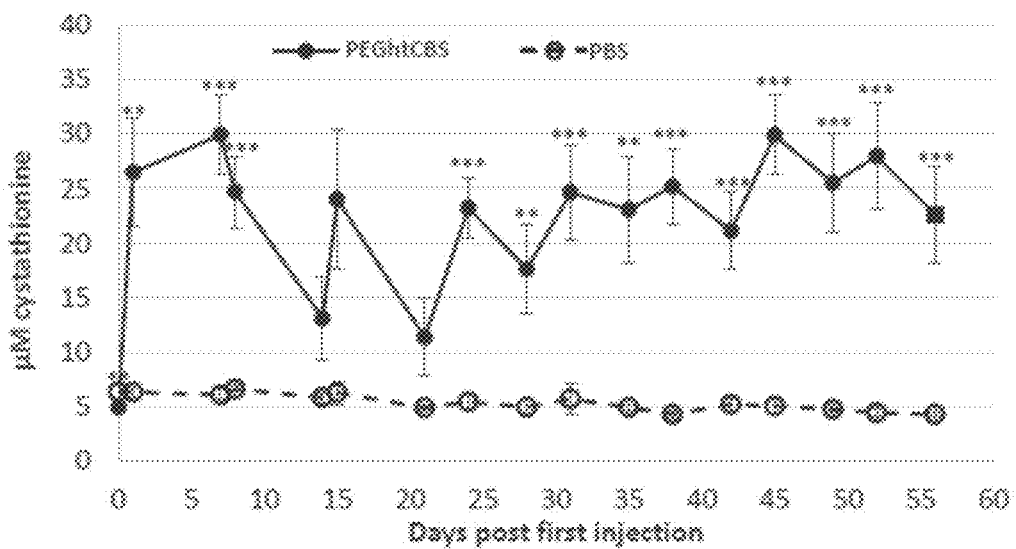
Figure 4C:
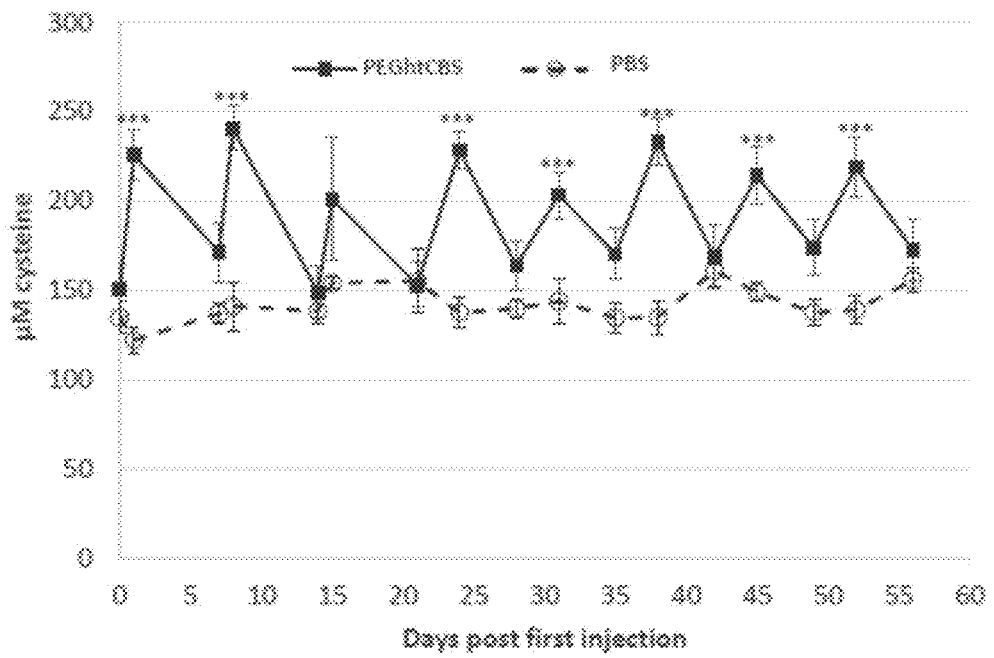
Figure 4D:
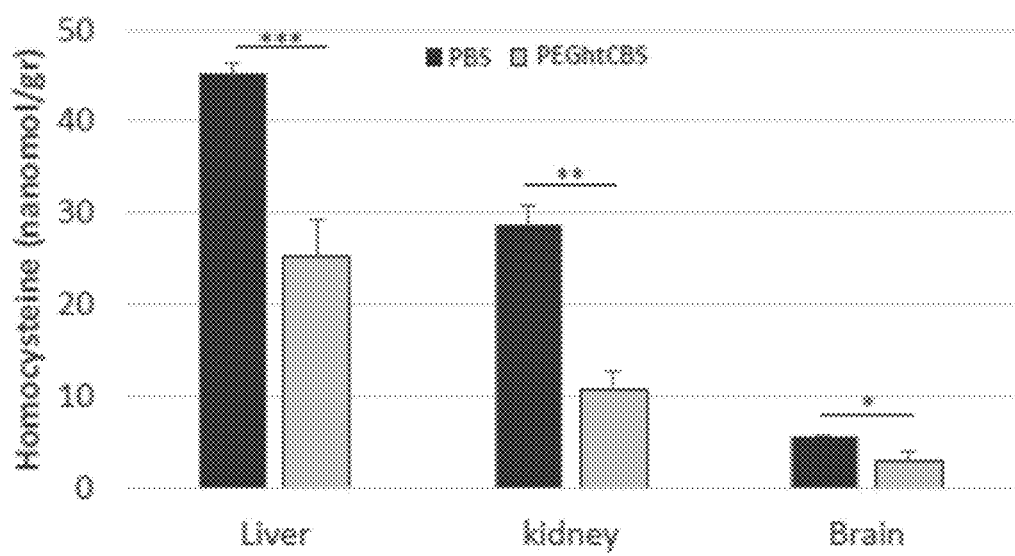

The long term effect of PEGhtCBS administration was monitored using HO mice. The PEGhtCBS enzyme was administered to 8 HO mice at a dose of 7.5 mg/kg, twice a week (Monday and Thursday) for the first two weeks, and then three times a week (Monday, Wednesday and Friday) for 6 weeks. Blood samples were collected 24 hours (Tuesday) and 72 hours (Monday) post injection (FIG. 4A-4C). FIG. 4A shows that plasma tHcy was reduced from 212 μM at time 0 to an average in the range of 62-103 μM 24 hours after injections, and was at a range of 141-189 μM 72 hours post the last weekly injection. From day 28 on, the 72 hour post injections values were significantly lower than the time 0 value (P≤0.02). Cystathionine and cysteine levels were positively influenced as well. Cystathionine increased from 6 μM to as high as 30 μM and cysteine was constantly above 200 μM 24 hours post injection (FIG. 4C). Interestingly, from day 24 on, fluctuations in cystathionine concentration were much less pronounced as compared to the first three weeks of treatment. In addition to analysis of plasma metabolites levels, liver, kidney and brain tissue samples from the injected mice were analyzed as well to determine the levels of non-protein bound homocysteine (free and disulfide-linked forms). As shown in FIG. 4D, in the long term injected animals, a reduction of 44%, 63% and 47% was demonstrated for liver, kidney, and brain tissues, respectively. Thus, long term repeated injection of the PEGhtCBS significantly impacts homocysteine, cystathionine and cysteine plasma levels.

Figure 5A:
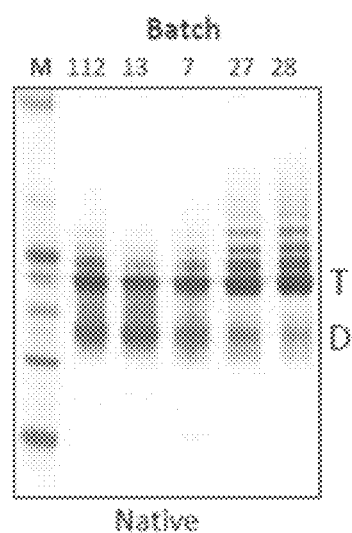
FIG. 5A-5H illustrate that the PEGylated htCBS mutant (also referred to as PEGC15S) and PEGylated htCBS prevents protein aggregation, forms mainly dimers and exhibits a reproducible PEGylation pattern.
Figure 5B:
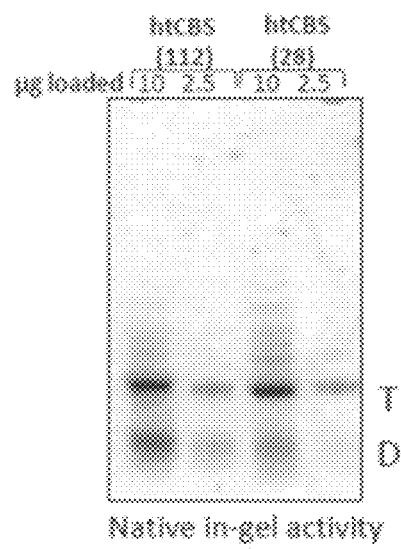
Figure 5C:
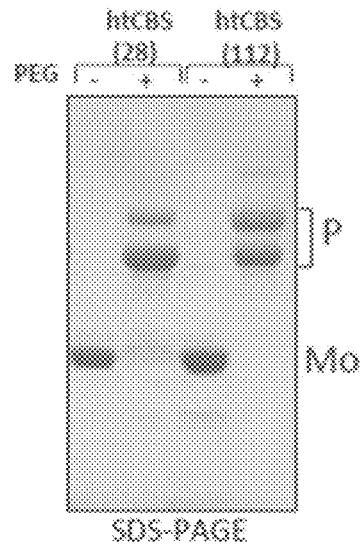
Figure 5D:
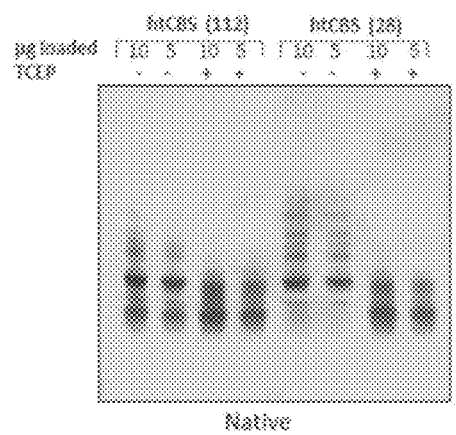
Figure 5E:
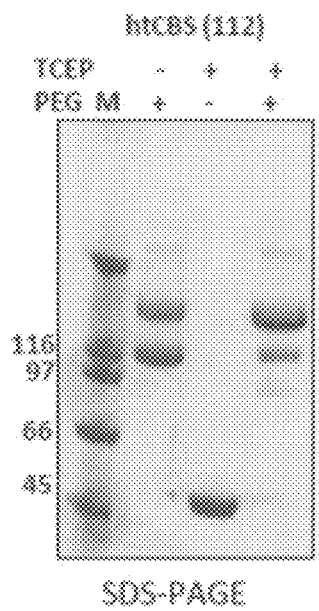
Figure 5F:
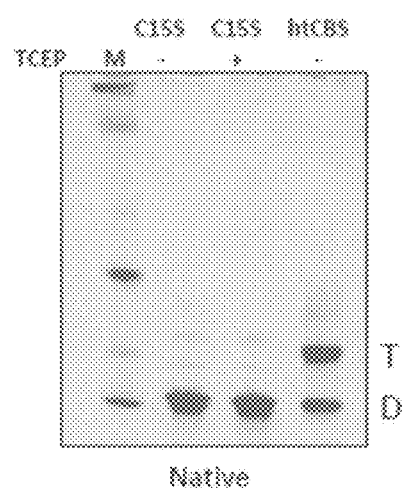
Figure 5G:
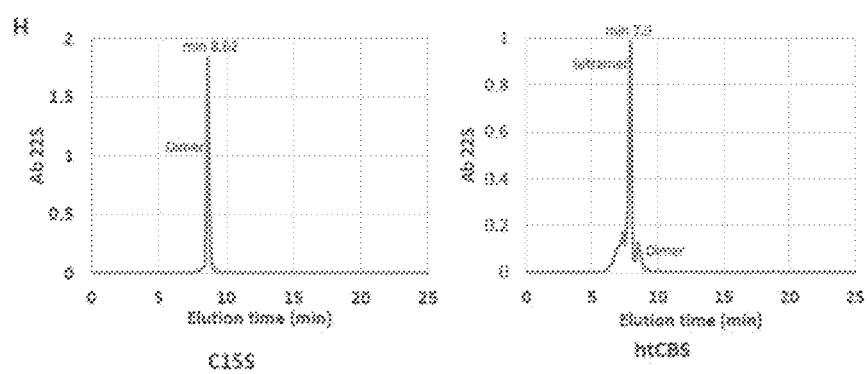
Figure 5H:
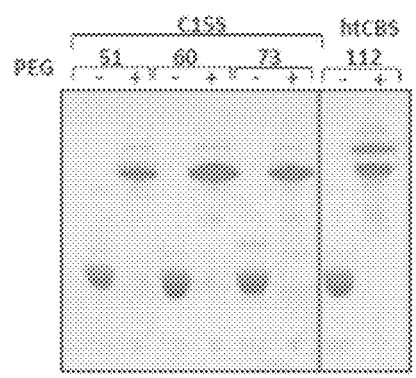

Example 4. htCBS Mutant (C15S) Shows Preferential Aggregation and PEGylation Patterns A. C15S Mutated htCBS Exhibits No Aggregation and a Uniform PEGylation Pattern Although it was previously reported that the htCBS enzyme is less prone to aggregation as compared to the full length protein (Frank et al., 2006, *Biochemistry* 45:11021-11029), it still forms tetramers and higher aggregates. This may stimulate immune defensive mechanisms and lead to e.g. amyloid deposition (D'Souza et al., 2014, "Amyloid: the international journal of experimental and clinical investigation. The official journal of the International Society of Amyloidosis" 21:71-75), but also affect purification, handling, and consistency. FIG. 5A (previously disclosed as FIG. 5A of WO2014120770, the contents of which are herein incorporated by reference in its entirety) depicts a Coomassie-stained native-PAGE showing that different batches of htCBS exhibited different dimer/tetramer ratios, with varying degrees of higher aggregates. FIG. 5B (previously disclosed as FIG. 5B of WO2014120770, the contents of which are herein incorporated by reference in its entirety) is an in-gel activity assay demonstrated that these aggregates exhibit CBS activity. FIG. 5C (previously disclosed as FIG. 5C of WO2014120770, the contents of which are herein are incorporated by reference in its entirety) shows that aggregation causes non-consistent PEGylation products. PEGylation resulted in two distinct bands, presumably reflecting varying degrees of PEGylation as aggregation may act to obscure the available PEGylation sites. Accordingly, due to a more pronounced aggregation of batch 28 (FIG. 5A) its PEGylation resulted in a more pronounced lower band, i.e less PEGylated, on SDS-PAGE (FIG. 5C), whereas PEGylation of batch 112, comprised of both tetramers and dimers (FIG. 5A), resulted in a more pronounced upper band as compared to batch 28 (FIG. 5C). FIG. 5D shows a Coomassie-stained native gel, indicating that incubation of both enzyme batches with the reducing agent tris(2-carboxyethyl)phosphine (TCEP) converted much of the tetramers and higher aggregates to a dimeric form. These data imply that aggregation is driven by exposed cysteines on the surface of htCBS. Thus, TCEP treatment was believed to also result in a more extensive PEGylation, as more dimers are generated from higher MW forms, giving rise to exposure of additional PEGylation sites on the surface of htCBS. Indeed, as shown in FIG. 5E the ratio between the upper/lower PEGylation bands on a Coomassie-stained SDS-PAGE is significantly shifted towards the upper band following TCEP treatment as compared to PEGylation in the absence of TCEP. Accordingly, htCBS aggregation is believed to be driven, at least partially, by formation of intramolecular disulfide bridges. Thus, C15 was mutated to serine, generating the C15S htCBS mutant; C15 was previously shown to be the most reactive cysteine on the surface of CBS (Frank et al., 2006, Biochemistry 45:11021-11029). FIG. 5F (previously disclosed as FIG. 6A of WO2014120770, the contents of which are herein incorporated by reference by its entirety) depicts a Coomassie-stained native gel, in which two main bands (dimers and tetramers) are observed for htCBS whereas the C15S htCBS mutant exhibits a single band, which as expected is not affected by treatment with TCEP. This observation was further substantiated by HPLC size exclusion chromatography (HPLC-SEC). CBS preparations were separated on a Yana SEC-3000, 300*7.8 mm size exclusion column (Phenomenex, CA, USA). The column was calibrated and operated in 100 mM sodium phosphate pH=6.8, at a flow rate of 1 ml/min at room temperature. HPLC-SEC analysis, FIG. 5G (previously disclosed as part of FIG. 7A and FIG. 7B of WO2014120770, the contents of which are herein incorporated by reference in its entirety), shows the differences in htCBS C15S (FIG. 5G, left panel) and htCBS dimer/tetramer ratio (FIG. 5G, right panel). The single peak for the dimeric C15S htCBS mutant eluted at 8.62 min while the main peak for the htCBS eluted at 7.9 min, corresponding to a tetramer. FIG. 4H shows a Coomassie-stained SDS-PAGE gel showing reproducibility of htCBS C15S PEGylation between different batches and comparison to htCBS. The absence of aggregates in the C15S htCBS resulted in a more consistent PEGylation pattern between different batches with almost exclusively one PEGylated band that appears on SDS-PAGE. Direct comparison between PEGhtCBS and the PEGC15S both in vivo and in vitro showed no difference in performance.

Figure 6A:
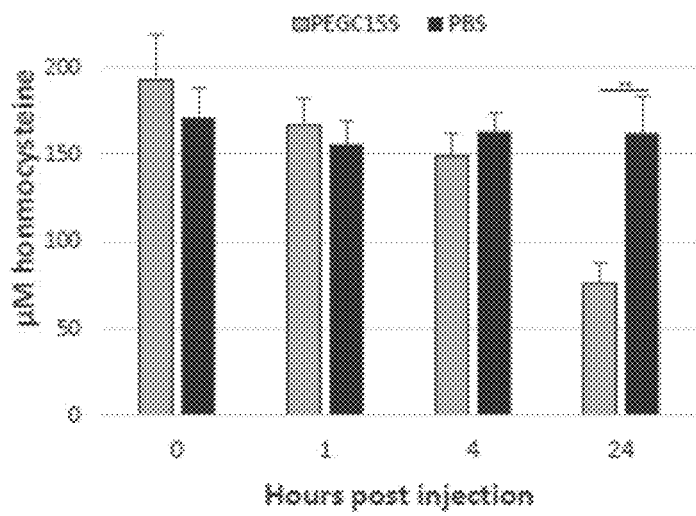
FIG. 6A-6C show the effect of PEGylated htCBS mutant (also referred to as PEGC15S) on homocysteine and its metabolites at 1, 4 and 24 hours post injection.
Figure 6B:
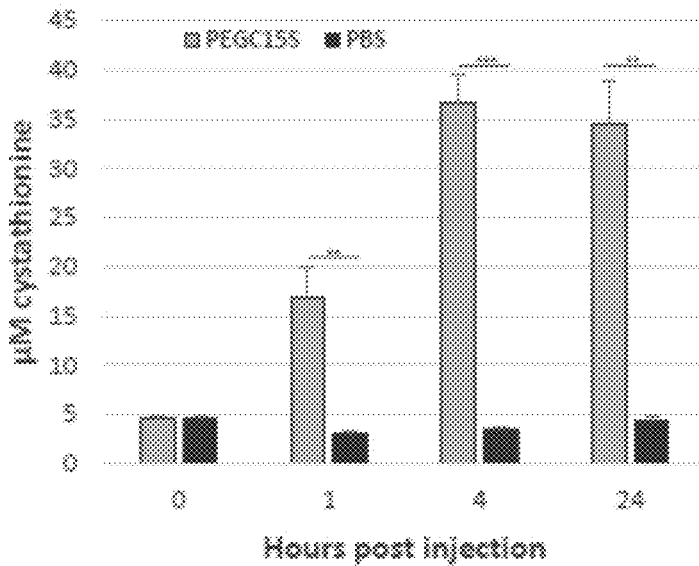
Figure 6C:
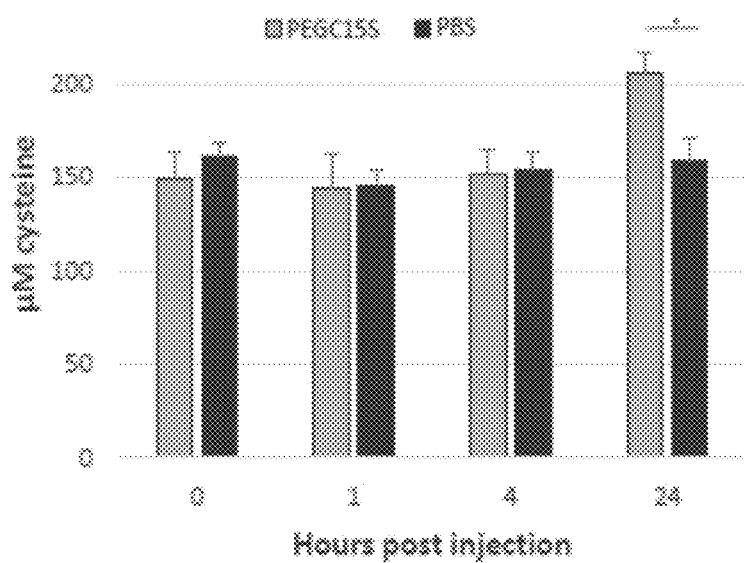

The effect of PEGC15S on metabolites was also tested at 1, 4 and 24 hours post injection (FIG. 6A-FIG. 6C). The levels of tHcy (FIG. 6A), cystathionine (FIG. 6B), and cysteine (FIG. 6C) in HO mice injected with 7.5 mg/kg of PEGC15S or PBS (n=5) 1, 4 and 24 hours post injection were measured. Data is presented as mean±SEM and each time point is compared between the two groups using unpaired Student's t test. *p=0.05, p≤0.01, and *p≤0.001. The effect on tHcy and cysteine was observed only 24 hours post injection (FIG. 6A and FIG. 6C), however a significant increase in cystathionine was already observed at 1 and 4 hours post injection (FIG. 6B).

Example 5. PEGC15S and Betaine Operate Synergistically In Vivo

To evaluate the effect of betaine and the combination therapy, betaine, PEGC15S, and a combination of betaine+PEGC15S treatments were conducted and metabolites of the transsulfuration pathway were compared.

Figure 7A:
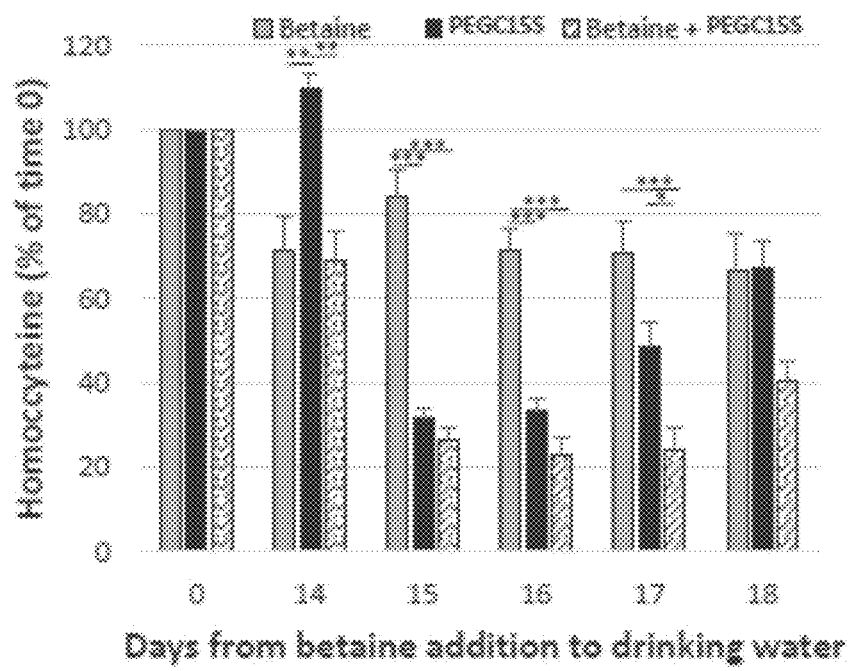
FIG. 7A-7B show that treatment with PEGylated htCBS mutant (also referred to as PEGC15S) and betaine synergistically reduce and maintain low homocysteine levels in HO mice and their effect on cystathionine levels.
Figure 7B:
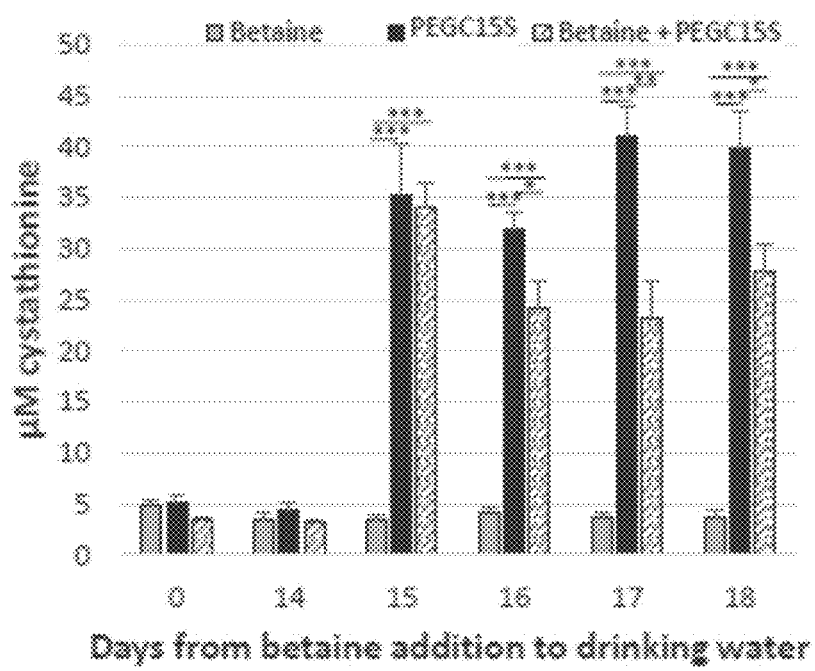

The betaine and betaine+PEGC15S groups were treated with 2% betaine in the drinking water throughout the 18 days of the experiment, and the latter group was injected with 7.5 mg/kg PEGC15S on days 14 and 15. The PEGC15S single treatment group was maintained on regular water and injected on days 14 and 15 as well. As shown in FIG. 7A, 14 days of betaine treatment resulted in a 29% and 32% decrease in tHcy for the betaine treated groups. The betaine single treatment group maintained these levels of tHcy to day 18. Injection of the PEGC15S on the background of betaine resulted in a more pronounced reduction of 74%, 77%, 76% and 40% on days 15, 16, 17 and 18, respectively. Treatment with PEGC15S alone resulted in a reduction of 69%, 67%, 52% and 33% on days 15, 16, 17 and 18, respectively. According to these data, injection of PEGC15S with or without betaine treatment is far superior to betaine treatment alone. In addition, the combination of betaine+PEGC15S was superior to treatment with PEGC15S alone. As shown in FIG. 7B, the difference between these two groups became statistically significant 48 hours post second injection (on day 17). Thus, the combination of PEGC15S with betaine allows for maintaining lower tHcy levels for an extended period of time.

Betaine treatment alone did not result in an increase of cystathionine throughout the 18 days of the experiment. In contrast, an increase was observed for the two groups that were treated with the PEGC15S (with or without betaine). Interestingly, the combination of PEGC15S with betaine, resulted in an increase which starting on day 16 and on, was significantly lower than in the group that received PEGC15S single therapy. This is due to the fact that treatment with PEGC15S alone channels homocysteine to condensation with serine to form cystathionine. Combination with betaine channels some of the available homocysteine through the re-methylation pathway to produce methionine, and thus less homocysteine may be available for PEGC15S to be converted to cystathionine.

Example 6. PEGC15S Rescues KO Mice From Early Death and Improves Liver Disease

A. Reduction of Early Death

Figure 8A:
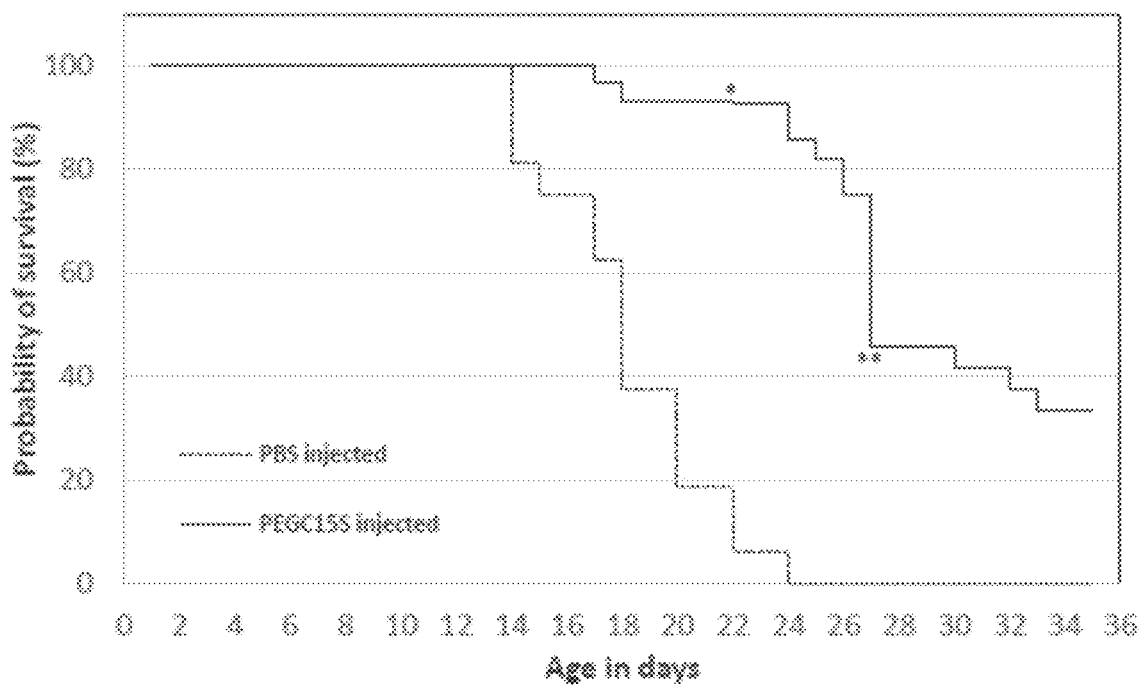
FIG. 8A-8B show that PEGylated htCBS mutant (also referred to as PEGC15S) administration rescues CBS complete knockout mice from early lethality and ameliorates liver pathology.

The majority of complete CBS-knockout mice (KOs) die within 2-3 weeks after birth. A Kaplan Meyer survival curve of KO mice injected twice weekly with PEGC15S versus mice that were injected with PBS was plotted. Mice were maintained on betaine water until day 21, and the ability of the injected enzyme to rescue KO pups was tested. KO pups were injected twice weekly with PEGC15S or with PBS. All mice were on betaine in drinking water up to day 21 (weaning day). As shown in FIG. 8A, on day 21, only 18% of the mice survived in the PBS-injected group as opposed to 93% of those that were injected with the enzyme. No PBS-injected animal survived to day 24, while 86% survival was recorded for the enzyme-injected group. From day 24 and on, the numbers of the enzyme-injected animals began to decline as well, with 45% survival on day 29 and 33% on day 35, although use of a different PEG molecule and dosing regimen was observed to greatly impact these results as shown in additional examples below (e.g., FIGS. 11A and 11C).

B. Liver Disease

It was previously demonstrated that KO mice suffer severe liver damage (Maclean et al., 2010a, *Mol. Genet. Metab* 101, 163-171; Watanabe et al., 1995, *Proc. Natl. Acad. Sci. U.S.A.* 92:1585-1589). Prolonged survival of KO mice, may be thus correlated with improvement in liver disease after CBS treatment. Accordingly, histological analysis of liver sections from animals that were injected with PEGC15S for 35 days were performed. Animals were sacrificed on day 36 and liver samples were processed for histological analysis by optical microscopy. PBS-injected animals did not survive to day 35, but liver samples were taken from two animals immediately after death, and were processed. The experiments were carried out in a blinded fashion. Livers were removed and were fixed for 24 hours with 4% paraformaldehyde in PBS (pH 7.4). Tissue blocks for histology were trimmed, dehydrated with an ethanol series followed by acetone, acetone-xylene mixture and xylene and then embedded in paraffin. In parallel, small tissue blocks (around 4 mm×2 mm) fixed with paraformaldehyde were rapidly frozen in petrol ether cooled with dry ice, and stored at −50° C. for detection of apolar lipids. Paraffin sections 4 μm thick were deparaffinized in xylene and after isopropyl alcohol step rehydrated with ethanol (96%, 70%, 60%). Tissue sections were stained with hematoxylin and eosin (H&E) to evaluate histopathological changes. Masson trichrome staining was performed for detection of fibrosis. Steatosis was verified using Oil Red O staining for detection of apolar lipids in fixed-frozen sections, 10 μm thick and cut with a Leica Cryomicrotome (CM 1850). The sections were viewed and photographed in a Nikon light microscope (E800) equipped with Olympus digital camera (DP70).

Figure 8B:
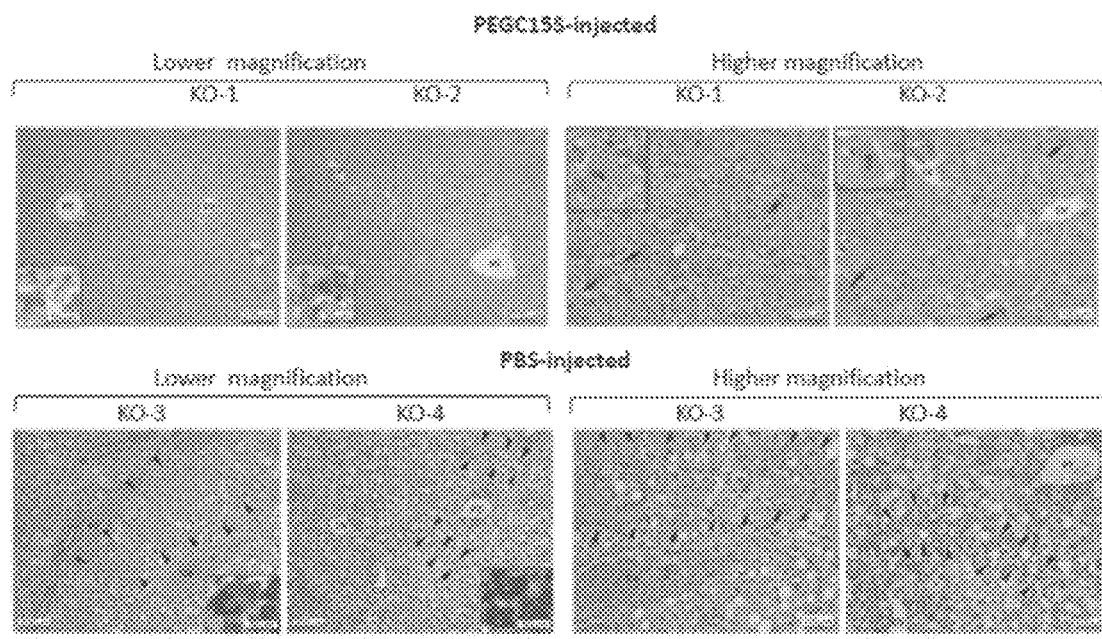

FIG. 8B shows the liver histology of two PEGC15S-injected KO mice sacrificed on day 35 versus livers from two PBS-injected KO animals that died on days 17 and 24 (hematoxylin and eosin stain). Low power views of the liver parenchyma (FIG. 8B, left columns) show moderate changes with slightly irregular liver cell plates and mild to moderate steatosis in PEGC15S-injected KO-1 and KO-2 contrasting with massive zonal necroses of hepatocytes (FIG. 8B, KO-3, marked by arrowheads) and diffuse steatosis with multiple dispersed necroses (FIG. 8B, KO-4, necroses marked by arrowheads) in PBS-injected KOs. A specific stain for apolar lipids in the cytoplasm of hepatocytes is shown in the inserts. Higher power views (right columns) demonstrate presence of frequent mitoses (marked by arrows and showed in a detail in inserts) and enlarged pleiomorphic nuclei with prominent nucleoli in PEGC15S-injected KOs. Higher power views of the liver parenchyma in PBS-injected KOs demonstrate confluent hepatocellular necroses with a sparse inflammatory infiltration (FIG. 8B, KO-3, marked by arrowheads) or multiple dispersed necroses accompanied with a prominent resorptive inflammatory reaction (FIG. 8B, KO-4, marked by arrowheads). The remaining liver parenchyma displays micro and macrovesicular steatosis in PBS-injected KOs. (PT=portal tract, CV=central vein).

PBS-injected animals developed severe hepatopathy characterized by pronounced microvesicular to macrovesicular steatosis and significant death of hepatocytes, with minimal or no fibrosis. Multiple mono or oligo cellular necroses of hepatocytes dispersed throughout the liver lobule accompanied by a prominent inflammatory resorptive reaction were found in one animal, whereas massive confluent necroses of hepatocytes mainly in periportal zones with a sparse inflammatory infiltrate dominated a feature in the other. Signs of liver parenchyma regeneration were minimal in both animals. The two PEGC15S-injected animals showed moderate changes in the liver with minor signs of parenchyma damage but with prominent regeneration, and were correctly recognized by the examiner as receiving therapy. Changes indicative of liver parenchyma regeneration (slightly irregular architecture of the liver lobule, basophilic cytoplasm of hepatocytes, frequent mitoses and binucleated hepatocytes, nuclear pleomorphy and enlargement with prominent nucleoli) were the most conspicuous feature. The overall morphology was consistent with increased proliferation, transcription and translation in hepatocytes. Besides, rare focal necroses of hepatocytes and mild steatosis of a microvesicular type were detected and fibrosis was minimal.

Example 7. Biochemical Characterization of 20NHS PEG-htCBS C15S

Biochemical characteristics of 20NHS PEG-htCBS C15S were determined prior to studies on the effects of in vivo administration of the molecule.

A. N-Terminal Sequencing and Intact Mass Analysis

Five batches of unmodified htCBS C15S were analyzed using N-terminal sequencing. The obtained sequences were identical for all the batches, and compared to the reference sequence, they all lacked the initial methionine residue. The N-terminus of htCBS C15S was observed to be PSETP, and not MPSETP as is found in the sequence of the wild-type CBS.

The intact mass determined by the deconvoluted mass spectra of htCBS C15S corroborated results from the N-terminal sequencing by identifying only one major peak at 45290 Da in the five batches. This value matches the molecular mass of the htCBS C15S monomer without the N-terminal methionine (theoretical molecular weight: 45289.7 Da).

Sequence alignment was further carried out by the software Geneious 9.1.5 (Free Version), using the Geneious alignment type "Global alignment with end gaps" and a Cost Matrix Blosum62 to compare the protein sequences of htCBS C15S in humans, rats, monkeys, and mice. Results confirmed that the N-terminus of 20NHS PEG-htCBS C15S is PSETP and not MPSETP as is found in the sequence of the wild-type truncated CBS in humans, monkeys, rats, and mice. htCBS C15S was observed to share a 96% sequence identity, including 1 gap (at the start codon), with truncated monkey CBS. The following differences between the sequences were observed in the htCBS C15S used herein and truncated monkey CBS based on UniProtKB/Swiss-Prot: Q58H57. Amino acid position (based on the alignment of the sequences) 18 R→L (htCBS C15S used herein→truncated monkey sequence), position 25 K→Q, position 32 S→L, position 34 E→G, position 69 A→V, position 71 A→E, position 90 V→I, position 133 D→A, position 157 A→T, position 242 Q→R, position 354 V→M, and position 403 T→V.

htCBS C15S was observed to share an 84% sequence identity, including 5 gaps (in the rat sequence), with truncated rat CBS. The following differences between the sequences was observed from the htCBS C15S used herein and truncated rat CBS based on UniProtKB/Swiss-Prot: P32232. Amino acid position (based on alignment of sequences) 4 E→G (htCBS C15S used herein→truncated rat sequence), position 6 P→S, position 8 A→C, position 10 V→D, position 12 P→S, position 13 T→A, position 15 S→C, positions 17-24 HRSGPHSA→QDLEVQPE, position 26 S→Q, position 32-34 SPE→ASG, position 38-42 AKEPL→R - - - V, position 45 R→S, position 48 A→T, positions 60-62 ASE→MAD, position 66 H→Y, position 69 A→V, position 71 A→T, position 82 K→R, position 86 D→N, position 94 K→R, position 96 G→S, position 98-99 KF→NA, position 133 D→A, position 161 R→K, position 175 S→M, position 235 T→D, position 238 D→E, position 248 L→V, positon 255 V→A, position 276 R→K, position 300 T→A, position 318 T→A, position 322 K→R, position 329-331 EEA→DDS, position 333 T→A, position 340 and 350 A→S, position 353-354 TV→AM, position 365 Q→K, position 383 T→S, position 389 R→K, position 397 L→M, position 401 D→-, position 403-404 TE→SV, and position 406 K→R.

htCBS C15S was observed to share an 84% sequence identity, including 5 gaps (in the mouse sequence), with truncated rat CBS. The following differences between the sequences was observed from the htCBS C15S used herein and truncated mouse CBS based on UniProtKB/Swiss-Prot: Q91W9. Amino acid position (based on alignment of sequences) 4 E→G (htCBS C15S used herein→truncated mouse sequence) position 6 P→S, position 8 A→C, position 10 V→D, positions 12-13 PT→SA, positions 15-21 SPHRSGP→GFQHLDM, position 24 A→E, position 26-27 GS→RQ, positions 32-34 SPE→PSG, positions 37-42 EAKEPL→DR - - - V, position 48 A→T, positions 59-62 PASE→AMAD, position 66 H→Y, positions 69-71 APA→VLT, position 82 K→R, position 86 D→N, position 96 G→S, position 98-99 KF→NA, position 133 D→A, position 161 R→K, position 175 S→M, position 235 T→D, position 238 D→E, position 255 V→A, position 276 R→K, position 300 T→A, position 318 T→A, positions 330-331 EA→DS, position 333 T→A, position 350 A→S, position 353-354 TV→AM, position 383 T→S, position 389 R→K, position 397 L→M, position 401 D→-, position 403-404 TE→SV, position 406 K→R, and position 411 H→R.

Results above show that rat and mouse sequences share many of the same differences compared to the htCBS C15S PEGylated with 20NHS PEG-htCBS C15S used in the examples herein. The truncated monkey sequence shared the greatest similarity with the sequence of 20NHS PEG-htCBS C15S.

B. NHS Ester PEGylation Mapping of PEGC15S

The PEGylation sites of three lots of 20NHS PEG-htCBS C15S were mapped: RC-6-67A (6.3 mg/ml), RC-6-67B (6.7 mg/ml), and RC-8-14 (3.8 mg/ml). The samples were de-PEGylated in alkali, reduced and alkylated, digested with Asp-N endopeptidase and analyzed by LC/UV/MS.

Reverse phase chromatography was performed for an injection amount of 33 μg in a mobile phase A of 0.1% TFA (ThermoFisher) in water and a mobile phase B of 0.1% TFA (ThermoFisher) in acetonitrile (Burdick and Jackson) with a XBridge BEH130 C18 3.5 μm, 4.6×150 mm column (Waters) at a column temperature of 60° C. Table 6 shows the gradient for high performance liquid chromatography (HPLC).

TABLE 6

| HPLC gradient | | |
|---|---|---|
| Time (min) | Solvent B % | Flow Rate (mL/min) |
| 0 | 3 | 0.5 |
| 6 | 3 | 0.5 |
| 51 | 25 | 0.5 |
| 87 | 34 | 0.5 |
| 98 | 45 | 0.5 |
| 99 | 98 | 0.5 |
| 104 | 98 | 0.5 |
| 105 | 3 | 0.5 |
| 120 | 3 | 0.5 |

The ESI-QTOF mass spectrometer (Agilent, model 6538) was set to high-resolution 4 GHz and positive ion mode having a MS Scan range of 330 to 3200 m/z prior to LC/UV/MS using Agilent calibration tuning mix. Voltages were set as follows: fragmentor −250 V, skimmer −65 V, and octopole RF voltage 750 V. The gas temperature was 350° C. All masses were calibrated to within ±1 ppm before testing could proceed. Dynamic mass axis calibration was also employed throughout all LC/MS/MS experiments by continuous infusion of a reference standard. Lock mass ions were employed: 922.009798.

A non-PEGylated htCBS C15S protein was processed in parallel as a control. The peptide map was observed to cover 97.8% of the amino acid sequence for each of the four samples, including all 30 lysine residues. Twelve peptides were identified as having been PEGylated based on the mass additions of 1-2 PEG linkers, and the extent of PEGylation was estimated to be in the range of 4.5 to 5.5 PEGs/CBS subunit for these three lots.

The samples were first de-PEGylated under conditions (pH 11.5, 37° C., 22 hours) optimized in PEGylation site-occupancy analysis of PEGylated htCBS C15S by LC/MS/MS. After de-PEGylation, the formerly PEGylated sites are left with a linker having the formula: $C_5H_6O_3$ (monoisotopic molecular weight of 114.0317 Da), which can be identified by peptide mapping. The de-PEGylated sample was reduced, alkylated, digested with Asp-N endopeptidase and analyzed by LC/UV/MS as described above.

The extent of PEGylation was estimated using the following calculation: # of PEGs per peptide=(Abundance (1*Linker)+2×Abundance(2*Linker))/(Abundance(no Linker)+Abundance(1*Linker)+Abundance(2*Linker)). Table 7 provides the LC/UV/MS results.

TABLE 7

| Extent of PEGylation in the three samples measured by estimated PEG/peptide | | | |
|---|---|---|---|
| | Estimated PEG/peptide | | |
| Peptide | RC-6-67A | RC-6-67B | RC-8-14 |
| 2-34 | 1.06 | 1.24 | 1.29 |
| 9-34 | 0.84 | 0.98 | 1.03 |
| 35-46 | 0.17 | 0.18 | 0.22 |
| 47-78 | 0.26 | 0.31 | 0.37 |
| 79-85 | 0.02 | 0.03 | 0.03 |
| 86-106 | 0.54 | 0.61 | 0.63 |
| 198-220 | 0.02 | 0.03 | 0.03 |
| 245-248 | 0.39 | 0.48 | 0.49 |
| 270-301 | 0.27 | 0.29 | 0.39 |
| 321-327 | 0.21 | 0.21 | 0.31 |
| 388-400 | 0.04 | 0.05 | 0.05 |
| 401-413 | 0.59 | 0.71 | 0.74 |

Lysines 25, 30, 211, 247, 271, and 405-406 were unequivocally identified as PEGylated to a certain extent in all three 20NHS PEG-htCBS C15S batches. Each of the groups of lysines 72 and 75; 82 and 83; 94, 97-98, and 102; 322 and 325; and 394 and 398 were within the same peptide, and the analysis herein was not able to determine which lysine was PEGylated to what extent.

Some peptide cleavages not specific to Asp-N endopeptidase (N-terminal of Asp and Glu) were also observed, for example 107 A-K 119 and 333 A-K 348, which may be attributable to basic hydrolysis of the protein during de-PEGylation. A significant percentage of deamidation was observed for some peptides, which may also be attributed to the alkaline conditions used for the dePEGylation reaction.

Example 8. Biochemical Characterization of Maleimide PEGylation

Figure 9A:
FIG. 9A-9B show the profiles of different PEGylated species for C15S PEGylated with a maleimide PEG molecule (ME-200MA0B or ME-400MA) or an NHS ester PEG molecule (ME-200GS).

SDS-PAGE and native PAGE gel were performed to compare the reproducibility of PEGylation patterns for htCBS conjugated to ME-400MA and ME-200GS. Results showed a variable ratio between discrete PEG-CBS species and showed incomplete PEGylation when the maleimide PEG molecules of ME-400MA were used. Variable extents of PEGylation for the NHS ester PEG ME-200GS generated a high molecular weight "smear" of inseparable PEGylated species on SDS-PAGE (FIG. 9A) and native PAGE gels (FIG. 9B).

Figure 9B:
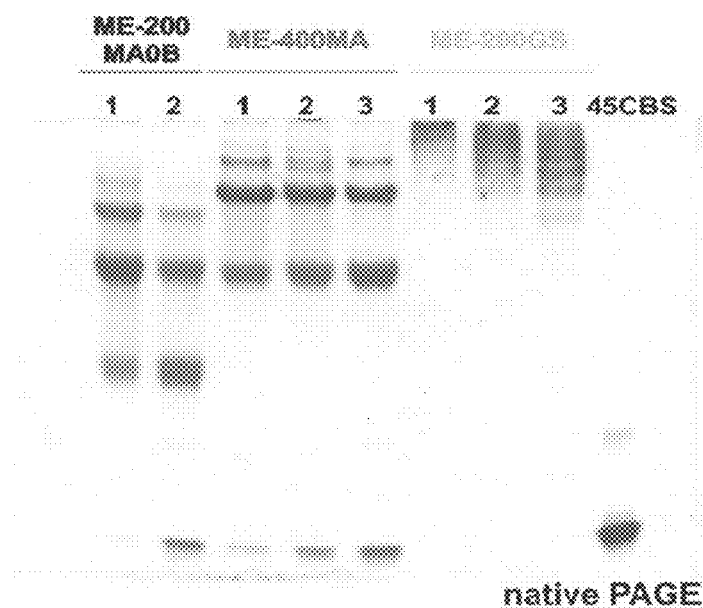

Unlike PEGylation of htCBS C15S with ME-200GS, PEGylation of htCBS C15S with ME-400MA was observed to yield three defined species when separated on a native PAGE (FIG. 9B). The heaviest species was observed to co-elute with the second species in htCBS C15S PEGylated with ME-200GS. The exact identity of the heaviest species was not determined because the relatively small amount of this species compared to others species and lack of separation precluded detailed pharmacodynamic (PD) characterization. The second species was identified to carry 1 PEG attached to each subunit in the native dimer, otherwise known as the homoPEGylated species. The lightest PEGylated species has been observed to carry only 1 PEG per dimer, otherwise known as the heteroPEGylated or hemiPEGylated species.

A. Maleimide PEGylation Mapping of PEGC15S

The first step of peptide mapping was accounting of each cysteine-containing peptide in two samples of htCBS C15S PEGylated with ME-400MA: RC-6-13 POOL1 and RC-6-13 POOL2. RC-6-13 POOL1 (BSL sample #1127) represents the homoPEGylated species (most likely PEGylated on the same residue). RC-6-13 POOL2 (BSL sample #1128) represents the hemiPEGylated species, therefore on SDS-PAGE there was observed to be about an equal proportion of the PEGylated and unmodified bands. This example determined the location of attachment of a ME-400MA, when the most accessible cysteine (C15) is replaced with serine.

A Lys-C digestion was performed on the reference protein (UnPEG RC-6-09 DIAFILTRATE) and simultaneously on the two PEGylated proteins (RC-6-13 POOL1/RC-6-13 POOL2). Eight cysteine-containing peptides were identified from a reduced/alkylated LC/MS peptide map. Seven cysteine-containing peptides yielded similar relative abundances in all three samples as shown in Table 8 below, indicating these 7 cysteine peptides are unlikely to have been PEGylated.

Only one cysteine-containing peptide was observed to have significantly decreased relative abundance in each of the two PEGylated samples. Table 8 provides the relative abundances of non-PEGylated peptides in each sample.

Peptide 272-322 was observed to contain two cysteine residues. PEGylated residues were observed at Cys272 and/or Cys275 residing on Lys-C peptide 272-322. To further differentiate whether Cys272 and/or Cys275 are PEGylated, the two residues were separated onto different peptides, the reference (UnPEG RC-6-09 DIAFILTRATE) and the two PEGylated proteins (RC-6-13 POOL1/RC-6-13 POOL2) were treated with reagent 2-Nitro-5-thio-cyanobenzoic acid (NTCB). Because NTCB cleaves N-terminally to free cysteine residues, PEGylated cysteine does not form the cyanylated end product and thus blocks the cleavage.

Seven cysteine-containing peptides were identified from the NTCB treated C8 LC-MS peptide map. As the chemical digestion efficiency was relatively low compared to enzyme digestion, the target peptide peaks were small in the chromatogram, and side reactions were also observed (results not shown). The cysteine-related peptide peaks were located and quantified using manual ion searching. Compared to the reference protein only one cysteine containing peptide showed a significant decrease in the RC-6-13 POOL1 sample. The peptide, identified as residues 244-271, signifies that site 272 was blocked, lowering the yield for the 244-271 peptide. Two cysteine-containing peptides showed a decrease in relative abundance for the RC-6-13-POOL2 sample; however, the ratio is close between these two. It is possible both cysteines are involved in the PEGylation or that the peak abundance is too low to draw a solid conclusion. Results in Table 9 provide evidence that the PEGylation resides are on Cys272, although Cys275 was not completely ruled out as the location of PEGylation.

TABLE 9

Comparison of PEGylation of Cys272 and Cys275

| | Reference protein | | 1127 RC-6-13 POOL1 | | | 1128 RC-6-13 POOL2 | | |
|---|---|---|---|---|---|---|---|---|
| Peptide (amino acid residues) | Delta mass ppm | Relative abundance | Delta mass ppm | Relative abundance | Ratio reference vs. sample | Delta mass ppm | Relative abundance | Ratio reference vs. sample |
| 52-102 | −1.25 | 0.006 | −1.92 | 0.0054 | 1.2 | 1.45 | 0.0054 | 1.2 |
| 103-108 | −0.57 | 0.002 | −1.86 | 0.0014 | 1.6 | −3.00 | 0.0024 | 1.0 |
| 244-271 | 1.28 | 0.003 | −0.90 | 0.0011 | 2.7 | 1.73 | 0.0021 | 1.4 |
| 275-345 | 0.76 | 0.001 | 0.64 | 0.0006 | 1.6 | 0.93 | 0.0007 | 1.4 |
| 370-413 | 0.67 | 0.045 | −1.28 | 0.037 | 1.2 | 0.31 | 0.040 | 1.1 |

TABLE 8

Relative abundance of non-PEGylated cys-containing Lys-C peptides

| Peptide | Reference protein relative abundance | 1127 relative abundance | 1128 relative abundance |
|---|---|---|---|
| 40-72 | 0.40 | 0.36 | 0.40 |
| 103-108 | 0.05 | 0.04 | 0.04 |
| 109-119 | 0.07 | 0.06 | 0.07 |
| 120-172 | 0.15 | 0.13 | 0.14 |
| 212-247 | 0.21 | 0.20 | 0.21 |
| 272-322 | 0.25 | 0.08 | 0.17 |
| 326-359 | 0.14 | 0.12 | 0.13 |
| 360-384 | 0.12 | 0.11 | 0.12 |

Example 9. Pharmacokinetics and Pharmacodynamics of 400MA PEG-htCBS C15S and 20NHS PEG-htCBS C15S in HO Mice This example characterizes and compares the pharmacokinetic (PK) and pharmacodynamic (PD) properties of htCBS C15S PEGylated with either 20 kDa linear NHS ester-activated PEG (ME-200GS) or 40 kDa linear maleimide-activated PEG (ME-400MA). Each of the PEGC15S were purified on DEAE sepharose and buffer exchanged using tangential flow filtration (TFF) on a BioMax® 100 cartridge in 1× sterile PBS.

htCBS C15S modified with ME-400MA (400MA PEG-htCBS C15S) was concentrated to 7 mg/ml. The homoP- EGylated htCBS C15S modified with ME-400MA (Peak 1) was concentrated to 4.3 mg/ml, and the hemi/heteroPEGylated htCBS C15S modified with ME-400MA (Peak 2) was concentrated to 5.1 mg/ml. htCBS C15S modified with ME-200GS (20NHS PEG-htCBS C15S) was concentrated to 6 mg/ml.

For 20NHS PEG-htCBS C15S, HO mice were administered SQ a dose of 5, 10 or 15 mg/kg dose or were administered IV a dose of 10 mg/kg. For 400MA-htCBS C15S, HO mice received a single dose of 10 mg/kg either SC or IV of one of the three forms: (i) a mixture of all species, where no separation of individual forms has been attempted (mix), (ii) a homoPEGylated specie (Peak 1), and (iii) a hetero/hemiPEGylated species (Peak 2).

Both male and female HO mice were used in this example, and each group contained 3 to 4 mice. Two groups of mice designated "A" and "B" were used for each route of administration to minimize the blood volume taken from any one mouse. For SC administration, blood was collected from group A at 0.5, 3, 24, and 72 hours post-injection and from group B at 1, 6, 48, and 96 hours post-injection. For IV administration, blood was collected from group A at 0.25, 1, 6, and 48 hours post-injection and from group B at 0.5, 3, 24, and 72 hours post-injection.

A. Pharmacokinetics

The PK parameters calculated from the time-activity curves are outlined in Table 10 for the ME-200GS conjugate and in Table 11 for ME-400MA conjugate. The semi-logarithmic plots were linear for the intravenous groups and thus confirmed that all forms of the htCBS C15S enzyme cleared from the plasma by first order kinetics (data not shown).

The bioavailability was calculated by dividing the area under the curve (AUC) for the SC or IP route by the AUC observed after IV administration. Table 10 provides the PK parameters after IV and SC administration of 20NHS PEG-htCBS C15S.

TABLE 10

| PK parameters for experiments conducted with 20NHS PEG-htCBS C15S | | | | | |
|---|---|---|---|---|---|
| PK Parameter | Units | SC | SC | SC | IV |
| Dose Amount | Mg/Kg | 5 | 10 | 15 | 10 |
| AUC(0-t) (obs area) | mU-hr/μL | 3062 ± 158 | 4788 ± 626 | 5754 ± 160 | 7431 ± 154 |
| AUC/dose | | 612 | 479 | 384 | |
| Bioavailability | % | 82.6% | 64.6% | 51.6% | NA |
| E Half-life | hr | 137 ± 95 | 17.5 ± 1.27 | 22.0 ± 1.7 | 47.6 ± 14.6 |
| A Half-life | hr | 5.3 ± 1.1 | 12.7 ± 0.6 | 11.9 ± 1.2 | NA |
| $c_{max}$ (obs) | mU/μL | 51.3 ± 3.7 | 89.9 ± 10.2 | 104.2 ± 11.3 | 371.6 ± 11.2 |
| $c_{max}$/dose | | 10.3 | 9.0 | 6.9 | |
| MRT (area) | hr | 194 ± 128 | 44.8 ± 1.7 | 49.0 ± 1.4 | 52 ± 13 |
| CL (obs area) | μL/hr | 1636 ± 86 | 2113 ± 280 | 2609 ± 72 | 1346 ± 27.3 |
| Time to steady state* | hr | | 343 | | |
| Peak at SS* | mU/μL | | 162 | | |
| Trough at SS* | mU/μL | | 85 | | |

The * indicates that the value was modeled for a 10 mg/kg dose with a 48 hour dosing interval and a 17.5 hour half-life.

For 20NHS PEG-htCBS C15S, the area under the curve was 3062, 4788 and 5754 for the 5, 10, and 15 mg/kg doses, respectively. The fraction of htCBS C15S enzyme that reached the systemic circulation after extravascular (SC) dosing was 82.6% in the 5 mg/kg 20NHS PEG-htCBS C15S SC dose-group but decreased to 64.6% and 51.6% in the 10 and 15 mg/kg dose groups. Thus, the increase was less than dose proportional which is reflected in the proportion of increase in AUC, $c_{max}$, and bioavailability. These results are likely explained by a slight decrease in the total absorption of 20NHS PEG-htCBS C15S with increasing dose.

The elimination half-life in the IV dose group was 48 hours meaning that half of the drug concentration in the plasma will clear every 48 hours. The data were completely linear when plotted as concentration with time on a log scale with correlation coefficients of >0.98 suggesting that this is a close estimate of the elimination half-life for 20NHS PEG-htCBS C15S. The half-life determinations in the SC dose groups were variable, and ranging from 17.5 to 137 hours. These estimates are confounded by a slow biphasic absorption/distribution phase. The average circulating time of a single enzyme molecule (MRT) was calculated to range between 44 and 194 hours for 20NHS PEG-htCBS C15S.

The time to reach steady state (constant peak and trough levels) was modeled from the 10 mg/kg SC data set assuming a dosing interval of 48 hours and a 17.5 hour half-life. The time to reach absolute steady state was estimated to be 343 hours (i.e. after about 7 SC injections every 2 days), but changes in the peak and trough plasma levels were very close to steady state levels by 144 hours. At steady state, the peak and trough levels were simulated to be 162 and 85 mU/μL after a 10 mg/kg dose administered SC once every two days. However, very similar levels were reached in 144 hours post-injection i.e. after 3 SC administrations of PEGylated enzyme every 2 days.

Figure 10A:
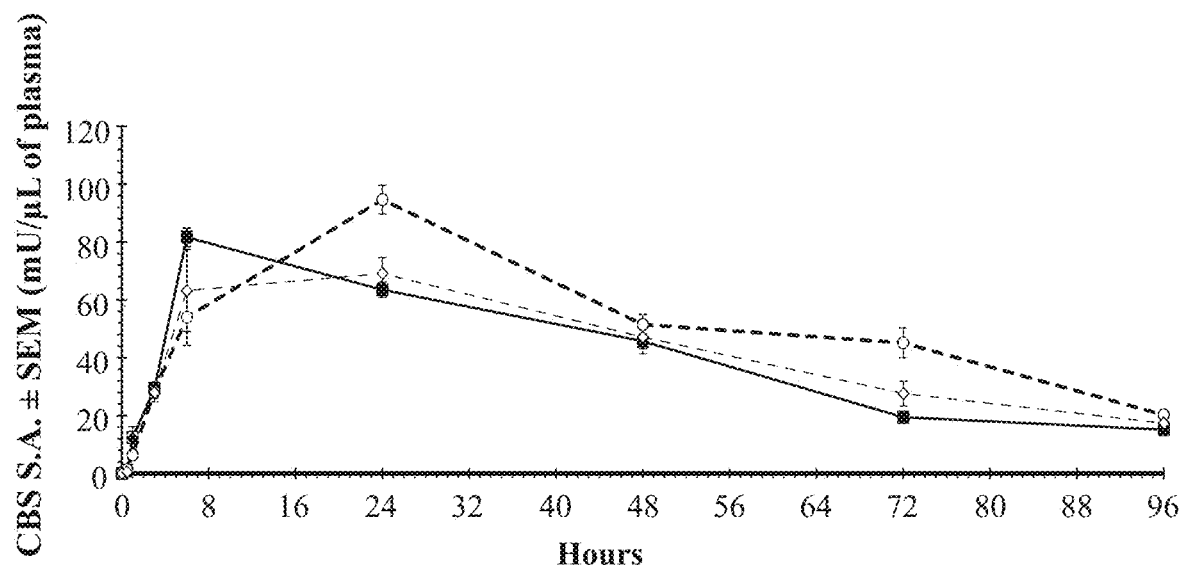
FIG. 10A-10E show the specific activity and plasma metabolite levels and CBS activity after a single subcutaneous (SC) injection of 20NHS PEG-htCBS C15S (htCBS C15S PEGylated with ME-200GS PEG) or 400MA PEG-htCBS C15S (htCBS C15S PEGylated with ME-400MA PEG) to HO mice.

The plasma levels of 400MA PEG-htCBS C15S for peak 1 representing the homoPEGylated species (2 PEG moieties per htCBSdimer), peak 2 representing the hemiPEGylated species (a single PEG moiety per htCBS C15S dimer) were compared in FIG. 10A. The mix is represented as a solid line with squares indicating the collection points. Peak 1 is represented by a dashed line with circles indicating the collection points, and peak 2 is represented by a dashed line with diamonds indicating collection points.

Table 11 provides the PK parameters calculated after SC and IV administration of 10 mg/kg of 400MA PEG-htCBS C15S.

TABLE 11

| PK parameters for experiments conducted with 400MA PEG-htCBS C15S | | | | | |
|---|---|---|---|---|---|
| Pharmacokinetic Parameter | Units | SC Mixed | SC Peak 1 | SC Peak 2 | IV Mixed |
| Dose Amount | Mg/Kg | 10 | 10 | 10 | 10 |
| AUC(0-t) (obs area) | mU-hr/μL | 3805 ± 656 | 5193 ± 519 | 4201 ± 436 | 6888 ± 268 |
| Bioavailability | % | 55.2% | NA | NA | NA |
| E Half-life | hr | 83.1 ± 47 | 22.0 ± 5.3 | 104.9 ± 122.3 | 39.0 ± 12.9 |
| A Half-life | hr | 9.4 ± 14.8 | 12.1 ± 1.26 | 6.3 ± 5.5 | NA |
| Tmax (or Cp0 for IV) | hr | 10.5 | 24 | 18 ± 10 | NA |
| $c_{max}$ (obs) | mU/μL | 75.8 ± 12.3 | 94.6 ± 8.6 | 75.8 ± 14.5 | 330.6 ± 40.0 |
| MRT (area) | hr | 99.3 ± 54.0 | 50.6 ± 2.57 | 135 ± 129 | 48.2 ± 11.4 |
| CL (obs area) | μL/hr | 2698 ± 534 | 1939 ± 205 | 2398 ± 259 | 1453 ± 57.6 |

The bioavailability calculated for the mixed 400MA PEG-htCBS C15S was observed to be 55.2%. $T_{max}$ is the time of $c_{max}$ (initial peak plasma level). The elimination half-life was calculated to be 39 hours from the IV dataset. The PK parameters were not dramatically different for the individual PEGylated species designated as Peak 1 (hemiPEGylated) and Peak 2 (homoPEGylated).

B. Comparison of ME-200GS and ME-400MA PEGylated Forms of htCBS C15S

Figure 10B:
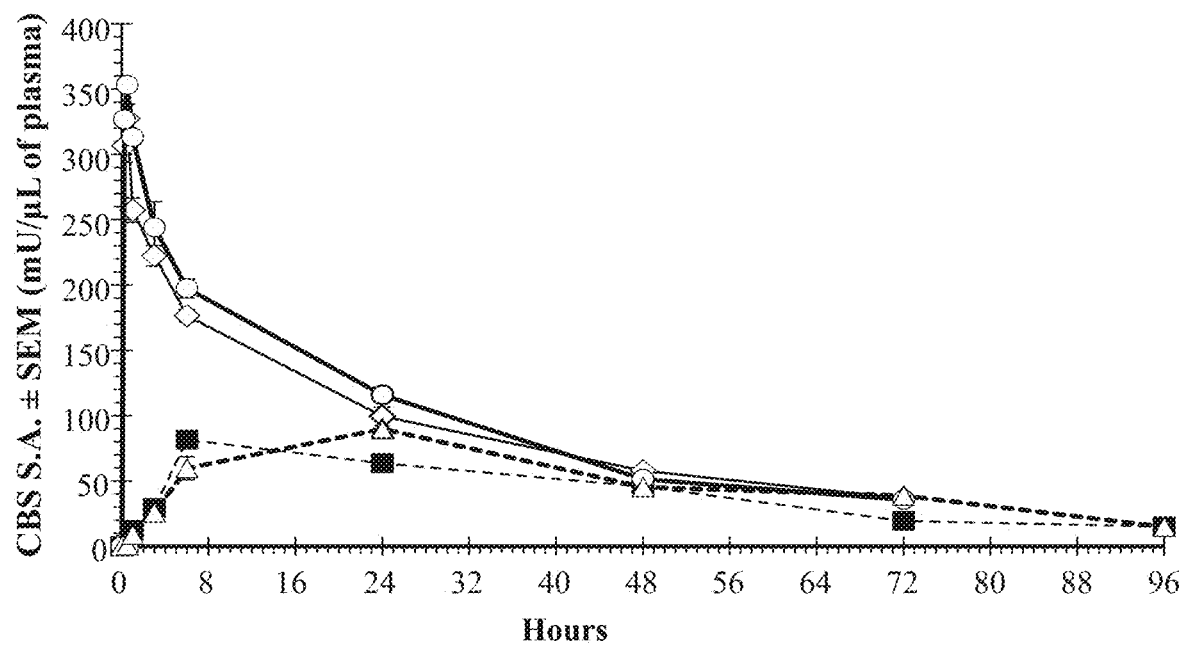

The PK parameters were not observed to be perceptibly different for the two PEGylated forms of htCBS C15S (ME-200GS and ME-400MA) compared herein. The specific activity versus time curves for the 10 mg/kg IV and SC doses of each enzyme were also observed to be similar as shown in FIG. 10B. The activities after IV dosing are shown as solid lines and after SC dosing are shown as dashed lines. The circles (IV) and triangles (SC) represent collection times for mice administered 20NHS PEG-htCBS C15S, and the diamonds (IV) and squares (SC) represent collection times for mice administered 400MA-htCBS C15S.

Figure 10C:
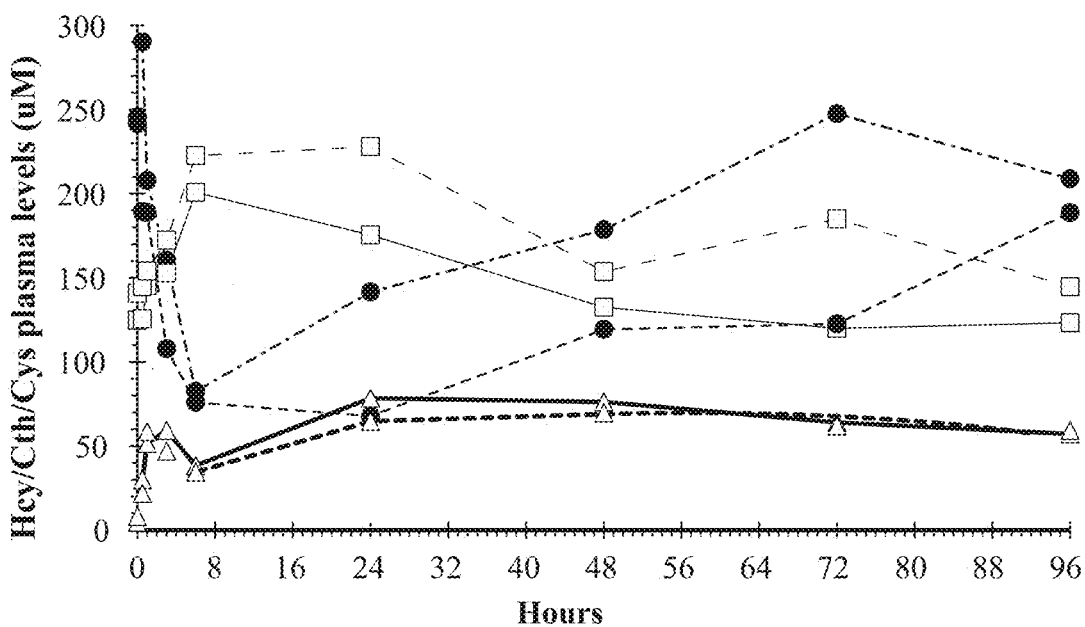

However, the metabolite profiles depicted in FIG. 10C show that 20NHS PEG-htCBS C15S was more efficacious in terms of normalizing plasma levels of homocysteine (circles) and cysteine (squares) after a single 10 mg/kg SC dose. The levels of cystathionine, represented by the triangles in the graph of FIG. 10C, were not significantly different between the two conjugates. Generally, the responses follow the plasma levels measured by the activity assay.

The response for 20NHS PEG-htCBS C15S was observed to occur more rapidly and was observed to be more prolonged compared to the response to 400MA PEG-htCBS C15S. Both PEGylated enzymes were observed to improve plasma levels of Hcy and Cys to roughly the same extent for 6 hours after SC administration, and plasma levels of Hcy were observed to remain decreased up to 72 hours after administration of 20NHS PEG-htCBS C15S compared to the gradual normalization from 24 hours and total return to pre-injection levels at 72 hours following administration of 400MA PEG-htCBS C15S. A similar pattern was reflected by plasma levels of Cys for both PEGylated enzymes.

Increased dosing was not observed to significantly improve the PD profile of either form of CBS suggesting that maximal efficacy of the enzyme is not governed solely by its plasma level concentrations, but is also influenced by factors such as enzyme kinetics, substrate availability, and concentration.

20NHS PEG-htCBS C15S was observed to provide the most favorable profile after SC administration compared to 400MA PEG-htCBS C15S. Specifically, the half-life in circulation was 47 hours for 20NHS PEG-htCBS C15S compared to 39 hours (i.e. 20% longer half-life) for 400MA PEG-htCBS C15S, and bioavailability after SC administration of equal amount (10 mg/kg) was 64.6% for 20NHS PEG-htCBS C15S compared to 55.2% for a mixture (i.e. 17% better bioavailability).

C. Comparison of Different Doses of 20NHS PEG-htCBS C15S

Figure 10D:
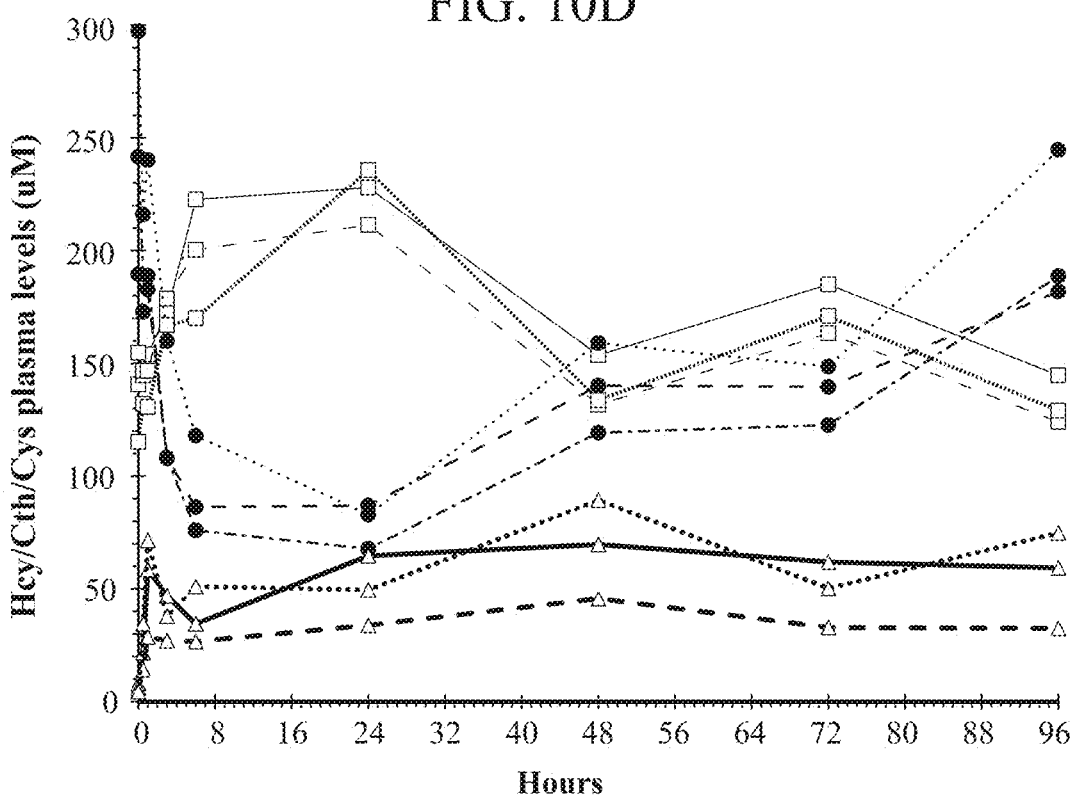

The PD response generally was observed to occur in direct proportionality to peak plasma levels and decreases proportionally with half-life. However, the dose-relationship in peak responses was observed to approach maximal levels at 5 mg/kg such that doses of 10 or 15 mg/kg resulted in little increase in the peak efficacy as determined by both homocysteine and cystathionine levels as shown in FIG. 10D. A wavy pattern of elimination was observed in each of the elimination phases that was the same in each curve, such that the plasma activity reached a trough at 48 hours and then recovered (or was similar) at 72 hours, only to drop off again at 96 hours. This unusual elimination pattern observed after SC dosing of htCBS C15S may be possibly due to the clearance of the biphasic absorption phase consisting of an early rapid and slower late absorption phase.

Figure 10E:
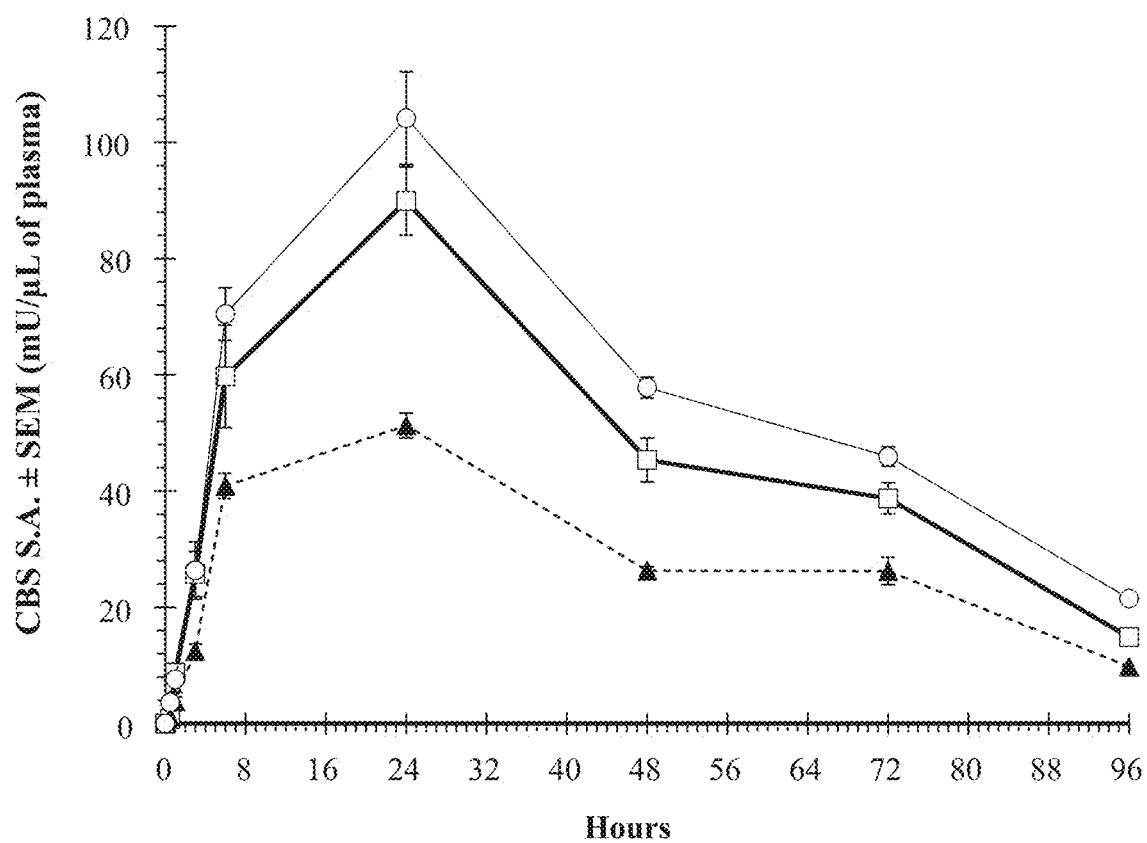

Increased dosing of 20NHS PEG-htCBS C15S was observed to show a roughly 2-fold higher CBS activity in plasma for dose of 10 mg/kg compared to 5 mg/kg, but it was not linear for the higher dose of 15 mg/kg, which is shown in FIG. 10E. There is discernable difference between the PD responses of the 10 and 15 mg/kg dose groups for each metabolite. In fact, many of the time points in the higher dose group were observed to produce a response that trended below that of the 5 mg/kg dose group. These differences were not accounted for by the lower bioavailability (decreased absorption per unit dose) observed with increasing doses of 20NHS PEG-htCBS C15S. In conclusion, a single dose between 5 and 10 mg/kg was observed to produce a maximal efficacy response in the HO mouse model.

Example 10. Pharmacodynamics of PEGC15S During Long-Term Administration in HO Mice This example assesses and compares the pharmacodynamic efficacy and potential immunogenic responses of long-term exogenously administered htCBS C15S PEGylated with either ME-200MA0B, ME-200GS, GL4-400MA, ME-400MA, or ME-050GS in HO mice. When human proteins are engineered into the mouse genome and expressed in neonatal animals, as is the case for the HO mouse, immune responses are more likely to have clinical relevance to the human response. See, Guidance for Industry, Immunogenic assessment of therapeutic protein products, CEBR (August 2014). The HO mice express small amounts of the human CBS protein and are likely to be more similar to human patients in terms of their adaptive immune response to PEG htCBS enzymes than complete knock-out or wild-type mice.

In one set of experiments, htCBS C15S PEGylated with either ME-200MA0B, ME-200GS, GL4-400MA, or ME-400MA was evaluated. Six groups of HO mice were used to conduct these studies: two groups received 200MA0B PEG-htCBS C15S (Groups 1 and 3), one group received 20NHS PEG-htCBS C15S (Group 4), one group received GL4-400MA PEG-htCBS C15S (Group 5), and two groups received 400MA PEG-htCBS C15S (Group 6 and 7). Both male and female HO mice were used (total n=6 to 8 mice per group) in these studies.

For Group 1, the mice received 2 bouts of 5 daily subcutaneous injections of 200MA0B PEG-htCBS C15S on days 1, 2, 3, 4, and 5 (week 1) and days 15, 16, 17, 18, and 19 (week 3). The dose for this experiment was 5 mg/kg/day. A saline control group (Group 2) was included in this experiment. All other groups received 3 bouts of 5 daily subcutaneous injections on days 1, 2, 3, 4, and 5 (week 1); days 15, 16, 17, 18, and 19 (week 3); and days 29, 30, 31, 32 and 33 (week 5). The dose for these experiments was 7.5 mg/kg/day.

In a separate set of experiments, htCBS C15S PEGylated with ME-200MA0B or ME050GS was evaluated. Two groups of male and female HO mice (1M/5F) received 3 bouts of 5 daily subcutaneous injections of either 200MA0B PEG-htCBS C15S (Group 8) or 050GS PEG-htCBS (Group 9) on days 1, 2, 3, 4, and 5 (week 1); days 15, 16, 17, 18, and 19 (week 3); and days 29, 30, 31, 32 and 33 (week 5). The dose was 7.5 mg/kg/day.

In all sets of experiments, each 5-day dosing cycle was followed by a 10-day "washout period". Blood was sampled using a submandibular lancet on Monday, Wednesday, and Friday of the dosing weeks (1, 3, and 5) and on the first day (Monday) of each 10-day washout period. All blood sampling procedures and subcutaneous injections were conducted at 3 P.M. to avoid artifacts due to diurnal variations. On days where both blood sampling and injection were conducted the blood sampling procedure was conducted prior to enzyme administration.

The pharmacodynamic response in HO mice to each PEGylated htCBS C15S conjugate was assessed for each bout of dosing by quantitating plasma levels of metabolites homocysteine, cystathionine, and cysteine, which are associated with the transsulfuration pathway, at baseline and after treatment. Quantification was performed by stable-isotope-dilution liquid chromatography mass spectrometry (LC/MS) as described in Example 1. The maximal percent change of homocysteine, cystathionine, and cysteine was calculated compared to baseline values for each dose week.

ME-200MA0B: Three independent studies were conducted with 200MA0B PEG-htCBS C15S (Groups 1, 3 and 8). In Group 1, plasma levels of Hcy were observed to drop by 68% compared to baseline levels during the first week of dosing, but were observed to drop by only 24% compared to baseline levels during the second series of 200MA0B PEG-htCBS C15S injections during week 3 with a 10-day washout period in between (Table 12). A similar decline in efficacy was suggested by attenuated elevation of both Cth and Cys levels during the second round of injections (Table 13 and Table 14). A second study (Group 3) was conducted to determine if attenuated efficacy was observed with a different set of naïve HO mice. The total Hcy levels in Group 3 were observed to decline to 82% below baseline during the first cycle of injections. During the second and third cycle of injections during week 3 and week 5, the Hcy levels were observed to decline to only 57% and 50% of baseline values, respectively. Similarly, the additional lot of 200MA0B PEG-htCBS C15S administered to Group 8 was observed to decrease plasma levels of Hcy by 80% compared to baseline levels in the first week of dosing, but only by 61% of the baseline values during week 3 of dosing. During week 5 of dosing, the plasma levels of Hcy were observed to drop to 50% of baseline values (Table 12). A similar decline in efficacy was suggested by attenuated elevations of Cys levels during week 3 and week 5 injections (Table 13 and Table 14), compared to week 1. A similar trend of attenuated efficacy was observed in Group 1, 3, and 8, although the magnitude of the attenuated response was observed to be more dramatic in Group 1 compared to Group 3 and 8.

ME-200GS: Administration of 20NHS PEG-htCBS C15S in experiment Group 4 was observed to decrease plasma levels of Hcy by 77% compared to baseline levels in the first week of dosing, 70% during the third week of dosing, and 66% during the fifth week of dosing (Table 12). A similar decline in efficacy was shown by attenuated elevations of Cth and Cys levels during the third and fifth week of dosing (Table 13 and Table 14) compared to week 1. However, for 20NHS PEG-htCBS C15S, the decline in efficacy observed in week 3 and week 5 of dosing was the least compared to the other PEG htCBS C15S conjugates and was statistically insignificant.

GL4-400MA: Administration of GL4-400MA-htCBS C15S in Group 5 resulted in an average of a 75% decrease in plasma levels of Hcy compared to baseline levels in the first week of dosing, but only 41% during the third week of dosing and 34% during week 5 of dosing (Table 12). A similar decline in efficacy was shown by attenuated elevation of Cth and Cys levels during week 3 and week 5 of dosing (Table 13 and Table 14) compared to week 1.

ME-400MA: Two independent experiments were conducted with 400MA PEG-htCBS C15S (Group 6 and 7). In Group 6, the percent decrease of Hcy levels was observed to be 73% compared to baseline levels in week 1, and subsequently declined to 65% and 59% during week 3 and week 5 of dosing respectively. The magnitude of the decline in efficacy was more dramatic in Group 7 as shown by the attenuated decreases of Hcy levels during the three bouts of dosing (Table 12). Similar trends of attenuated efficacy were observed in the changes of the Cth and Cys levels for Group 6 and Group 7 (Table 13 and Table 14).

ME-050GS: Administration of 050GS PEG-htCBS C15S in Group 9 was observed to decrease plasma levels of Hcy by 75% compared to baseline levels in week 1 of dosing, but only decreased by 59% of baseline levels during week 3 of dosing. During week 5 of dosing, the plasma levels of Hcy was observed to decrease to 42% of baseline levels (Table 12). A similar decline in efficacy was shown by attenuated elevations of Cth and Cys levels during week 3 and 5 of dosing (Table 13 and Table 14) compared to week 1.

Table 12, Table 13, and Table 14 present the percent changes in plasma homocysteine, cystathionine, and cysteine metabolite levels after each bout of the subcutaneous injections of different forms of PEGylated htCBS C15S. In these tables, baseline values are presented as mean±Standard Error of the Mean (SEM) in µM, and changes are presented as the mean maximal percent change from baseline for each 5-day dosing cycle (weeks 1, 3 and 5). n.d. stands for "not determined". Table 12 provides the percent change in total homocysteine after long-term treatment with PEGC15S.

TABLE 12

Change in total Hcy levels after PEGC15S treatment in HO mice

| Group | PEG Moiety | Baseline (µM) Day 0 | Percent Decrease at Trough | | |
|---|---|---|---|---|---|
| | | | Week 1 | Week 3 | Week 5 |
| 1 | ME-200MA0B | 155.3 ± 15.7 | 68% | 24% | n.d. |
| 2 | Saline | 176.1 ± 20.9 | −8% | −8% | n.d. |
| 3 | ME-200MA0B | 239.9 ± 26.2 | 82% | 57% | 50% |
| 4 | ME-200GS | 164.4 ± 15.9 | 77% | 70% | 66% |
| 5 | GL4-400MA | 169.7 ± 14.4 | 75% | 41% | 34% |
| 6 | ME-400MA | 134.0 ± 22.2 | 73% | 65% | 59% |
| 7 | ME-400MA | 239.1 ± 11.4 | 75% | 52% | 42% |
| 8 | ME-200MA0B | 224.0 ± 14.0 | 80% | 61% | 50% |
| 9 | ME-050GS | 192.1 ± 17.1 | 75% | 59% | 42% |

Table 13 provides the percent change in cystathionine after long-term treatment with PEGC15S.

TABLE 13

Change in cystathionine levels after PEGC15S treatment in HO mice

| | | Baseline | Percent Increase at Peak | | |
|---|---|---|---|---|---|
| | | Study (μM) | | | |
| Group | PEG Moiety | Day 0 | Week 1 | Week 3 | Week 5 |
| 1 | ME-200MA0B | 4.1 ± 0.2 | 796% | 508% | n.d. |
| 2 | Saline | 4.5 ± 0.4 | −1% | −19% | n.d. |
| 3 | ME-200MA0B | 4.8 ± 0.4 | 700% | 866% | 335% |
| 4 | ME-200GS | 5.0 ± 0.6 | 676% | 492% | 432% |
| 5 | GL4-400MA | 3.2 ± 0.3 | 715% | 723% | 449% |
| 6 | ME-400MA | 5.0 ± 0.5 | 383% | 329% | 365% |
| 7 | ME-400MA | 4.1 ± 0.4 | 696% | 649% | 443% |
| 8 | ME-200MA0B | 3.6 ± 0.4 | 1023% | 764% | 1100% |
| 9 | ME-050GS | 4.0 ± 0.5 | 978% | 795% | 833% |

Table 14 provides the percent change in cysteine after long-term treatment with PEGC15S.

TABLE 14

Change in cysteine levels after PEGC15S treatment in HO mice

| | | Baseline | Percent increase at Peak | | |
|---|---|---|---|---|---|
| | | Study (μM) | | | |
| Group | PEG Moiety | Day 0 | Week 1 | Week 3 | Week 5 |
| 1 | ME-200MA0B | 170.7 ± 8.5 | 36% | 16% | n.d. |
| 2 | Saline | 166.2 ± 8.7 | −18% | 5% | n.d. |
| 3 | ME-200MA0B | 149.5 ± 7.0 | 72% | 38% | 32% |
| 4 | ME-200GS | 147.3 ± 10.0 | 59% | 61% | 51% |
| 5 | GL4-400MA | 114.5 ± 8.6 | 98% | 48% | 52% |
| 6 | ME-400MA | 184.3 ± 16.1 | 17% | 6% | 8% |
| 7 | ME-400MA | 122.8 ± 4.5 | 72% | 44% | 44% |
| 8 | ME-200MA0B | 123.8 ± 7 | 77% | 77% | 58% |
| 9 | ME-050GS | 128.5 ± 11.9 | 71% | 75% | 36% |

The results of these studies show a decrease in plasma Hcy levels in concert with an increase in plasma Cth and Cys in all groups, suggesting a normalization of metabolites in response to the PEG-C15S treatment. In all Groups, the maximal efficacy was observed during the first week of dosing. Hcy levels were observed to decrease significantly (about 68% to about 82%) below baseline for all experimental groups, as shown in Table 12. The peak percent increase in the Cth and Cys levels was also maximal during week 1, as shown in Table 13 and Table 14. The magnitude of the pharmacodynamic response declined during subsequent cycles of PEG-C15S injection during week 3 and further on week 5. Overall, the highest and most enduring pharmacodynamic response was observed for 20NHS PEG-htCBS C15S.

Attenuated efficacy was observed during the second bout of PEGylated htCBS C15S dosing administered during dosing week 3 for all studied conjugates with the exception of 20NHS PEG-htCBS C15S. A further decline in efficacy was observed during the third cycle of dosing conducted during week 5 compared to week 3. Although antibody formation was not measured directly in these studies, this slow decline in efficacy following repeated administration is a classic indication of adaptive immunity. Thus, the likely explanation for the attenuation was an immune response directed at the htCBS C15S PEGylated with ME-200MA0B, MA-400ME, GL4-400MA, or ME-050GS.

Of the conjugates tested, 20NHS PEG-htCBS C15S was observed to have the most robust and long-lived efficacy. The ME-200GS is hypothesized to be able to more efficiently mask immunogenic epitopes on the htCBS C15S compared to the other PEGs. Therefore, 20NHS PEG-htCBS C15S form was observed to be the most potent and least immunogenic form of the various PEGylated htCBS C15S conjugates tested.

Example 11. htCBS C15S PEGylated with ME-200MA0B, ME-400MA, or ME-200GS Rescues KO Mice from Early Death A survival study was performed in the KO mouse model described herein to compare the efficacy of various PEGylated htCBS C15S conjugates.
A. Survival of KO Pups Up to Day 21/35

A Kaplan Meyer survival curve was plotted of KO mice injected three times weekly with 7.5 mg/kg htCBS C15S PEGylated with ME-200MA0B (n=24), ME-400MA (n=31=13F+18M), or ME-200GS (n=28=14F+14M), and a group of KO mice (n=44) that was injected with PBS as a control. Lactating mothers were maintained on betaine water, and after weaning, the pups (day 21) were put on regular water with no betaine. The ability of the injected enzyme to rescue KO pups was tested.

Figure 11A:
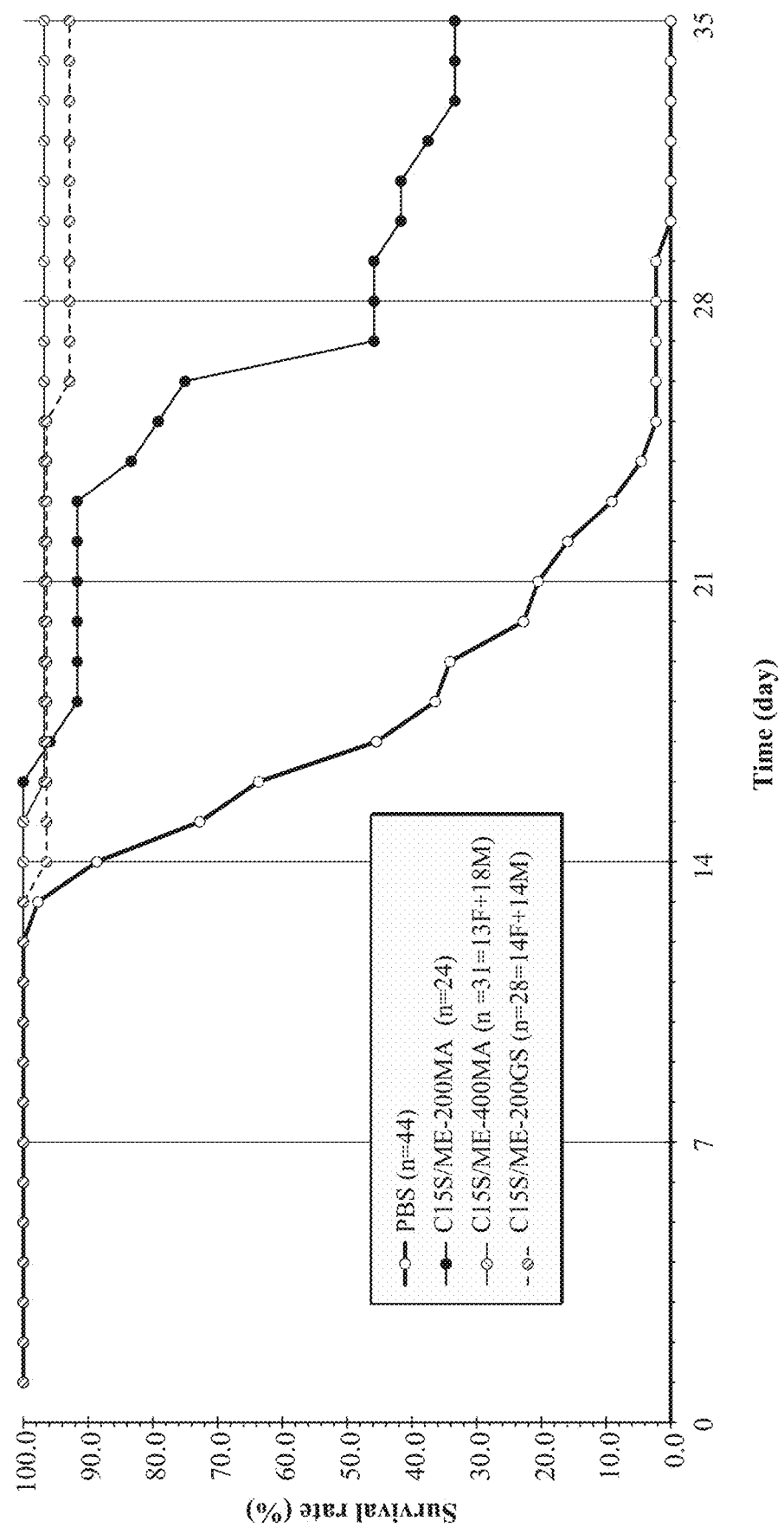

As shown in FIG. 11A, on day 21, only about 20% of the mice survived in the PBS-injected group as opposed to about 92% of those that were injected with 200MA0B PEG-htCBS C15S (C15S/ME-200MA) and about 97% of those that were injected with 400MA PEG-htCBS C15 (C15S/400MA) or 20NHS PEG-htCBS C15S (C15S/200GS).
B. Metabolite Levels After a Weekend Washout (trough) and 24 Hours After the Last Injection (Peak)

Metabolite levels in surviving KO mice at age of about 4-5 weeks were measured after a weekend washout (trough) and 24 hours after the last injection (peak) using the experimental procedure in Example 1.

The levels measured were compared to levels in similarly treated healthy KO +/−littermates as shown in FIG. 11B. The plasma levels of Hcy in 400MA PEG-htCBS C15S-treated KO mice ranged 256±8 μM 72 hours post-dose (ME-400MA) (bar on far left for each metabolite) to 145±6 μM 24 hours post-dose (ME-400MA 24 h) (bar second from left for each metabolite). The plasma levels of Hcy in 20NHS PEG-htCBS C15S-treated KO mice ranged 179±10 μM at 72 hours post-dose (ME-200GS) (bar third from left) to 96±8 μM 24 hours post-dose (ME-200GS 24 h) (bar fourth from left). Thus, the maximal response for both htCBS C15S conjugates was observed 24 hours post-dose and was observed to decline 72 hours post-dose. Treatment with either conjugate was observed to significantly (p<0.001) decrease the plasma levels of the toxic Hcy by about half. In contrast, plasma levels of homocysteine in the treated healthy heterozygous littermates were observed to be about 5 μM at both timepoints.

Levels of Cth were observed within the range of 57 and 77 μM in KO mice treated with PEGylated htCBS C15S conjugates. These plasma levels were roughly 12-fold higher than those observed in the untreated heterozygous mice. The difference between peak and trough plasma levels of Cth was observed to be small, which is evidence that the pharmacodynamic effect of the enzyme on cystathionine levels may persist beyond 72 hours and/or Cth may be more slowly cleared from the plasma compared with the other metabolites where larger differences were observed. Plasma levels of Cys 72 hours post-dose in both 400MA PEG-htCBS C15S-treated and 20NHS PEG-htCBS C15S-treated KO mice were observed to be significantly (p<0.001) decreased to 83±4 and 106±6 μM compared to healthy heterozygous littermates (151±6), respectively. Plasma levels of Cys were observed to be increased in treated KO mice 24 hours post-dose for both conjugates indicating a partial normalization of circulating sulfur metabolites. Plasma levels of Cys were observed to increase to 157±6 24 hours post-400MA PEG-htCBS C15S administration and to 176±6 µM 24 hours post-20NHS PEG-htCBS C15S administration. Methionine plasma levels were slightly elevated in KO mice compared to healthy heterozygous controls and did not change significantly between trough and peak levels.

C. Life Span After an Initial or Continuous Treatment

After an initial 35 days (5 weeks) long treatment to prevent neonatal lethality of KO mice, the KO mice treated with 20NHS PEG-htCBS C15S were divided into two groups. One group (5 W) stopped receiving any treatment apart from the initial one, while the other group (CONT) continued with the same regimen for up to 120 days of age (7.5 mg/kg, SC, 3× a week).

Figure 11C:
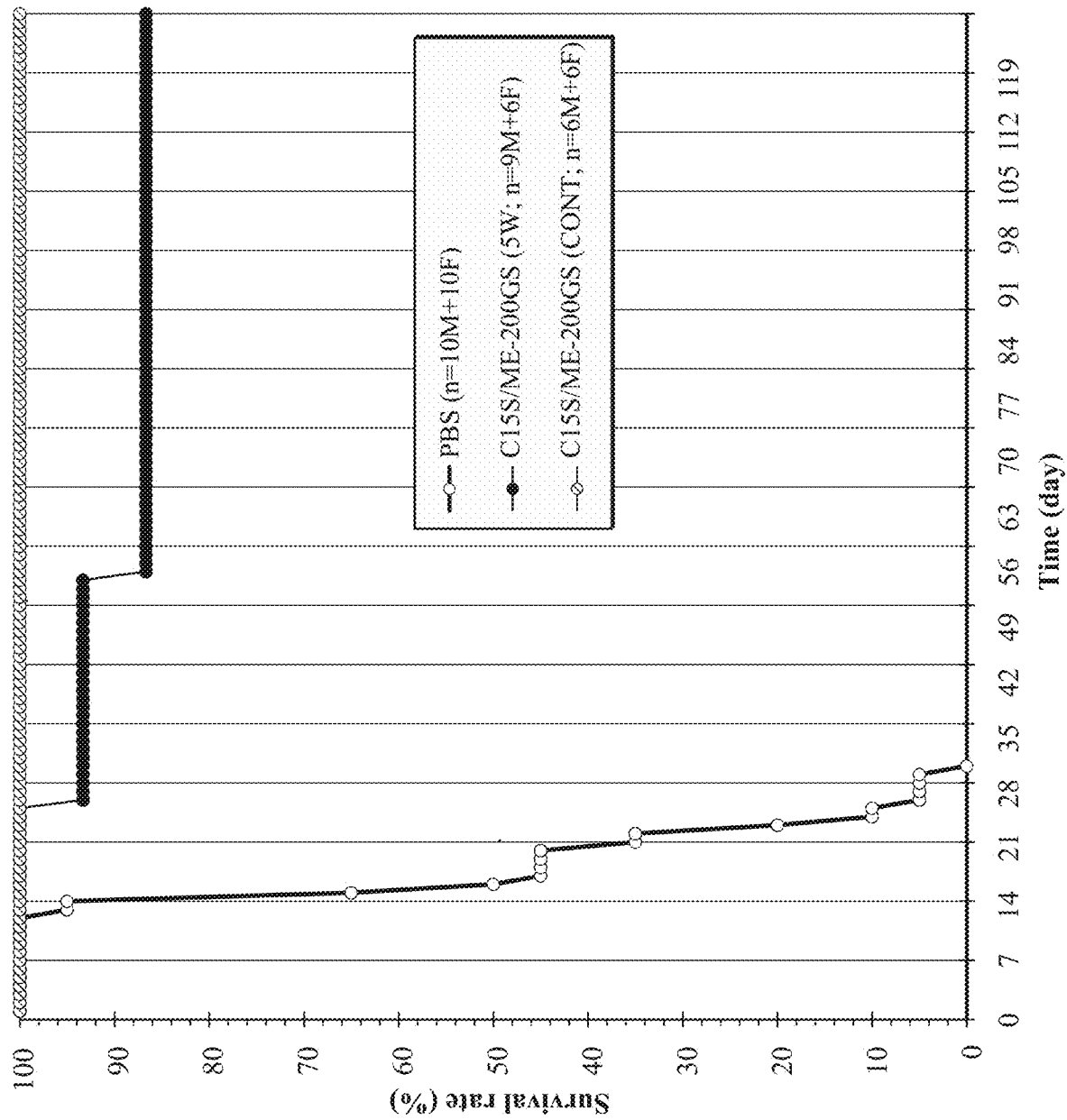

The survival of these groups of KO pups for up to 4 months was observed and plotted in FIG. 11C. All KO mice that were continuously administered 20NHS PEG-htCBS C15S (C15S/ME-200GS) survived at least 119 days as shown in FIG. 11C. Termination of the treatment after initial 35 days resulted in about 85% survival at 119 days of age.

D. Total Weight and Weight Gain of CBS-Treated KO Mice vs. +/- Healthy Mice

The total weight and amount of weight gain of the KO mice (male n=16 and female n=11) administered 20NHS PEG-htCBS C15S three times weekly at a dose of 7.5 mg/kg was determined and compared with similarly treated +/- healthy littermates (males n=14 and females n=13). The total weight and weight gain were measured in mice after weaning from day 21 to day 36.

Heterozygous male mice were observed to have the greatest total weight from days 23-35 ranging from about 10.5 g to about 18 g, although the 20NHS PEG-htCBS C15S-treated KO male mice had the highest total weight at day 21 (about 10 g). The 20NHS PEG-htCBS C15S-treated KO female mice had the lowest total weight after day 23 ranging from about 10 g to about 14 g.

Healthy male mice (n=14) also had the greatest amount of weight gain starting at day 23 ranging from about 2 g to about 9.5 g. The amount of weight gain in the 20NHS PEG-htCBS C15S-treated KO male mice (n=16) and 20NHS PEG-htCBS C15S-treated KO female mice (n=11) was significantly lower than the amount of weight gain for both control groups.

Example 12. PEGylated htCBS C15S Delays, Prevents, and Reverses Facial Alopecia in I278T Mice Model I278T -/- homozygous mouse model of homocystinuria was observed to exhibit specific phenotypic traits such as facial alopecia in addition to a typical metabolite's profile, unlike other homocystinuric mouse models. Facial alopecia is defined as a loss of hair from the face and head. The onset of facial alopecia is around 90 days (W12), typically fully developed around 120 days of age (W17).

Facial alopecia is hypothesized to be related to homocystinuria and the related metabolic profile; therefore, administration of enzyme replacement therapy (ERT; PEG-CBS) should rescue this phenotype by slowing the progress, preventing/delaying the onset, and/or reversing the damage already caused.

A. Delay the Onset of Facial Alopecia

3 W old mice not showing any signs of facial alopecia were split into 2 groups. The first group (n=3 males) was injected with 7.5 mg/kg three times per week with 200MA0B PEG-htCBS C15S for a period of 6 weeks. Physical look was recorded before the experiment and monitored weekly, then bi-weekly after the 6 W injection regimen. Metabolite levels were checked before the experiment and 24 hours after the last injection, i.e. after the 6 W injection regimen.

Figure 12A:
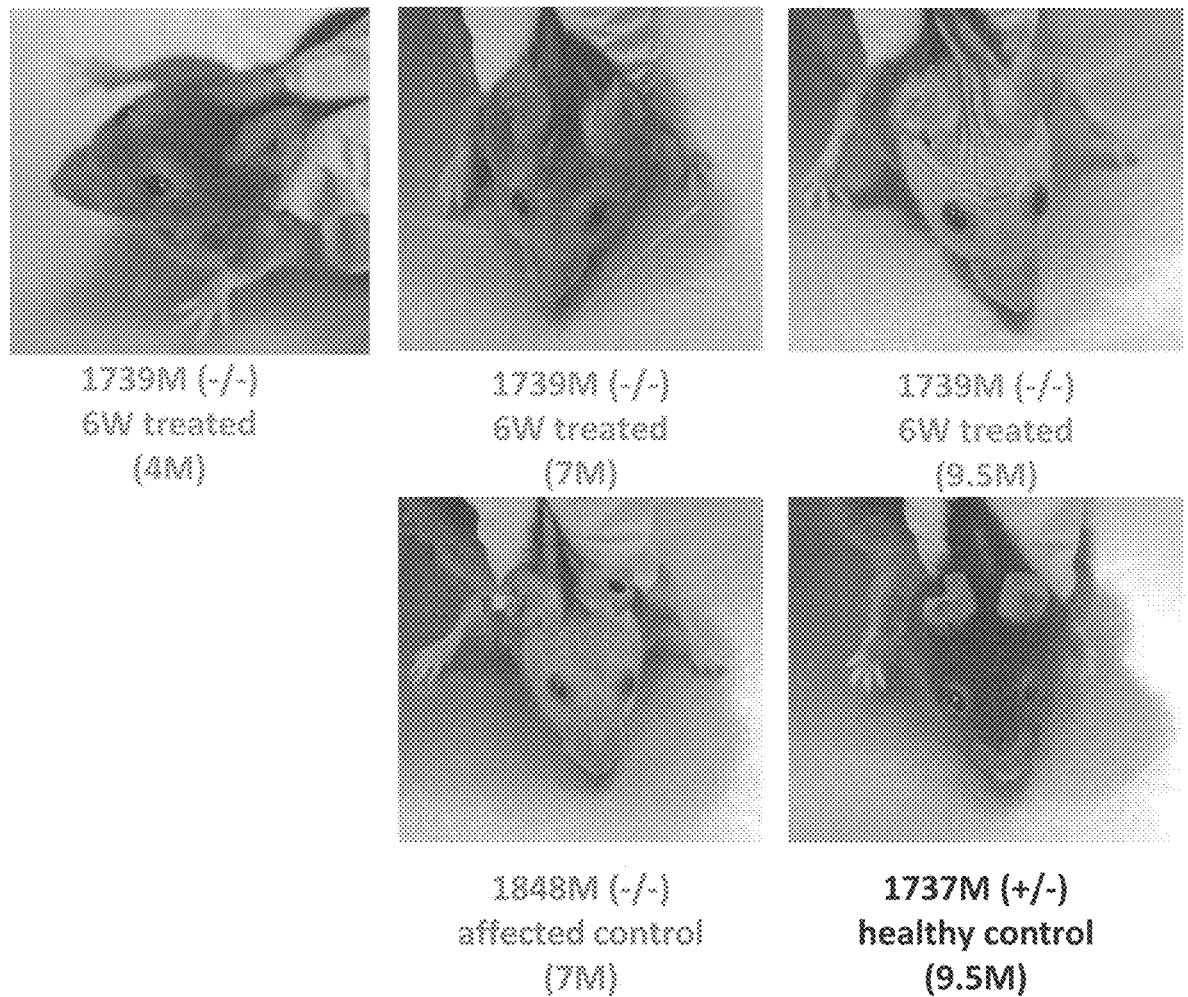
FIG. 12A-12E shows complete prevention and delay of onset of facial alopecia in groups of I278T −/− homozygous mice that were continuously administered C15S PEGylated with either ME-200MA0B, ME-400MA or ME-200GS.

Administration of 200MA0B PEG-htCBS C15S for a period of 6 weeks from age 3 W was observed to delay the onset of facial alopecia in FIG. 12A. I278T affected (-/-) or healthy (+/-) mice were observed to be indistinguishable at that age, and the -/- mice had no signs of facial hair loss. Untreated I278T +/- healthy heterozygous mice were not observed to suffer from a loss of facial hairs at 19 W and only mild hair loss at 34 W, unlike untreated I278T -/- affected homozygous mice, which were observed to have fully developed facial alopecia by 38 W. Typically, facial alopecia becomes apparent at 12 W and is fully developed by the age of 17 W.

Administration of 200MA0B PEG-htCBS C15S for 6 weeks (age of mice during injection was 4 W-10 W) was observed to delay the onset of alopecia for about the same time as the duration of the treatment (6 weeks) as evidenced by I278T -/- affected homozygous mice being observed to show no signs of facial hair loss at the age of 4M and only initial signs at the age of 7M. These results provide evidence that administration of 200MA0B PEG-htCBS C15S for 6 weeks delayed the onset of facial alopecia in I278T mice.

B. Total Prevention of Developing the Facial Alopecia

The second group (n=3; 2 males, 1 female) was continuously injected with 7.5 mg/kg of 200MA0B PEG-htCBS C15S administered subcutaneously from 3 W of age until 41 weeks of age. Weight was initially monitored weekly. Physical look was recorded before the experiment and was monitored weekly or bi-weekly after the initial 6 W injection regimen. Metabolite levels were checked before the experiment and 24 hours after the last injection of initial 6 W injection regiment and then followed weekly or bi-weekly.

Figure 12B:
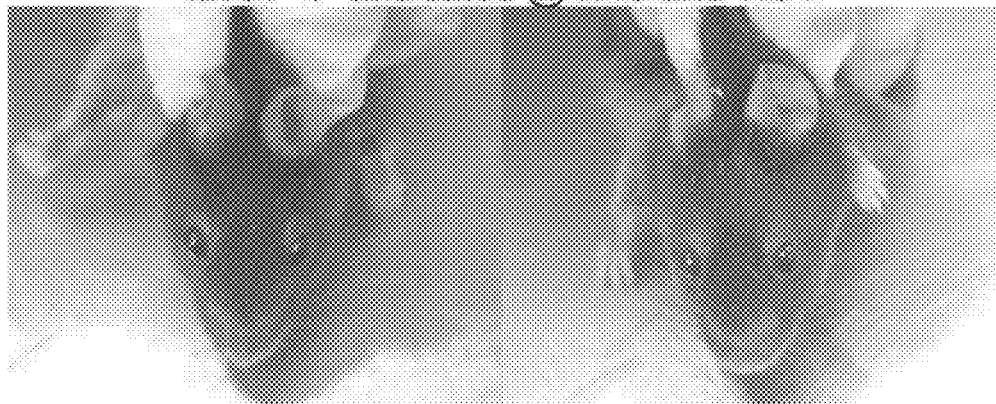
Figure 12B:
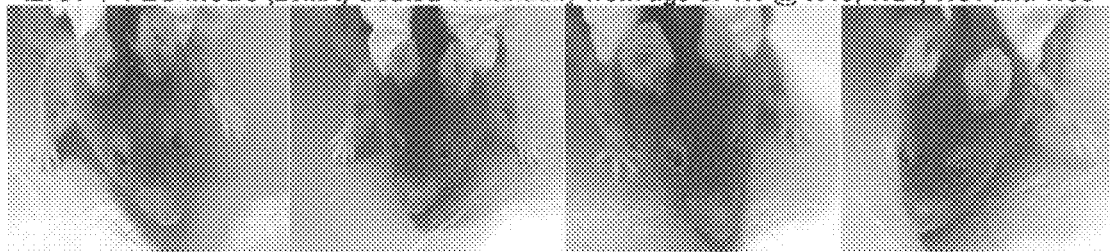
Figure 12B:

Continuous administration of 200MA0B PEG-htCBS C15S to I278T -/- homozygous mice was observed to completely prevent the onset and development of facial alopecia in mice observed at W19, W24, W31, and W35 of age as shown in FIG. 12B. The physical looks of such treated mice resemble those typically observed for healthy I278T +/- heterozygous mice, and significantly differ from the physical looks of both untreated I278T -/- controls and I278T -/- homozygous at age W36 and older treated for a 6 week period only.

Figure 12C:
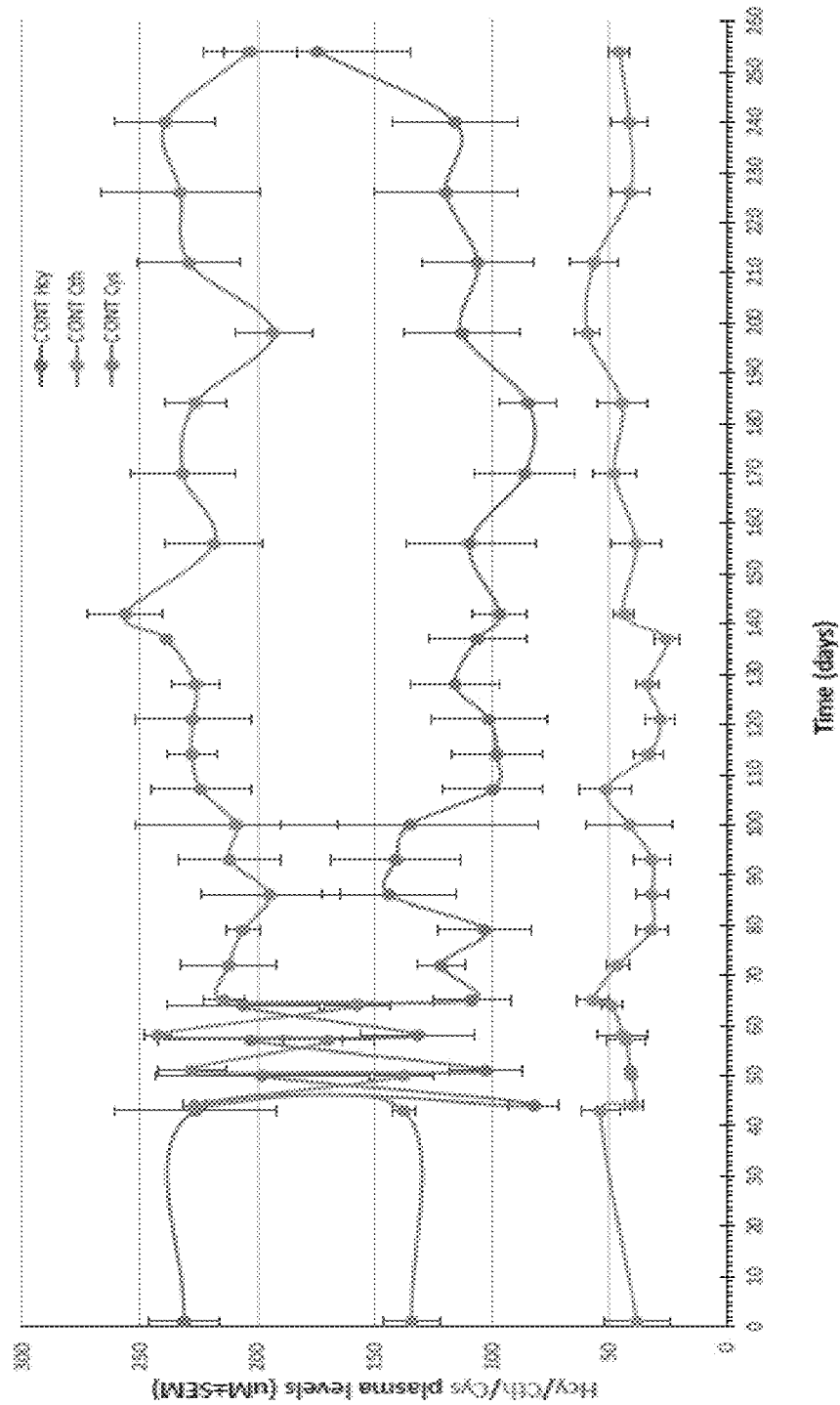

Metabolite measurements in FIG. 12C show that continuous administration of 200MA0B PEG-htCBS C15S resulted in a significant decrease of Hcy levels compared to the levels before the treatment (about 300 µM) and stabilization at levels of around 100 µM of total Hcy (middle line). Cys levels (top line) were normalized with the treatment (from about 130 µM to about 240 µM) and maintained throughout at levels around 230 µM.

C. Reversal/normalization of Phenotype Once the Facial Alopecia Has Been Fully Developed The I278T mice, which were at least 120D (W17) old and had visible, fully developed facial alopecia, were split into 2 groups. Group A (n=6; 3 males and 3 females) was injected 3 times per week with 400MA PEG-htCBS C15S, and Group B (n=4; 2 males, 2 females) was injected 3 times per week with 20NHS PEG-htCBS C15S up to an age of about 1 year. Metabolite levels were determined prior to the treatment initiation and measured during the study 24 hours after the injection, and weight and physical look were initially monitored weekly, and later bi-weekly.

For the reversal of facial alopecia in I278T −/− homozygous mice (otherwise known as normalization of phenotype), the treatment of mice already fully expressing facial alopecia phenotype was initiated. The age of animals at the beginning of the study ranged from W24 to W28 of age, which is beyond the typical age for onset of alopecia (120D or W17).

Figure 12D:
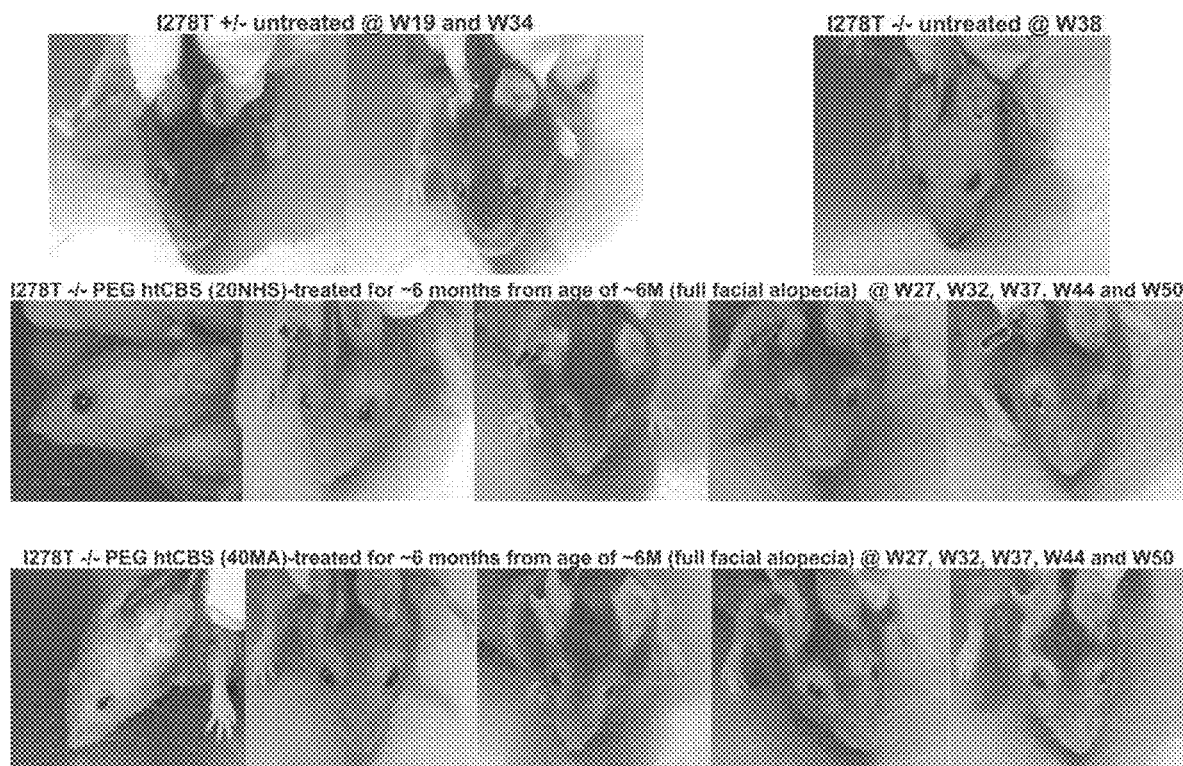

Continuous administration of either of the PEG-CBS conjugate for 3 times a week significantly ameliorated the facial alopecia as shown in FIG. 12D, even though it did not completely normalize it compared to the untreated unaffected I278T +/− heterozygous controls. 20NHS PEG-htCBS C15S was observed to perform better than 400MA PEG-htCBS C15S because all animals treated with 20NHS PEG-htCBS C15S responded to the treatment (4 out of 4), while only 5 out of 6 animals responded to treatment with 400MA PEG-htCBS C15S. In addition, a subjective observation of the mice provides that thickness and glossiness of the mice coat was better for those administered 20NHS PEG-htCBS C15S.

Figure 12E:
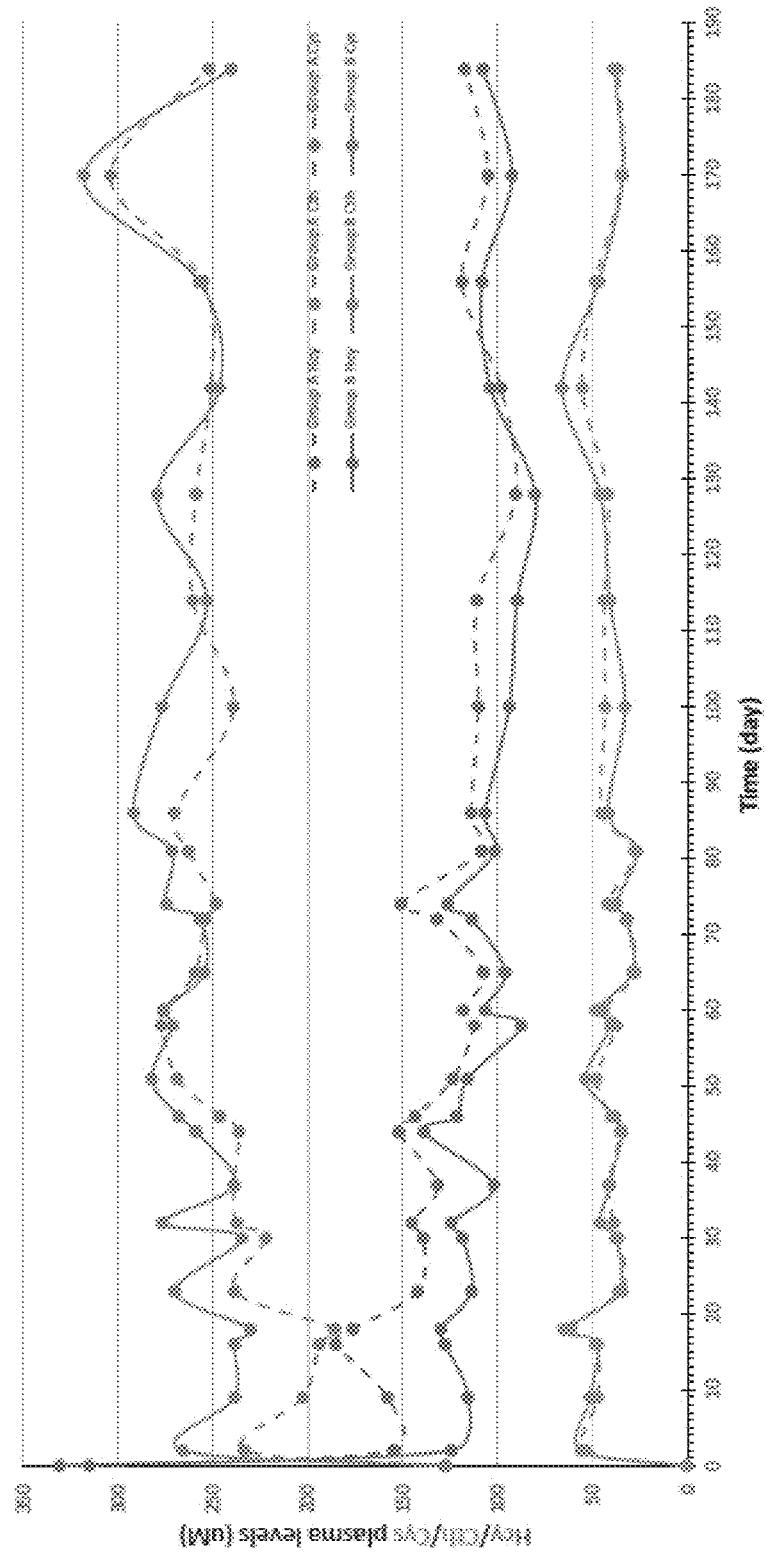

Furthermore, metabolite measurements in FIG. 12E shows that, while both PEG-CBS molecules were effective, 20NHS PEG-htCBS C15S (Group B) was observed to decrease Hcy levels and increase Cys levels more substantially than 400MA PEG-htCBS C15S (Group A).

D. Conclusions

Administration of PEG-CBS regardless of the PEG moiety resulted in improvement of facial alopecia, which is a phenotypic trait typical for untreated I278T −/− homozygous mice as mentioned above. ERT administration for 6 weeks resulted in delay in onset of facial alopecia. Continuous ERT administration to the mice before the onset of facial alopecia completely prevented its development and such animals were indistinguishable from unaffected healthy I278T +/− heterozygous mice. Continuous ERT administration to the mice with already fully developed facial alopecia resulted in significant improvement of their physical looks. In all cases, the positive effect on facial alopecia was accompanied with or caused by at least partial (Hcy) or full (Cys) normalization of plasma metabolites levels.

Example 13. 20NHS PEG-htCBS C15S Improves Liver Disease in KO Mice

Histological analysis was performed for liver sections from KO mice that had been subcutaneously (SC) injected with 7.5 mg/kg of 20NHS PEG-htCBS C15S or PBS three times a week from 2 days of age and euthanized at age of 17-19 days and compared to livers of age-matched +/− healthy control mice.

A. Light Microscopy

Figure 13A:
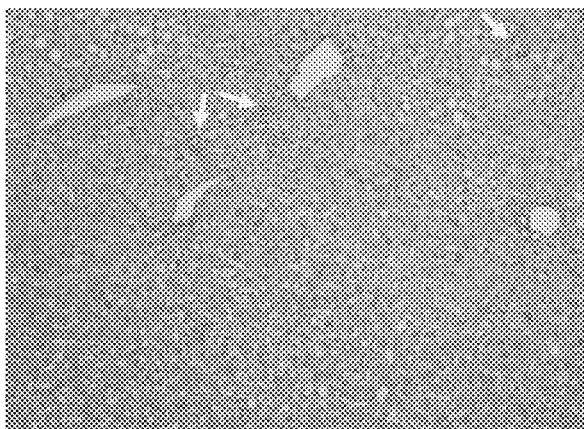
FIG. 13A-13B shows improved liver disease in 20NHS PEG-htCBS C15S-treated KO mice compared to PBS-treated KO mice and a healthy control.
Figure 13A:
Figure 13A:
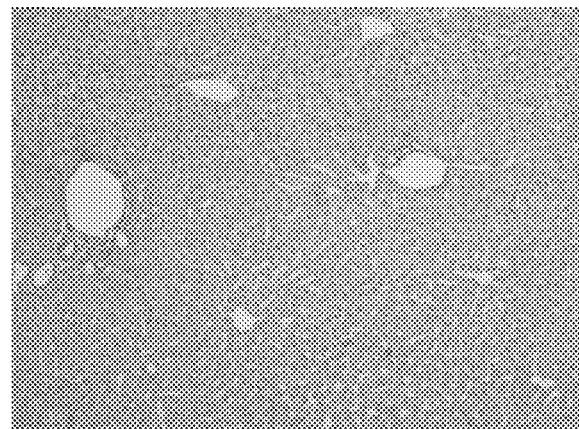

Animals were sacrificed on day 17-19 and liver samples were processed for histological analysis by optical microscopy. The liver parenchyma of the PBS-injected KO mice, as shown in FIG. 13A, was observed to have slightly irregular architecture of liver lobules with moderate to severe steatosis, focal hepatocellular necroses, and resorptive inflammatory reaction, which is indicated by the arrow. The liver parenchyma of the healthy heterozygous mice and 20NHS PEG-htCBS C15S-treated KO mice, also shown in FIG. 13A, were observed to have regular liver architecture and minimal anizokaryosis.

Figure 13B:
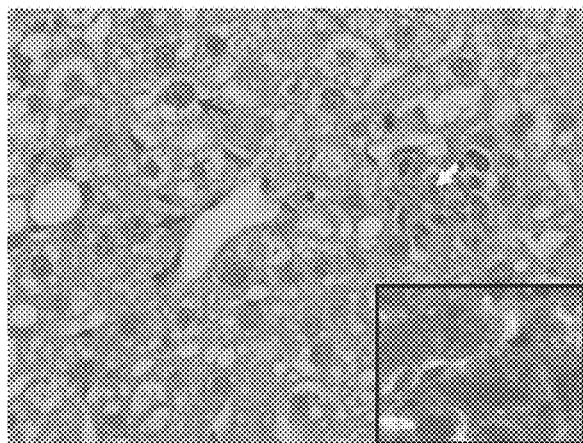
Figure 13B:
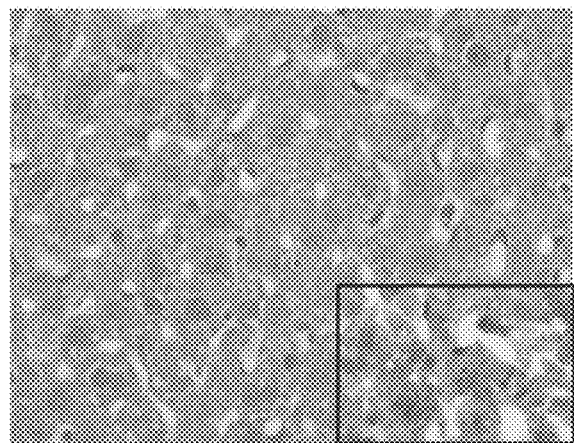
Figure 13B:
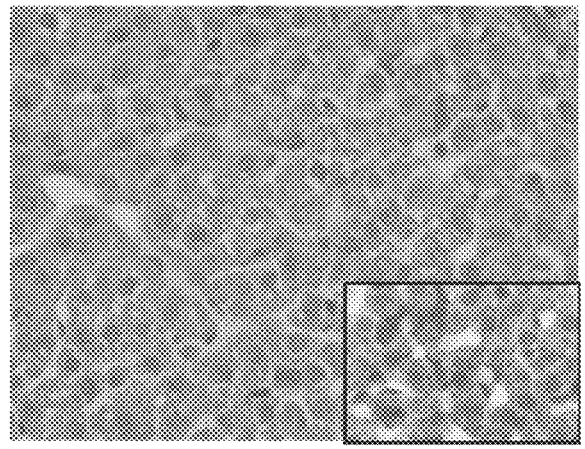

The greater detail provided by a higher magnification of the identical liver section shown in FIG. 13A are shown in FIG. 13B with insets showing Oil Red O staining for lipids. PBS-injected KO mice were observed to have micro- and macro-vesicular steatosis, anizokaryosis, focal necroses of hepatocytes, and a resorptive inflammatory reaction. These features are pointed out by the arrows. The liver parenchyma of the 20NHS PEG-htCBS C15S-treated KO mice was observed to have minimal anizokaryosis, as evidenced by the nuclei of the 20NHS PEG-htCBS C15S-treated KO and the healthy heterozygous mice both having regularly sized and shaped with fine chromatin and inconspicuous nucleoli. The discrete lipid droplets seen in the cytoplasm of hepatocytes of the treated and healthy mice were detectable using Oil Red O stain (see inserts in FIG. 13B).

B. Electron Microscopy

Figure 14A:
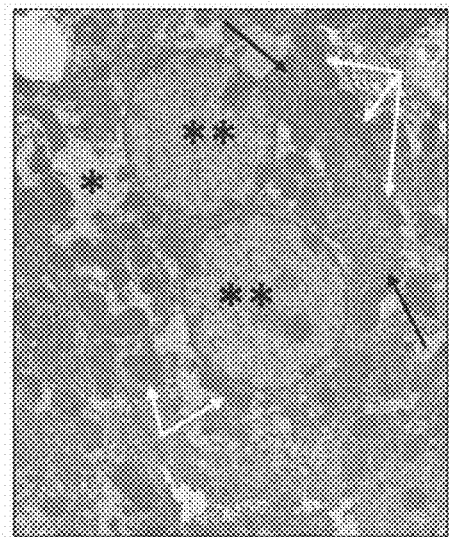
FIG. 14A-14B show the liver samples in FIG. 13A-13B as observed by electron microscopy.
Figure 14A:
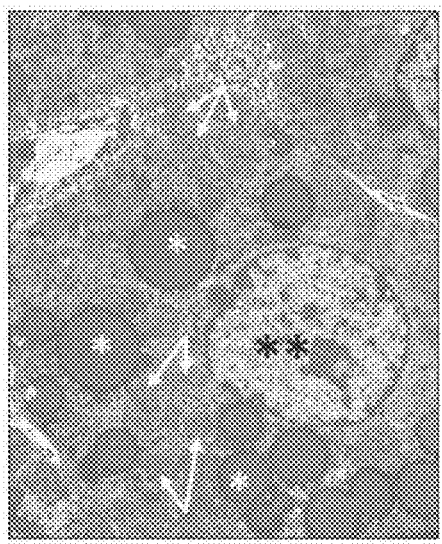
Figure 14A:
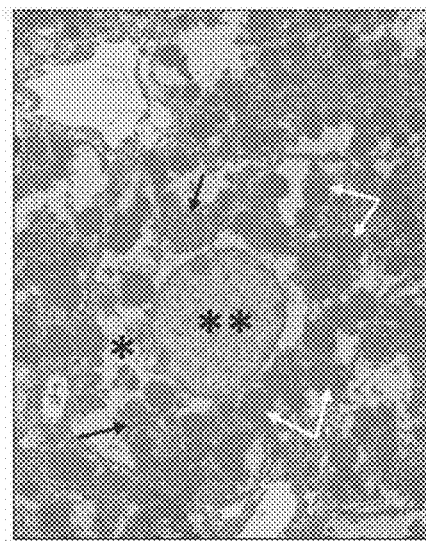

Liver tissue from a healthy heterozygous (+/−) mouse, a PBS-treated KO mouse, and a 400MA PEG-htCBS C15S-treated KO mouse was also observed using electron microscopy at 3000× magnification. Captured electron microscopy images are shown in FIG. 14A. In FIG. 14A, the black arrows indicate the rough endoplasmic reticulum (ER), and the white arrows indicate mitochondria (MT). The black asterisks indicate cytosolic glycogen, and the double black asterisks indicate nuclei. The white asterisks indicate lipid droplets.

The +/− mouse was observed to have a binucleated hepatocyte with normal cytoplasm composition and nuclei with normal morphology. The cisternae of rough ER were observed to be slim and regularly organized, and the MT were observed to be normally sized and shaped. The nuclei were observed to be regular and normochromatic with inconspicuous nucleoli.

The PBS-treated KO mouse was observed to have steatosis, an increased number of cytoplasmic organelles, and an irregular hyperchromatic nucleus of the hepatocyte. The cytoplasm was observed to be rich in organelles and to contain numerous lipid droplets (white asterisks) and edematous MT. The nucleus was observed to have coarse chromatin, an irregular outline, and a prominent nucleolus.

The 400MA PEG-htCBS C15S-treated mouse was observed to have a normal cytoplasm composition in the hepatocyte and a regular normochromatic nucleus. Like the +/− mouse, the cisternae of the ER were observed to be slim and regularly organized, the MT was normally sized and shaped, and the nucleus appeared normal with fine chromatin.

Figure 14B:
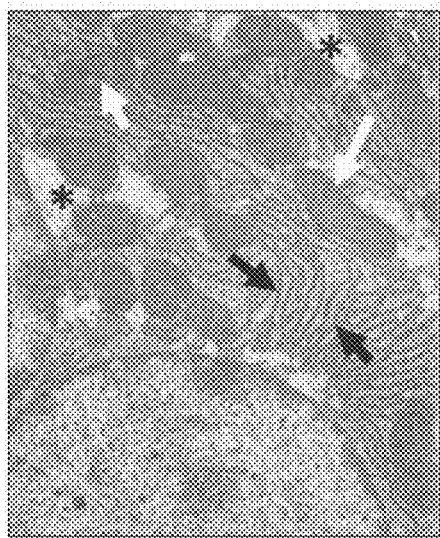
Figure 14B:
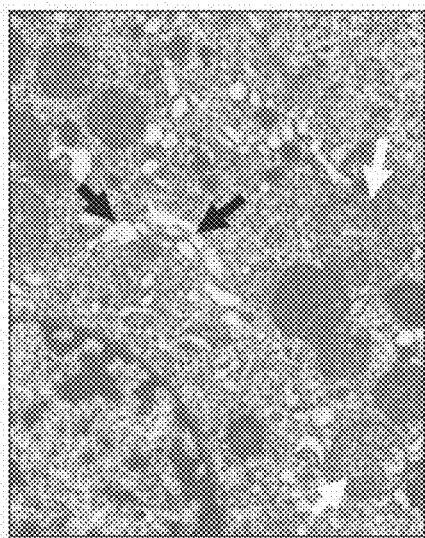
Figure 14B:
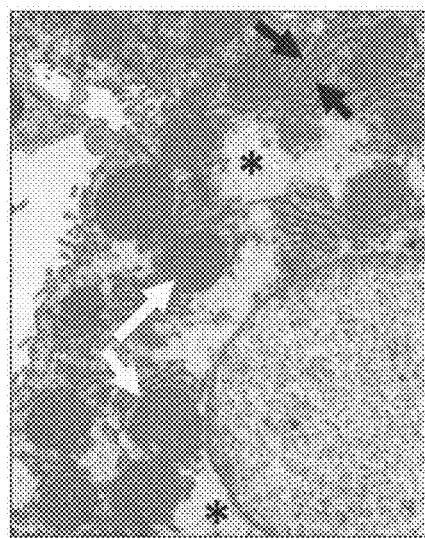

Electron microscopy images at 8000× magnification confirm these findings in greater detail, as shown in FIG. 14B. In FIG. 14B, the black arrows indicate the endoplasmic reticulum (ER), and the white arrows indicate mitochondria (MT). The black asterisks indicate cytosolic glycogen. The 400MA PEG-htCBS C15S-treated and +/− mice were observed to have slim and normally organized rough ER cisternae and regular MT. The PBS-treated KO mouse was observed to be rich in cisternae and vesicles. The ER cisternae were observed to have variably increasing widths. The MT were observed to be pleiomorphic and swollen with disorganized cristae.

C. Comparison of Metabolite Levels in Plasma and Tissues in KO Mice at 18-19 Days of Age Plasma and tissue metabolites were measured in the groups of wild-type mice (control), untreated homozygous −/− affected KO mice, and 400MA PEG-htCBS C15S-treated KO mice. The treated group was administered subcutaneous injections of 400MA PEG-htCBS C15S 3 times per week at a dose of 7.5 mg/kg from the age of 2 days. Plasma and tissues were harvested 24 hours after the last injection. Table 15 shows the levels of Hcy, Cys, Cth, and Met in plasma.

TABLE 15

Metabolite levels in plasma [μM ± SEM]

| Genotype | Treatment | Homocysteine | Cystathionine | Cysteine | Methionine |
|---|---|---|---|---|---|
| Wild type | None | 10.1 ± 0.7 | 2.8 ± 0.1 | 237.9 ± 9.2 | 87.7 ± 5.6 |
| KO$^{+/-}$ | None | 11.7 ± 0.7 | 1.7 ± 0.1 | 236.8 ± 2.7 | 93.4 ± 12.6 |
| KO | None* | 261.4 ± 12.9 | 0.06 ± 0.02 | 95.9 ± 8.1 | 483.7 ± 51.7 |
| KO | 20NHS PEG-htCBS C15S** | 52.8 ± 6.8 | 133.2 ± 9.1 | 211.7 ± 11.5 | 99.2 ± 5.4 |
| * vs. **, p-value | | 0.0001 | 0.001 | 0.0001 | 0.0018 |

Table 16 shows the levels of Hcy, Cys, Cth, and Met in liver tissue.

TABLE 16

Metabolite levels in liver tissue [nmols/g ± SEM]

| Genotype | Treatment | Homocysteine | Cystathionine | Cysteine | Methionine |
|---|---|---|---|---|---|
| Wild type | None | 9.2 ± 0.4 | 24.9 ± 7.8 | 257.8 ± 13.7 | 39.2 ± 2.1 |
| KO$^{+/-}$ | None | 8.9 ± 5.2 | 28.5 ± 19.3 | 326.7 ± 147.9 | 26.9 ± 9.8 |
| KO | None* | 63.4 ± 8.6 | 0.48 ± 0.1 | 110.6 ± 13.0 | 511.0 ± 66.8 |
| KO | 20NHS PEG-htCBS C15S** | 22.4 ± 3.4 | 18.9 ± 1.8 | 205.2 ± 27.4 | 25.5 ± 3.4 |
| * vs. **, p-value | | 0.01 | 0.0005 | 0.0355 | 0.0019 |

Table 17 shows the levels of Hcy, Cys, Cth, and Met in kidney tissue.

TABLE 17

Metabolite levels in kidney tissue [nmols/g ± SEM]

| Treatment | Homocysteine | Cystathionine | Cysteine | Methionine |
|---|---|---|---|---|
| None | 5.58 ± 0.18 | 6.67 ± 1.01 | 225.6 ± 10.8 | 61.2 ± 13.2 |
| None | 0.92 ± 0.04 | 5.38 ± 2.10 | 370.8 ± 102.6 | 65.9 ± 6.2 |
| None* | 30.6 ± 7.1 | 0.47 ± 0.06 | 239.8 ± 34.5 | 466.2 ± 112.8 |
| 20NHS PEG-htCBS C15S** | 6.76 ± 4.42 | 256.0 ± 77.5 | 282.8 ± 17.1 | 53.3 ± 2.9 |
| | 0.0460 | 0.0300 | 0.3285 | 0.0216 |

Table 18 shows the levels of Hcy, Cys, Cth, and Met in brain tissue.

TABLE 18

Metabolite levels in brain tissue [nmols/g ± SEM]

| Genotype | Treatment | Homocysteine | Cystathionine | Cysteine | Methionine |
|---|---|---|---|---|---|
| Wild type | None | 4.0 ± 0.9 | 69.0 ± 18.3 | 55.0 ± 3.6 | 61.6 ± 1.4 |
| KO$^{+/-}$ | None | 0.17 ± 0.02 | 34.3 ± 5.0 | 54.3 ± 1.5 | 56.6 ± 11.2 |
| KO | None* | 24.8 ± 7.5 | 1.3 ± 0.3 | 51.4 ± 1.4 | 616.0 ± 71.1 |
| KO | 20NHS PEG-htCBS C15S** | 1.1 ± 0.1 | 8.5 ± 1.1 | 56.8 ± 3.0 | 68.6 ± 4.7 |
| * vs. **, p value | | 0.0388 | 0.0027 | 0.1760 | 0.0015 |

Example 14. Effects of Continuous Administration of 20NHS PEG-htCBS C15S Using an ALZET® Osmotic Pump in HO Mice ALZET® osmotic pumps provide steady, controlled delivery of the 20NHS PEG-htCBS C15S for a prolonged period of time in fresh and naïve HO mice. The htCBS C15S PEGylated with ME-200GS was administrated using four different models of micro-osmotic ALZET® pumps, which continuously dispensed a volume of enzyme per hour instead of repeated subcutaneous injections: Model 1002 (0.25 μl/h), Model 2002 (0.5 μl/h), Model 2004 (0.25 μl/h), and Model 2006 (0.15 μl/h).

For pain relief, pre- and post-operatively, animals were also administered TYLENOL® (2 mg/ml) in water bottles ad libitum for 48 hours before and after surgery for implantation of the ALZET® pump. In addition, the animals received 5 mg/kg of carprofen subcutaneously every 24 hours, and for 48 hours postoperatively. For anesthesia during surgery, 5% isoflurane was administered by inhalation and maintained at 2-3% during surgery. While mice were anesthetized, they each received a medical grade ALZET® osmotic pump implanted under sterile conditions in a biological safety cabinet. Pumps were implanted subcutaneously in the loose skin area on the ventral side of the neck. Prior to implanting the pump, the mice were shaved and the skin area was prepped with BETADINE®. Pump implantation required a small surgical incision (5 mm) made with sterile scissors. The incision was closed with wound clips, which were removed after 1 week when the skin had fully healed. Blood samples were taken at 1, 3, 6, 9, 12, 15, 19, and 20 days for pumps Model 1002 and 2002. Models 2004 and 2006 of the pumps were surgically removed at the end of designated life cycle of the pump (4 and 6 weeks for Model 2004 and 2006, respectively). Collection of blood samples was therefore adjusted for each pump: 1, 3, 5, 12, 19, 26, 31, 32, 33, and 36 days for Model 2004 explanted at study day 30 and 1, 3, 5, 12, 19, 26, 33, 40, 45, 46, 47 and 50 days for Model 2006 explanted at study day 44. Plasma samples were used for determination of CBS activity in plasma and measuring Hcy, Cth, and Cys levels.

The administered enzyme for Models 1002 and 2002 was 20NHS PEG-htCBS C15S at a concentration of 21 µg/µl and having a specific activity of 673.9+13.2 U/mg. In these experiments, Model 1002 had a mean pumping rate of 0.25+0.01 µl/hr for a period of 14 days and the mean fill volume was 110.7+6.5 µl. The rate of administration of the enzyme was 5.25 µg/hr of the enzyme, which is equivalent to 126 µg/day or about 3.5 U/hr equaling 85 U/day.

Model 2002 had a mean pumping rate of 0.48±0.02 µl/hr for a period of 14 days and the mean fill volume was 207±7 µl. The rate of administration was 0.5 µg/hr of the enzyme, which is equivalent to 252 µg/day or about 7 U/hr equaling 168 U/day.

Figure 15A:
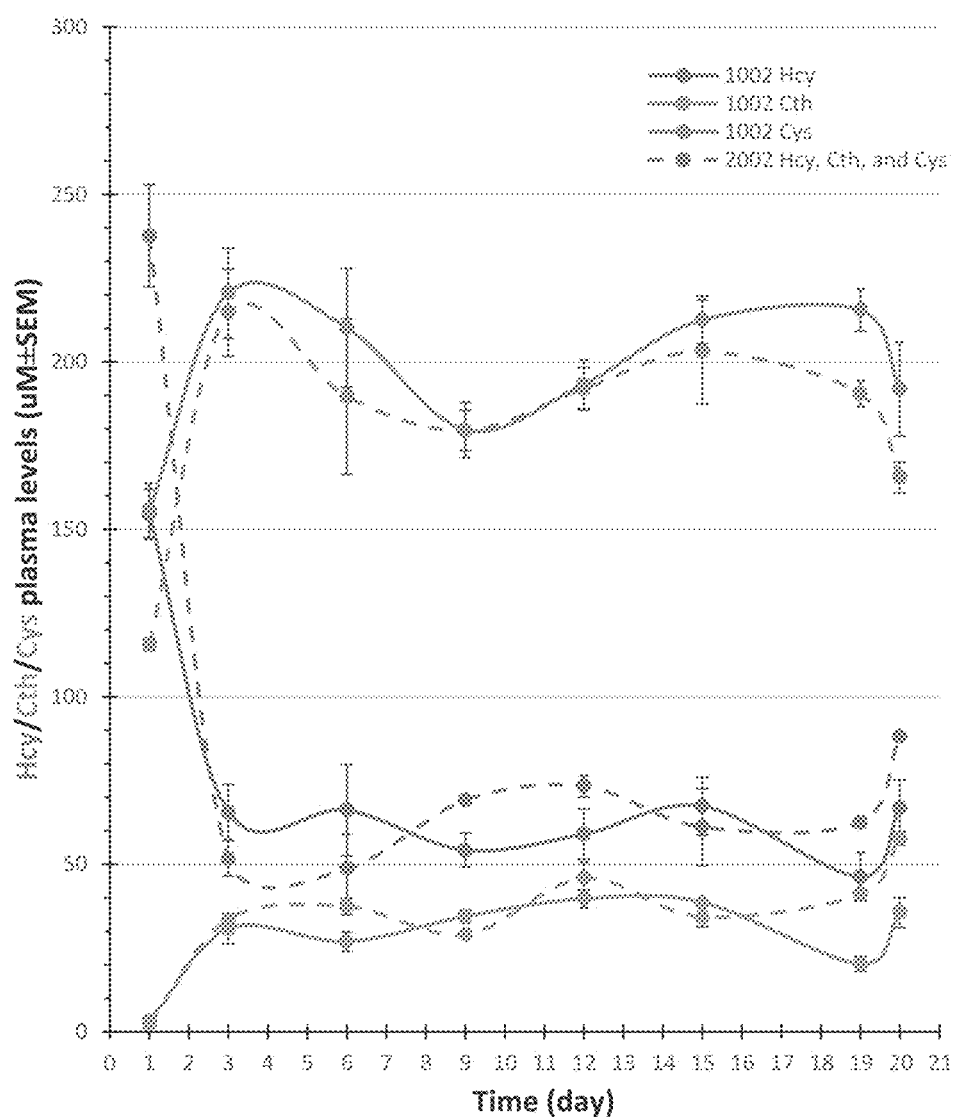
FIG. 15A-15D shows the effects of continuous administration of 20NHS PEG-htCBS C15S in HO mice on CBS activity and sulfur amino acid metabolites in plasma using different models of ALZET® osmotic pumps.
Figure 15B:
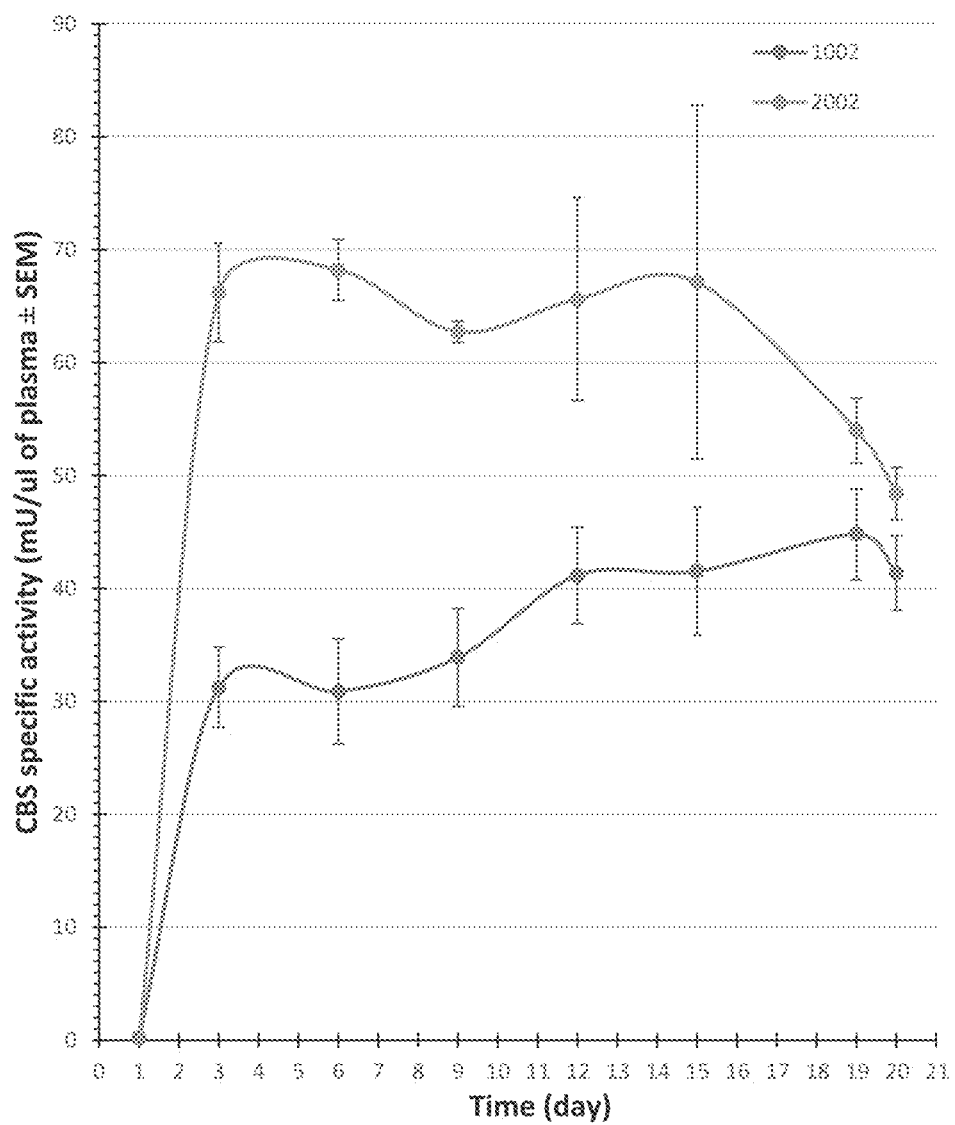

FIG. 15A is a graph comparing the plasma levels of Hcy and Cys between HO mice implanted with either a Model 1002 or a Model 2002 ALZET® osmotic pump. An overlap of metabolite levels in the plasma of both groups was observed. FIG. 15B is a graph comparing the specific activity of the 20NHS PEG-htCBS C15S in plasma after continuous administration with either a Model 1002 or a Model 2002 ALZET® osmotic pump. CBS activity in plasma of HO mice implanted with Model 2002 pumps was observed to be roughly doubled compared to the mice implanted with Model 1002. However, twice the amount of CBS activity in plasma of mice implanted with the Model 2002 pump resulted to a similar improvement of plasma metabolites as was achieved in mice implanted with the Model 1002 pump and having roughly half of the plasma CBS activity compared to Model 2002 group.

The administered enzyme for Models 2004 and 2006 was ME-200GS PEGylated htCBS C15S at a concentration of 18 µg/µl and having a specific activity of 623.2+16.4 U/mg. Model 2004 had a mean pumping rate of 0.23+0.01 µl/hr for a period of 28 days and the mean fill volume was 237.7+4.6 µl. The rate of administration of the enzyme was 4.5 µg/hr of the enzyme, which is equivalent to 108 µg/day or about 2.8 U/hr equaling 67 U/day. The ALZET® osmotic pump Model 2004 was explanted at 30 days.

Model 2006 had a mean pumping rate was 0.15+0.01 µl/hr for a period of 42 days, and the mean fill volume was 237.2+3.0 µl. The rate of administration of the enzyme was 2.7 µg/hr of the enzyme, which is equivalent to 65 µg/day or about 1.7 U/hr equaling 40 U/day. The ALZET® osmotic pump Model 2006 was explanted at 44 days.

Figure 15C:
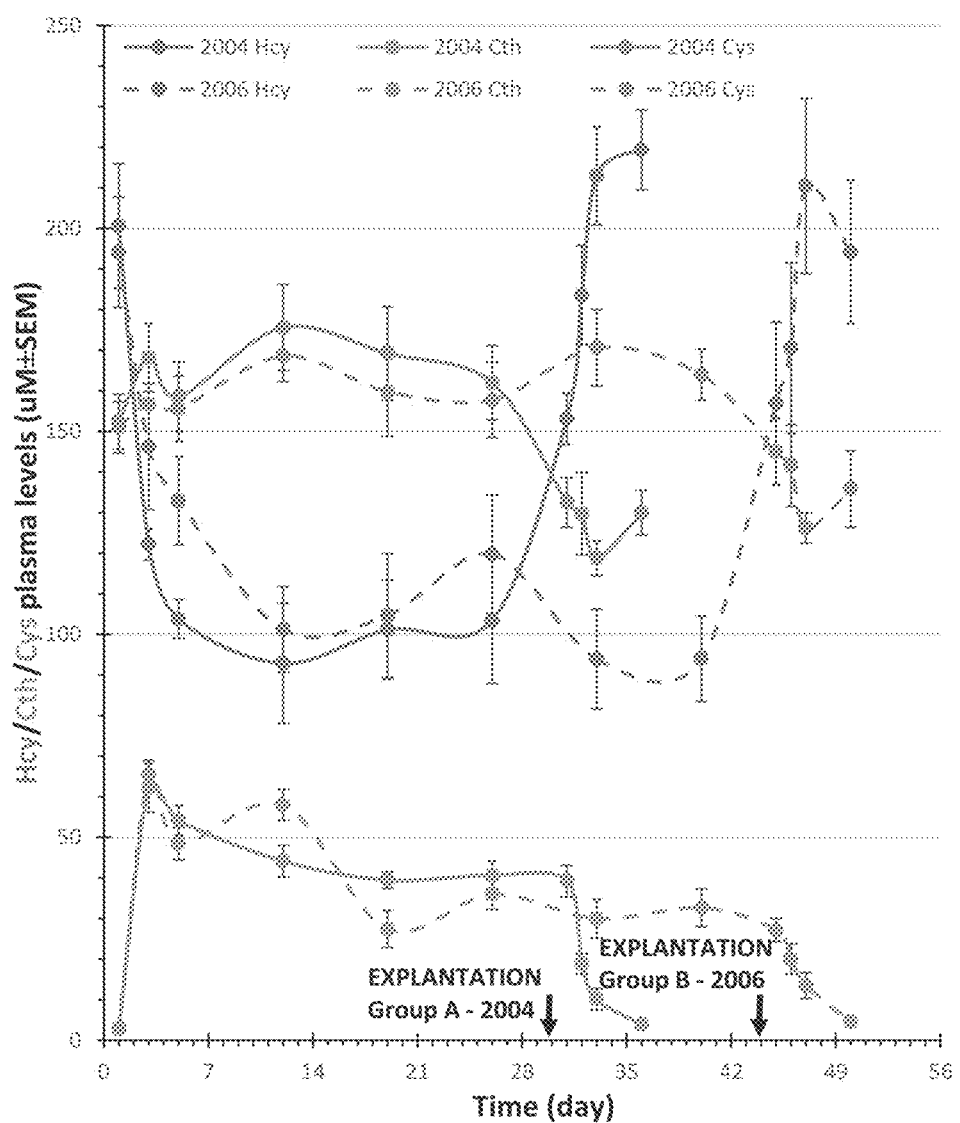
Figure 15D:
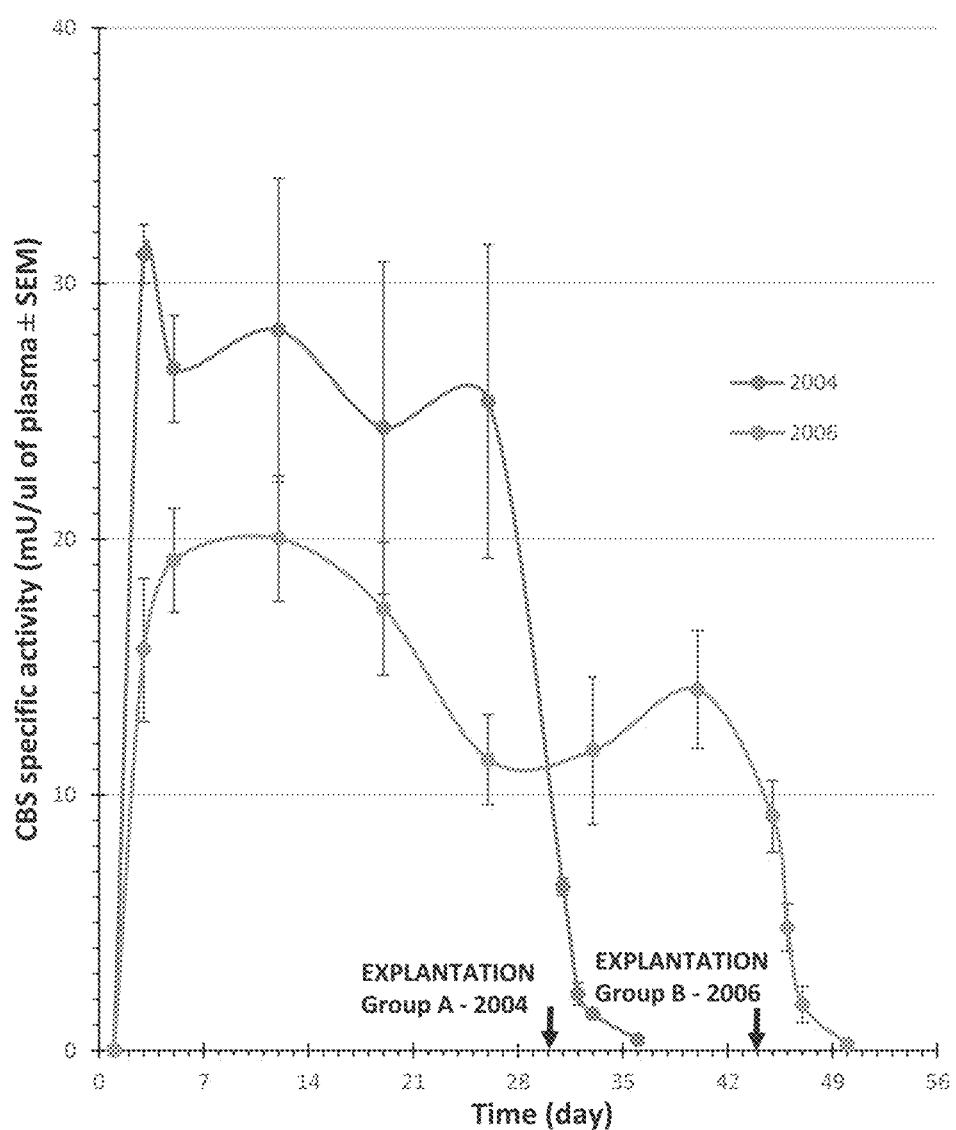

FIG. 15C and FIG. 15D show graphs comparing metabolite levels and CBS activity, respectively, in the plasma of mice that have been administered 20NHS PEG-htCBS C15S with either Model 2004 or Model 2006 ALZET® osmotic pumps. Despite Model 2004 dispensing 67% more enzyme than Model 2006 pump, both groups of mice were observed to have similar plasma metabolite profiles. The plasma levels of Hcy were observed to be substantially reduced in 20NHS PEG-htCBS C15S-treated mice, yet there was only a modest increase in Cys plasma levels.

Example 15. Lone-Term Continuous Administration of 20NHS PEG-htCBS C15S Prevents Osteoporosis in KO and I278T Mice The effects of long-term continuous administration of 20NHS PEG-htCBS C15S in KO and I278T mice was analyzed using dual-energy x-ray absorptiometry (DEXA) using the protocol in Example 1.

A. Bone Mineralization and Body Composition in KO Mice

The bone mineral density (BMD) and bone mineral content (BMC) were analyzed by DEXA for three groups of mice: +/− healthy heterozygous controls (n=4M+6F), affected KO controls (n=5M+13F), and 20NHS PEG-htCBS C15S (C15S/ME-200GS)-treated KO mice (n=6M+15F). The 20NHS PEG-htCBS C15S-treated mice were administered 7.5 mg/kg subcutaneously (SC) three times a week from day 2 to about 5 months. All −/− KO mice were treated for the initial 5 W (from 2 to 35 days of age) to prevent neonatal lethality.

FIG. 16A, FIG. 16B, FIG. 16C, FIG. 16D, and FIG. 16E are graphs comparing BMD (g/cm$^2$), BMC (g), total mass (g), lean mass (g), and fat content (%), respectively, among the three groups of mice. Table 19 provides the P-values used to determine significance for the differences in the treated group compared to the two control groups.

TABLE 19

| P-values for DEXA determined parameters in KO mice | | | | | |
|---|---|---|---|---|---|
| | BMD | BMC | Total mass | Lean mass | Fat content |
| +/− healthy vs. −/− affected | <0.001 | 0.011 | 0.045 | 0.675 | <0.001 |
| +/− healthy controls vs. treated | 0.006 | 0.609 | 0.749 | 0.160 | 0.071 |
| −/− affected controls vs. treated | <0.001 | <0.001 | 0.027 | 0.049 | 0.045 |

A P-value of 0.05 was set as a threshold to determine significance. The treated group had a significantly higher BMD than both control groups. The treated group also had a significantly higher BMC, total mass, lean mass, and fat content than the knock-out control. Therefore, treatment of KO mice with 20NHS PEG-htCBS C15S completely prevented profound osteoporosis and improved body composition (total mass, lean mass & fat content).

B. Plasma Metabolites in KO Mice

Figures 16A, 16B:
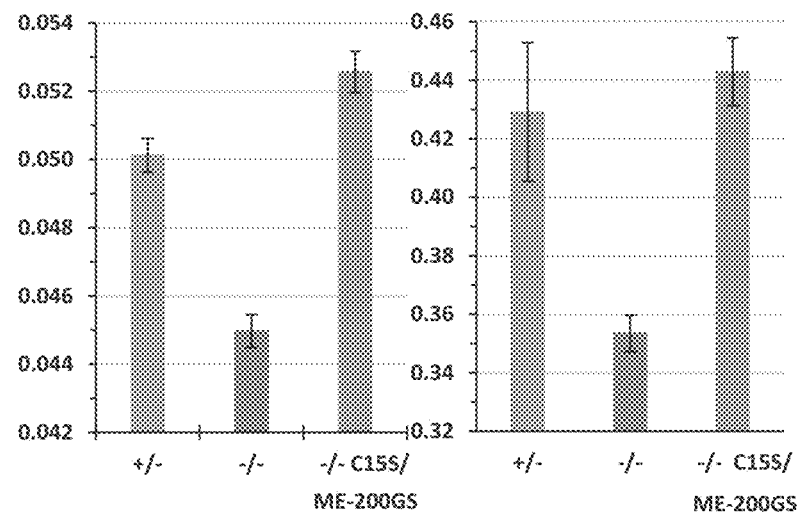
FIG. 16A-16G show results of the dual-energy X-ray absorptiometry (DEXA or DXA) study of continuous long-term administration of 20NHS PEG-htCBS C15S in KO mice.
Figures 16C, 16D, 16E:
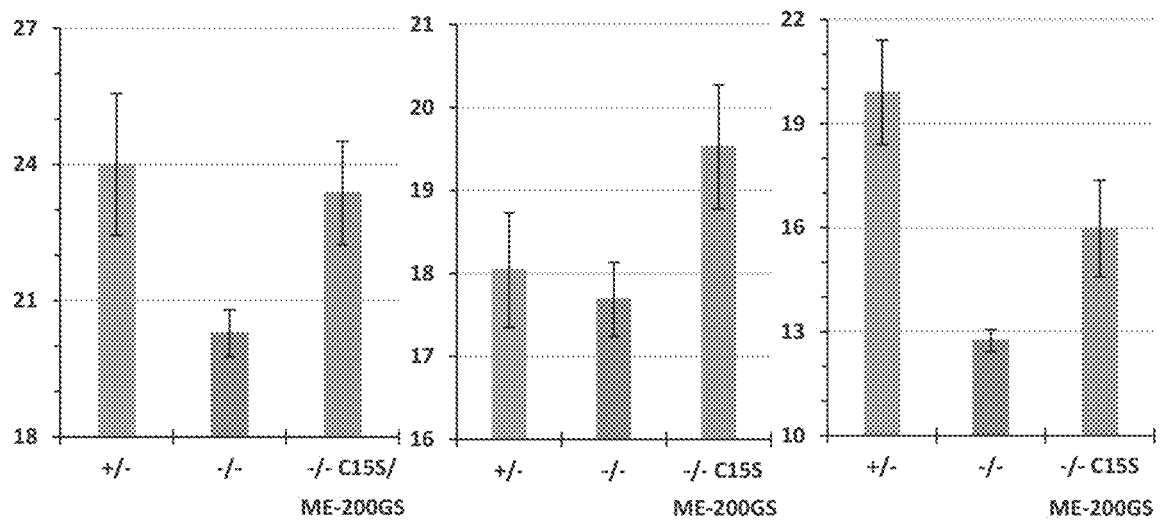
Figure 16F:
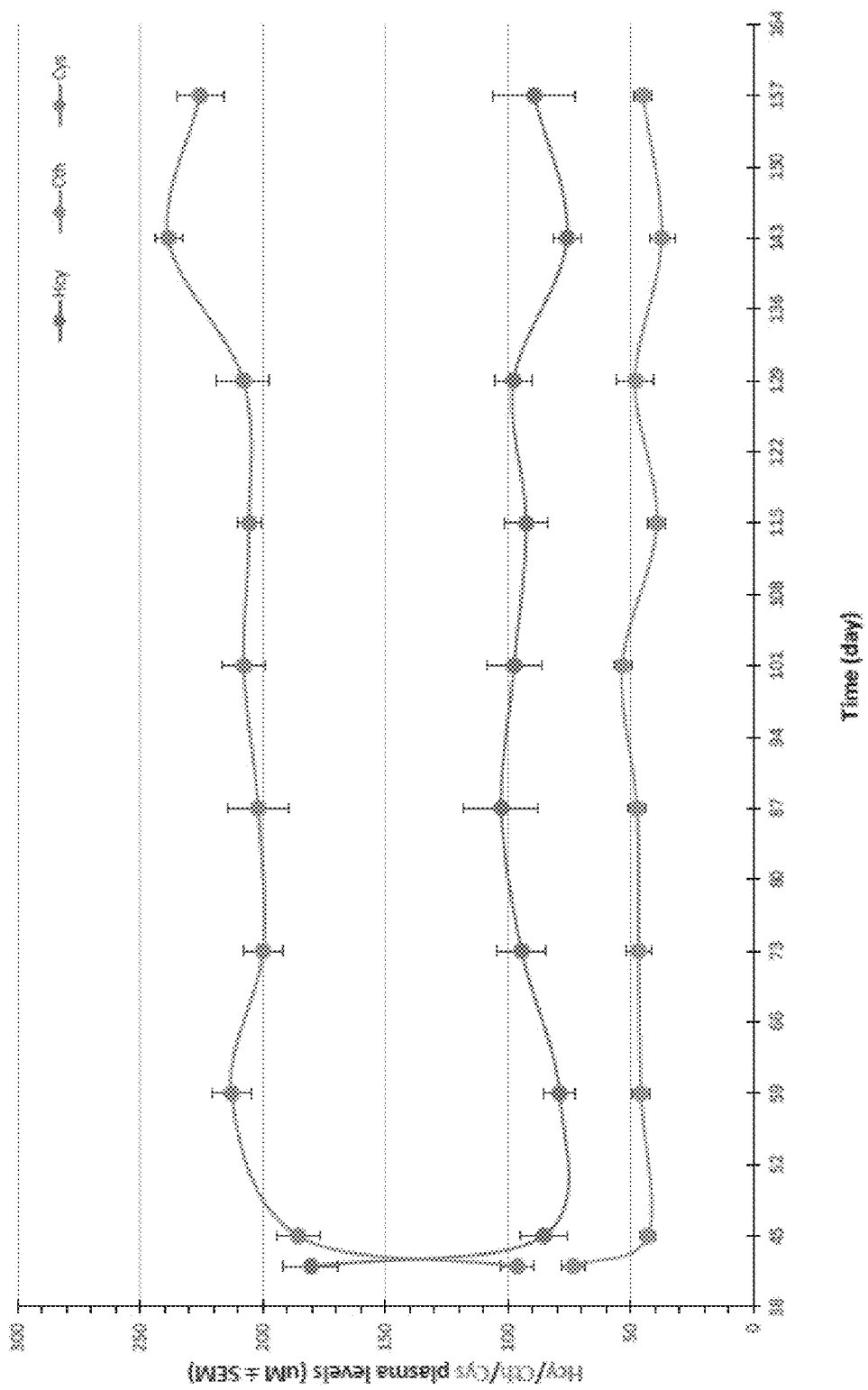

In 20NHS PEG-htCBS C15S-treated KO mice, the plasma levels of Hcy, Cth, and Cys were measured biweekly over the course of the study and are shown in FIG. 16F. A blood sample was initially taken at day 41 (does not represent a true time zero, rather metabolite levels 72 hours after injection), then beginning at day 45, a sample was taken every two weeks. The level of Hcy (middle line) was observed to decrease from about 180 µM at day 45 to about 90 µM at day 45 and remained steady at those levels throughout the study. The level of Cys (top line) normalized with the treatment from less than 100 µM at day 45 to about 200 µM at day 45 and sustained over the course of the study.

The level of Cth (bottom line) oscillated around 50 µM throughout the duration of the study.

Figure 16G:
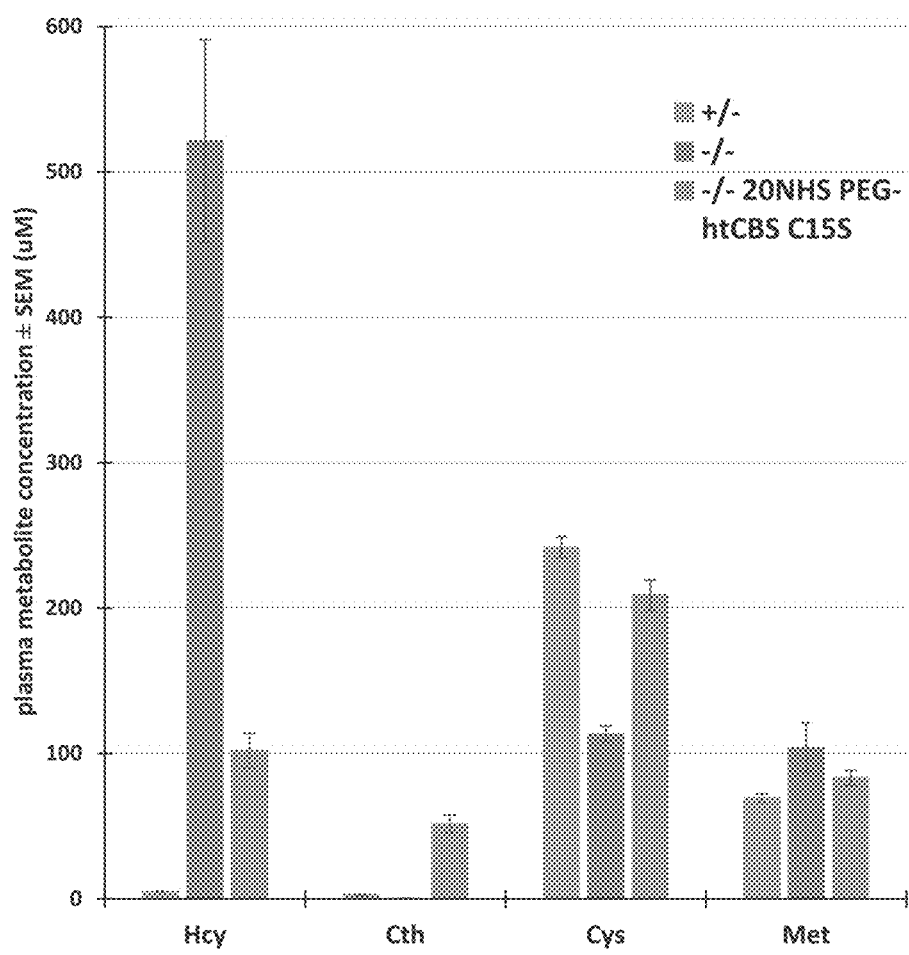

Plasma metabolites were determined using the same mice/groups as described above. The end-point levels of metabolites Hcy, Cth, Cys, and Met were determined 24 hours after the last injection to the 20NHS PEG-htCBS C15S-treated KO mice (right bar for each metabolite) and compared with untreated healthy +/− (left bar) and affected −/− KO mice (middle bar), as shown in FIG. 16G. Table 20 provides the P-values used to determine significance for the differences in metabolite levels in the treated group compared to the two control groups.

TABLE 20

P-values for metabolite level changes in KO mice

|  | Hcy | Cth | Cys | Met |
|---|---|---|---|---|
| +/− healthy controls vs. −/− affected controls | <0.001 | <0.001 | <0.001 | 0.133 |
| +/− healthy controls vs. −/− treated | <0.001 | <0.001 | 0.024 | 0.039 |
| −/− affected controls vs. −/− treated | 0.005 | 0.005 | 0.005 | 0.005 |

A P-value of 0.01 was set as a threshold to determine significance. The levels of Hcy were observed to drop significantly, Cth levels were observed to increase significantly, and Cys levels were normalized in KO mice receiving 20NHS PEG-htCBS C15S compared to the untreated KO mice. The Met levels were observed to be slightly elevated in untreated KO mice, but not significantly different among the groups.

Therefore, continuous long-term administration of 20NHS PEG-htCBS C15S to KO mice was observed to significantly improve Hcy, Cth, and Cys plasma levels compared to the untreated −/− KO mice. Plasma levels of Cys were normalized (i.e. not significantly different from) to the healthy +/− mice values. Metabolites data were observed to correlate with the determined phenotype by DEXA.

C. Bone Mineralization and Body Composition in I278T Mice

The bone mineral density (BMD) and bone mineral content (BMC) were analyzed by DEXA for three groups of I278T mice: +/− healthy heterozygous controls (n=10M+11F), −/− affected homozygous I278T controls (n=6M+8F), and 20NHS PEG-htCBS C15S-treated I278T mice (n=6M+6F). The 20NHS PEG-htCBS C15S (C15S/ME-200GS)-treated I278T mice were administered 7.5 mg/kg subcutaneously (SC) 3 times per week from the age of 6 months up to the age of 13 months. FIG. 17A, FIG. 17B, FIG. 17C, FIG. 17D, and FIG. 17E are graphs comparing BMD (g/cm$^2$), BMC (g), total mass (g), lean mass (g), and fat content (%), respectively, among the three groups of mice. Table 21 provides the P-values used to determine significance of the differences in the treated group compared to the control groups.

TABLE 21

P-values for DEXA determined parameters in I278T mice

|  | BMD | BMC | Total mass | Lean mass | Fat content |
|---|---|---|---|---|---|
| +/− healthy vs. −/− affected | <0.001 | <0.001 | <0.001 | 0.001 | <0.001 |
| +/− healthy controls vs. −/− treated | 0.473 | 0.832 | <0.001 | 0.037 | <0.001 |
| −/− affected controls vs. −/− treated | <0.001 | <0.001 | 0.027 | 0.331 | <0.001 |

A P-value of 0.05 was set as a threshold to determine significance. All DEXA determined parameters were significantly decreased in affected I278T mice compared to healthy heterozygous mice. The treatment of I278T mice with 20NHS PEG-htCBS C15S resulted in a significant correction of all parameters except amount of lean mass compared to untreated I278T mice. In fact, bone mineralization (BMD) values were observed to be indistinguishable between healthy heterozygous controls and 20NHS PEG-htCBS C15S-treated I278T mice. Therefore, treatment of I278T mice with 20NHS PEG-htCBS C15S also prevented profound osteoporosis and improved body composition (total mass, lean mass & fat content).

D. Plasma Metabolites in I278T Mice

Figures 17A, 17B, 17C:
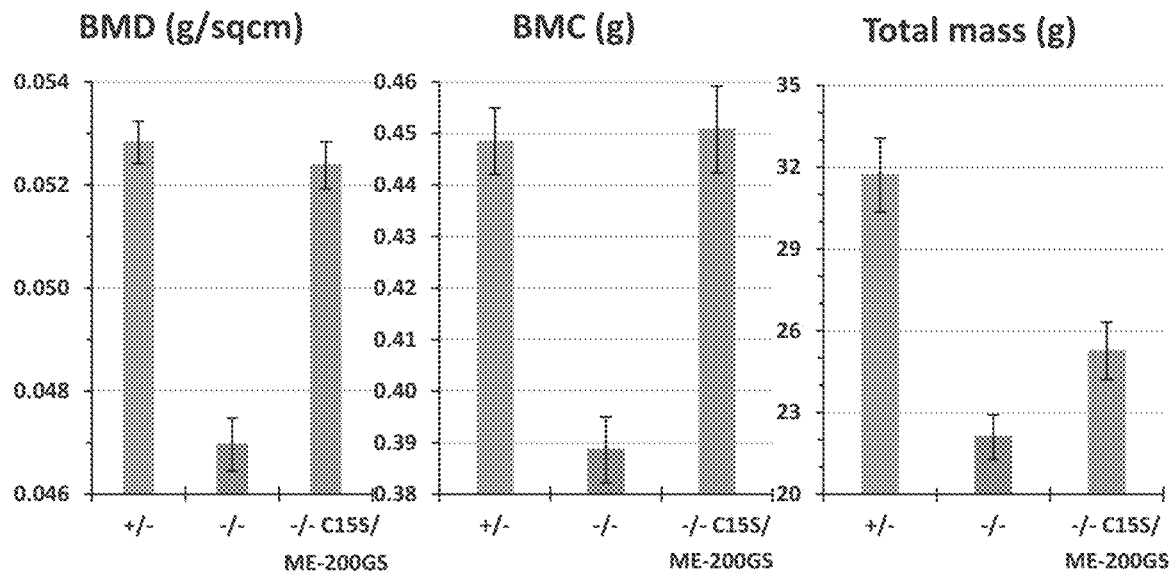
FIG. 17A-17F show results of the dual-energy X-ray absorptiometry (DEXA or DXA) study of continuous long-term administration of 20NHS PEG-htCBS C15S in I278T mice.
Figures 17D, 17E:
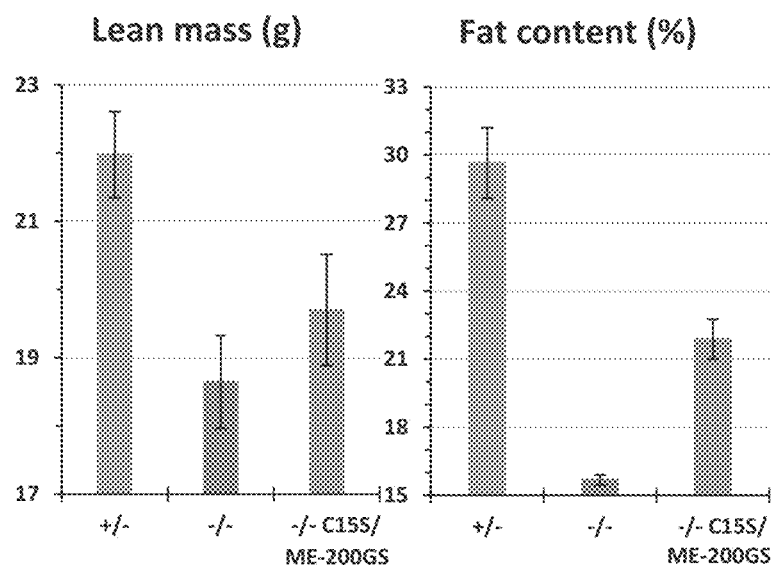
Figure 17F:
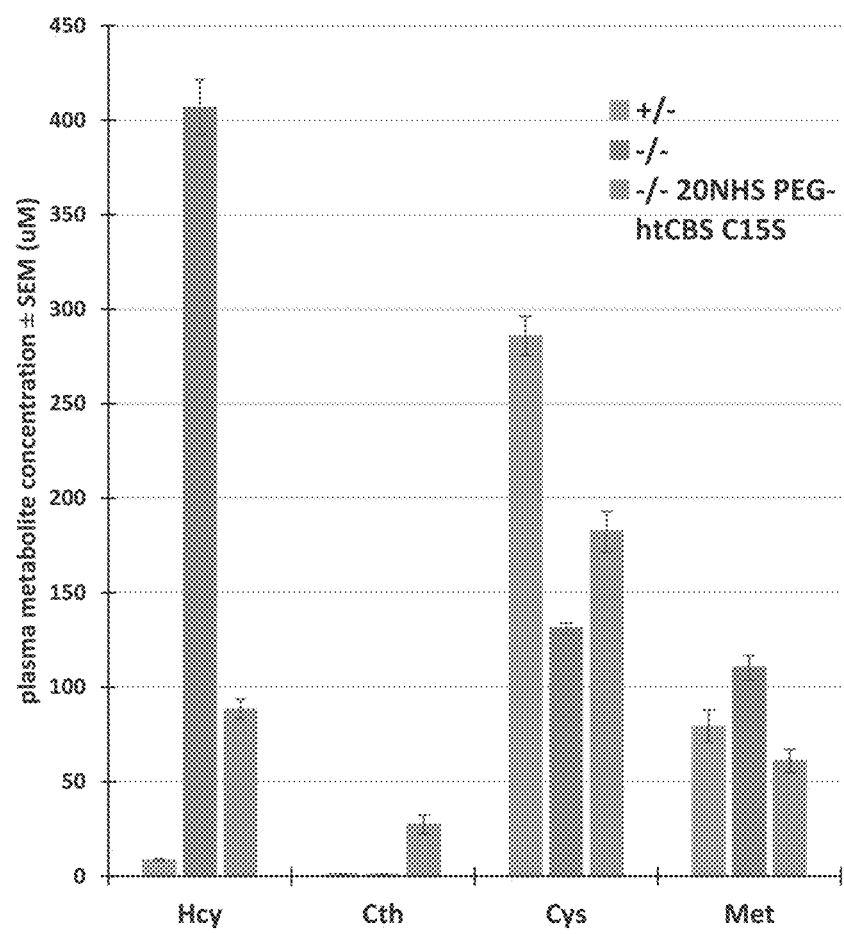

Plasma metabolites were determined in the same mice/groups as described above and compared to each other. The plasma levels of metabolites Hcy, Cth, Cys, and Met are shown in FIG. 17F. The left bar represents the level of metabolite for +/− healthy controls, and the middle bar represents the level of metabolite for −/− affected controls. The levels of each metabolite in 20NHS PEG-htCBS C15S-treated mice is represented by the right bar. Table 22 shows the P-values used to determine significance for the differences in plasma metabolite levels among the +/− healthy controls, −/− affected controls, and 20NHS PEG-htCBS C15S-treated I278T mice.

TABLE 22

P-values of changes in plasma metabolites

|  | Hcy | Cth | Cys | Met |
|---|---|---|---|---|
| +/− healthy vs. −/− affected | <0.001 | 0.667 | <0.001 | 0.021 |
| +/− healthy controls vs. treated | <0.001 | <0.001 | <0.001 | 0.140 |
| −/− affected controls vs. treated | <0.001 | <0.001 | <0.001 | <0.001 |

A P-value of 0.01 was set as a threshold to determine significance. The levels of Hcy were observed to decrease significantly, Cth levels were observed to increase significantly, and Cys levels were significantly improved, but not normalized, in I278T mice receiving 20NHS PEG-htCBS C15S compared to the untreated affected I278T controls. The Met levels were slightly elevated in untreated affected I278T mice and were significantly normalized to +/− heterozygous mice levels in I278T mice after treatment.

These results are similar to the results in the DEXA study with KO mice, except that normalization of Cys levels to +/− levels was not observed in the treated I278T group. Therefore, continuous long-term 20NHS PEG-htCBS C15S administration to I278T mice significantly improved Hcy, Cth, Cys, as well as Met plasma levels compared to untreated −/− homozygous affected mice. These metabolite data were observed to corroborate the phenotype assessed by DEXA.

Therefore, long-term continuous administration of 20NHS PEG-htCBS C15S prevents osteoporosis and improves body composition in both KO and I278T mouse models, and is efficacious to improve metabolite levels that are associated with homocystinuria.

Example 16. Continuous Long-Term Administration of 200MA0B PEG-htCBS C15S Improves Liver Metabolism and Function, Reduces Inflammation, and Normalizes Plasma Lipids in I278T Mice Administration of 200MA0B PEG-htCBS C15S to I278T mice was observed to improve liver glucose metabolism, redox status, and methylation potential as well as lipid metabolism. Liver function was observed to be unaffected, and the inflammatory cytokines and plasma lipids were observed to be normalized by the treatment.

A. Effects of Long-Term Administration of 200MA0B PEG-htCBS C15S on Liver Function and Lipid Metabolism in I278T Mice Plasma biomarkers were measured in I278T mice following long-term treatment with 200MA0B PEG-htCBS C15S to analyze liver function, inflammation, and plasma lipid levels. Three groups of I278T mice were analyzed: +/− healthy heterozygous control (n=3), −/− affected homozygous control (n=3), and 200MA0B PEG-htCBS C15S-treated I278T mice (n=3). The 200MA0B PEG-htCBS C15S-treated mice were administered 7.5 mg/kg subcutaneously (SC) 3 times per week from the age of 6 months up to the age of 13 months. The enzyme activities of alanine aminotransferase (ALT), aspartate aminotransferase (AST), and alkaline phosphatase (ALP); the concentrations of cytokines IL-12 (p40), IL-12 (p20), IL-13, G-CSF, MCP-1, and TNF-α; and the concentrations of plasma lipids (total, HDL and LDL cholesterols, and triglycerides) were measured in plasma (results not shown). Liver function was observed to be unaffected as the AST, ALT and ALP plasma activities were within the reference range. The inflammatory cytokines, particularly IL-12 (p40) and IL-13, were observed to be elevated in untreated I278T mice and normalized with the treat group. The plasma lipid panel showed that untreated I278T mice has significantly higher total, HDL and LDL cholesterols, while substantially decreased triglycerides compared to healthy +/− controls. The lipid profile was entirely normalized in 200MA0B PEG-htCBS C15S-treated I278T mice.

B. Effects of Long-Term Administration of 200MA0B PEG-htCBS C1 5S on Liver Metabolism in I278T Mice In addition to biomarkers described above, nuclear magnetic resonance (NMR) metabolomics was performed to analyze liver tissue of the same mice to investigate the effect of long-term treatment with 200MA0B PEG-htCBS C15S on I278T mice. Metabolites from liver tissues were extracted into hydrophilic and lipophilic solvents and quantified separately using NMR.

Figure 18A:
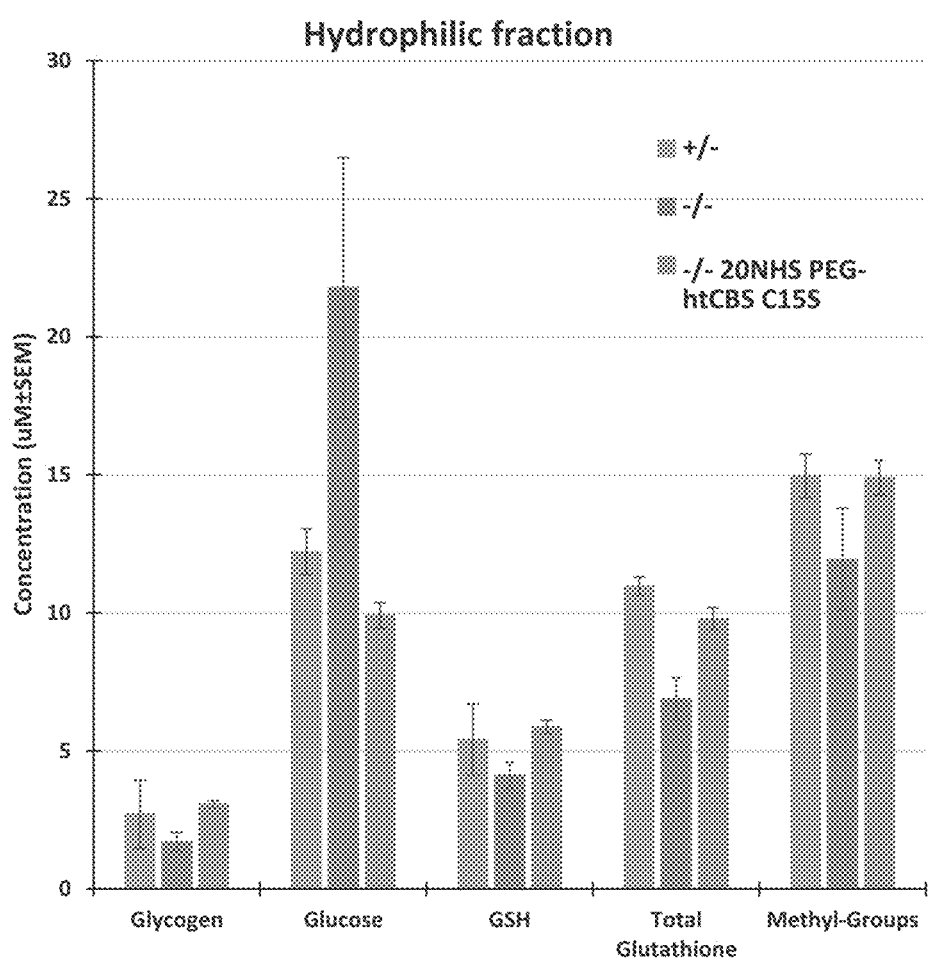
FIG. 18A-18B show concentrations of selected liver metabolites analyzed using NMR metabolomics in I278T mice after continuous long-term administration of 20NHS PEG-htCBS C15S and compared to healthy heterozygous and affected homozygous controls.
Figure 18B:
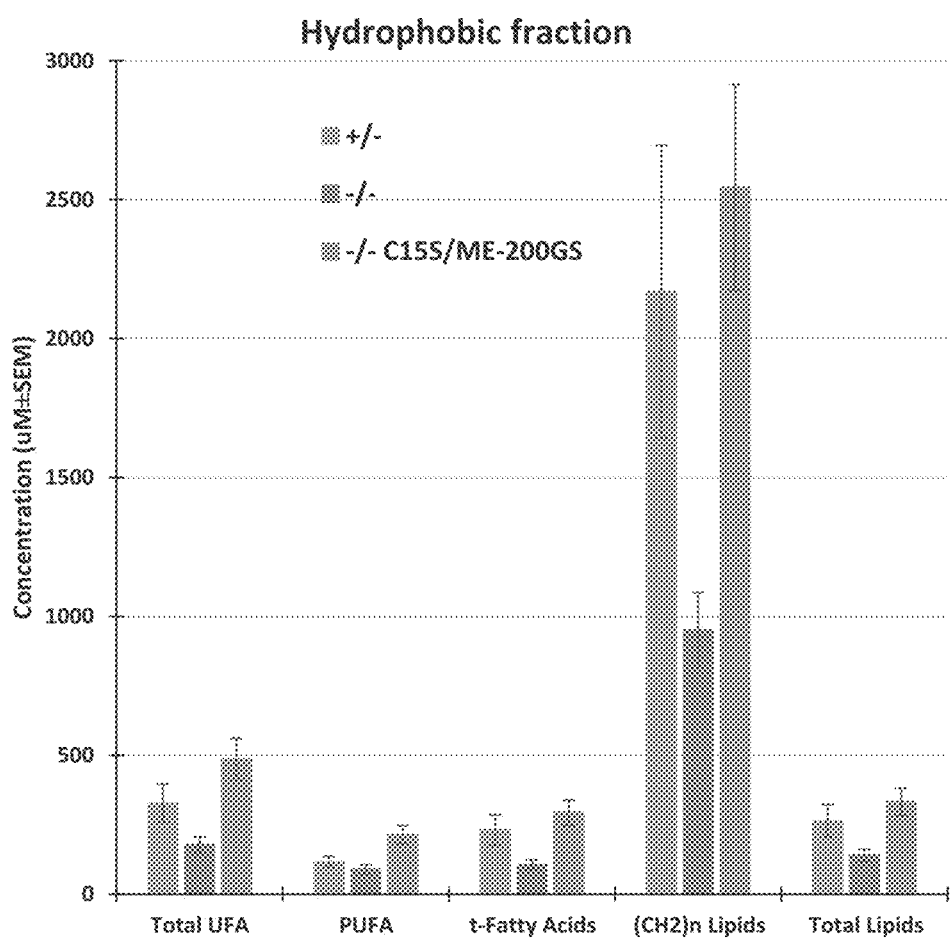

The concentrations of glycogen, glucose, glutathione (GSH), total glutathione, and methyl-groups in the hydrophilic fraction are shown in FIG. 18A. The left bar represents the concentrations in +/− healthy controls, and the middle bar represents the concentrations in −/− affected controls. The concentrations in 20NHS PEG-htCBS C15S-treated mice are represented by the right bar. For the hydrophobic fraction, the total unsaturated fatty acids (UFA), polyunsaturated fatty acids (PUFA), t-fatty acids, $(CH_2)_n$ lipids, and total lipids are shown in FIG. 18B. The left bar represents the concentrations in +/− healthy controls, and the middle bar represents the concentrations in −/− affected controls. The concentrations in 20NHS PEG-htCBS C15S-treated mice are represented by the right bar. Administration of 200MA0B PEG-htCBS C15S to I278T mice was observed to improve liver glucose metabolism, redox status, and methylation potential as well as lipid metabolism.

Figure 19A:
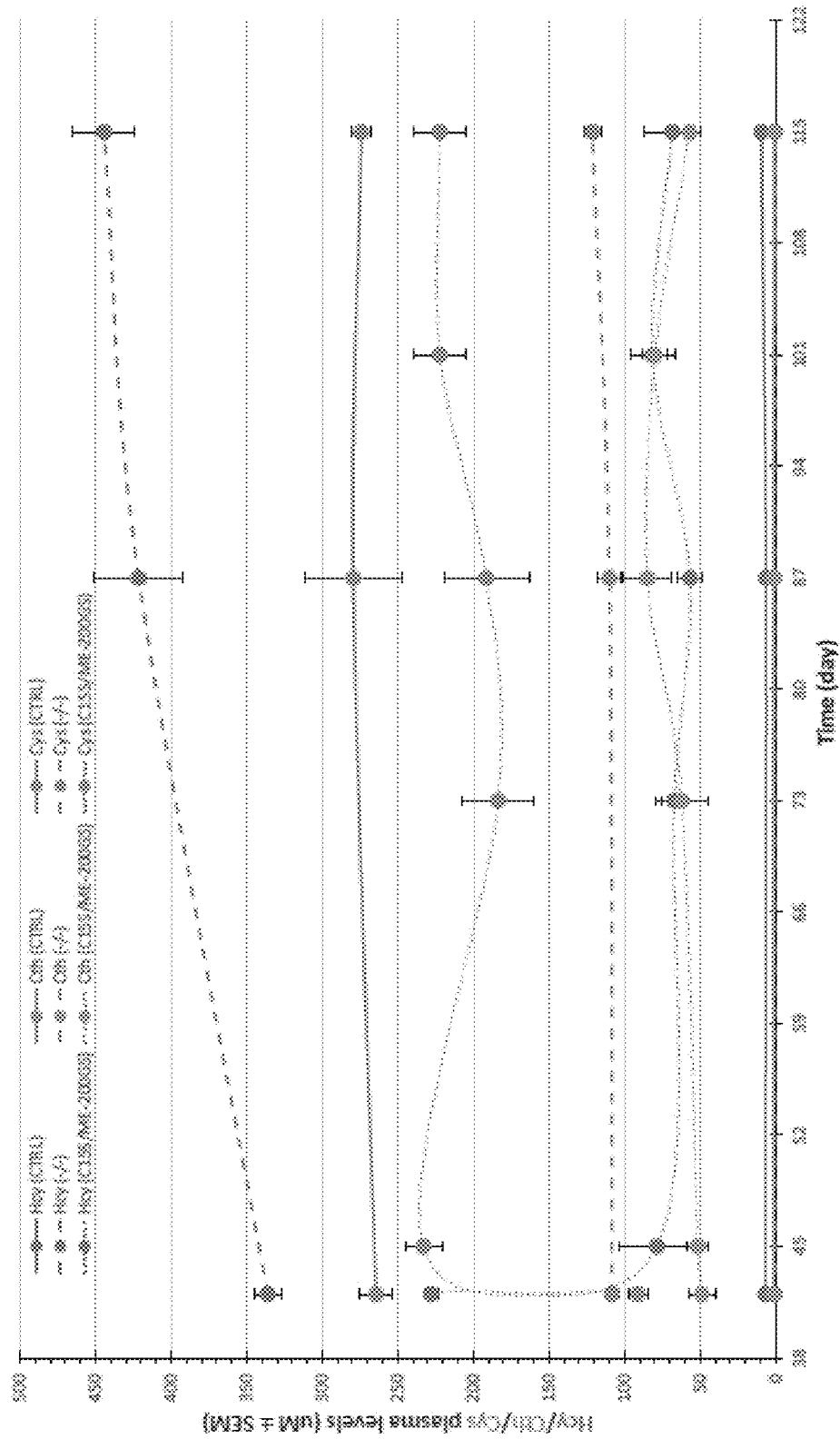
FIG. 19A-19E show the effects of administration of 20NHS PEG-htCBS C15S on eye defects in I278T mice.

Example 17. Long-Term Treatment With 20NHS PEG-htCBS C15S Improves Eye Defects in I278T Mice The changes in metabolite levels in plasma were measured in I278T (+/−) healthy heterozygous control mice, untreated −/− affected homozygous control mice, and 20NHS PEG-htCBS C15S-treated −/− homozygous I278T mice. The 20NHS PEG-htCBS C15S (C15S/ME-200GS)-treated mice were administered 7.5 mg/kg subcutaneously (SC) 3 times per week from the age of 2 days up to the age of 4 months. Changes in plasma metabolite levels from 6 weeks to 4 months are shown in FIG. 19A. Levels measured beginning at 72 hours after the injection as mice were on the treatment from 2 days of age.

As expected, the untreated homozygous I278T control had significantly elevated Hcy level and reduced Cys level compared to the healthy heterozygous controls as shown in FIG. 19A. The Hcy level in the untreated homozygous I278T mice fluctuated around 400 μM to 440 μM during the study, which is evidence of a continuous accumulation of Hcy due to the lack of functional CBS. In the 20NHS PEG-htCBS C15S-treated I278T mice, Hcy level decreased from 230 μM to about 70 μM and maintained this level throughout the rest of the study. In addition, activity of 20NHS PEG-htCBS C15S resulted in accumulation of plasma Cth to around 50 μM throughout the study and more importantly normalization of plasma Cys levels to around 230 μM, which was maintained throughout the study.

Figure 19B:
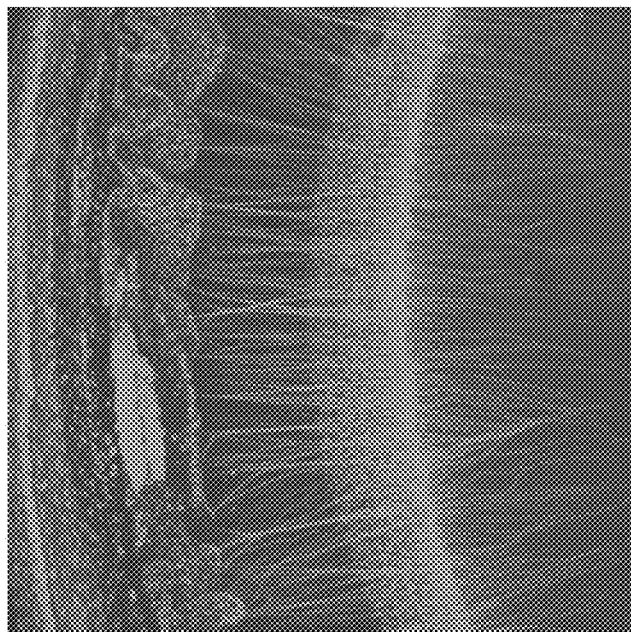
Figure 19C:
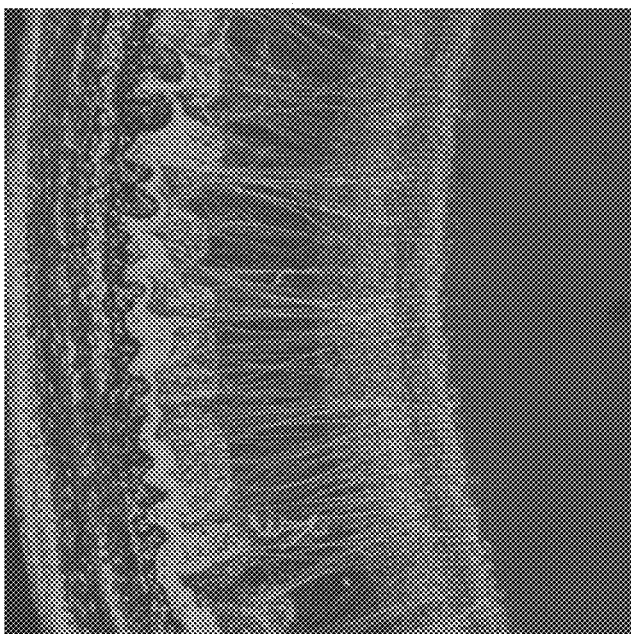
Figure 19D:
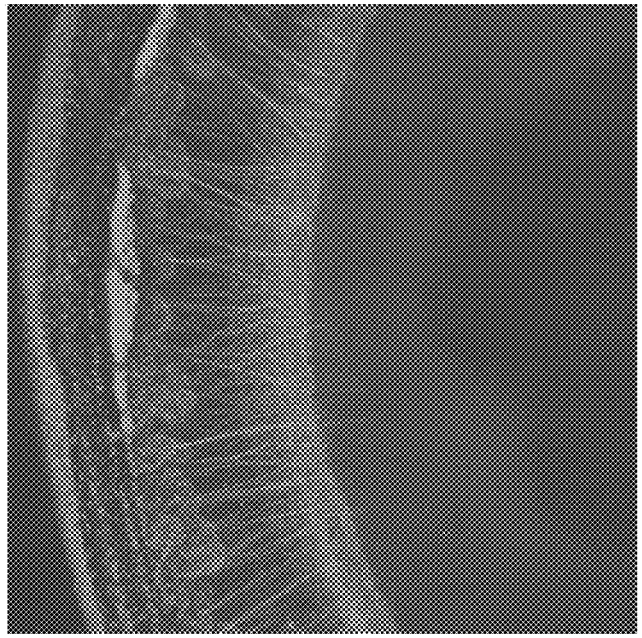
Figure 19E:
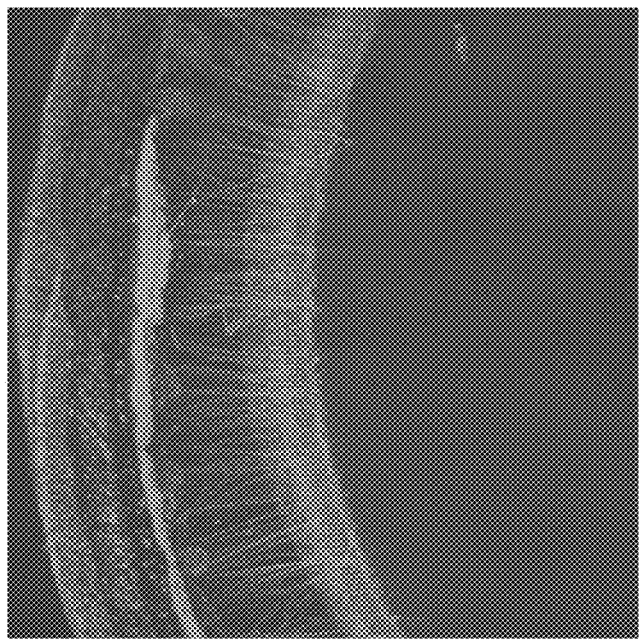

Eyes from I278T mice were analyzed and compared among the three groups. The healthy heterozygous control and the untreated −/− affected I278T control are compared in FIG. 19B and FIG. 19C, respectively, the untreated homozygous control was observed to have fewer and thinner zonular fibers, which terminated at the lens equator just above the meridional rows and did not grow on the posterior surface of the lens. In the samples from the 20NHS PEG-htCB S C15S-treated mice shown in FIG. 19D and FIG. 19E, enrichment of the density of zonular fibers and signs of "regrowth" of zonular fibers onto the back surface of the lens were observed. These observations are evidence that long-term treatment with 20NHS PEG-htCBS C15S had a positive effect on the eye defects in the I278T homozygous mice.

Example 18. Combination of Administration of 20NHS PEG-htCBS C15S and a Met-Restricted Diet Normalizes Hcy Levels in I278T Mice A diet study was performed in I278T mice and analyze them. Plasma metabolites of 10 weeks old mice: +/− I278T (control), −/− I278T (negative control), and −/− treated with 20NHS PEG-htPBS (OT-58) mice. Each group was further divided into subgroups: one on a regular diet (8.2 g/kg Met TD.01084 diet+zinc water) (REG) and one on a methionine-restricted diet (0.5 g/kg Met TD.110591 diet+betaine water) (MRD). Treatment was begun at W5 of age.

Figure 20A:
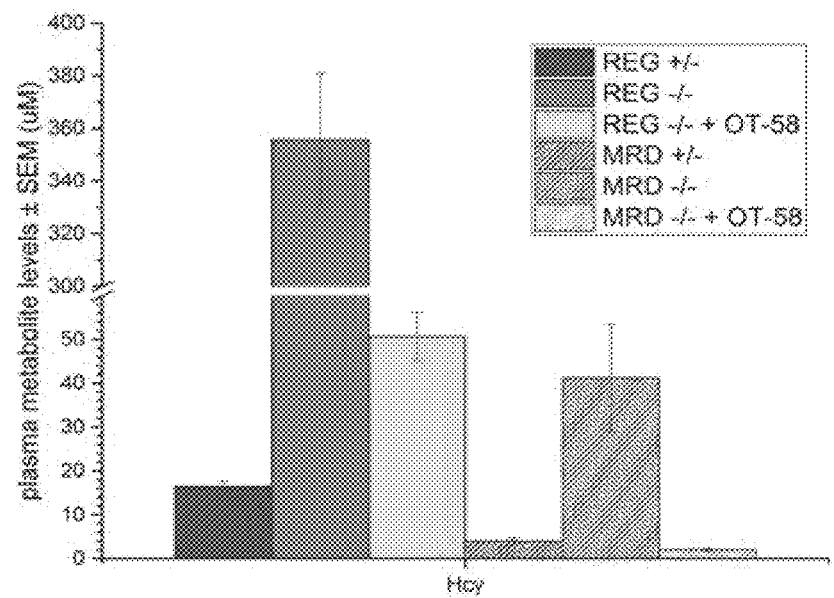
FIG. 20A-20D show plasma metabolite levels in I278T mice that are treated with 20NHS PEG-htCBS and are maintained on either a regular diet or on a metabolite restricted diet.

FIG. 20A shows the levels of Hcy among the 6 groups. A high level of Hcy (356 μM, which is consistent with the experiments above using I278T mice) were observed in −/− mice on a REG diet. The level of Hcy was observed to be substantially lower (51 μM) in the treated group on the REG diet. A relatively high level of Hcy (41 μM) was also observed in −/− mice on a MRD diet, which was normalized by the OT-58 treatment (2 μM versus 4 μM in +/− on MRD).

Figure 20B:
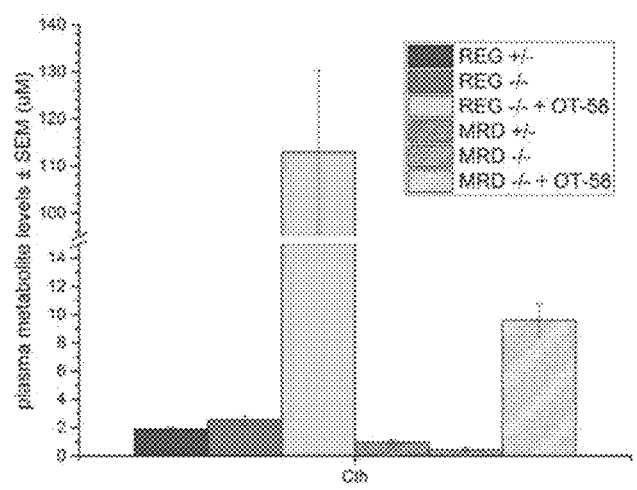

FIG. 20B shows the levels of Cth among the 6 groups. A high level of Cth was observed in the −/− OT-58-treated mice on both diets, 113 μM for REG versus 10 μM for the MRD diet, and the level was higher in mice on REG diet due to substrate availability. A similar trend between REG versus MRD diet was observed for the remaining groups, which is evidence that high levels of Cth (particularly in −/− on REG) result from the diet I believe.

Figure 20C:
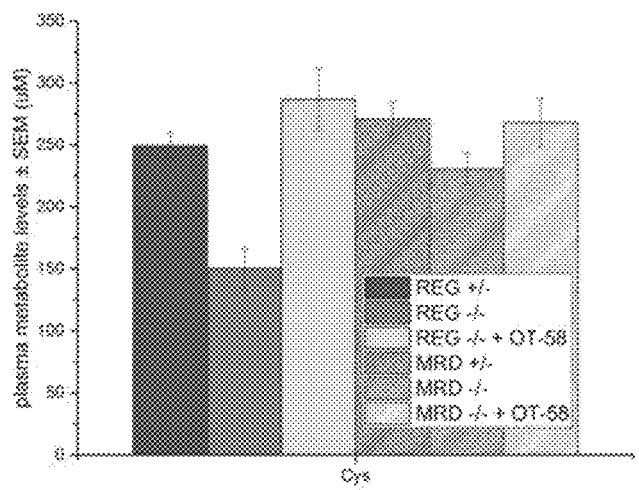

FIG. 20C shows the levels of Cys among the 6 groups. Cys levels were observed to be substantially decreased only in −/− mice on a REG diet, while a MRD diet and/or OT-58 treatment was observed to normalize plasma levels of Cys.

Figure 20D:
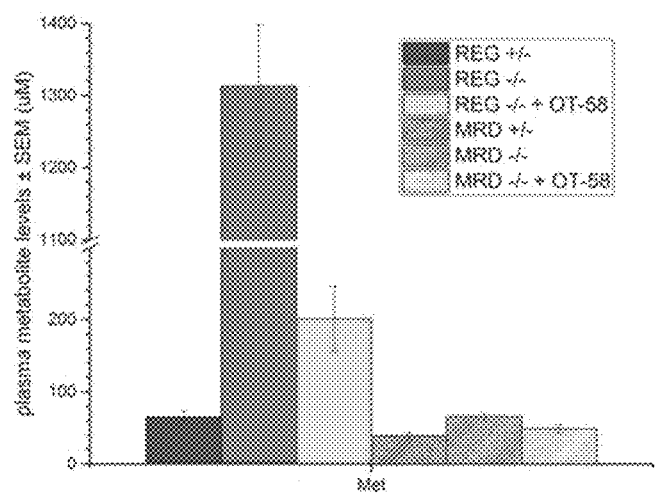

FIG. 20D shows the levels of Met among the 6 groups. Plasma levels of Met were observed to be high (1313 μM) in −/− mice on a REG diet, which had not been previously observed in I278T mice on a standard diet. Such a higHesh level of Met had only been previously observed in D17-19 untreated CBS KO mice. The high Met levels in −/− I278T mice on a REG diet receiving PBS injections was likely the result of a higher content of Met in REG diet used as control diet in this experiment compared to the STD diet provided by the animal facility.

Nevertheless, OT-58 treatment in −/− mice on a REG diet was observed to decrease the level of Met (201 μM to 66 μM) substantially, though it did not normalize the levels. Met levels in mice on MRD diet were observed to be normal or lower than normal showing only a slight effect from treatment.

Therefore, the combination of a Met-restricted diet and administration of 20NHS PEG-htCBS C15S was observed to normalize metabolite levels in I278T mice. Co-administration of 20NHS PEG-htCBS C15S (OT-58) with an unrestricted (not just eased) diet in homocystinuric subjects resulted in a reduction of Hcy to 50 μM.

Example 19: Pharmacokinetics of 20NHS PEG-htCBS C15S in Rats

A. Single Dose Pharmacokinetics

In order to assess the pharmacokinetics of 20NHS PEG-htCBS C15S in rats, wild-type Sprague Dawley rats were injected with a single dose of 20NHS PEG-htCBS C15S through intra-vascular (IV) or sub-cutaneous (SC) routes. Three separate single dose PK studies were combined using an identical or very similar study design as those shown in Table 23. The design of a third (repeated dose) PK study (groups 7-9) was adjusted to allow extraction of data after the first dose and thus their combination with a single dose PK study (groups 1-6). Plasma was collected at designated times as listed in Table 23 and analyzed for CBS activity using methods detailed in Example 1.

TABLE 23

The design of single dose (groups 1-6) and repeated dose (groups 7-9) PK studies on Sprague Dawley rats using 20NHS PEG-htCBS C15S

| Group | Rats (nM/nF) | Route | Dose (mg/kg) | Sampling (hours post first injection) |
|---|---|---|---|---|
| 1 | 2M/2F | IV | 4 | 0, 0.083, 0.167, 0.25, 0.5, 1, 2, 4, 8, 12, 24, 72, 120 |
| 2 | | SC | 8 | 0, 0.5, 2.4, 8, 12, 24, 48, 72, 96, 120, 168 |
| 3 | | SC | 24 | |
| 4 | 3M/0F | IV | 4 | 0, 0.083, 0.167, 0.25, 0.5, 1, 2, 4, 8, 12, 24, 72, 120 |
| 5 | | SC | 8 | 0, 0.5, 2.4, 8, 12, 24, 48, 72, 96, 120, 168 |
| 6 | | SC | 24 | |
| 7 | 3M/3F | SC | 4 | Main groups: 0, 24, 48, 240, 264, 288, 312, 336, 360, 384, 408 |
| 8 | (main) + | SC | 8 | Recovery groups: 0, 8, 12, 32, 38, 404, 432, 476, 527, 577 |
| 9 | 3M/3F (recovery) | SC | 24 | |

Figure 21A:
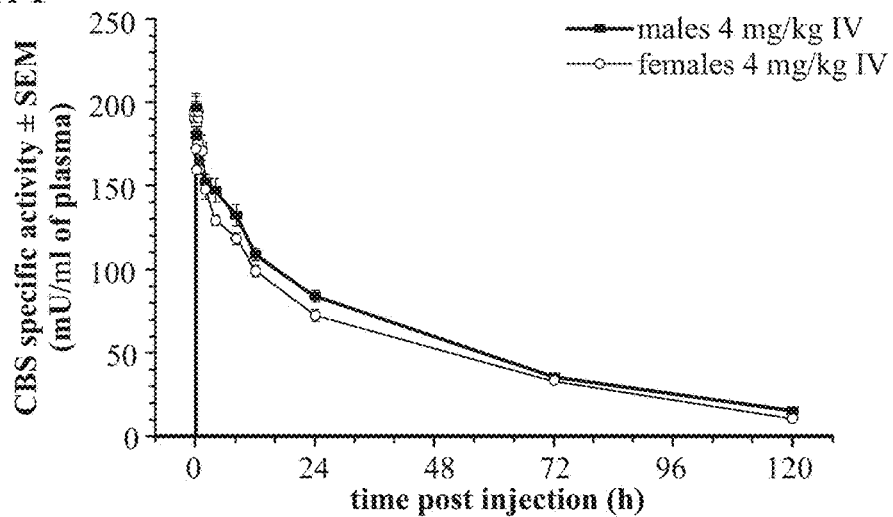
FIG. 21A-21B show the specific activity of 20NHS-htCBS C15S in male and female rats after an IV or SC bolus dose of 4 (IV), 8 (SC), and 24 (SC) mg/kg.
Figure 21B:
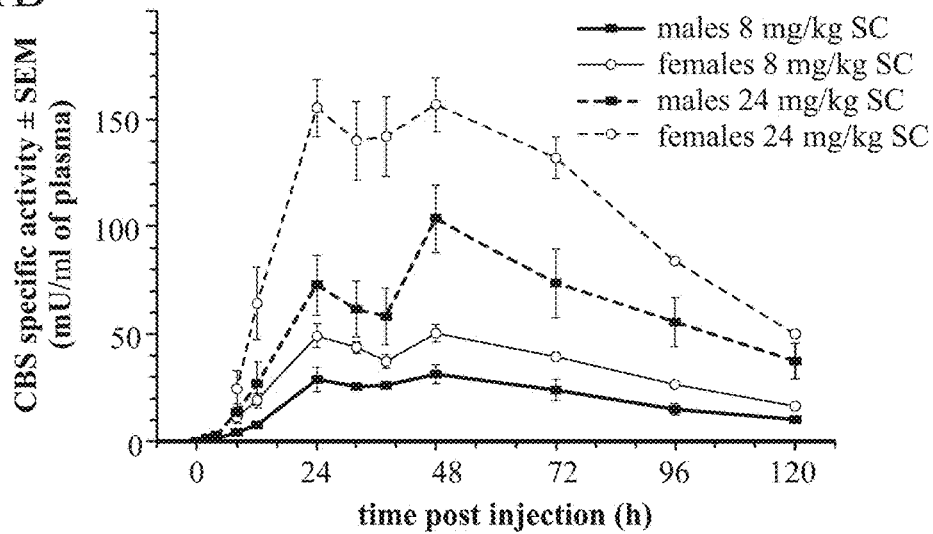

The specific activity of 20NHS PEG-htCBS C15S in male and female rats after a single IV or SC bolus dose of 4 (IV), 8 (SC), and 24 mg/kg (SC) are shown in FIG. 21A and FIG. 21B. Results from administration of 20NHS PEG-htCBS C15S via IV injection to male and female rats was almost superimposable. However, substantial differences were observed between males and females after a single administration of 8 or 24 mg/kg of 20NHS PEG-htCBS C15S via SC route. PK parameters for both IV and SC routes in males and females calculated from the results in FIG. 21A (4 mg/kg IV) and FIG. 21B (8 mg/kg and 24 mg/kg SC) are shown in Table 24. The bioavailability of 20NHS PEG-htCBS C15S from SC in rats was strongly sex-dependent with males absorbing less (19-21%) than females (about 36%), and the bioavailability was substantially lower in rats compared to what was observed in HO mice (52-83%).

TABLE 24

PK parameters of 20NHS PEG-htCBS C15S in Sprague Dawley rats

| PK Parameter | Unit | SC males | SC females | SC males | SC females | IV males | IV females |
|---|---|---|---|---|---|---|---|
| Dose | mg/kg | 8 | 8 | 24 | 24 | 4 | 4 |
| $AUC_{0-t}$ (obs area) | mU-h/µl | 2703 | 4505 | 9269 | 13135 | 7231 | 6165 |
| $AUC_{0-\infty}$/dose | mU-h/µl/(mg/kg) | 338 | 563 | 386 | 547 | 1808 | 1541 |
| Bioavailability | % | 18.7 | 36.5 | 21.3 | 35.5 | 100 | 100 |
| $t_{1/2-A}$ | h | 14.6 | 8.9 | 13.6 | 13.0 | N/A | N/A |
| $t_{1/2-E}$ | h | 44.2 | 40.1 | 51.2 | 41.1 | 40.0 | 34.8 |
| $t_{max}$ (obs) | h | 48 | 24 | 38 | 48 | N/A | N/A |
| $c_{max}$ | mU/µl | 32.7 | 58.2 | 110.0 | 166.3 | N/A | N/A |
| $c_{p0}$ | mU/µl | N/A | N/A | N/A | N/A | 182.1 | 186.2 |
| $c_{max}$/dose | mU/µl/(mg/kg) | 4.1 | 7.3 | 4.6 | 6.9 | N/A | N/A |
| MRT (area) | h | 65.6 | 76.8 | 66.1 | 79.8 | 52.9 | 45.5 |

B. Repeated Dose Pharmacokinetics

To further evaluate rats as a species for conducting long-term toxicity studies, the pharmacokinetics of 20NHS PEG-htCBS C15S was determined in three groups of Sprague Dawley rats receiving a total of 9 SC injections every 48 hours of either 4 mg/kg (low), 8 mg/kg (mid), or 24 mg/kg (high) 20NHS PEG-htCBS C15S. The study design is outlined in Table 23. The experiment was conducted for a length of 24 days. Plasma was collected and analyzed for CBS activity using methods detailed in Example 1.

Figure 21C:
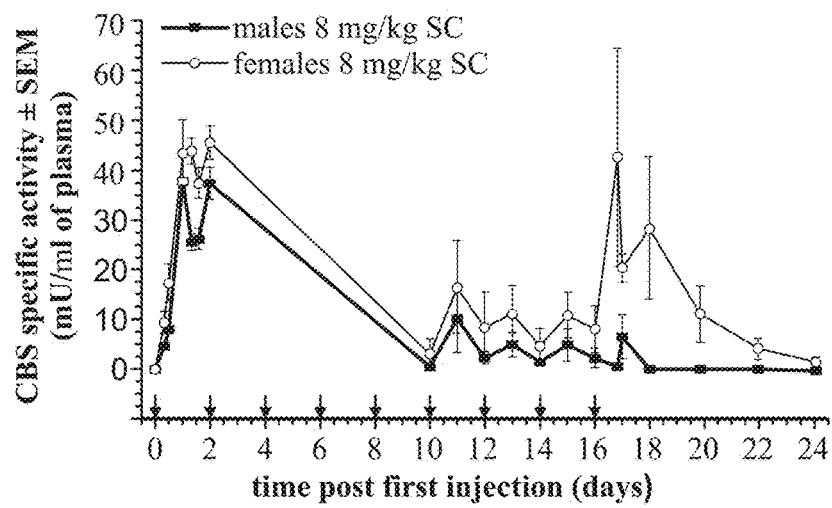
FIG. 21C shows specific activity of 20NHS PEG-htCBS C15S after the initial injection and at steady-state levels for individual wild-type Sprague Dawley rats receiving a total of 9 injections at a dose of 8 mg/kg.

The CBS specific activities for the repeated dose PK study plotted over time are exemplified on mid-dose 8 mg/kg as shown in FIG. 21C (similar phenomena was observed for low (4 mg/kg) as well as high dose (24 mg/kg groups). The arrows indicate an injection. No accumulation of CBS activity was observed in plasma, and a substantial decline in peak CBS activities was observed after the first 6 injections was observed. This unexpected inability of rats to achieve predicted steady-state levels of CBS activity in plasma was observed to be more profound in males than females, most likely due to their decreased bioavailability (see the single dose PK data above). The substantial attenuation of CBS activity in the subsequent administrations of 20NHS PEG-htCBS C15S was likely due to an immune response, which was evidence that rats are not a suitable species for long-term toxicity studies.

Example 20. Pharmacokinetics and Pharmacodynamics of 20NHS PEG-htCBS C15S in Monkeys To evaluate a non-human primate model for long-term toxicity studies and to estimate of human efficacious dose via allometric scaling, pharmacokinetic and pharmacodynamic studies of 20NHS PEG-htCBS C15S were conducted in wild type cynomolgus monkeys (*Macaca fascicularis*).

A. Single Dose Pharmacokinetics and Pharmacodynamics of 20NHS PEG-htCBS C15S in Monkey For the single dose PK study, three experimental groups of 4 (n=2M+2F) monkeys each were used to conduct the experiments. The first group received 2 mg/kg 20NHS PEG-htCBS C15S via IV injection. Blood was collected at 0, 0.083, 0.16, 0.25, 0.5, 1, 2, 4, 8, 24, 72, 120, and 192 hours post IV injection. The second and third groups received either 2 mg/kg or 6 mg/kg 20NHS PEG-htCBS C15S via SC injection. Blood was collected at 0, 1, 2, 4, 8, 24, 48, 72, 96, 120, 192, 240, and 336 hours post SC injection. Collected plasma was analyzed for CBS activity and sulfur amino acid metabolite (homocysteine, cystathionine and cysteine) levels were determined using methods described in Example 1.

Figure 22A:
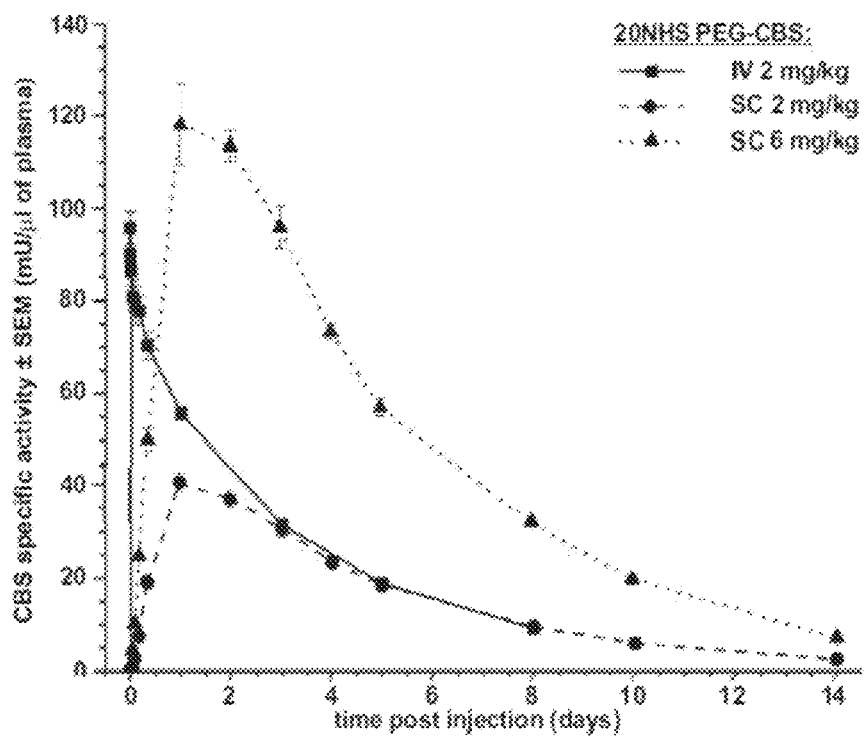
FIG. 22A-22B show the plasma concentration of Cth and the specific activity of 20NHS PEG-htCBS C15S in wild type cynomolgus monkeys (*Macaca fascicularis*) after a single IV or SC injection of a dose of 2 or 6 mg/kg.

The CBS specific activity over time curves in monkeys after receiving a single 2 mg/kg dose of IV administration or a 2 mg/kg or 6 mg/kg dose of SC administration of 20NHS PEG-htCBS C15S are shown in FIG. 22A. The calculated PK parameters for both IV and SC administration after a single injection are summarized in Table 25. The bioavailability of 20NHS PEG-htCBS C15S in monkeys was calculated to be approximately 80%, which is almost identical to the bioavailability in HO mice administered with SC dose of 5 mg/kg (83%). The elimination half-life of 20NHS PEG-htCBS C15S from plasma in monkeys was calculated to be 67 hours from the IV dataset and 73 hours from the SC dataset. $c_{max}$ was calculated to be 40.8 mU/µL at an SC dose of 2 mg/kg and 114.9 mU/µL at an SC dose of 6 mg/kg.

Table 25 lists PK parameters obtained from a single dose experiments conducted with 20NHS PEG-htCBS C15S in monkeys.

TABLE 25

PK parameters after a single IV and SC injection of 20NHS
PEG-htCBS C15S to a cynomolgus monkey

| PK Parameter | Unit | SC | SC | IV |
|---|---|---|---|---|
| Dose | mg/kg | 2 | 6 | 2 |
| AUC0-t (obs area) | mU-h/μl | 5263 ± 299 | 15743 ± 629 | 5942 ± 156 |
| AUC0-t/dose | mU-h/μl/(mg/kg) | 2761 ± 160 | 2727 ± 119 | 2971 ± 78 |
| Bioavailability | % | 80.8 ± 4.7 | 79.9 ± 3.5 | 100 |
| t1/2-A | h | 7.9 ± 1.0 | 9.7 ± 1.0 | N/A |
| t1/2-E | h | 72.9 ± 1.1 | 72.8 ± 1.7 | 66.7 ± 1.2 |
| tmax (obs) | h | 26.2 ± 2.6 | 32.4 ± 2.4 | N/A |
| $C_{max}$ | mU/μl | 40.8 ± 2.0 | 114.9 ± 7.5 | N/A |
| cp0 | mU/μl | N/A | N/A | 96.5 ± 2.8 |
| $c_{max}$/dose | mU/μl/(mg/kg) | 20.4 ± 1.0 | 19.2 ± 1.3 | N/A |
| MRT (area) | h | 116.3 ± 2.4 | 116.2 ± 5.0 | 89.9 ± 2.4 |
| CL (obs area) | μl/h/kg | N/A | N/A | 933 ± 53 |

Figure 22B:
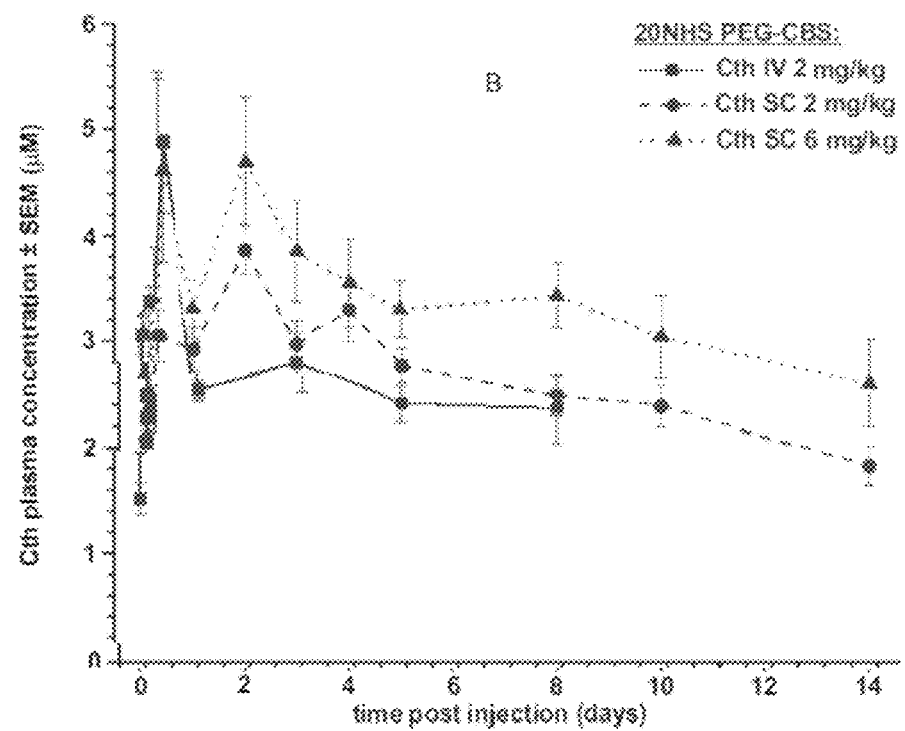

Since the injected monkeys were healthy wild-types and had naturally low Hcy levels (3-5 μM compared to 150-500 μM in murine models of homocystinuria), a pharmacodynamics effect after a single IV or SC dose of 20NHS PEG-htCBS C15S was not expected. No significant changes in plasma levels of Hcy and Cys were observed in injected monkeys. However, significant spikes were observed in plasma of Cth 8 hours after IV administration, and 8 and 48 hours after SC administration compared to the initial levels, which was evidence of a PD effect even in unaffected healthy monkeys (FIG. 22B). The spikes in Cth plasma levels likely originated from the administration of 20NHS PEG-htCBS C15S because CBS is the only enzyme known to form Cth. In addition, CBS enzyme does not normally circulate and function in the plasma. Cth formed in plasma by administered 20NHS PEG-htCBS C15S was observed to be cleared more slowly than Cys or Hcy. Therefore, the metabolites, particularly Cth, were further monitored in a multi-dose study to determine whether the observed PD effect were more pronounced or dose-dependent.

B. Repeated Dose Pharmacokinetics and Pharmacodynamics of 20NHS PEG-htCBS C15S in Monkeys Repeated dose experiments were performed in which three groups of 4 monkeys (1M+1F in main subgroup and 1M+1F in recovery subgroup) received a total of 6 consecutive SC doses every 72 hours of either 1 mg/kg (low), 3 mg/kg (mid), or 10 mg/kg (high) 20NHS PEG-htCBS C15S. Blood was collected from monkeys in main subgroups at 0, 32, 72, 104, 144, 176, 216, 248, 288, 320, 360, 392, and 408 hours post first injection, while the animals in recovery subgroups were bled at additional times of 432, 456, 480, 528, and 696 hours post first injection. Plasma was collected and analyzed for CBS activity and sulfur amino acid (homocysteine, cystathionine, cysteine, lanthionine, and homolanthionine) levels using methods described in Example 1.

Figure 23A:
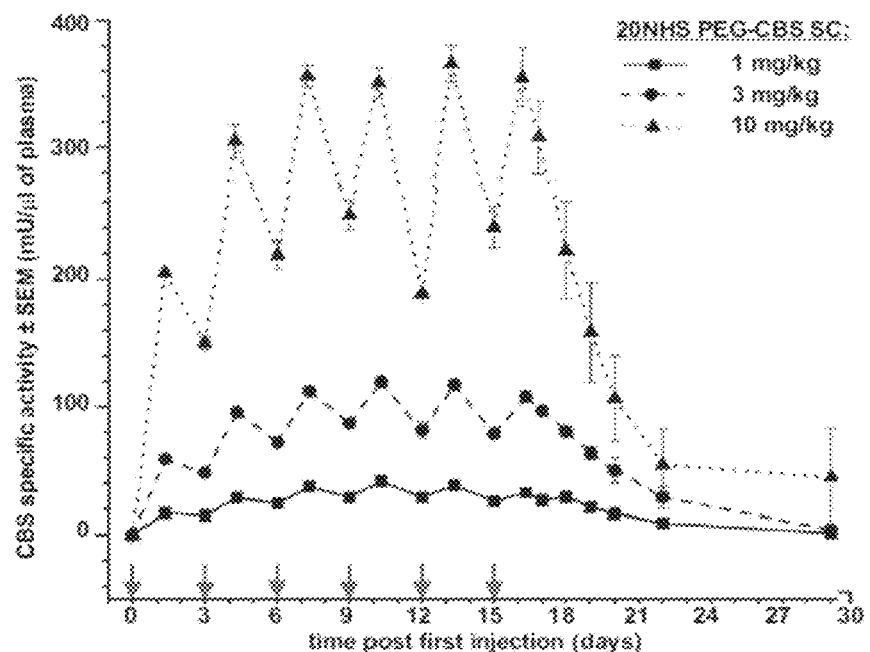
FIG. 23A-23B the specific activity and plasma levels of cystathionine (Cth) in wild type cynomolgus monkeys (*Macaca fascicularis*) after multiple SC administrations of a 1, 3, or 10 mg/kg dose of 20NHS PEG-htCBS C15S.

The 20NHS PEG-htCBS C15S specific activity over time curves for low (1 mg/kg), mid (3 mg/kg) and high (10 mg/kg) dose groups after 6 consecutive SC injections every 3 days are shown in FIG. 23A. The subcutaneous administration of 20NHS PEG-htCBS C15S to cynomolgus monkeys led to predictable and dose-dependent plasma levels of CBS activity after 6 doses given every 3 days for 16 days. In contrast to results in the rat repeated dose PK study, no attenuation of CBS activity was detected after repeated administrations of 20NHS PEG-htCBS C15S to wild-type monkeys. Each subsequent administration of the enzyme resulted in a completely predictable accumulation of CBS activity in plasma and essentially reached steady state levels after first three doses. Further dosing was observed to maintain the steady state, where the rate of elimination was equivalent to the rate of absorption leading to constant peak and trough plasma levels. The mean peak plasma concentration at steady state ($c_{max-ss}$) was normalized for doses ranging from 36 to 39 mU/μl and the trough plasma levels normalized for doses at steady state ($c_{mm-ss}$) ranging from 23 to 28 mU/μl. The elimination rate of 20NHS PEG-htCB S C15S was observed to be log-linear thus conforming to first order kinetics such that the time required for half the plasma 20NHS PEG-htCBS C15S activity to decrease was constant (data not shown). The elimination half-life was estimated in the recovery animals after the last dose at day 16 and was between 49 and 64 hours, i.e., similar to the half-life observed in monkeys after a single SC dose of 20NHS PEG-htCBS C15S (73 hours), which was evidence that multiple doses did not change the elimination rate.

Figure 23B:
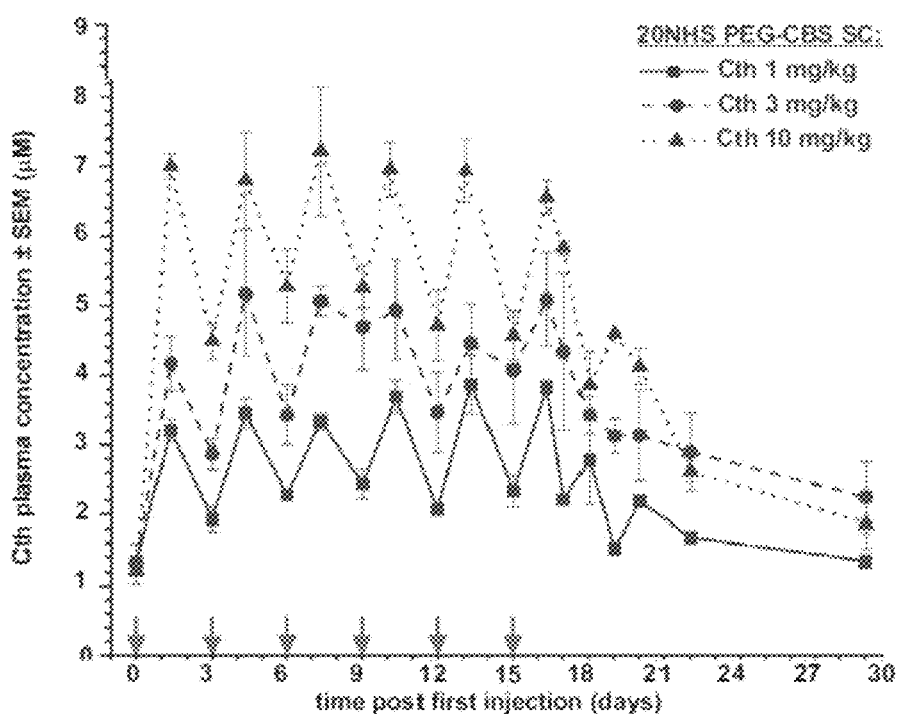

The plasma levels of cystathionine, a biomarker found indicative of 20NHS PEG-htCB S C15S activity even in unaffected healthy monkeys (see single dose monkey data). Results in monkeys receiving 6 injections 72 hours apart for low (1 mg/kg), mid (3 mg/kg), and high (10 mg/kg) doses are presented in FIG. 23B. The levels of Cth correlated well with peaks and troughs of 20NHS PEG-htCBS C15S activity in plasma and were observed to be dose-dependent as well. No clear differences were observed between dose groups for homocysteine and cysteine (data not shown).

In addition to thioether cystathionine produced by CBS, two thioethers lanthionine and homolanthionine, which were chosen as surrogate markers of hydrogen sulfide production, were measured in monkey plasma samples from repeated dose study at selected time points. Hydrogen sulfide is an emerging and important signaling molecule in many physiological processes and thus has been studied extensively in recent years for therapeutical applications.

Table 26 presents the plasma levels of cystathionine, lanthionine, and homolanthionine in wild-type monkeys after repeated administration of 20NHS PEG-htCBS C15S at different doses via the SC route. Metabolite levels at 0 hours (pre-dose), 176 hours and 392 hours after the first injection are reported. Data are presented as mean±standard error of the mean (SEM) in μM (n=4).

TABLE 26

Plasma levels of thioethers cysthathionine, lanthionine and homolanthionine in monkeys after repeated administration of 20NHS PEG-htCBS C15S

| Metabolite | 1 mg/kg | | | 3 mg/kg | | | 10 mg/kg | | |
|---|---|---|---|---|---|---|---|---|---|
| | 0 h | 176 h | 392 h | 0 h | 176 h | 392 h | 0 h | 176 h | 392 h |
| Cystathionine | 982 ± 72 | 4010 ± 236 | 4272 ± 333 | 982 ± 72 | 5629 ± 284 | 5893 ± 390 | 982 ± 72 | 7098 ± 12 | 9318 ± 288 |
| Lanthionine | 25 ± 2 | 46 ± 9 | 69 ± 7 | 25 ± 2 | 103 ± 7 | 109 ± 9 | 25 ± 2 | 281 ± 43 | 353 ± 38 |
| Homolanthionine | 38 ± 5 | 64 ± 7 | 72 ± 5 | 38 ± 5 | 64 ± 4 | 60 ± 10 | 38 ± 5 | 50 ± 3 | 53 ± 4 |

Repeated administration of 20NHS PEG-htCBS C15S to wild-type monkeys was observed to increase plasma levels of cystathionine and lanthionine, but levels of homolanthionine were not significantly affected. The increase of cystathionine and lanthionine was observed to be directly proportional to the dose, and the dose dependency was observed to be more prominent for lanthionine than cystathionine.

C. LC/MS/MS C15S Activity Assay

The bioanalytical method developed using LC/MS/MS for the determination of cystathionine M+4 as product of the CBS activity using cystathionine M+8 ($^{13}C_2D_6$) as an internal standard has been developed and validated for both monkey and human plasma samples and thus can be used to determine CBS activity in samples from pharmacokinetic and toxicology studies as well as clinical trials. The enzymatic assay was essentially performed as described in Example 1 with the following modifications. Deuterated D,L-homocysteine M+4 was used to initiate the reaction with unlabeled L-serine in the reaction mixture. After 30 min incubation at 37° C., the enzymatic reaction was stopped by acidification using 6N HCl and labeled product of the reaction (cystathionine M+4) was extracted using EZ:faast kit (Phenomenex, USA). Briefly, 50 µl of sample (calibration standard, QC sample or enzymatic reaction) was mixed in tube on ice and protected from light with 100 µl of internal standard solution (cystathionine M+8, 0.25 ng/µl) and 250 µl water. The mix was extracted with MCX cartridge columns (Waters). Eluted medium (6N ammonia in methanol) was evaporated to dryness at 45° C. The dry residue was dissolved in eluent medium of the EZ:faast kit, derivatized and liquid-liquid extracted following the kit manufacturer's protocol. The solid phase extraction was automatized with extraction plates to increase throughput and save time. Measurable concentrations of cystathionine M+4 were observed regardless of origin of the enzyme (htCBS C15S or C15S/ME-200GS present in plasma samples or controls or traces of endogenous monkey/human CBS in plasma samples). Much attention was paid to the calibration range since the incurred determinations were in the higher part of the concentration range qualified (5.00 to 1500 nM).

Tables 12-14 below show the comparison of C15S/ME-200GS specific activity determined by LC/MS/MS using D,L-homocysteine M+4 as a substrate and by radiometric assay using L-[$^{13}$C-U]-serine as a substrate. The enzyme's specific activity is presented in mU/µl. The "n.d." stands for "not determined". Table 27 shows comparison of the C15S/ME-200GS specific activities in a set of plasma samples from cynomolgus monkey injected IV with a single dose of 2 mg/kg.

TABLE 27

Comparison of C15S/ME-200GS specific activities determined by two assays in monkey plasma samples after a single IV dose of 2 mg/kg

| Time (h) | LC/MS/MS assay | Radiometric assay | Difference (%) |
|---|---|---|---|
| 0.083 | 88.865 | 95.741 | 7.182 |
| 0.167 | 81.065 | 90.049 | 9.977 |
| 0.25 | 80.315 | 88.891 | 9.648 |
| 0.5 | 81.815 | 85.342 | 5.243 |
| 1 | 75.415 | 80.992 | 6.887 |
| 2 | 71.765 | 78.984 | 9.140 |
| 4 | 67.415 | 77.809 | 13.359 |
| 8 | 61.715 | 70.357 | 12.283 |
| 24 | 47.815 | 55.865 | 14.411 |
| 72 | 28.915 | 31.601 | 8.500 |
| 120 | 17.180 | 18.908 | 9.142 |
| 192 | 8.490 | 9.182 | 7.534 |

Table 28 shows comparison of the C15S/ME-200GS specific activities in a set of plasma samples from cynomolgus monkey injected SC with a single dose of 2 mg/kg.

TABLE 28

Comparison of C15S/ME-200GS specific activities determined by two assays in monkey plasma samples after a single SC dose of 2 mg/kg

| Time (h) | LC/MS/MS assay | Radiometric assay | Difference (%) |
|---|---|---|---|
| 1 | n.d. | 2.842 | n.d. |
| 2 | 6.479 | 5.801 | 11.694 |
| 4 | 11.108 | 11.207 | 0.884 |
| 8 | 19.913 | 22.164 | 10.155 |
| 24 | n.d. | 40.293 | n.d. |
| 48 | 32.538 | 36.658 | 11.238 |
| 72 | 27.888 | 30.670 | 9.069 |
| 96 | 20.768 | 23.536 | 11.758 |
| 120 | 16.958 | 18.608 | 8.866 |
| 192 | 9.063 | 9.496 | 4.551 |
| 240 | 5.908 | 5.963 | 0.915 |
| 336 | 2.273 | 2.441 | 6.900 |

Table 29 shows comparison of the C15S/ME-200GS specific activities in a set of plasma samples from cynomolgus monkey injected SC with a single dose of 6 mg/kg (relates to Example 20).

TABLE 29

Comparison of C15S/ME-200GS specific activities determined by two assays in monkey plasma samples after a single SC dose of 6 mg/kg

| Time (h) | LC/MS/MS assay | Radiometric assay | Difference (%) |
|---|---|---|---|
| 1 | 3.065 | 3.739 | 18.029 |
| 2 | 7.640 | 9.180 | 16.778 |
| 4 | 18.365 | 22.263 | 17.877 |
| 8 | 41.090 | 50.194 | 18.138 |
| 24 | 85.190 | 111.081 | 23.308 |
| 48 | 86.090 | 109.292 | 21.229 |
| 72 | 74.840 | 95.722 | 21.815 |
| 96 | 59.940 | 73.072 | 17.971 |
| 120 | 56.340 | 56.427 | 0.154 |
| 192 | 24.190 | 31.513 | 23.238 |
| 240 | 14.440 | 19.203 | 24.801 |
| 336 | 4.784 | 5.807 | 17.608 |

Example 21. Extrapolation of PK/PD Data From Animals to Humans

In most cases, the plasma levels of a drug required to elicit a pharmacodynamic response are different across species due to species-specific sequence variations in the receptor or enzyme target. For example, an antibody against a human protein may have very different affinity for the murine and human target protein due to species differences in the target protein sequence. In the case of 20NHS PEG-htCBS C15S, the biological target is the amino acid, Hcy, which is identical across species. Furthermore, the distribution of a drug to the target tissue may vary across species and may not be easily predicted by drug plasma levels due to species-specific biodistribution. However, the "target tissue" for 20NHS PEG/C15S is the plasma lending a high degree of certainty to the prediction of extrapolated human values from interspecies comparison of the pharmacokinetic parameters in plasma.

Studies herein were conducted in mice using a SC dose of 7.5 mg/kg, and dose-response studies demonstrated that a dose of 5 mg/kg maximized efficacy in terms of modulating the plasma levels of biomarkers: Hcy, Cth and Cys. Using a dose of 5 mg/kg and correcting for the difference in body surface area between humans (70 kg) and mice (0.025 kg), a dose of 0.4 mg/kg was estimated to be the efficacious human equivalent dose (HED). At this dose the peak plasma levels were 50 mU/μL in mice with an AUC of 3060 mU−h/mL. Since the substrate for 20NHS PEG-htCBS C15S activity (Hcy and serine) was the same across species and the site of action was the blood pool itself, these parameters provide an accurate estimate of the target human plasma levels required for efficacy in a 20NHS PEG-htCBS clinical trial.

Pharmacokinetic studies were conducted in murine animal models of CBSDH, normal Sprague Dawley rats, and normal cynomolgus monkeys after either single and multiple SC injections at various dose-levels. In addition, single dose pharmacokinetic studies were conducted in all 3 species after IV administration of 20NHS PEG-htCBS C15S to evaluate bioavailability in all 3 species after SC administration. A summary of the pharmacokinetic parameters bioavailability (F %) corrected for dose in mouse, rat, and monkey models after SC administration are provided in Table.

TABLE 30

PK parameters for OT-58 (htCBS C15S ME-200GS) across species and the predicted human values from body surface area scaling

| Parameter:<br>Units: | $T_{1/2}$<br>h | AUC/dose<br>(mU-h/mL)/(mg/kg) | $C_{max}$/dose<br>(mU/μL)/(mg/kg) | $t_{max}$<br>h | F % |
|---|---|---|---|---|---|
| Species/Sex | | | | | |
| Mouse/both sexes | 20 | 612 | 10 | 24 | 83% |
| Rat/Male | 48 | 363 (1452)* | 4.4 (17)** | 35 | 20% |
| Rat/Female | 41 | 555 (1233)* | 7.1 (16)** | 29 | 36% |
| Monkey/both sexes | 73 | 2744 | 20 | 29 | 81% |
| Human predicted value | 177 | 7474 | 34 | NA | NA |

*indicates that the average AUC/dose in rats was corrected to 80% bioavailability equaling 1343 (mU-h/mL)/(mg/kg).
**indicates that the average $c_{max}$/dose in rats was corrected to 80% bioavailability equaling 16.5 (mU/μL)/(mg/kg).

According to these results, 20NHS PEG-htCBS C15S was slowly absorbed into the bloodstream after SC administration in all 3 species. The absorption half-life was similar across species ranging between 5 and 12 hours in the mouse, between 10 and 16 hours in the rat, and between 8 and 10 hours in the monkey after a single SC injection, which led to $T_{max}$ values that ranged between 24 hours and 48 hours in individual animals. The elimination half-life ($T_{1/2}$) was 20 hours in mice, 44.5 hours in rats, and 73 hours in monkeys. The percentage of 20NHS PEG-htCBS C15S absorbed into the blood after SC administration (F %) was >80% in both mouse (5 mg/kg dose) and monkey (at doses of 1, 3 or 10 mg/kg) models. However, the percentage of 20NHS PEG-htCBS C15S absorbed into the blood was only 20% in male rats and 36% in female rats. In Table 30, the AUC/dose and Cmax/dose in rat were corrected to 80% bioavailability (parenthetic values in Table 30) to allow interspecies comparisons to be made at the same F %.

Interspecies comparisons were conducted based upon body surface area scaling assuming an 80% bioavialability in all 3 species (mouse, rat and monkey) to determine if a linear correlation existed between the log body weight and the log of various PK parameters (AUC/dose, Cmax per dose and $T_{1/2}$). A linear correlation in these parameters indicated that the pharmacokinetic parameters for 20NHS PEG-htCBS C15S were scaled to body surface area, and thus would likely be predictive of human values. Linear correlations allow predictions of the clinical dose and dosing regimen from the preclinical data to be made.

Figure 24A:
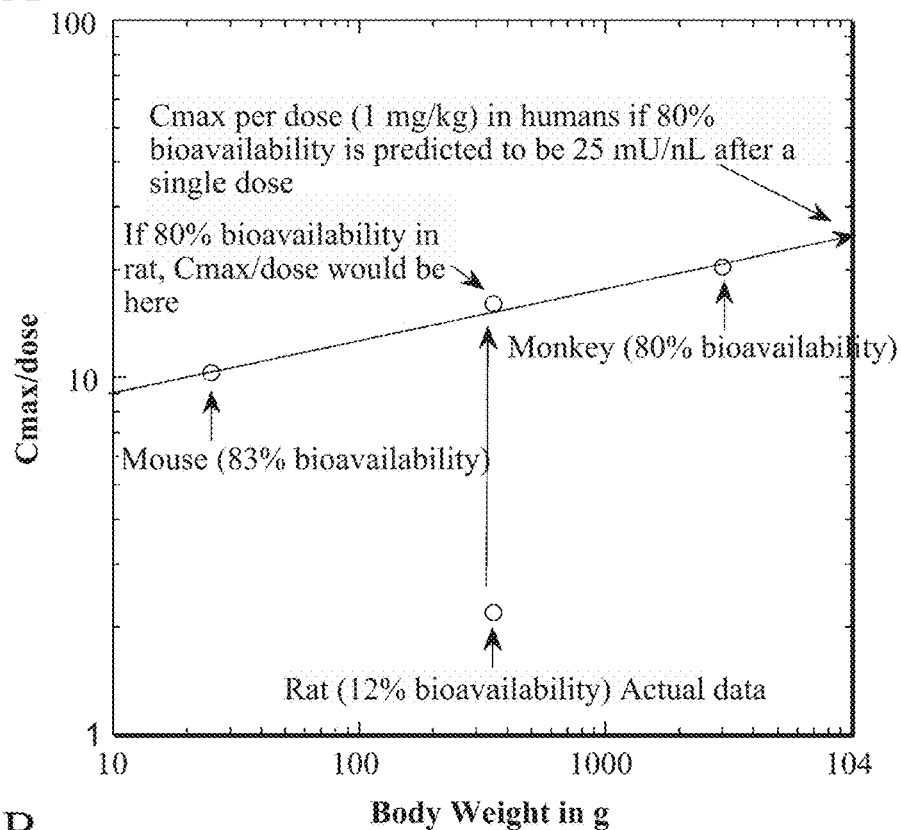
FIG. 24A-24G shows allometric scaling results to estimate an efficacious dose of 20NHS PEG-htCBS in humans based on the results for the mouse, rat, and monkey models herein.
Figure 24B:
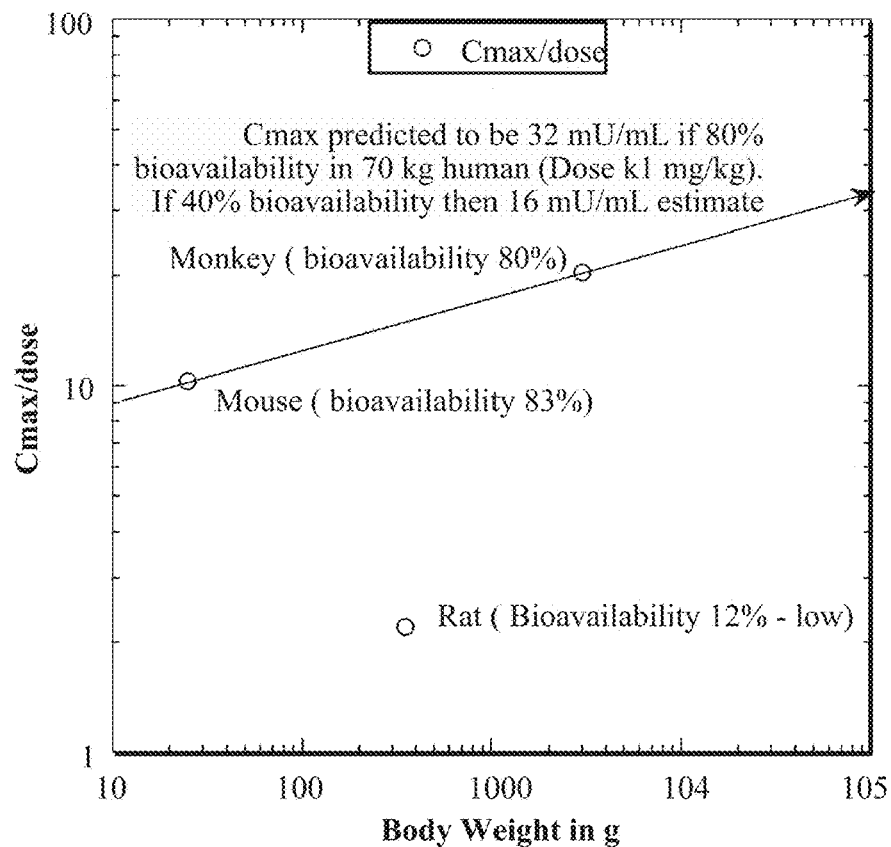
Figure 24C:
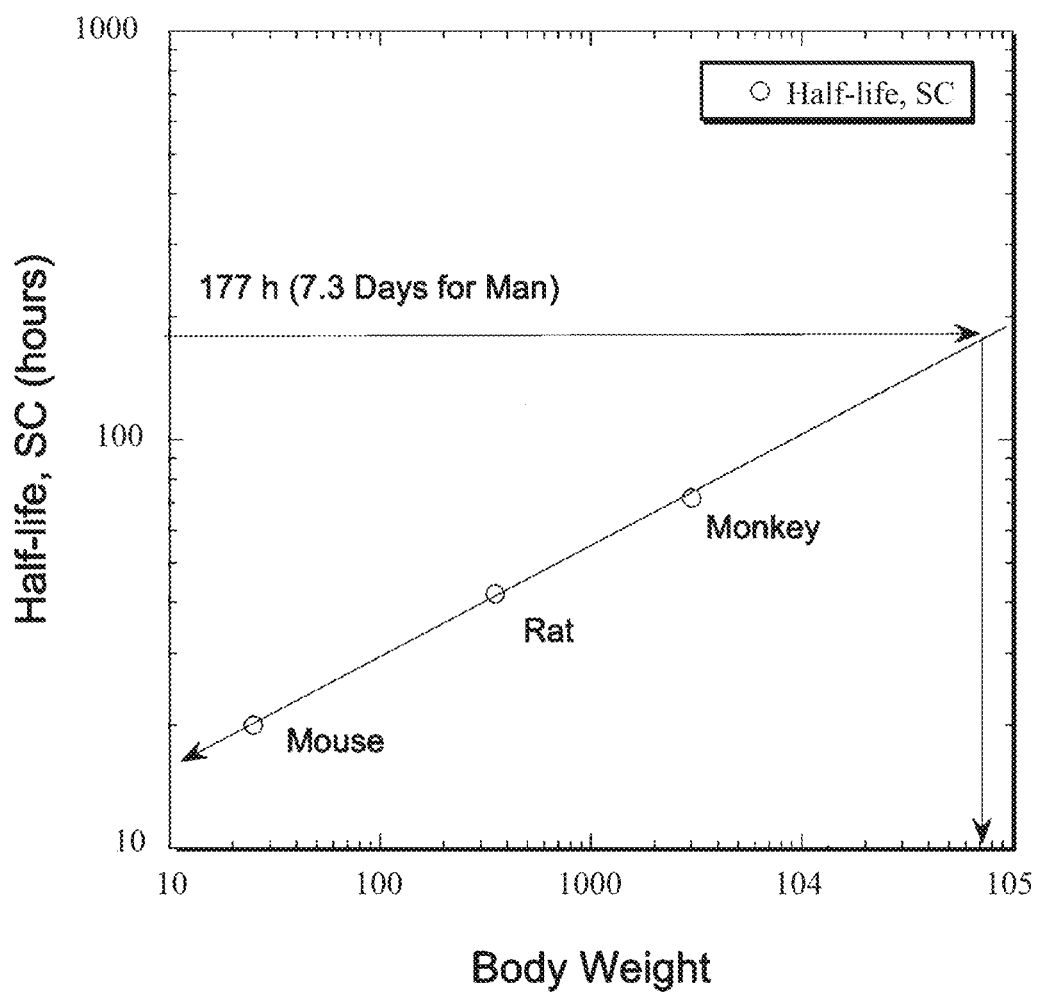

A linear correlation was observed for the pharmacokinetic parameters AUC, Cmax and $T_{1/2}$ across species for 20NHS PEG-htCBS C15S. As shown in FIG. 24A (AUC/dose), FIG. 24B (Cmax/dose), and FIG. 24C ($T_{1/2}$), an excellent linear correlation was observed between log body weight of each species against their associated PK parameters corrected for dose. By extrapolating to the log body weight for humans (70 kg) for each parameter, the AUC/dose, Cmax/dose, and $T_{1/2}$ was calculated for human subjects. The predictive human values are provided in Table 30.

Figure 24D:
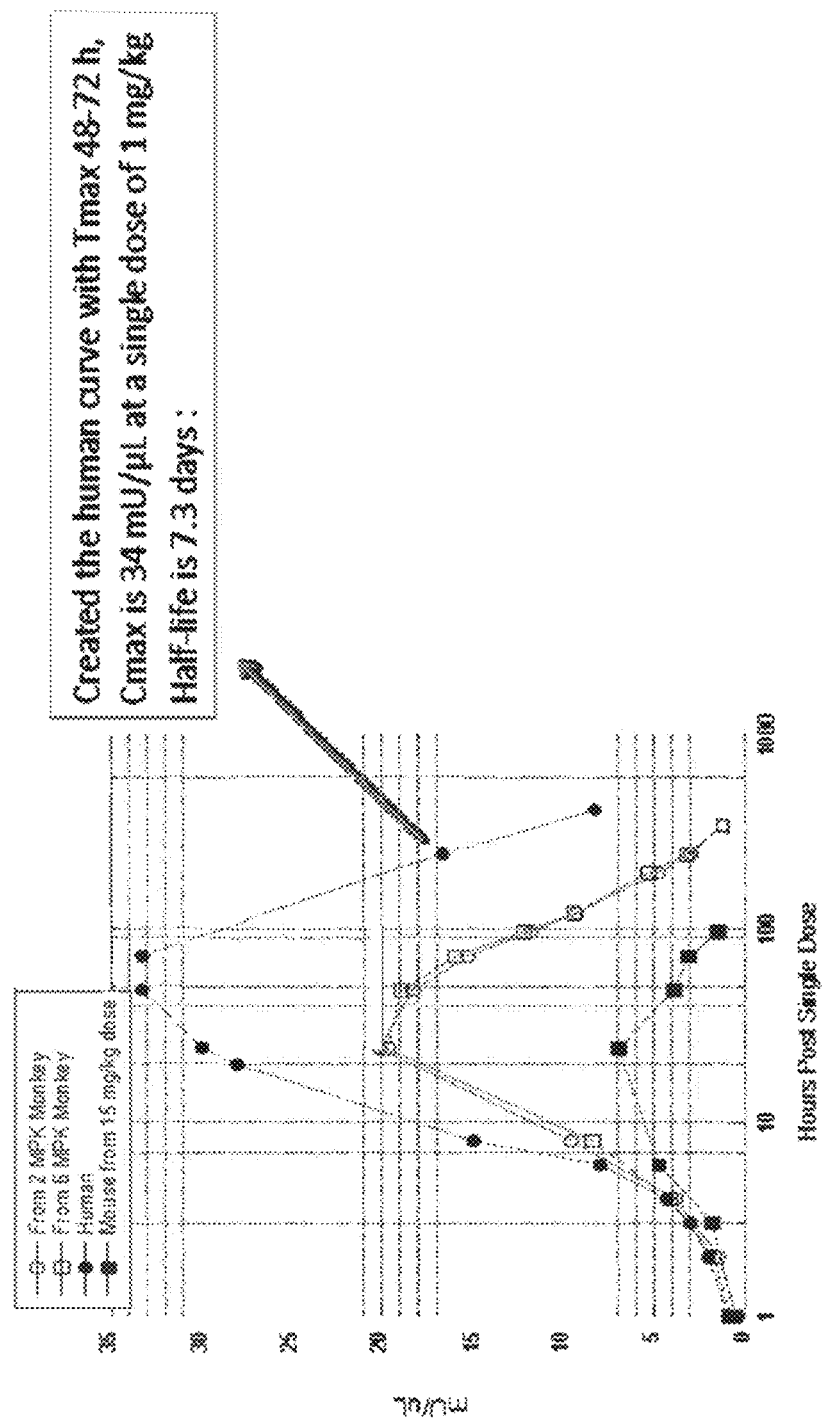

The extrapolated/predicted half-life in humans was about 175 hours or 7.3 days. The human predicted efficacious dose was calculated from the efficacious dose in mice (5 mg/kg) by allometric scaling to be 0.4 mg/kg in a 70 kg human. Using the predicted human $c_{max}$ of 34 mU/μL (per mg/kg) and a $T_{max}$ range of 48 to 72 hours, a hypothetical curve was constructed for a single dose PK curve in humans, which is shown in FIG. 24D. The E intercept was 43.079 mg/μL, and the half-life was 176.737 hours. Data from mice and monkeys are also shown for comparative purposes in FIG. 24D. Table 31 provides the extrapolated concentrations estimated for humans.

TABLE 31

Extrapolated concentrations for humans

| Time (hours) | Concentration (mg/μL) |
|---|---|
| 0 | 0 |
| 1 | 0.9 |
| 2 | 2 |
| 4 | 4.3 |
| 8 | 8 |
| 20 | 20 |
| 48 | 33.3 |
| 72 | 34 |
| 96 | 28 |
| 240 | 16.7 |
| 336 | 12 |
| 408 | 8.5 |

Figure 24E:
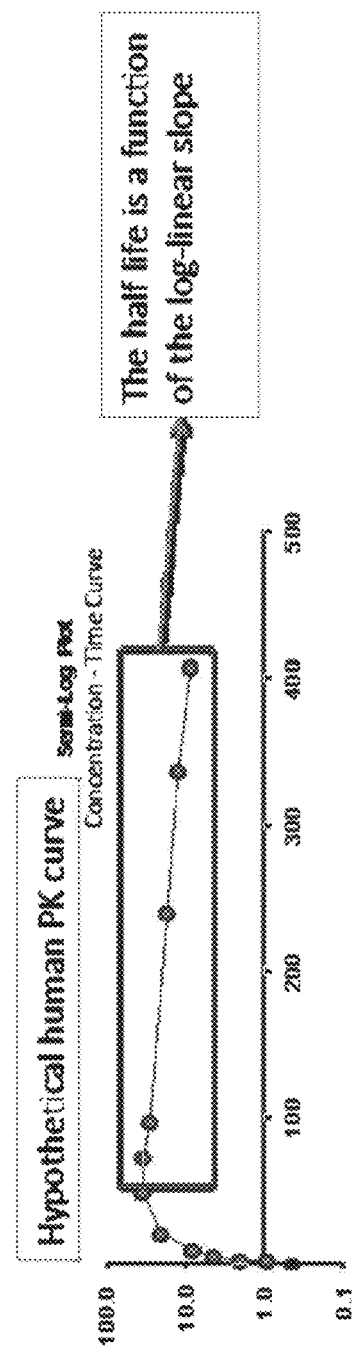

From the PK parameters derived from FIG. 24D, a multiple dose PK curve was modeled assuming first order kinetics in humans, which is shown in FIG. 24E.

A. Hypothetical Repeated Dose PK Curve in Humans

Figure 24F:
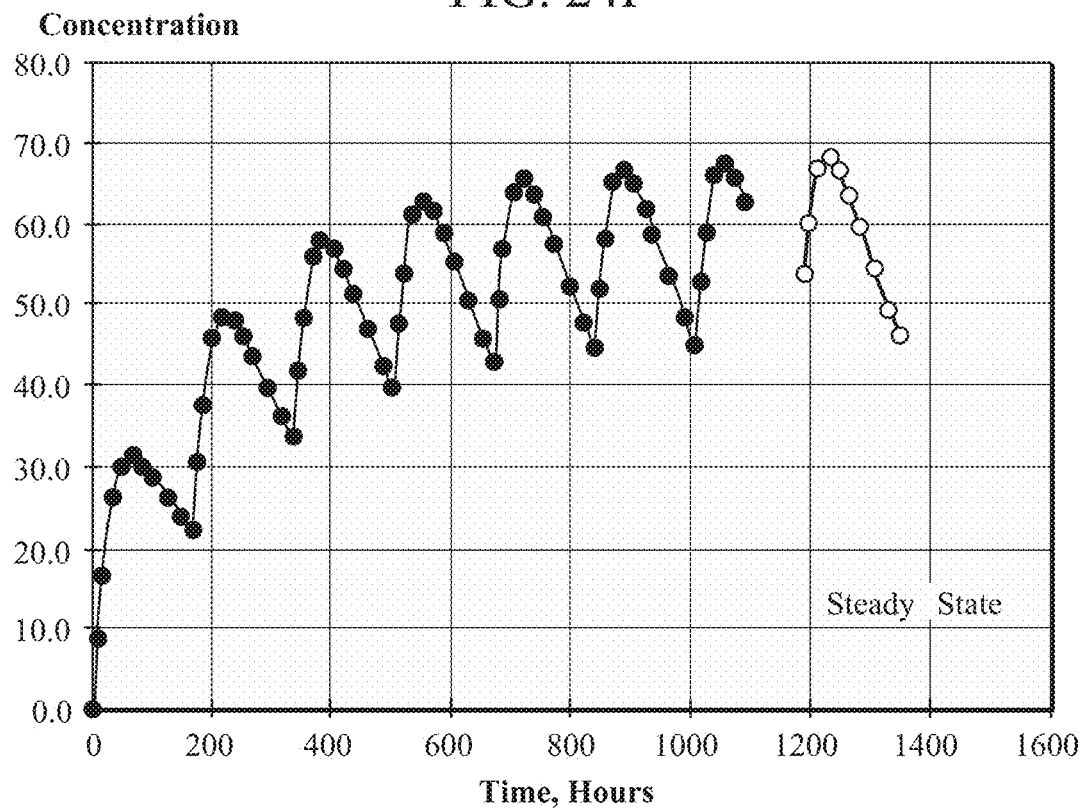
Figure 24G:
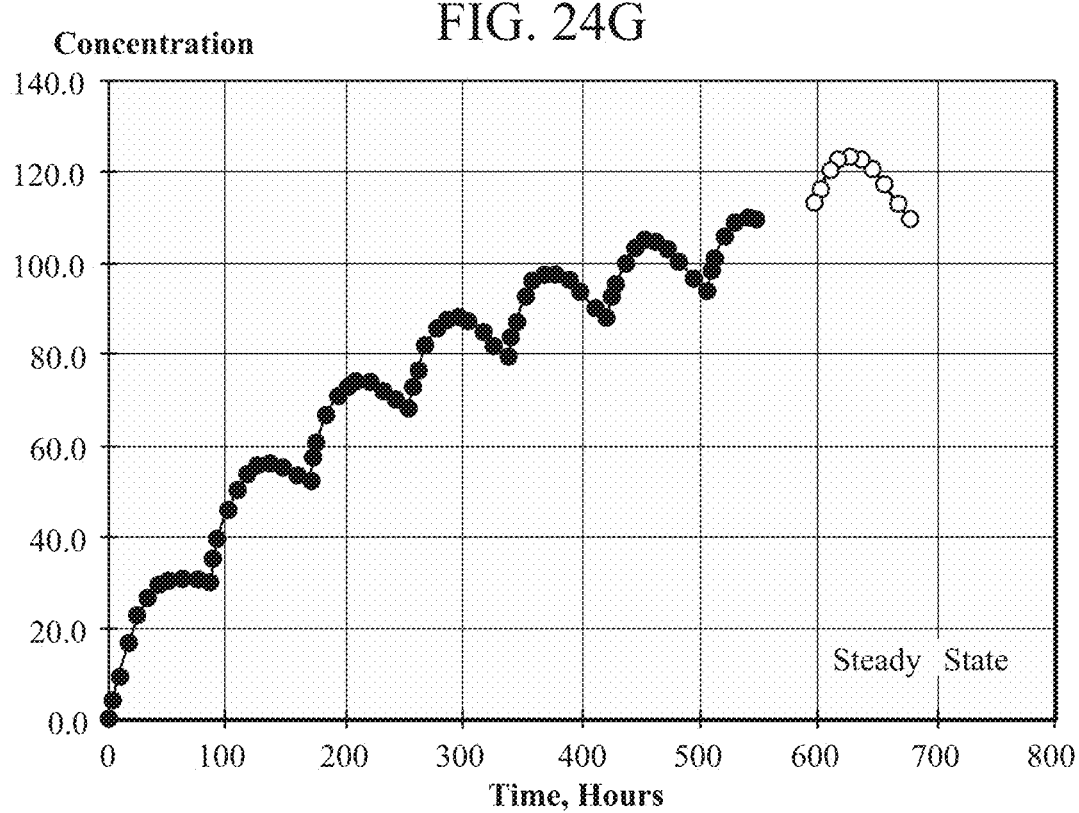

FIG. 24F shows predicted PK values for 20NHS PEG-htCBS C15S in humans at a SC dose of 1 mg/kg administered once per week during the approach to steady state plasma levels and the predicted peak and trough levels at steady state (light gray). FIG. 24G shows predicted PK values for 20NHS PEG-htCBS C15S in humans at a SC does of 1 mg/kg administered twice per week during the approach to steady state plasma levels and the predicted peak and trough levels in humans at this dosing interval (light gray). Table 32 compares the predicted peak and trough plasma levels of 20NHS PEG-htCBS C15S in humans at SC doses of 0.33, 0.66, and 1 mg/kg administered once per week and twice per week (assuming 80% bioavailability in humans).

TABLE 32

Predicted plasma levels in humans (assuming 80% bioavailability)

| Human dose | 1 mg/kg | | 0.66 mg/kg | | 0.33 mg/kg | |
|---|---|---|---|---|---|---|
| Dosing interval | 1x/wk (168 h) | 2x/wk (84 h) | 1x/week (168 h) | 2x/week (84 h) | 1x/week (168 h) | 2x/week (84 h) |
| Initial Cmax, mU/μL | 34 | 34 | 22.6 | 22.6 | 11.3 | 11.3 |
| Peak @ SS, mU/μL | 67.9 | 123 | 45.2 | 82 | 22.6 | 41 |

TABLE 32-continued

Predicted plasma levels in humans (assuming 80% bioavailability)

| Human dose | 1 mg/kg | | 0.66 mg/kg | | 0.33 mg/kg | |
|---|---|---|---|---|---|---|
| Dosing interval | 1x/wk (168 h) | 2x/wk (84 h) | 1x/week (168 h) | 2x/week (84 h) | 1x/week (168 h) | 2x/week (84 h) |
| Trough @ SS, mU/µL | 46.2 | 109 | 30.8 | 69 | 15.4 | 34.5 |
| C1min | 22.3 | 29.0 | | | | |
| Tmax @ SS (hr) | 38.2 | 27.4 | | | | |

From these calculations, a dose of 0.66 mg/kg 20NHS PEG-htCBS C15S administered SC to human patients once a week was predicted to result in plasma levels that range between 31 and 45 mU/µL at steady state. Similarly, a dose of 0.33 administered twice weekly was predicted to result in plasma levels ranging between 35 and 41 mU/µL at steady state (after about 8 doses). These predictions assume a subcutaneous bioavailability of 80% as was observed in both mice and monkeys. These doses of 20NHS PEG-htCBS C15S are also expected to produce peak and trough plasma levels in the efficacious range for the plasma levels similar to those in mice (peak levels of 50 mU/µL). Additionally, these doses correspond to the human efficacious dose predicted from the murine studies alone of 0.4 mg/kg. The linear correlation of body weight and the PK parameters across the preclinical species, allowed allometric scaling (body surface area scaling) to predict the PK parameters AUC, Cmax and the elimination half-life in humans by comparing values across species.

Both methods of predicting the efficacious dose in humans (directly from the mouse data and allometric scaling across 3 species) were observed to agree in terms of efficacious dose predictions (HED). Thus, assuming an 80% bioavailability, a proposed dose of 0.33 mg/kg administered twice weekly or 0.66 mg/kg administered once weekly will likely be effective doses in human clinical trials.

The foregoing examples of the related art and limitations related therewith are intended to be illustrative and not exclusive. Other limitations of the related art will become apparent to those of skill in the art upon a reading of the specification and a study of the drawings.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, scientific articles and the like, cited or identified in this application are hereby incorporated by reference in their entirety in order to describe more fully the state of the art to which the present application pertains.

What is claimed is:

1. A method of treating homocystinuria in a human subject comprising administering an isolated human truncated cystathionine beta synthase (htCBS) mutant polypeptide to the subject, wherein:
    (a) the isolated htCBS mutant polypeptide comprises amino acids 2-413 of the amino acid sequence of SEQ ID NO:13 and is conjugated to a PEG moiety, and
    (b) the isolated htCBS mutant polypeptide is administered in a dose between 0.33 mg/kg and 10 mg/kg at least once a week for at least six weeks.

2. The method of claim 1, wherein the PEG is a low molecular weight linear PEG of about 2 kDa.

3. The method of claim 1, wherein the PEG is a high molecular weight four arm branched PEG of about 40 kDa.

4. The method of claim 1, wherein the PEG is a 20 kDa NHS ester-activated PEG.

5. The method of claim 1, wherein the isolated htCBS mutant polypeptide is administered at least twice a week.

6. The method of claim 1, wherein the isolated htCBS mutant polypeptide is co-administered with betaine.

7. The method of claim 1, wherein betaine is administered prior to the isolated htCBS mutant polypeptide.

8. A method of increasing the cystathionine and/or cysteine in a human subject comprising administering an isolated human truncated cystathionine beta synthase (htCBS) mutant polypeptide to the subject, wherein:
    (a) the isolated htCBS mutant polypeptide comprises amino acids 2-413 of the amino acid sequence of SEQ ID NO:13 and is conjugated to a PEG moiety, and
    (b) the isolated htCBS mutant polypeptide is administered in a dose between 0.33 mg/kg and 10 mg/kg at least once a week for at least six weeks.

9. The method of claim 8, wherein the PEG is a low molecular weight linear PEG of about 2 kDa.

10. The method of claim 8, wherein the PEG is a high molecular weight four arm branched PEG of about 40 kDa.

11. The method of claim 8, wherein the PEG is a 20 kDa NHS ester-activated PEG.

12. The method of claim 8, wherein the isolated htCBS mutant polypeptide is administered at least twice a week.

13. The method of claim 8, wherein the isolated htCBS mutant polypeptide is co-administered with betaine.

14. The method of claim 8, wherein betaine is administered prior to the isolated htCBS mutant polypeptide.

15. A method of decreasing homocysteine, methionine, and/or S-adenosyl homocysteine in a human subject comprising administering an isolated human truncated cystathionine beta synthase (htCBS) mutant polypeptide to the subject, wherein:
    (a) the isolated htCBS mutant polypeptide comprises amino acids 2-413 of the amino acid sequence of SEQ ID NO:13 and is conjugated to a PEG moiety, and
    (b) the isolated htCBS mutant polypeptide is administered in a dose between 0.33 mg/kg and 10 mg/kg at least once a week for at least six weeks.

16. The method of claim 15, wherein the PEG is a low molecular weight linear PEG of about 2 kDa.

17. The method of claim 15, wherein the PEG is a high molecular weight four arm branched PEG of about 40 kDa.

18. The method of claim 15, wherein the PEG is a 20 kDa NHS ester-activated PEG.

19. The method of claim 15, wherein the isolated htCBS mutant polypeptide is administered at least twice a week.

20. The method of claim 15, wherein the isolated htCBS mutant polypeptide is co-administered with betaine or betaine is administered prior to the isolated htCBS mutant polypeptide.

* * * * *